United States Patent
Cowen et al.

(10) Patent No.: US 7,572,789 B2
(45) Date of Patent: *Aug. 11, 2009

(54) SALTS OF POTASSIUM ATP CHANNEL OPENERS AND USES THEREOF

(75) Inventors: Neil M. Cowen, Carlsbad, CA (US); Kenneth B. Kashkin, Sparta, NJ (US); Khaled A. Yamout, Carlsbad, CA (US)

(73) Assignee: Essentialis, Inc., Carlsbad, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 12/391,990

(22) Filed: Feb. 24, 2009

(65) Prior Publication Data

US 2009/0148526 A1    Jun. 11, 2009

Related U.S. Application Data

(63) Continuation of application No. 11/614,044, filed on Dec. 20, 2006.

(60) Provisional application No. 60/756,941, filed on Jan. 5, 2006, provisional application No. 60/854,740, filed on Oct. 27, 2006.

(51) Int. Cl.
*A61K 31/549* (2006.01)
*C07D 285/22* (2006.01)

(52) U.S. Cl. ............... 514/223.2; 544/12

(58) Field of Classification Search ............... 514/223.2; 544/12
See application file for complete search history.

(56) References Cited

U.S. PATENT DOCUMENTS

| | | | |
|---|---|---|---|
| 2,678,311 A * | 5/1954 | Delmar et al. ............... 544/273 |
| 2,986,573 A | 5/1961 | Topliss et al. |
| 3,265,573 A | 8/1966 | Goldberg |
| 3,269,906 A | 8/1966 | Topliss et al. |
| 3,304,228 A | 2/1967 | Topliss |
| 3,345,365 A * | 10/1967 | Topliss et al. ............... 544/12 |
| 4,029,780 A | 6/1977 | Nishimura et al. |
| 4,184,039 A | 1/1980 | Soldati et al. |
| 4,880,830 A | 11/1989 | Rhodes et al. |
| 5,284,845 A | 2/1994 | Paulsen |
| 5,356,775 A | 10/1994 | Hebert et al. |
| 5,378,704 A | 1/1995 | Weller et al. |
| 5,399,359 A | 3/1995 | Baichwal |
| 5,415,871 A | 5/1995 | Pankhania et al. |
| 5,629,045 A | 5/1997 | Veech |
| 5,744,594 A | 4/1998 | Adelman et al. |
| 6,022,562 A | 2/2000 | Autant et al. |
| 6,197,765 B1 | 3/2001 | Vardi et al. |
| 6,197,976 B1 | 3/2001 | Harrington et al. |
| 6,225,310 B1 | 5/2001 | Nielsen et al. |
| 6,255,459 B1 | 7/2001 | Lester et al. |
| 6,309,855 B1 | 10/2001 | Duprat et al. |
| 6,313,112 B1 | 11/2001 | Busija |
| 6,329,367 B1 | 12/2001 | Hansen et al. |
| 6,361,795 B1 | 3/2002 | Kuczynski et al. |
| 6,894,043 B1 | 5/2005 | Pirotte et al. |
| 7,053,180 B2 | 5/2006 | Johnson et al. |
| 7,268,130 B2 | 9/2007 | Desos et al. |
| 7,378,414 B2 | 5/2008 | Hutchinson et al. |
| 2002/0035106 A1 | 3/2002 | Hansen et al. |
| 2002/0173636 A1 | 11/2002 | Chen |
| 2003/0035106 A1 | 2/2003 | Yeh al. |
| 2004/0097492 A1 | 5/2004 | Pratt et al. |
| 2004/0167123 A1 | 8/2004 | Pratt et al. |
| 2004/0204472 A1 | 10/2004 | Briggs et al. |
| 2004/0229803 A1 | 11/2004 | Stephenson et al. |
| 2004/0266822 A1 | 12/2004 | Wang et al. |
| 2005/0075331 A1 | 4/2005 | Pratt et al. |
| 2005/0089473 A1 | 4/2005 | Black et al. |
| 2005/0203072 A1 | 11/2005 | Rudolph et al. |
| 2006/0051418 A1 | 3/2006 | Cowen et al. |
| 2006/0148037 A1 | 7/2006 | Johnson et al. |
| 2006/0263805 A1 | 11/2006 | Terzic et al. |
| 2007/0191351 A1 * | 8/2007 | Cowen et al. ............ 514/223.2 |
| 2007/0254863 A1 | 11/2007 | Antel et al. |
| 2007/0254871 A1 | 11/2007 | Gehenne et al. |

FOREIGN PATENT DOCUMENTS

| | | |
|---|---|---|
| DE | 2757925 | 6/1979 |
| EP | 0 327 263 B1 | 8/1989 |
| EP | 0 618 209 B1 | 5/1994 |

(Continued)

OTHER PUBLICATIONS

Berge "Pharmaceutical salts" J. Pharm. Sciences v.66(1) p. 1-19 (1977).*

(Continued)

*Primary Examiner*—Celia Chang
(74) *Attorney, Agent, or Firm*—Foley & Lardner LLP

(57) ABSTRACT

Provided are immediate or prolonged administration of certain salts of $K_{ATP}$ channel openers such as diazoxide to a subject to achieve novel pharmacodynamic, pharmacokinetic, therapeutic, physiological, metabolic and compositional outcomes in the treatment of diseases or conditions involving $K_{ATP}$ channels. Also provided are pharmaceutical formulations, methods of administration and dosing of the salts that achieve these outcomes and reduce the incidence of adverse effects in treated individuals. Further provided are method of co-administering the salts with other drugs to treat diseases of humans and animals.

14 Claims, 51 Drawing Sheets

FOREIGN PATENT DOCUMENTS

| GB | 982072 | 3/1961 |
|---|---|---|
| JP | 59-95212 | 6/1984 |
| WO | WO 93/21171 | 10/1993 |
| WO | WO 98/10786 | 3/1998 |
| WO | WO 02/50085 A1 | 6/2002 |
| WO | WO 03/099801 | 12/2003 |
| WO | WO 03/103606 A2 | 12/2003 |
| WO | WO 03/105896 A1 | 12/2003 |
| WO | WO 2004/099217 A1 | 11/2004 |
| WO | WO 2006/000607 A1 | 5/2006 |
| WO | WO 2006/045799 A2 | 5/2006 |
| WO | WO 2007/081521 | 7/2007 |

OTHER PUBLICATIONS

Delmar et al. "Theophylline salts" CA49:32579 (1955).*
Cowen et al "salts of potassium ATP . . . " CA 150:114355 (2009).*
Calesnick et al., "Importance of Dissolution Rates in Producing Effective Diazoxide Blood Levels in Man", *Journal of Pharmaceutical Sciences*, 1965, vol. 54, No. 7, pp. 1277-1280.
Chernykh et al., "Synthesis and Properties of 3-substituted 2H-1,2,4-Benzothiadiazine 1,1 Dioxide", *Khimiya Geterotsiklicheskikh Soedineii (Chemistry of Heterocyclic Compounds)*, 1976, vol. 4, pp. 479-483. (English Translation provided).
Drogovoz et al., "Relation Between the Structure and Diuretic Activity of 2H-1,2,4-benzothiadiazine-1,1-dioxide-3-carboxylic Acid Derivatives", *Farmzkologiya I Toksikologiya (Pharmacology & Toxicology)*, 1977, vol. 40, No. 1, pp. 73-76. (English Translation provided).
Loubatiérés et al., "Etude Expérimentale d'un Sulfamide Hyperglycéemiant, le Diazoxide (Experimental Study of Diazoxide, a Hyperglycemic Sulfonamide" *Societe de Biologie*, Jan. 17, 1996, vol. 160, pp. 165-168. (English Translation provided).
Petyunin et al., "Use of 2-Sulphamoyl Oxanilic Acid Esters as a Basis for the Synthesis of Derivatives of 2-H-1,2,3-Benzothiadizine-1,1-dioxo-3-carboxylic acid Derivatives", *Khimiya Geterotsiklicheskikh Soedineii (Chemistry of Heterocyclic Compounds), Report LVII from Heterocyclic Chemistry Research series*, 1976, vol. 8, pp. 1056-1059. (English Translation provided).
Pruitt et al., "Metabolism of Diazoxide in Man and Experimental Analysis", *Journal of Pharmacology and Experimental Therapeutics*, 1974, vol. 188, No. 1, pp. 248-256.
Raffa et al., "1,2,4-Benzothiadiazine Derivatives Research. Note XIII. Reaction Between 3-chloroalkyl-1,2,4-benzothiadiazine, 1-dioxide and Amines," *Farmaco Edizione Scientifica*, 1960, vol. 15, pp. 700-715. (English Translation provided).
Raffa et al., "1,2,4-Benzothiadiazine Derivatives Research, Note XIV. Relation Between Chemistry and Flavor", *Farmaco Edizione Scientifica*, 1960, vol. 15, pp. 716-725. (English Translation provided).
Raffa et al., "1,2,4-Benzothiadiazine Derivatives Research: Note XV. Relation Between 3-chloroalkyl-1,2,4-benzothiadiazine 1,1-dioxide and Tertiary Amines", *Farmaco Edizione Scientifica*, 1960, vol. 15, pp. 845-855. (English Translation provided).
Supuran et al., "Complexes with Biologically Active Ligands. Part 1. Synthesis of Coordination Compounds of Diazoxide with Transition- and Main-group Cations", *Metal Based Drugs*, 1996, vol. 3, No. 1, pp. 25-30.
Tait et al., "1,2,4-Benzothiadiazine Derivatives as $\alpha_1$ and $5\text{-HT}_{1A}$ Receptor Ligands," *Bioorganic & Medicinal Chemistry Letters*, 2005, vol. 15, No. 4, pp. 1185-1188.
Aishima et al., "Actions of ZD0947, a Novel ATP-sensitive K+ Channel Opener, on Membrane Currents in Human Detrusor Myocytes", *British Journal of Pharmacology*, Nov. 2006, vol. 149, No. 5, pp. 542-550.
Aizawa et al., "Prophylaxis of Genetically Determined Diabetes by Diazoxide: A Study in a Rat Model of Naturally Occurring Obese Diabetes", *J of Pharma Exp Therapy*, 1995, vol. 275, No. 1, pp. 194-199.
Alemzadeh et al., "Modification of Insulin Resistance by Diazoxide in Obese Zucker Rats", *Endocrinology*, 1993, vol. 133, pp. 705-712.
Alemzadeh et al., "Antiobesity Effect of Diazoxide in Obese Zucker Rats", *Metabolism*, 1996, vol. 45, No. 3, pp. 334-341.
Alemzadeh et al., "Beneficial Effect of Diazoxide in Obese Hyperinsulinemic Adults", *J Clin Endocr Metab.*, 1998, vol. 83, pp. 1911-1915.
Alemzadeh et al., "Effect of Diazoxide on Brain Capillary Insulin Reeptor Binding and Food Intake in Hyperphagic Obese Zucker Rats", *Endocrinology*, 1999, vol. 140, pp. 3197-3202.
Alemzadeh et al., "Chronic Suppression of Insulin by Diazoxide Alters the Activities of Key Enzymes Regulating Hepatic Gluconeogenesis in Zucker Rats", *Endocrinology*, 2002, vol. 146, pp. 871-879.
Alemzadeh et al., "Diazoxide Enhances Adipose Tissue Protein Kinase B Activation and Glucose Transporter-4 Expression in Obese Zucker Rats", *Med Sci Monit*, 2004, vol. 10, No. 3, pp. BR53-60.
Alemzadeh et al., "Modulation of Adipoinsular Axis in Prediabetic Zucker Diabetic Fatty Rats by Diazoxide", *Endocrinology*, 2004, vol. 145, No. 12, pp. 5476-5484.
Babenko et al., "A View of $SUR/K_{IR}6.X$, $K_{ATP}$ Channels", *Annu. Rev. Physiol.*, 1998, vol. 60, pp. 667-687.
Babenko et al., "Pharmaco-topology of Sulfonylurea Receptors, Separate Domains of the Regulatory Subunits of $K_{ATP}$ Channel Isoforms are Required for Selective Interaction with $K^+$ Channel Openers", *J Biol Chem*, 2000, vol. 275, No. 2, pp. 717-720.
Ball et al., "Alterations of Insulin Secretion Following Long-Term Manipulation of ATP-sensitive Potassium Channels by Diazoxide and Nateglinide", *Biochemical Pharmacology*, Jan. 1, 2005, vol. 69, No. 1, pp. 59-63.
Bertolino et al., "Modulation of AMPA/Kainate Receptors by Analogues of Diazoxide and Cyclothiazide in Thin Slices of Rat Hippocampus", *Receptors and Channels*, 1993, vol. 1, pp. 267-278.
Bjork et al., "Induction of β-Cell Rest in Type 1 Diabetes", *Diabetes Care*, 1998, vol. 21, No. 3, pp. 427-430.
Bjorklund et al.,"Glucose-Induced $[Ca^{2+}]i$ Abnormalities in Human Pancreatic Islets, Important Role of Overstimulation", *Diabetes*, 2000, vol. 49, pp. 1840-1848.
Bombieri et al., "Structural Studies on Benzothiadiazine Derivatives: 3-aminomethyl-1,2,4-benzothiadiazine 1,1-dioxide and 6-aminomethyl-3-methyl-1,2,4-benzothiadiazine 1,1-dioxide Hydrochloride Monohydrate", *Journal of Crystallographic and Spectroscopic Research*, 1990, vol. 20, No. 5, pp. 457-463.
Braghiroli et al., "Rigid Analogs of Taurine as Potential Taurine Antagonists", *Farmaco*, 1990, vol. 45, No. 6, pp. 631-645.
Bryan et al., "Toward Understanding the Assembly and Structure of $K_{ATP}$ Channels", *Physiological Review*, 1998, vol. 78, No. 1, pp. 227-245.
Cosgrove et al., "BPDZ 154 Activates Adenosine 5'-Triphosphate-Sensitive Potassium Channels: In Vitro Studies Using Rodent Insulin-Secreting Cells and Islets Isolated from Patients with Hyperinsulinism", *J. Clin. Endocrinol. Metab.*, 2002, vol. 87, pp. 4860-4868.
D'Hahan et al., "Pharmacological Plasticity of Cardiac ATP-sensitive Potassium Channels toward Diazoxide Revealed by ADP", 1999, PNAS, vol. 96, No. 21, pp. 12162-12167.
Dabrowski et al., "A Novel SUR1/Kir6.2 Specific KATP Channel Opener", Proceedings of the Scientific Meeting of the Physiological Society Mar. 19-21, 2001, *Journal of Physiology* (Cambridge), Reprint May 2001, No. 533P., p. 115P.
Dabrowski et al., "The Novel Diazoxide Analog 3-Isopropylamino-7-Methoxy-4H-1,2,4-Benzothiadiazine 1,1-Dioxide Is a Selective Kir6.2/SUR1 Channel Opener", *Diabetes*, 2002, vol. 51, pp. 1896-1906.
De Tullio et al., "Toward Tissue-Selective Pancreatic B-Cells $K_{ATP}$ Channel Openers Belonging to 3-Alkylamino-7-halo-4H-1,2,4-benzothiadiazine 1,1-Dioxides", *J. Med. Chem.*, 2003, vol. 46, pp. 3342-3353.
Dong et al., "L-OROS® Softcap™ for Controlled Release of Non-Aqueous Liquid Formulations", Drug Delivery Technologies online article.
Escande et al., "The Potassium Channel Opener Cromakalim (BRL 34915) Activates ATP-Dependent $K^+$ Channels in Isolated Cardiac Myocytes", *Biochem Biophys Res Commun*, 1988, vol. 154, pp. 620-625.

Fozard et al., "Potassium Channel Openers, Agents for the Treatment of Airway Hyperreactivity", *Prog. Res Research*, 2001, vol. 31, pp. 77-80.

Girard et al., "Aminomethyl-1,2,4-benzothiadiazines as Potential Analogs of γ-aminobutyric Acid. Unexpected discovery of a Taurine Antagonist", *Journal of Medicinal Chemistry*, 1982, vol. 25, No. 2, pp. 113-116.

Guldstand et al., "Improved Beta Cell Function After Short-Term Treatment with Diazoxide in Obese Subjects with Type 2 Diabetes", *Diabetes and Metabolism*, 2002, vol. 28, pp. 448-456.

Hanley et al., "KATP Channel Opener Diazoxide Inhibits Succinate Dehydrogenase in the Mammalian Heart", Proceedings of the Scientific Meeting of The Physiological Society Mar. 19-21, 2001, *Journal of Physiology*, Reprint May 2001, No. 533P, pp. 33P-34P.

Hanley et al., "KATP Channel-independent Targets of Diazoxide and 5-Hydroxydecanoate in the Heart," *Journal of Physiology*, Aug. 2002, vol. 542, No. 3, pp. 735-741.

International Search report for PCT Application PCT/US2006/048711.

Isomoto et al., "A Novel Sulfonylurea Receptor Forms with BIR (Kir6.2) a Smooth Muscle Type ATP-sensitive $K^+$ Channel", *J. Biol. Chem.*, 1996, vol. 271, No. 40, pp. 24321-24324.

Kratzl et al., "Tetracyclic 1,2,4-benzothiadiazines. II. Nitro and chloro Derivatives", *Monatshefte fuer Chemie*, 1965, vol. 96, No. 5, pp. 1592-1595. . (German only—no English translation provided).

Lawrence et al., "The KATP Channel Opener Diazoxide Protects Cardiac Myocytes During Metabolic Inhibition Without Causing Mitochondrial Depolarization or Flavoprotein Oxidation", *British Journal of Pharmacology*, Oct. 2001, vol. 34, No. 3, pp. 535-542.

Lebrun et al., "A Potent Diazoxide Analogue Activating ATP-Sensitive $K^+$ Channels and Inhibiting Insulin Release", *Diabetologia*, Jun. 2000, vol. 43, No. 6, pp. 723-732.

Leonard, "Effects of Digitalis on Intracellular Potassium", *Cardiovascular Drug Therapy*, 1965, pp. 419-423.

Marugo et al., "II Diazossido Nella Terapia Dell Obesita (Diazoxide in the Treatment of Obesity)", *Boll Spec It Biol Sper*, 1977, vol. 53, pp. 1860-1866. (Italian only—no English translation provided).

Ortqvist et al., "Temporary Preservation of β-Cell Function by Diazoxide Treatment in Childhood Type 1 Diabetes", *Diabetes Care*, 2004, vol. 27, No. 9, pp. 2191-2197.

Ouedraogo et al., "2-Alkyl-3-Alkylamino-2H-Benzo- and Pyridothiadiazine 1, 1-Dioxides: From K+ ATP Channel Openers to Ca++ Channel Blockers", *Biol. Chem.*, 2002, vol. 383, pp. 1759-1768.

Petegnief et al., "Taurine Analog Modulation of Taurine Uptake by Two Different Mechanisms in Cultured Glial Cells", *Biochemical Pharmacology*, 1995, vol. 49, No. 3, pp. 399-410.

Qvigstad et al., Nine Weeks of Bedtime Diazoxide is Well Tolerated and Improves β-cell Function in Subjects with Type 2 Diabetes, *Diabetic Medicine*, 2004, vol. 21, pp. 73-76.

Raffa et al., "1,2-Benzothiadiazine Derivatives Research. Note XI. Reaction of 3-chloroalkyl-1,2,4-benzothiadiazine 1,1-dioxide with dialkylaminoalcohols", *Farmaco Edizione Scientifica*, 1960, vol. 15, pp. 655-667. (Italian only—no English translation provided).

Raffa et al., "1,2,4-Benzothiadiazine Derivatives Research. Note XII. Action of diazomethane on 6-chloro-7-sulfamyl-3-oxodihydro-1,2,4-benzo-thiadiazine 1,1-dioxide", *Farmaco Edizione Scientifica*, 1960, vol. 15, pp. 668-679. (Italian only—no English translation provided).

Raffa et al., "1,2,4-Benzothiadiazine Derivatives Research. Note XVI. Relation between 3-oxodihydro-1,2,4-benzothiadiazine 1,1-dioxide or its Derivatives and Heterocyclic Bases in Presence of Arylsulfonyl Chlorides", *Farmaco Edizione Scientifica*, 1961, vol. 16, pp. 3-13. (Italian only—no English translation provided).

Raffa et al., "Cardiovascular action of 1,2,4-benzothiadiazine 1,1-dioxides. II", *Farmaco Edizione Scientifica*, 1965, vol. 20(9), pp. 647-661. (Italian only—no English translation provided).

Ratzmann et al., "Effect of Pharmacological Suppression of Insulin Secretion on Tissue Sensitivity to Insulin in Subjects with Moderate Obesity", *Int J Obesity*, 1983, vol. 7, No. 5, pp. 453-458.

Reddy et al., "Once-Daily Sustained-Release Matrix Tablets of Nicorandil: Formulation and In Vitro Evaluation", *AAPS Pharm Sci Tech*, 2003, vol. 4, No. 4, pp. 1-98.

Remington, "The Science and Practice of Pharmacy", *Remington's Pharmaceutical Sciences*, 19th ed., Mack Publishing Co., Easton, PA, 1995, vol. 2, p. 1457.

Schou et al., "Synthesis and Pharmacological Evaluation of 4H-1,4-benzothiazine-2-carbonitrile 1,1-dioxide and N-(2-cyanomethylsulfonylphenyl)acylamide Derivatives as Potential Activators of ATP Sensitive Potassium Channels", *Bioorg. Med. Chem.*, 2005, vol. 13, pp. 141-155.

Schwanstecher et al., "Potassium Channel Openers Require ATP to Bind to and Act through Sulfonylurea Receptors", *EMBO J.*, 1998, vol. 17, pp. 5529-5535.

Stadnicka et al., "Isoflurane Sensitizes the Cloned Pancreatic KATP Channel to Diazoxide", Anesthesiology Abstracts of Scientific Papers Annual Meeting Oct. 16-18, 2000, *American Society of Anesthiologists*, Reprint 2002, Abstract No. 683.

Stanridge et al., Diazoxide Down-regulates Leptin and Lipid Metabolizing Enzymes in Adipose Tissue of Zucker Rats, *FASEB J*, 2000, vol. 14, pp. 455-460.

Surwit et al., "Diazoxide Restores $\beta_3$-Adrenergic Receptor Function in Diet-Induced Obesity and Diabetes", *Endocrinology*, 2000, vol. 141, pp. 3630-3637.

Trube et al., "Opposite Effects of Tolbutamide and Diazoxide on the ATP-dependent $K^+$ Channel in Mouse Pancreatic β-cells", *Pfluegers Arch Eur J Physiol*, 1996, vol. 407, pp. 493-499.

U.S. Pharmacopeia, Chapter 711 Dissolution/Physical Tests, 2005, pp. 2412-2414.

Vansheidt et al., "Polymerization of Cyclin trimer N-methyleneacrylamide in Solutions and in the Crystalline State, and Plastics based on it", *Zhurnal Prikaldnoi Khimii* (Sankt-Peterburg, Russian Federation), 1961, vol. 34, pp. 895-902. (Russian only—no English translation provided).

Wessberg et al., "Effects of Taurine and a Taurine Antagonist on some Respiratory and Cardiovascular Parameters", *Life Sciences*, 1983, vol. 33, No. 17, pp. 1649-1655.

Wigand et al., "Downregulation of Insulin Receptors in Obese Man", *Diabetes*, 1979, vol. 28, No. 4, pp. 287-291.

Yarbrough et al., Neuropharmacological Characterization of a Taurine Antagonist, *Journal of Pharmacology and Experimental Therapeutics*, 1981, vol. 219, No. 3, pp. 604-613.

Office Action dated Apr. 24, 2009 for Chinese Application No. 200580035520.5 (with English Translation).

* cited by examiner

SALTS OF POTASSIUM ATP CHANNEL OPENERS AND USES THEREOF

RELATED PATENT APPLICATIONS

This application is a Continuation of U.S. application Ser. No. 11/614,044 filed Dec. 20, 2006, which claims the benefit of U.S. Provisional Application No. 60/854,740 filed Oct. 27, 2006, and U.S. Provisional Application No. 60/756,941 filed Jan. 5, 2006, all of which are incorporated herein by reference in their entireties and for all purposes.

FIELD OF THE INVENTION

The present invention relates to salts of potassium ATP ($K_{ATP}$) channel openers, methods of preparing such salts, and methods of use thereof for treatment of a variety of diseases and conditions, including for example, diabetes and obesity.

BACKGROUND OF THE INVENTION

The following description of the background of the invention is provided as an aid in understanding the invention and is not admitted to describe or constitute prior art to the invention.

ATP-sensitive potassium ($K_{ATP}$) channels play important roles in a variety of tissues by coupling cellular metabolism to electrical activity. The $K_{ATP}$ channel has been identified as an octameric complex of two unrelated proteins, which assemble in a 4:4 stoichiometry. The first is a pore forming subunit, Kir6.x, which forms an inwardly rectifying $K^+$ channel; the second is an ABC (ATP binding cassette) transporter, also known as the sulfonylurea receptor (SURx) (Babenko et al., *Annu. Rev. Physiol.*, 60:667-687 (1998)). The Kir6.x pore forming subunit is common for many types of $K_{ATP}$ channels, and has two putative transmembrane domains (identified as TM1 and TM2), which are linked by a pore loop (H5). The subunit that comprises the SUR receptor includes multiple membrane-spanning domains and two nucleotide-binding folds.

According to their tissue localization, $K_{ATP}$ channels exist in different isoforms or subspecies resulting from the assembly of the SUR and Kir subunits in multiple combinations. The combination of the SUR1 with the Kir6.2 subunits (SUR1/Kir6.2) typically forms the adipocyte and pancreatic B-cell type $K_{ATP}$ channels, whereas the SUR2A/Kir6.2 and the SUR2B/Kir6.2 or Kir6.1 combinations typically form the cardiac type and the smooth muscle type $K_{ATP}$ channels, respectively (Babenko et al., *Annu. Rev. Physiol.*, 60:667-687 (1998)). There is also evidence that the channel may include Kir2.x subunits. This class of potassium channels are inhibited by intracellular ATP and activated by intracellular nucleoside diphosphates. Such $K_{ATP}$ channels link the metabolic status of the cells to the plasma membrane potential and in this way play a key role in regulating cellular activity. In most excitatory cells, $K_{ATP}$ channels are closed under normal physiological conditions and open when the tissue is metabolically compromised (e.g. when the (ATP:ADP) ratio falls). This promotes $K^+$ efflux and cell hyperpolarization, thereby preventing voltage-operated $Ca^{2+}$ channels (VOCs) from opening. (*Prog. Res Research*, (2001) 31:77-80).

Potassium channel openers (PCOs or KCOs; also referred to as channel activators or channel agonists), are a structurally diverse group of compounds with no apparent common pharmacophore linking their ability to antagonize the inhibition of $K_{ATP}$ channels by intracellular nucleotides. Diazoxide is a PCO that stimulates $K_{ATP}$ channels in pancreatic β-cells (see Trube et al., *Pfluegers Arch Eur J Physiol*, 407, 493-99 (1986)). Pinacidil and chromakalim are PCOs that activate sarcolemmal potassium channels (see Escande et al., *Biochem Biophys Res Commun*, 154, 620-625 (1988); Babenko et al., *J Biol Chem*, 275(2), 717-720 (2000)). Responsiveness to diazoxide has been shown to reside in the $6^{th}$ through $11^{th}$ predicted transmembrane domains (TMD6-11) and the first nucleotide-binding fold (NBF1) of the SUR1 subunit.

Diazoxide, which is a nondiuretic benzothiadiazine derivative having the formula 7-chloro-3-methyl-2H-1,2,4-benzothiadiazine 1.1-dioxide (empirical formula $C_8H_7ClN_2O_2S$), is commercialized in three distinct formulations to treat two different disease indications: (1) hypertensive emergencies and (2) hyperinsulinemic hypoglycemic conditions. Hypertensive emergencies are treated with Hyperstat IV, an aqueous formulation of diazoxide for intravenous use, adjusted to pH 11.6 with sodium hydroxide. Hyperstat IV is administered as a bolus dose into a peripheral vein to treat malignant hypertension or sulfonylurea overdose. In this use, diazoxide acts to open potassium channels in vascular smooth muscle, stabilizing the membrane potential at the resting level, resulting in vascular smooth muscle relaxation.

Hyperinsulinemic hypoglycemic conditions are treated with Proglycem®, an oral pharmaceutical version of diazoxide useful for administration to infants, children and adults. It is available as a chocolate mint flavored oral suspension, which includes 7.25% alcohol, sorbitol, chocolate cream flavor, propylene glycol, magnesium aluminum silicate, carboxymethylcellulose sodium, mint flavor, sodium benzoate, methylparaben, hydrochloric acid to adjust the pH, poloxamer 188, propylparaben and water. Diazoxide is also available as a capsule with 50 or 100 mg of diazoxide including lactose and magnesium stearate.

Several experimental formulations of diazoxide have been tested in humans and animals. These include an oral solution tested in pharmacodynamic and pharmacokinetic studies and a tablet formulation under development in the early 1960's as an anti-hypertensive, but never commercialized (see Calesnick et al., *J. Pharm. Sci.* 54:1277-1280 (1965); Reddy et al., *AAPS Pharm Sci Tech* 4(4):1-98, 9 (2003); U.S. Pat. No. 6,361,795).

Current oral formulations of diazoxide are labeled for dosing two or three times per day at 8 or 12 hour intervals. Most subjects receiving diazoxide are dosed three times per day. Commercial and experimental formulations of diazoxide are characterized by rapid drug release following ingestion with complete release in approximately 2 hours. Unless indicated differently, the term "approximately" when used in the context of a numeric value, refer to the stated numeric value +/−10%. In the context of two-theta angles from XRPD studies, the term approximately refers to +/−5% of the stated numeric value.

Current oral formulations of diazoxide in therapeutic use result in a range of adverse side effects including dyspepsia, nausea, diarrhea, fluid retention, edema, reduced rates of excretion of sodium, chloride, and uric acid, hyperglycemia, vomiting, abdominal pain, ileus, tachycardia, palpitations, and headache. (See e.g., current packaging insert for the Proglycem®). Oral treatment with diazoxide is used in individuals experiencing serious disease where failure to treat results in significant morbidity and mortality. The adverse side effects from oral administration are tolerated because the benefits of treatment are substantial. The adverse side effects profile of oral diazoxide limit the utility of the drug in treating obese subjects at doses within the labeled range of 3 to 8 mg/kg per day.

The effect of diazoxide in animal models of diabetes and obesity (e.g. obese and lean Zucker rats) has been previously reported. See e.g. Alemzadeh et al., *Endocrinology* 133:705-712 (1993); Alemzadeh et al., *Metabolism* 45:334-341 (1996); Alemzadeh et al., *Endocrinology* 140:3197-3202 (1999); Stanridge et al., *FASEB J* 14:455-460 (2000); Alemzadeh et al., *Med Sci Monit* 10(3): BR53-60 (2004); Alemzadeh et al, *Endocrinology* 145(12):3476-3484 (2004); Aizawa et al., *J of Pharma Exp Ther* 275(1): 194-199 (1995); and Surwit et al., *Endocrinology* 141:3630-3637 (2000).

The effect of diazoxide in humans with obesity or diabetes has been previously reported. See e.g., Wigand et al., *Diabetes* 28(4):287-291 (1979), evaluation of diazoxide on insulin receptors; Ratzmann et al., *Int J Obesity* 7(5):453-458 (1983), glucose tolerance and insulin sensitivity in moderately obese patients; Marugo et al., *Boll Spec It Biol Sper* 53:1860-1866 (1977), moderate dose diazoxide treatment on weight loss in obese patients; Alemzadeh et al., *J Clin Endocr Metab* 83:1911-1915 (1998), low dose diazoxide treatment on weight loss in obese hyperinsulinemic patients; Guldstrand et al., *Diabetes and Metabolism* 28:448-456 (2002), diazoxide in obese type II diabetic patients; Ortqvist et al., *Diabetes Care* 27(9):2191-2197 (2004), beta-cell function measured by circulating C-peptide in children at clinical onset of type 1 diabetes; Bjork et al., *Diabetes Care* 21(3):427-430 (1998), effect of diazoxide on residual insulin secretion in adult type I diabetes patients; and Qvigstad et al., *Diabetic Medicine* 21:73-76 (2004).

U.S. Pat. No. 5,284,845 describes a method for normalizing blood glucose and insulin levels in an individual exhibiting normal fasting blood glucose and insulin levels and exhibiting in an oral glucose tolerance test, elevated glucose levels and at least one insulin level abnormality selected from the group consisting of a delayed insulin peak, an exaggerated insulin peak and a secondary elevated insulin peak. According to this reference, the method includes administering diazoxide in an amount from about 0.4 to about 0.8 mg/kg body weight before each meal in an amount effective to normalize the blood glucose and insulin levels.

U.S. Pat. No. 6,197,765 describes administration of diazoxide for treatment for syndrome-X, and resulting complications, that include hyperlipidemia, hypertension, central obesity, hyperinsulinemia and impaired glucose intolerance. According to this reference, diazoxide interferes with pancreatic islet function by ablating endogenous insulin secretion resulting in a state of insulin deficiency and high blood glucose levels equivalent to that of diabetic patients that depend on exogenous insulin administration for normalization of their blood glucose levels.

U.S. Pat. No. 2,986,573 describes the preparation of diazoxide and its use for the treatment of hypertension. The patent asserts that alkali metal salts may be prepared by methods well-known in the art for the preparation of a salt of a strong base with a weak acid. It also alleges a specific method for making a sodium salt of diazoxide. This patent does not provide any evidence to support the formation of any salt of diazoxide.

U.S. Pat. No. 5,629,045 describes diazoxide for topical ophthalmic administration.

WO 98/10786 describes use of diazoxide in the treatment of X-syndrome including obesity associated therewith.

U.S. Patent publication no. 2003/0035106 describes diazoxide containing compounds for reducing the consumption of fat-containing foods.

U.S. Patent Publication No. 2004/0204472 describes the use of a Cox-2 inhibitor plus diazoxide in the treatment of obesity. Also described therein is the use of a Cox-2 inhibitor plus a pharmaceutically acceptable salt of diazoxide, wherein acceptable cations include alkali metals and alkaline earth metals.

U.S. Patent Publication No. 2002/0035106 describes use of $K_{ATP}$ channel agonists for reducing the consumption of fat containing food. This application mentions pharmaceutically acceptable acid addition salts, pharmaceutically acceptable metal salts and optionally alkylated ammonium salts, but does not disclose or describe how to prepare any such salts. This patent also does not provide any evidence to support the formation of any salt of a $K_{ATP}$ channel agonist.

U.K. Patent GB982072 describes the preparation and use of diazoxide and derivatives for the treatment of hypertension and peripheral vascular disorders. This patent mentions non-toxic alkali metals salts but does not disclose or describe how to prepare any such salts. This patent does not provide any evidence to support the formation of any salt of diazoxide or its derivatives.

SUMMARY OF THE INVENTION

The current invention relates to methods of preparation and use of alkali metal, tertiary amine and ammonium salts of diazoxide and diazoxide derivatives. It has been surprisingly found that it is difficult to produce salts of diazoxide and derivatives. In particular, the inventors have been unable to reproduce formation of a diazoxide salt using the method asserted in U.S. Pat. No. 2,986,573. Contrary to what is reported in the literature, salt formation with diazoxide and derivatives depends on a proper selection of solvent and counter-ion.

Provided herein are pharmaceutical formulations of $K_{ATP}$ channel openers and their use for treatment of various diseases and conditions including diabetes and obesity. Such formulations are characterized as being bioavailable. A $K_{ATP}$ channel opener as used herein has any one or more of the following properties: (1) opening SURx/Kir6.y potassium channels, where x=1, 2A or 2B and y=1 or 2; (2) binding to the SURx subunit of $K_{ATP}$ channels; and (3) inhibiting glucose induced release of insulin following administration of the compound in vivo. Preferably, $K_{ATP}$ channel openers are $K_{ATP}$ channel openers with all three properties. $K_{ATP}$ channel openers as defined herein are preferably salts prepared from the compounds of Formulae I-VIII, as set forth below.

The present invention also provides salts of the compounds defined by Formulae I-VIII. Salts of Formulae I-IV provided herein include monovalent alkali metal salts and monovalent and divalent salts of organic compounds, preferably organic compounds which include an ammonium moiety. Salts of Formulae V-VIII are also provided herein, preferably prepared with monovalent and divalent counter-ions.

$K_{ATP}$ channel openers defined by Formula I are as follows:

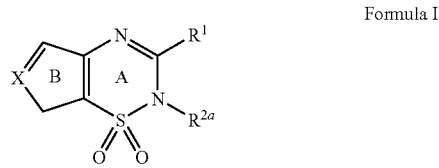

Formula I wherein:

$R^1$ is selected from the group consisting of hydrogen, lower alkyl, substituted lower alkyl, cycloalkyl, and substituted cycloalkyl provided however that when $R^1$ is a substituted lower alkyl or a substituted cycloalkyl, then the substituent does not include an amino group;

$R^{2a}$ is hydrogen;

X is a 1, 2 or 3 atom chain, wherein each atom is independently selected from carbon, sulfur and nitrogen, and each atom is optionally substituted with halogen, hydroxyl, lower alkyl, substituted lower alkyl, lower alkoxy, cycloalkyl, substituted cycloalkyl, or substituted lower alkoxy, provided however that when an atom of the chain is substituted with substituted lower alkyl, substituted lower alkoxy or substituted cycloalkyl, then the substituent does not include an amino group;

wherein ring B is saturated, monounsaturated, polyunsaturated or aromatic;

and all bioequivalents including salts, prodrugs and isomers thereof.

In particular embodiments of Formula I, X is $C(R^a)C(R^b)$, wherein $R^a$ and $R^b$ are independently selected from the group consisting of hydrogen, halogen, lower alkyl, substituted lower alkyl, cycloalkyl, substituted cycloalkyl, lower alkoxy, substituted lower alkoxy, sulfonyl, and the like. In further embodiments, $R^a$ and $R^b$ are independently selected from the group consisting of hydroxyl, substituted oxy, substituted thiol, alkylthio, substituted alkylthio, sulfinyl, sulfonyl, substituted sulfinyl, substituted sulfonylalkylsulfinyl, alkylsulfonyl, and the like. In a preferred embodiment, Ring B does not include any heteroatoms.

Salts of embodiments of the channel openers defined by Formula I may be prepared from the following: (a) metal hydroxides, preferably alkali metal hydroxides (e.g., NaOH and KOH) and (b) organic hydroxides, preferably organic compounds which include at least one tertiary amine or at least one quaternary ammonium ion (e.g., diethylamine ethanol, triethylamine, hydroxyethylpyrrolidine, choline and hexamethylhexamethylenediammonium, and the like).

$K_{ATP}$ channel openers defined by Formula II are as follows:

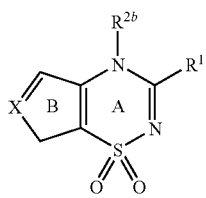

Formula II wherein:

$R^1$ is selected from the group consisting of hydrogen, lower alkyl, substituted lower alkyl, cycloalkyl, and substituted cycloalkyl provided however that when $R^1$ is a substituted lower alkyl or a substituted cycloalkyl, then the substituent does not include an amino group;

$R^{2b}$ is hydrogen;

X is a 1, 2 or 3 atom chain, wherein each atom is independently selected from carbon, sulfur and nitrogen, and each atom is optionally substituted with halogen, hydroxyl, lower alkyl, substituted lower alkyl, lower alkoxy, cycloalkyl, substituted cycloalkyl, or substituted lower alkoxy, provided however that when an atom of the chain is substituted with substituted lower alkyl, substituted cycloalkyl or substituted lower alkoxy, then the substituent does not include an amino group;

wherein ring B is saturated, monounsaturated, polyunsaturated or aromatic;

and all bioequivalents including salts, prodrugs and isomers thereof.

In particular embodiments of Formula II, X is $C(R^a)C(R^b)$, wherein $R^a$ and $R^b$ are independently selected from the group consisting of hydrogen, halogen, lower alkyl, substituted lower alkyl, cycloalkyl, substituted cycloalkyl, lower alkoxy, substituted lower alkoxy, sulfonyl, and the like. In further embodiments, $R^a$ and $R^b$ are independently selected from the group consisting of hydroxyl, substituted oxy, substituted thiol, alkylthio, substituted alkylthio, sulfinyl, sulfonyl, substituted sulfinyl, substituted sulfonyl, alkylsulfinyl, alkylsulfonyl, nitro and the like. In preferred embodiment, Ring B does not include any heteroatoms.

Salts of embodiments of the channel openers defined by Formula II may be prepared from the following: (a) metal hydroxides, preferably alkali metal hydroxides (e.g., NaOH and KOH) and (b) organic hydroxides, preferably organic compounds which include at least one tertiary amine or at least one quaternary ammonium ion (e.g., diethylamine ethanol, triethylamine, hydroxyethylpyrrolidine, choline and hexamethylhexamethylenediammonium, and the like).

$K_{ATP}$ channel openers defined by Formula III are as follows:

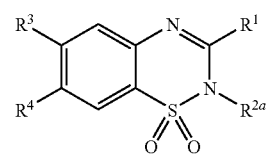

Formula III wherein:

$R^1$ is selected from the group consisting of hydrogen, lower alkyl, substituted lower alkyl, and cycloalkyl provided however that when $R^1$ is a substituted lower alkyl, then the substituent does not include an amino group;

$R^{2a}$ is hydrogen;

$R^3$ is selected from the group consisting of hydrogen, halogen, lower alkyl, substituted lower alkyl, cycloalkyl and substituted cycloalkyl provided however that when $R^3$ is a substituted lower alkyl, then the substituent does not include an amino group;

$R^4$ is selected from the group consisting of hydrogen, halogen, lower alkyl, substituted lower alkyl, cycloalkyl and substituted cycloalkyl provided however that when $R^4$ is a substituted lower alkyl, then the substituent does not include an amino group;

and all bioequivalents including salts, prodrugs and isomers thereof.

In particular embodiments of Formula III, $R^1$ is a lower alkyl, (preferably ethyl or methyl); $R^{2a}$ is hydrogen; and $R^3$ and $R^4$ are each independently halogen.

In another embodiment of Formula III, $R^1$ is methyl; $R^{2a}$ is hydrogen; $R^3$ is selected from the group consisting of hydrogen, halogen, lower alkyl, substituted lower alkyl, cycloalkyl, and substituted cycloalkyl; and $R^4$ is chlorine.

Salts of embodiments of the channel openers defined by Formula III may be prepared from the following: (a) metal hydroxides, preferably alkali metal hydroxides (e.g., NaOH and KOH) and (b) organic hydroxides, preferably organic compounds which include at least one tertiary amine or at least one quaternary ammonium ion (e.g., diethylamine ethanol, triethylamine, hydroxyethylpyrrolidine, choline and hexamethylhexamethylenediammonium, and the like).

$K_{ATP}$ channel openers defined by Formula IV are as follows:

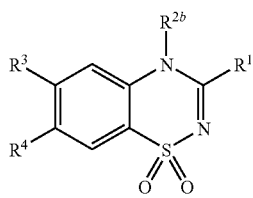

Formula IV wherein:
- $R^1$ is selected from the group consisting of hydrogen, lower alkyl, substituted lower alkyl, and cycloalkyl provided however that when $R^1$ is a substituted lower alkyl, then the substituent does not include an amino group;
- $R^{2b}$ is hydrogen;
- $R^3$ is selected from the group consisting of hydrogen, halogen, lower alkyl, substituted lower alkyl, cycloalkyl and substituted cycloalkyl provided however that when $R^3$ is a substituted lower alkyl, then the substituent does not include an amino group;
- $R^4$ is selected from the group consisting of hydrogen, halogen, lower alkyl, substituted lower alkyl, cycloalkyl and substituted cycloalkyl provided however that when $R^4$ is a substituted lower alkyl, then the substituent does not include an amino group;
- and all bioequivalents including salts, prodrugs and isomers thereof.

In particular embodiments of Formula IV, $R^1$ is a lower alkyl, (preferably ethyl or methyl); $R^{2b}$ is hydrogen; and $R^3$ and $R^4$ are each independently halogen.

In another embodiment of Formula IV, $R^1$ is methyl; $R^{2b}$ is hydrogen; $R^3$ is selected from the group consisting of hydrogen, halogen, lower alkyl, substituted lower alkyl, cycloalkyl, and substituted cycloalkyl; and $R^4$ is chlorine.

Salts of embodiments of the channel openers defined by Formula IV may be prepared from the following: (a) metal hydroxides, preferably alkali metal hydroxides (e.g., NaOH and KOH) and (b) organic hydroxides, preferably organic compounds which include at least one tertiary amine or at least one quaternary ammonium ion (e.g., diethylamine ethanol, triethylamine, hydroxyethylpyrrolidine, choline and hexamethylhexamethylenediammonium, and the like).

$K_{ATP}$ channel openers defined by Formula V are as follows:

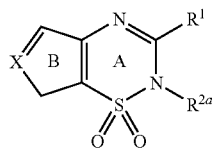

Formula V wherein:
- $R^1$ is selected from the group consisting of optionally substituted amino, optionally substituted alkyl, optionally substituted cycloalkyl, optionally substituted heterocyclyl, optionally substituted heterocyclylalkyl, optionally substituted aryl, optionally substituted heteroaryl, and optionally substituted heteroarylalkyl;
- $R^{2a}$ is selected from the group consisting of hydrogen, and lower alkyl;
- X is a 1, 2 or 3 atom chain, wherein each atom is independently selected from carbon, sulfur and nitrogen, and each atom is optionally substituted with halogen, hydroxyl, optionally substituted lower alkyl, optionally substituted lower alkoxy, optionally substituted cycloalkyl, or optionally substituted amino;
- wherein ring B is saturated, monounsaturated, polyunsaturated or aromatic;
- wherein at least one of $R^1$ or a substituent of X includes an amino group;
- and all bioequivalents including salts, prodrugs and isomers thereof.

In particular embodiments of Formula V, X is $C(R^a)C(R^b)$, wherein $R^a$ and $R^b$ are independently selected from the group consisting of hydrogen, halogen, optionally substituted lower alkyl, optionally substituted cycloalkyl, optionally substituted lower alkoxy, amino, sulfonylamino, aminosulfonyl, sulfonyl, and the like. Preferably $R^1$ includes at least one substituent containing an amino group. In further embodiments, $R^a$ and $R^b$ are independently selected from the group consisting of hydroxyl, substituted oxy, substituted thiol, alkylthio, substituted alkylthio, sulfinyl, sulfonyl, substituted sulfinyl, substituted sulfonyl, substituted sulfonylamino, substituted amino, substituted amine, alkylsulfinyl, alkylsulfonyl, alkylsulfonylamino, and the like. In a preferred embodiment, Ring B does not include any heteroatoms.

$K_{ATP}$ channel openers defined by Formula VI are as follows:

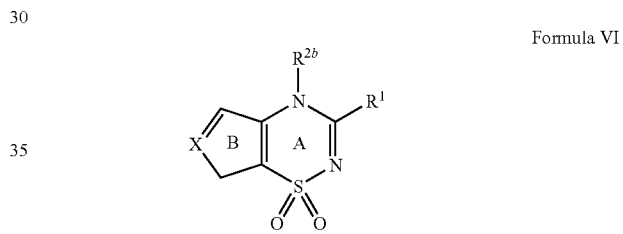

Formula VI wherein:
- $R^1$ is selected from the group consisting of optionally substituted amino, optionally substituted alkyl, optionally substituted cycloalkyl, optionally substituted heterocyclyl, optionally substituted heterocyclylalkyl, optionally substituted aryl, optionally substituted heteroaryl, and optionally substituted heteroarylalkyl;
- $R^{2b}$ is selected from the group consisting of hydrogen and lower alkyl;
- X is a 1, 2 or 3 atom chain, wherein each atom is independently selected from carbon, sulfur and nitrogen, and each atom is optionally substituted with halogen, hydroxyl, optionally substituted lower alkyl, optionally substituted lower alkoxy, optionally substituted cycloalkyl, or optionally substituted amino;
- wherein ring B is saturated, monounsaturated, polyunsaturated or aromatic;
- wherein at least one of $R^1$ or a substituent of X includes an amino group;
- and all bioequivalents including salts, prodrugs and isomers thereof.

In particular embodiments of Formula VI, X is $C(R^a)C(R^b)$, wherein $R^a$ and $R^b$ are independently selected from the group consisting of hydrogen, halogen, lower alkyl, substituted lower alkyl, cycloalkyl, substituted cycloalkyl, lower alkoxy, substituted lower alkoxy, amino, sulfonylamino, aminosulfonyl, sulfonyl, and the like. In further embodiments, $R^a$ and $R^b$ are independently selected from the group consisting of hydroxyl, substituted oxy, substituted thiol, alkylthio, substituted alkylthio, sulfinyl, sulfonyl, substituted sulfinyl, substituted sulfonyl, substituted sulfonylamino, substituted amino, substituted amine, alkylsulfinyl, alkylsulfonyl, alkylsulfonylamino, and the like. Preferably $R^1$ includes at least one substituent containing an amino group. In a preferred embodiment, Ring B does not include any heteroatoms.

$K_{ATP}$ channel openers defined by Formula VII are as follows:

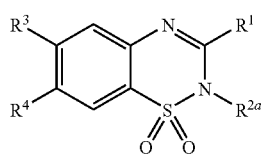

Formula VII wherein:
$R^1$ is selected from the group consisting of optionally substituted amino, optionally substituted alkyl, optionally substituted cycloalkyl, optionally substituted heterocyclyl, optionally substituted heterocyclylalkyl, optionally substituted aryl, optionally substituted heteroaryl, and optionally substituted heteroarylalkyl;

$R^{2a}$ is selected from the group consisting of hydrogen, lower alkyl, and substituted lower alkyl;

$R^3$ is selected from the group consisting of hydrogen, halogen, optionally substituted lower alkyl, optionally substituted amino, optionally substituted cycloalkyl and optionally substituted aryl;

$R^4$ is selected from the group consisting of hydrogen, halogen, optionally substituted lower alkyl, optionally substituted amino, optionally substituted cycloalkyl and optionally substituted aryl;

wherein at least one of $R^1$, $R^3$ and $R^4$ includes a substituent containing an amino group;

and all bioequivalents including salts, prodrugs and isomers thereof.

Preferably, $R^1$ includes a substituent containing an amino group. In particular embodiments of Formula VII; $R^1$ includes an amino substituent, $R^{2a}$ is hydrogen; and $R^3$ and $R^4$ are each independently halogen.

In another embodiment of Formula VII, $R^{2a}$ is hydrogen; $R^3$ is selected from the group consisting of hydrogen, halogen, lower alkyl, substituted lower alkyl, amino, substituted amino, cycloalkyl, and substituted cycloalkyl; and $R^4$ is chlorine.

$K_{ATP}$ channel openers defined by Formula VIII are as follows:

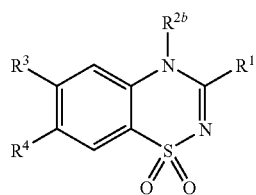

Formula VIII wherein:
$R^1$ is selected from the group consisting of optionally substituted amino, optionally substituted alkyl, optionally substituted cycloalkyl, optionally substituted heterocyclyl, optionally substituted heterocyclylalkyl, optionally substituted aryl, optionally substituted heteroaryl, and optionally substituted heteroarylalkyl;

$R^{2b}$ is selected from the group consisting of hydrogen, lower alkyl, and substituted lower alkyl;

$R^3$ is selected from the group consisting of hydrogen, halogen, optionally substituted lower alkyl, optionally substituted amino, optionally substituted cycloalkyl and optionally substituted aryl;

$R^4$ is selected from the group consisting of hydrogen, halogen, optionally substituted lower alkyl, optionally substituted amino, optionally substituted cycloalkyl and optionally substituted aryl;

wherein at least one of $R^1$, $R^3$ and $R^4$ includes a substituent containing an amino group;

and all bioequivalents including salts, prodrugs and isomers thereof.

Preferably $R^1$ includes a substituent containing an amino group. In particular embodiments of Formula VIII, $R^{2b}$ is hydrogen; and $R^3$ and $R^4$ are each independently halogen.

In another embodiment of Formula VIII, $R^{2b}$ is hydrogen; $R^3$ is selected from the group consisting of hydrogen, halogen, lower alkyl, optionally substituted lower alkyl, optionally substituted amino, and optionally substituted cycloalkyl; and $R^4$ is chlorine.

Unless otherwise indicated, reference in this application to $K_{ATP}$ channel openers should be understood to refer to $K_{ATP}$ channel openers based upon a salt of one of the compounds described by Formulae I-VIII and having one or more, and preferably all three, of the following properties: (1) opening SURx/Kir6.y potassium channels, wherein x=1, 2A or 2B and y=1 or 2; (2) binding to the SURx subunit of $K_{ATP}$ channels; and (3) inhibiting glucose induced release of insulin following administration of the compound in vivo. Such $K_{ATP}$ channel openers preferably have the structure of any of the compounds of Formula I-VIII, or more preferably Formula III-IV where ring B or its equivalent does not include any heteroatoms. More preferably, the structure is diazoxide. Structural variants or bioequivalents of any of the compounds defined by Formulae I-VIII, such as derivatives, salts, prodrugs or isomers, are also contemplated herein. Specifically, salts of compounds of Formula I-IV wherein the cation is selected from a cation of an alkali metal or an organic compound which includes a tertiary amine or a quaternary ammonium ion. Preferably, when the salt includes an anion of diazoxide and a sodium cation, the salt is not in a form suitable for intravenous use. In other embodiments, when the anion is diazoxide in a solution suitable for intravenous use, the cation is not sodium. In alternate embodiments, in solutions suitable for intravenous use, when the cation is sodium, the anion is not an anion of diazoxide. In certain embodiments, when the salt includes an anion of diazoxide and a sodium cation, the salt is not in liquid form. More preferably, $K_{ATP}$ channel openers contemplated herein are salts of compounds of Formulae III and IV wherein the cation is selected from sodium, potassium, choline or hexamethyl hexamethylene diammonium. Other $K_{ATP}$ channel openers that are contemplated for use herein include BPDZ 62, BPDZ 73, NN414, BPDZ 154.

Also provided herein are salts of compounds of Formula V-VIII, wherein at least one substituent of the compound of Formulae V-VIII includes an amino group. In another embodiment, the compound of Formula V-VIII forms the anion of the salt and a monovalent or divalent metal forms the cation. In other embodiments, the cation includes a tertiary amino or quaternary ammonium group.

In vitro analysis of glucose induced release of insulin via $K_{ATP}$ channel openers can be determined using rat islets as provided by De Tullio et al., *J. Med. Chem.*, 46:3342-3353 (2003), or by using human islets as provided by Björklund et al., *Diabetes*, 49:1840-1848 (2000).

Provided herein are formulations, such as controlled release pharmaceutical formulations, of $K_{ATP}$ channel openers and bioequivalents thereof, which include salts of the compounds of Formulae I-VIII. In one embodiment, the salt can be formulated for controlled release following oral administration. Such formulations contain in a single administration dosage between 10 and 100 mg, between 25 and 100 mg, between 100 and 200 mg, between 200 and 300 mg, between 300 and 500 mg or between 500 and 2000 mg of the salt of the $K_{ATP}$ channel openers provided in Formulae I-VIII. In certain embodiments, the dosage of the $K_{ATP}$ channel openers contained in a formulation may be determined based on the weight of the subject for which it is to be administered, i.e., the formulation may contain in a single administration dosage between 0.1-20 mg of the $K_{ATP}$ channel opener per kg of the subject's body weight, or between 0.1-0.5 mg of the $K_{ATP}$ channel opener per kg of the subject's body weight; or between 0.5-1 mg of the $K_{ATP}$ channel opener per kg of the subject's body weight; or between 1-2 mg of the $K_{ATP}$ channel opener per kg of the subject's body weight, or between 2-5 mg of the $K_{ATP}$ channel opener per kg of the subject's body weight, or between 5-10 mg of the $K_{ATP}$ channel opener per kg of the subject's body weight, or between 10-15 mg of the $K_{ATP}$ channel opener per kg of the subject's body weight, or between 15-20 mg of the $K_{ATP}$ channel opener per kg of the subject's body weight.

Also provided herein are controlled release pharmaceutical formulations containing $K_{ATP}$ channel openers selected from salts of Formulae I-VIII, which can be obtained by at least one of the following: (a) particle size reduction involving comminution, spray drying, or other micronising techniques, (b) use of an ion exchange resin, (c) use of inclusion complexes, for example cyclodextrin, (d) compaction of the $K_{ATP}$ channel opener with a solubilizing agent including a low viscosity hypromellose, low viscosity methylcellulose or similarly functioning excipient or combinations thereof, (e) associating the $K_{ATP}$ channel opener with a salt prior to formulation, (f) use of a solid dispersion of the $K_{ATP}$ channel opener, (g) use of a self emulsifying system, (h) addition of one or more surfactants to the formulation, (i) use of nanoparticles, or (j) combinations of these approaches.

Further provided herein are controlled release pharmaceutical formulations containing $K_{ATP}$ channel openers selected from salts of the compounds defined by Formulae I-VIII, which include at least one component that substantially inhibits release of the $K_{ATP}$ channel activator from the formulation until after gastric transit. As used herein, "substantially inhibits" means less than 15% release, more preferably at least less than 10% release, or even more preferably at least less than 5% release of the drug from the formulation during gastric transport. Release can be measured in a standard USP based in-vitro gastric dissolution assay in a calibrated dissolution apparatus. See e.g., U.S. Pharmacopeia, Chapter 711 (2005).

Also provided are oral pharmaceutical formulations of the $K_{ATP}$ channel openers selected from the salts of the compounds of Formulae I-VIII, which include at least one component that substantially inhibits release of the $K_{ATP}$ channel opener from the formulation until after gastric transit. Substantial inhibition of drug release during gastric transit is achieved by inclusion of a component in the formulation selected from the group consisting of: (a) a pH sensitive polymer or co-polymer applied as a compression coating on a tablet, (b) a pH sensitive polymer or co-polymer applied as a thin film on a tablet, (c) a pH sensitive polymer or co-polymer applied as a thin film to an encapsulation system, (d) a pH sensitive polymer or co-polymer applied to encapsulated microparticles, (e) a non-aqueous-soluble polymer or copolymer applied as a compression coating on a tablet, (f) a non-aqueous-soluble polymer or co-polymer applied as a thin film on a tablet, (g) a non-aqueous soluble polymer applied as a thin film to an encapsulation system, and (h) a non-aqueous soluble polymer applied to microparticles, wherein the pH sensitive polymer or co-polymer is resistant to degradation under acid conditions. Alternatively, substantial inhibition of drug release during gastric transport can also be achieved by incorporation of the formulation in an osmotic pump system, by use of systems controlled by ion exchange resins, or by combinations of any of the above approaches.

Also provided herein are controlled release pharmaceutical formulations of $K_{ATP}$ channel openers selected from salts of the compounds of Formulae I-VIII, wherein the formulation includes at least one component that contributes to sustained release of a $K_{ATP}$ channel opener over an extended period, e.g., over a period of 2-24 hours following administration, or over a period of 2-4 hours following administration, or over a period of 4-8 hours following administration, or over a period of more than 8-24 hours following administration. These formulations are characterized in having one of the following components: (a) a pH sensitive polymeric coating, (b) a hydrogel coating, (c) a film coating that controls the rate of diffusion of the drug from a coated matrix, (d) an erodable matrix that controls rate of drug release, (e) polymer coated pellets, granules or microparticles of drug which can be further encapsulated or compressed into a tablet, (f) an osmotic pump system containing the drug, (g) a compression coated tablet form of the drug, or (h) combinations of any of the approaches of (a)-(f) above.

As used herein, an erodable matrix is the core of a tablet formulation that, upon exposure to a suitable aqueous environment, begins a process of disintegration which facilitates the release of drug from the matrix. The rate of release of drug from the tablet is controlled both by the solubility of the drug and the rate of disintegration of the matrix.

The above formulations may further comprise one or more additional pharmaceutically active agents (other than $K_{ATP}$ channel openers selected from the salts of the compounds of Formulae I-VIII) useful for the treatment of a condition selected from the group consisting of obesity, prediabetes, diabetes, hypertension, depression, elevated cholesterol, fluid retention, other obesity associated co-morbidities, ischemic and reperfusion injury, epilepsy, cognitive impairment, schizophrenia, mania, other psychotic diseases, and the like.

Further provided is a controlled release pharmaceutical formulation of a $K_{ATP}$ channel opener selected from the salts of the compounds of Formulae I-VIII wherein administration to an obese, overweight or obesity prone subject results in at least one of the following: (a) inhibition of fasting insulin secretion, (b) inhibition of stimulated insulin secretion, (c) elevation of energy expenditure, (d) elevation of beta oxidation of fat, or (e) inhibition of hyperphagia for about 24 hours.

Additionally provided is a controlled release pharmaceutical formulation of a $K_{ATP}$ channel opener selected from the salts of the compounds of Formulae I-VIII wherein administration to an obese, overweight or obesity prone subject results in at least one of the following: (a) inhibition of fasting insulin secretion, (b) inhibition of glucose stimulated insulin secretion, (c) elevation of energy expenditure, (d) elevation of beta oxidation of fat, or (e) inhibition of hyperphagia for about 18 hours.

Still further provided is a controlled release pharmaceutical formulation of a $K_{ATP}$ channel opener selected from the salts of the compounds of Formulae I-VIII which upon administration to an obese, overweight or obesity prone subject results in at least one of the following: (a) inhibition of fasting insulin secretion, (b) inhibition of glucose stimulated insulin secretion, (c) elevation of energy expenditure, (d) elevation of beta oxidation of fat, or (e) inhibition of hyperphagia for about 24 hours.

Additionally provided is a controlled release pharmaceutical formulation of a $K_{ATP}$ channel opener selected from the salts of the compounds of Formulae I-VIII that upon administration to an obese, overweight or obesity prone subject results in at least one of the following: (a) inhibition of fasting insulin secretion, (b) inhibition of glucose stimulated insulin secretion, (c) elevation of energy expenditure, (d) elevation of beta oxidation of fat, or (e) inhibition of hyperphagia for about 18 hours.

Provided herein is a method of treating hypoglycemia, the method comprising orally administering to a subject in need thereof, a controlled release formulation of a $K_{ATP}$ channel opener selected from the salts of the compounds of Formulae I-VIII.

Further provided herein is a method of treating obesity associated co-morbidities in an obese, overweight or obesity prone subject, the method comprising administering a therapeutically effective amount of a solid oral dosage form of a $K_{ATP}$ channel opener selected from the salts of the compounds of Formulae I-VIII, or controlled release pharmaceutical formulation of a $K_{ATP}$ channel opener selected from the salts of the compounds of Formulae I-VIII. In a preferred embodiment, administration is no more than two times per 24 hours, or once per 24 hours.

Yet further provided herein is a method of achieving weight loss in an obese overweight, or obesity prone subject, the method comprising administering a therapeutically effective amount of a solid oral dosage form of a $K_{ATP}$ channel opener selected from the salts of the compounds of Formulae I-VIII or controlled release pharmaceutical formulation of a $K_{ATP}$ channel opener selected from the salts of the compounds of Formulae I-VIII. In a preferred embodiment, administration is no more than two times per 24 hours, or once per 24 hours. The daily dosage administered is preferably between 50 and 180 mg. In certain embodiments, the obese subject has a body mass index greater than 30 kg/m$^2$, or greater than 35 kg/m$^2$, or greater than 40 kg/m$^2$, or greater than 50 kg/m$^2$, or greater than 60 kg/m$^2$ at the time the method commences.

Also provided is a method of maintaining a weight loss in an obese overweight, or obesity prone subject, the method comprising administering a therapeutically effective amount of a solid oral dosage form of a $K_{ATP}$ channel opener selected from the salts of the compounds of Formulae I-VIII or controlled release pharmaceutical formulation of a $K_{ATP}$ channel opener selected from the salts of the compounds of Formulae I-VIII. It is preferable to maintain weight in an obese subject once some weight loss has occurred when the alternative is to regain weight. In a preferred embodiment, administration is no more than two times per 24 hours, or once per 24 hours.

Further provided is a method of elevating energy expenditure in an overweight, obese or obesity prone subject, the method comprising administering an effective amount of a solid oral dosage form of a $K_{ATP}$ channel opener selected from the salts of the compounds of Formulae I-VIII or controlled release pharmaceutical formulation of a $K_{ATP}$ channel opener selected from the salts of the compounds of Formulae I-VIII. In a preferred embodiment, administration is no more than two times per 24 hours, or once per 24 hours. In certain embodiments, the subject has a body mass index greater than 20 kg/m$^2$, or greater than 25 kg/m$^2$, or greater than 30 kg/m$^2$, or greater than 35 kg/m$^2$, or greater than 40 kg/m$^2$, or greater than 50 kg/m$^2$, or greater than 60 kg/m$^2$ at the time the method commences.

Additionally provided is a method of elevating beta oxidation of fat in an overweight, obese or obesity prone subject, the method comprising administering an effective amount of a solid oral dosage form of a $K_{ATP}$ channel opener selected from the salts of the compounds of Formulae I-VIII or controlled release pharmaceutical formulation of a $K_{ATP}$ channel opener selected from the salts of the compounds of Formulae I-VIII. In a preferred embodiment, administration is no more than two times per 24 hours, or once per 24 hours. In certain embodiments, the subject has a body mass index greater than 20 kg/m$^2$, or greater than 25 kg/m$^2$, or greater than 30 kg/m$^2$, or greater than 35 kg/m$^2$, or greater than 40 kg/m$^2$, or greater than 50 kg/m$^2$, or greater than 60 kg/m$^2$ at the time the method commences.

Yet further provided is a method of reducing visceral fat in an overweight, obese or obesity prone subject, the method comprising administering an effective amount of a solid oral dosage form of a $K_{ATP}$ channel opener selected from the salts of the compounds of Formulae I-VIII or controlled release pharmaceutical formulation of a $K_{ATP}$ channel opener selected from the salts of the compounds of Formulae I-VIII. In a preferred embodiment, administration is no more than two times per 24 hours, or once per 24 hours.

Still further provided is a method of delaying or preventing the transition to diabetes of a prediabetic subject comprising administering an effective amount of a $K_{ATP}$ channel opener selected from the salts of the compounds of Formulae I-VIII or controlled release pharmaceutical formulation of a $K_{ATP}$ channel opener selected from the salts of the compounds of Formulae I-VIII. In a preferred embodiment, administration is no more than two times per 24 hours, or once per 24 hours.

Additionally provided is a method of restoring normal glucose tolerance in a prediabetic subject comprising administering an effective amount of a $K_{ATP}$ channel opener selected from the salts of the compounds of Formulae I-VIII or controlled release pharmaceutical formulation of a $K_{ATP}$ channel opener selected from the salts of the compounds of Formulae I-VIII. In a preferred embodiment, administration is no more than two times per 24 hours, or once per 24 hours.

Further provided is a method of restoring normal glucose tolerance in a diabetic subject comprising administering an effective amount of a $K_{ATP}$ channel opener selected from the salts of the compounds of Formulae I-VIII or controlled release pharmaceutical formulation of a $K_{ATP}$ channel opener selected from the salts of the compounds of Formulae I-VIII. In a preferred embodiment, administration is no more than two times per 24 hours, or once per 24 hours.

Still further provided is a method of delaying or preventing progression of diabetes in an subject comprising administering an effective amount of a $K_{ATP}$ channel opener selected from the salts of the compounds of Formulae I-VIII or controlled release pharmaceutical formulation of a $K_{ATP}$ channel opener selected from the salts of the compounds of Formulae I-VIII. In a preferred embodiment, administration is no more than two times per 24 hours, or once per 24 hours.

Also provided is a method to prevent or treat weight gain, impaired glucose tolerance or dyslipidemia associated with the administration of anti-psychotics to a subject, said method including the co-administration of an effective amount of a $K_{ATP}$ channel opener selected from the salts of the compounds of Formulae I-VIII or controlled release pharmaceutical formulation of a $K_{ATP}$ channel opener selected from the salts of the compounds of Formulae I-VIII. In a preferred embodiment, administration is no more than two times per 24 hours, or once per 24 hours.

Further provided is a method to treat obesity, or hyperphagia in a Prader-Willi Syndrome patient, a Froelich's Syndrome patient, in a Cohen Syndrome patient, in a Summit Syndrome patient, in an Alstrom Syndrome patient, in a Borjeson Syndrome patient or in a Bardet-Biedl Syndrome patient comprising the administration of an effective amount of a $K_{ATP}$ channel opener selected from the salts of the compounds of Formulae I-VIII or controlled release pharmaceutical formulation of a $K_{ATP}$ channel opener selected from the salts of the compounds of Formulae I-VIII. In a preferred embodiment, administration is no more than two times per 24 hours, or once per 24 hours.

Still further provided is a method to treat obesity or elevated triglycerides in a patient suffering hyperlipoproteinemia type I, type II, type III or type IV comprising administering an effective amount of a $K_{ATP}$ channel opener selected from the salts of the compounds of Formulae I-VIII or controlled release pharmaceutical formulation of a $K_{ATP}$ channel opener selected from the salts of the compounds of Formulae I-VIII. In a preferred embodiment, administration is no more than two times per 24 hours, or once per 24 hours.

Also provided is a method of reducing the incidence of adverse effects from administration of a $K_{ATP}$ channel opener selected from the salts of the compounds of Formulae I-VIII in the treatment of diseases of a subject achieved by any of the following: (a) use of a dosage form that on administration reduces $C_{max}$ relative to the current Proglycem® oral suspension or capsule products in order to reduce the incidence of adverse side effects that are associated with peak drug levels, (b) use of a dosage form that delays release until gastric transit is complete in order to reduce the incidence of adverse side effects that are associated with the release of drug in the stomach, (c) initiating dosing at subtherapeutic levels and in a stepwise manner increasing dose daily until the therapeutic dose is achieved wherein the number of steps is 2 to 10 to reduce the incidence of adverse side effects that occur transiently at the initiation of treatment, (d) use of the lowest effective dose to achieve the desired therapeutic effect in order to reduce the incidence of adverse side effects that are dose dependent, or (e) optimizing the timing of administration of dose within the day and relative to meals.

Further provided is a method of preventing weight gain, dyslipidemia or impaired glucose tolerance in a subject treated with an anti-psychotic drug, the method comprising administering a pharmaceutical formulation of a $K_{ATP}$ channel opener selected from the salts of the compounds of Formulae I-VIII.

Yet further provided is a method of treating weight gain, dyslipidemia or impaired glucose tolerance in a subject treated with an anti-psychotic drug, the method comprising administering a pharmaceutical formulation of a $K_{ATP}$ channel opener selected from the salts of the compounds of Formulae I-VIII.

Also provided is a method of treating diseases characterized by obesity, hyperphagia, dyslipidemia, or decreased energy expenditure including (a) Prader-Willi Syndrome, (b) Froelich's syndrome, (c) Cohen syndrome, (d) Summit Syndrome, (e) Alstrom Syndrome, (f) Borjesen Syndrome, (g) Bardet-Biedl Syndrome, or (h) hyperlipoproteinemia type I, II, III, and IV comprising administering a pharmaceutical formulation of a $K_{ATP}$ channel opener selected from the salts of the compounds of Formulae I-VIII.

Further provided is a pharmaceutical formulation of a $K_{ATP}$ channel opener selected from the salts of the compounds of Formulae I-VIII further comprising a pharmaceutically active agent other than the $K_{ATP}$ channel opener. In this formulation, the other pharmaceutically active agent is an agent useful for the treatment of a condition selected from the group consisting of obesity, prediabetes, diabetes, hypertension, depression, elevated cholesterol, fluid retention, or other obesity associated co-morbidities, ischemic and reperfusion injury, epilepsy, cognitive impairment, schizophrenia, mania, and other psychotic condition.

The formulations containing $K_{ATP}$ channel openers selected from the salts of the compounds of Formulae I-VIII described herein provide for improved compliance, efficacy and safety, and for co-formulations with other agents. Included are co-formulations of $K_{ATP}$ channel openers selected from the salts of the compounds of Formulae I-VIII with one or more additional pharmaceutically active agents that have complementary or similar activities or targets. Other pharmaceutically active agents that can be combined with $K_{ATP}$ channel openers selected from the salts of the compounds of Formulae I-VIII to treat obesity or to maintain weight loss in an obesity prone subject include, but are not limited to: sibutramine, orlistat, phentermine, rimonabant, a diuretic, an antiepileptic, or other pharmaceutical active whose therapeutic utility includes weight loss. It is preferable to maintain weight in an obese subject once some weight loss has occurred when the alternative is to regain weight. Other pharmaceutically active agents that may be combined with $K_{ATP}$ channel openers selected from the salts of the compounds of Formulae I-VIII to treat type II diabetes, or prediabetes include acarbose, miglitol, metformin, repaglinide, nateglinide, rosiglitizone, proglitizone, ramipril, metaglidasen, or any other pharmaceutical active that improves insulin sensitivity or glucose utilization or glycemic control where the mode of action is not enhanced insulin secretion. Other pharmaceutical active agent that can be combined with $K_{ATP}$ channel openers selected from the salts of the compounds of Formulae I-VIII to treat obesity associated co-morbidities include a drug active used to lower cholesterol, a drug active used to lower blood pressure, an anti-inflammatory drug that is not a cox-2 inhibitor, a drug that is an antidepressant, a drug used to treat urinary incontinence, or other drug routinely used to treat disease conditions the incidence of which is elevated in overweight or obese patients as compared to normal weight subjects including, but not limited to, drugs to treat atherosclerosis, osteoarthritis, disc herniation, degeneration of knees and hips, breast, endometrium, cervical, colon, leukemia and prostate cancers, hyperlipidemia, asthma/reactive airway disease, gallstones, GERD, obstructive sleep apnea, obesity hypoventilation syndrome, recurrent ventral hernias, menstrual irregularity and infertility.

Also provided herein are methods for treating obesity or obesity associated co-morbidities or other diseases or conditions involving $K_{ATP}$ channels by co-administration to a subject in need thereof of an effective amount of any of the compounds according to Formulae I-VIII, or a salt of any of the compounds according to Formulae I-VIII or pharmaceutical formulation thereof, and a drug selected from the group consisting of an amphetamine or amphetamine mixture, Sibutramine, Orlistat, Rimonabant, a CB-1 agonist, a $5HT_2$, receptor agonist, a drug used to treat addiction, a beta adrenergic receptor agonist, an ACC inhibitor, leptin, a leptin analogue, a leptin agonist, a somatostatin agonist, an adiponectin agonist or secretagogue, Amylin, PYY or a PYY analogue, a ghrelin antagonist, a drug that inhibits gastrointestinal lipases or other digestive enzymes, a de-novo lipogenesis inhibitor, a drug that blocks absorption of dietary fat, growth hormone or a growth hormone analogue, a growth hormone secretagogue, a CCK agonist, an oleoylethanolamine receptor agonist, a fatty acid synthase inhibitor, a thyroid receptor agonist, a selective androgen receptor modulator, a PPAR agonist, oxyntomodulin, oleoylestrone, a NPY2 receptor antagonist, a NPY5 receptor antagonist, a NPY agonist, a monoamine uptake inhibitor, a MTP inhibitor, a MC4 receptor agonist, a MCH1 receptor antagonist, a 5HT-6 antagonist, a histamine-3 antagonist, a glycine analog, a fgf1 inhibitor, a DGAT-1 inhibitor, a carboxypeptidase inhibitor, an appetite suppressant, a non-thiazide diuretic, a drug that lowers cholesterol, a drug that raises HDL cholesterol, a drug that lowers LDL cholesterol, a drug that lowers blood pressure, a drug that is an anti-depressant, a drug that improves insulin sensitivity, a drug that improves glucose utilization or uptake, a drug that is an anti-epileptic, a drug that is an anti-inflammatory, a drug that is an appetite suppressant, a drug that lowers circulating triglycerides, a drug that is used to induce weight loss in an overweight or obese individual, and pharmaceutically acceptable salts thereof.

Also provided herein are polymorphic forms (i.e., "polymorphs") of the compounds of Formulae I-VIII, as exemplified by the X-ray Power Diffraction (XRPD) patterns shown in any of the figures.

Also provided are polymorphs of salts of diazoxide which include diazoxide and a cation selected from the group consisting of an alkali metal and a compound comprising a tertiary amine or quaternary ammonium group.

Also provided herein are methods for producing a diazoxide choline salt, which includes suspending diazoxide in a solvent and mixing with a choline salt, adding a co-solvent to the suspension under conditions sufficient to cause formation and precipitation of the diazoxide choline salt, and harvesting the precipitate to provide the diazoxide choline salt.

Also provided herein are methods of treating obesity or obesity-related co-morbidity in an obese subject, wherein the method comprising administering to a subject in need thereof an effective amount of a compound of Formula I-VIII.

Also provided herein are methods for treatment of a subject suffering from or at risk for Alzheimer's disease (AD), which methods include administration to a subject a therapeutically effective amount of a pharmaceutical formulation comprising a compound of any of Formulae I-VIII as provided herein. In some embodiments, the compound is diazoxide. Also provided herein are methods for treatment of a subject suffering from or at risk for AD, which methods include administration to a subject a therapeutically effective amount of a salt of a compound according to any of Formulae I-VIII. In some embodiments, the compound is a salt of diazoxide.

In another embodiment, the invention provides a method for treating hypoglycemia by administration of an effective amount of a pharmaceutical formulation comprising a salt selected from the group consisting of a) a salt comprising an anion of a $K_{ATP}$ channel opener selected from the group consisting of Formula I, Formula II, Formula III and Formula IV, and a cation selected from the group consisting of an alkali metal and a compound comprising a tertiary amine or ammonium group; b) a salt comprising an anion of a $K_{ATP}$ channel opener selected from the group consisting of Formula V, Formula VI, Formula VII and Formula VIII; and c) a salt comprising a cation of a $K_{ATP}$ channel opener selected from the group consisting of Formula V, Formula VI, Formula VII and Formula VIII, wherein at least one substituent comprises an amino group.

In further embodiments, the hypoglycemia is selected from the group consisting of a) nighttime hypoglycemia, b) hypoglycemia attributable to a defect in insulin secretion, c) attributable to an insulin secreting tumor, and d) drug-induced hypoglycemia.

In the present context, the term "therapeutically effective" or "effective amount" indicates that the materials or amount of material is effective to prevent, alleviate, or ameliorate one or more symptoms of a disease or medical condition, and/or to prolong the survival of the subject being treated.

The term "pharmaceutically acceptable" indicates that the identified material does not have properties that would cause a reasonably prudent medical practitioner to avoid administration of the material to a patient, taking into consideration the disease or conditions to be treated and the respective route of administration. For example, it is commonly required that such a material be essentially sterile, e.g., for injectables.

As used herein, the term "composition" refers to a formulation suitable for administration to an intended animal subject for therapeutic purposes that contains at least one pharmaceutically active compound and at least one pharmaceutically acceptable carrier or excipient. Other terms as used herein are defined below.

Adipocyte: An animal connective tissue cell specialized for the synthesis and storage of fat.

Agonist: A chemical compound that has affinity for and stimulates physiological activity at cell receptors normally stimulated by naturally occurring substances, triggering a biochemical response. An agonist of a receptor can also be considered an activator of the receptor.

About: is used herein to mean in quantitative terms plus or minus 10%.

Adipose tissue: Tissue comprised principally of adipocytes.

Adolescent: A person between 10 and 19 years of age.

Adiponectin: A protein hormone produced and secreted exclusively by adipocytes that regulates the metabolism of lipids and glucose. Adiponectin influences the body's response to insulin. Adiponectin also has anti-inflammatory effects on the cells lining the walls of blood vessels.

Alkali metal: refers to elements included in Group I of the periodic table, such as, lithium, sodium, potassium, rubidium, cesium and francium.

Amelioration of the symptoms of a particular disorder by administration of a particular pharmaceutical composition: refers to any lessening, whether permanent or temporary, lasting or transient that can be attributed to or associated with administration of the composition.

Analog: a compound that resembles another in structure but differs by at least one atom.

Antagonist: A substance that tends to nullify the action of another, as a drug that binds to a cell receptor without eliciting a biological response when confronted with an agonist for the receptor.

Atherosclerotic Plaque: A buildup of cholesterol and fatty material within a blood vessel due to the effects of atherosclerosis Bariatric Surgery: A range of surgical procedures which are designed to aid in the management or treatment of obesity and allied diseases.

Beta cell rest: Temporarily placing beta cells in a condition in which there is reduced metabolic stress due to suppressed secretion of insulin.

Bilaminate: A component of a pharmaceutical dosage form that consists of the lamination of two distinct materials.

Bioavailability: Refers to the amount or extent of therapeutically active substance that is released from the drug product and becomes available in the body at the intended site of drug action. The amount or extent of drug released can be established by the pharmacokinetic-parameters, such as the area under the blood or plasma drug concentration-time curve (AUC) and the peak blood or plasma concentration ($C_{max}$) of the drug.

Bioequivalent: Two formulations of the same active substance are bioequivalent when there is no significant difference in the rate and extent to which the active substance becomes available at the site of drug action when administered at the same molar dose under similar conditions. "Formulation" in this definition may include the free base of the active substance or different salts of the active substance. Bioequivalence may be demonstrated through several in vivo and in vitro methods. These methods, in descending order of preference, include pharmacokinetic, pharmacodynamic, clinical and in vitro studies. In particular, bioequivalence is demonstrated using pharmacokinetic measures such as the area under the blood or plasma drug concentration-time curve (AUC) and the peak blood or plasma concentration (Cmax) of the drug, using statistical criteria.

Cannabinoid Receptor: Receptors in the endocannabinoid (EC) system associated with the intake of food and tobacco dependency. Blocking the cannabinoid receptor may reduce dependence on tobacco and the craving for food.

Capsule: refers to a softgel, caplet, or any other encapsulated dosage form known to practitioners in the art, or a portion thereof. Softgel refers a soft gelatin capsule, in agreement with the accepted nomenclature adopted by the SoftGel Association. A softgel is a one-piece, sealed, soft gelatin (or other film-forming material) shell that contains a solution, a suspension, or a semi-solid paste.

Combination: Refers to any association between or among two or more items. The combination can be two or more separate items, such as two compositions or two collections. It can be a mixture thereof, such as a single mixture of the two or more items, or any variation thereof.

Composition: Refers to any mixture. It can be a solution, a suspension, liquid, powder, a paste, aqueous, non-aqueous or any combination thereof.

Compression tablet: Tablet formed by the exertion of pressure to a volume of tablet matrix in a die.

Compression coated tablet: A tablet formed by the addition of a coating by compression to a compressed core containing the pharmaceutical active. As used herein the term "tablet" is intended to mean the same as a compression tablet unless indicated otherwise.

Derivative: A chemical substance derived from another substance by modification or substitution.

Daily dosage: The total amount of a drug taken in a 24 hour period whether taken as a single dose or taken in multiple doses.

Diazoxide: 7-chloro-3-methyl-2-H-1,2,4-benzothiadiazine 1,1 dioxide (shown below with its tautomer) with the empirical formula $C_8H_7ClN_2O_2S$ and a molecular weight of 230.7.

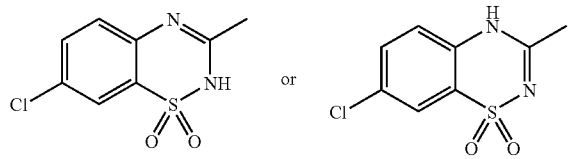

Encapsulation system: A structural feature that contains drug within such as a pharmaceutical capsule. A gel into which drug is incorporated also is considered an encapsulation system.

Equivalent amount: An amount of a derivative of a drug that in assays or upon administration to a subject produces an equal effect to a defined amount of the non-derivatized drug.

Fatty acid synthase: The central enzyme of a multienzyme complex that catalyses the formation of palmitate from acetylcoenzyme A, malonylcoenzyme A, and NADPH.

Gastric Lipase: An enzyme secreted into the gastrointestinal tract that catalyzes the hydrolysis of dietary triglycerides.

Glidant: An inactive component of a pharmaceutical formulation that prevents caking of the matrix during processing steps.

Hyperinsulinemia: Excessively high blood insulin levels, which is differentiated from hyperinsulinism, excessive secretion of insulin by the pancreatic islets. Hyperinsulinemia may be the result of a variety of conditions, such as obesity and pregnancy.

Hyperinsulinism: Excessive secretion of insulin by the pancreatic islets.

Hyperlipidemia: A general term for elevated concentrations of any or all of the lipids in the plasma, such as cholesterol, triglycerides and lipoproteins.

Hyperphagia: Ingestion of a greater than optimal quantity of food.

Ingredient of a pharmaceutical composition: Refers to one or more materials used in the manufacture of a pharmaceutical composition. Ingredient can refer to an active ingredient (an agent) or to other materials in the compositions. Ingredients can include water and other solvents, salts, buffers, surfactants, non-aqueous solvents, and flavorings.

Insulin resistance: A condition in which the tissues of the body are diminished in their ability to respond to insulin.

Ischemic injury: Injury to tissue that results from a low oxygen state usually due to obstruction of the arterial blood supply or inadequate blood flow leading to hypoxia in the tissue.

Ketoacidosis: Acidosis accompanied by the accumulation of ketone bodies (ketosis) in the body tissue and fluids, as in diabetic acidosis.

Kit: Refers to a packaged combination. A packaged combination can optionally include a label or labels, instructions and/or reagents for use with the combination.

Kir: Pore forming subunit of the $K_{ATP}$ channel. Also known as the inwardly rectifying subunit of the $K_{ATP}$ channel. Typically existing as Kir6.x and infrequently as Kir2.x subspecies.

$K_{ATP}$ channel: An ATP sensitive potassium ion channel across the cell membrane formed by the association of 4 copies of a sulfonylurea receptor and 4 copies of a pore forming subunit Kir. Agonizing the channel can lead to membrane hyperpolarization.

$K_{ATP}$ channel opener: As used herein refers to a compound of any of Formulae I-VIII, or a derivative, salt or prodrug thereof, having one or more or preferably all of the following three properties: (1) opening SURx/Kir6.y potassium channels, where x=1, 2A or 2B and y=1 or 2; (2) binding to the SURx subunit of $K_{ATP}$ channels; and (3) inhibiting glucose induced release of insulin following administration of the compound in vivo.

Leptin: Product (16 kD) of the ob (obesity) locus. It is found in plasma of mammals and exerts a hormonal action, which reduces food uptake and increases energy expenditure.

Lipogenesis: The generation of new lipids, primarily triacylglycerides. It is dependent on the action of multiple distinct enzymes and transport molecules.

Lipolysis: The breakdown of fat by the coordinated action of multiple enzymes.

Lipoprotein lipase: An enzyme of the hydrolase class that catalyses the reaction of triacyglycerol and water to yield diacylglycerol and a fatty acid anion. The enzyme hydrolyses triacylglycerols in chylomicrons, very-low-density lipoproteins, low-density lipoproteins, and diacylglycerols.

Lubricant: An inactive component of a pharmaceutical formulation that provides for the flow of materials in various processing steps, particularly tableting.

Microparticle: A small particulate formed in the process of developing pharmaceutical formulations that may be coated prior to producing the final dosage from.

Obesity: An increase in body weight beyond the limitation of skeletal and physical requirement, as the result of an excessive accumulation of fat in the body. Formally defined as having a body mass index greater than 30 kg/m2.

Obesity Prone: Subjects who because of genetic predisposition or prior history of obesity are at above average risk of becoming obese.

Obesity related co-morbidities: Any disease or condition of animals or humans that are increased incidence in obese or overweight subjects. Examples of such conditions include hypertension, prediabetes, type 2 diabetes, osteoarthritis and cardiovascular conditions.

Osmotically controlled release: A pharmaceutical dosage form in which the release of the active drug is principally achieved by the hydration of a swellable component of the formulation.

Overweight: An subject whose weight is above that which is ideal for their height but who fails to meet the criteria for classification as obese. In humans using Body Mass Index (kg/m2) an overweight subjects has a BMI between 25 and 30.

Oxidation of Fat: A series of reactions involving acyl-coenzyme A compounds, whereby these undergo beta oxidation and thioclastic cleavage, with the formation of acetyl-coenzyme A; the major pathway of fatty acid catabolism in living tissue.

Pharmaceutical composition: Refers to a composition that contains an agent and one or more other ingredients that is formulated for administration to a subject. An agent refers to an active ingredient of a pharmaceutical composition. Typically active ingredients are active for treatment of a disease or condition. For example, agents that can be included in pharmaceutical compositions include agents for treating obesity or diabetes. The pharmaceutically active agent can be referred to as "a pharmaceutical active."

Pharmaceutical effect: Refers to an effect observed upon administration of an agent intended for treatment of a disease or disorder or for amelioration of the symptoms thereof.

Pharmacodynamic: An effect mediated by drug action.

Pharmacokinetic: Relating to the absorption, distribution, metabolism and elimination of the drug in the body.

Polymorph: A crystalline form of a compound that exists in at least two crystalline forms. Polymorphic forms of any given compound are defined by the same chemical formula and/or composition and are as distinct in chemical structure as crystalline structures of two different chemical compounds. Such compounds may differ in packing or geometrical arrangement of respective crystalline lattices. The chemical and/or physical properties or characteristics of the various polymorphs may vary with each distinct polymorphic form, and may include, but are not limited to, variations in solubility, melting point, density, hardness, crystal shape, optical and electrical properties, vapor pressure, and stability.

Preadipocyte: A progenitor cell to adipocytes.

Prediabetic: A condition that precedes diagnosis of type TI diabetes. Type TI diabetes is a form of diabetes mellitus which is characterized by insulin insensitivity or resistance.

Prodrug: Refers to a compound which, when metabolized, yields the desired active compound. Typically, the prodrug is inactive, or less active than the active compound, but may provide advantageous handling, administration, or metabolic properties. For example, some prodrugs are esters of the active compound; during metabolysis, the ester group is cleaved to yield the active drug. Also, some prodrugs are activated enzymatically to yield the active compound, or a compound which, upon further chemical reaction, yields the active compound.

Prolonged Administration (prolonged basis): Administration of a pharmaceutically acceptable formulation of a drug for 7 or more days. Typically, prolonged administration is for at least two weeks, preferably at least one month, and even more preferably at least two months (i.e. at least 8 weeks).

Quick dissolving formulation: A pharmaceutical formulation which upon oral administration may release substantially all of the drug active from the formulation within 10 minutes.

Release formulation (sustained), (or "sustained release formulation"): A formulation of pharmaceutical product that, upon administration to animals, provides for release of the active pharmaceutical over an extended period of time than provided by formulations of the same pharmaceutical active that result in rapid uptake. Similar terms are extended-release, prolonged-release, and slow-release. In all cases, the preparation, by definition, has a reduced rate of release of active substance.

Release formulation (delayed), (or "delayed release formulation"): Delayed-release products are modified-release, but are not extended-release. They involve the release of discrete amount(s) of drug some time after drug administration, e.g. enteric-coated products, and exhibit a lag time during which little or no absorption occurs.

Release formulation (controlled), (or "controlled release formulation"): A formulation of pharmaceutical product that may include both delay of release of pharmaceutical active upon administration and control of release in the manner described for sustained release.

Salt: The neutral, basic or acid compound formed by the union of an acid or an acid radical and a base or basic radical. Used generally to describe any ionic compound not containing an oxide or hydroxide ion.

Solid oral dosage form: Pharmaceutical formulations designed for oral administration including capsules and tablets.

Subject: Refers to animals, including mammals, such as human beings, domesticated animals, and animals of commercial value.

Sulfonylurea receptor: A component of the $K_{ATP}$ channel responsible for interaction with sulfonylurea, other $K_{ATP}$ channel antagonists, diazoxide and other $K_{ATP}$ channel agonists.

Tablet: Pharmaceutical dosage form that is produced by forming a volume of a matrix containing pharmaceutical active and excipients into a size and shape suitable for oral administration.

Thermogenesis: The physiological process of heat production in the body.

Threshold Concentration: The minimum circulating concentration of a drug required to exert a specific metabolic, physiological or compositional change in the body of a treated human or animal.

Treatment: Any manner in which the symptoms of a condition, disorder or disease or other indication, are ameliorated or otherwise beneficially altered.

Triglyceride: Storage fats of animal and human adipose tissue principally consisting of glycerol esters of saturated fatty acids.

Type I diabetes: A chronic condition in which the pancreas makes little or no insulin because the beta cells have been destroyed.

Uncoupling protein: A family of proteins that allow oxidation in mitochondria to proceed without the usual concomitant phosphorylation to produce ATP.

Visceral fat: Human adipose tissues principally found below the subcutaneous fat and muscle layer in the body.

DETAILED DESCRIPTION OF THE INVENTION

Figure 1:
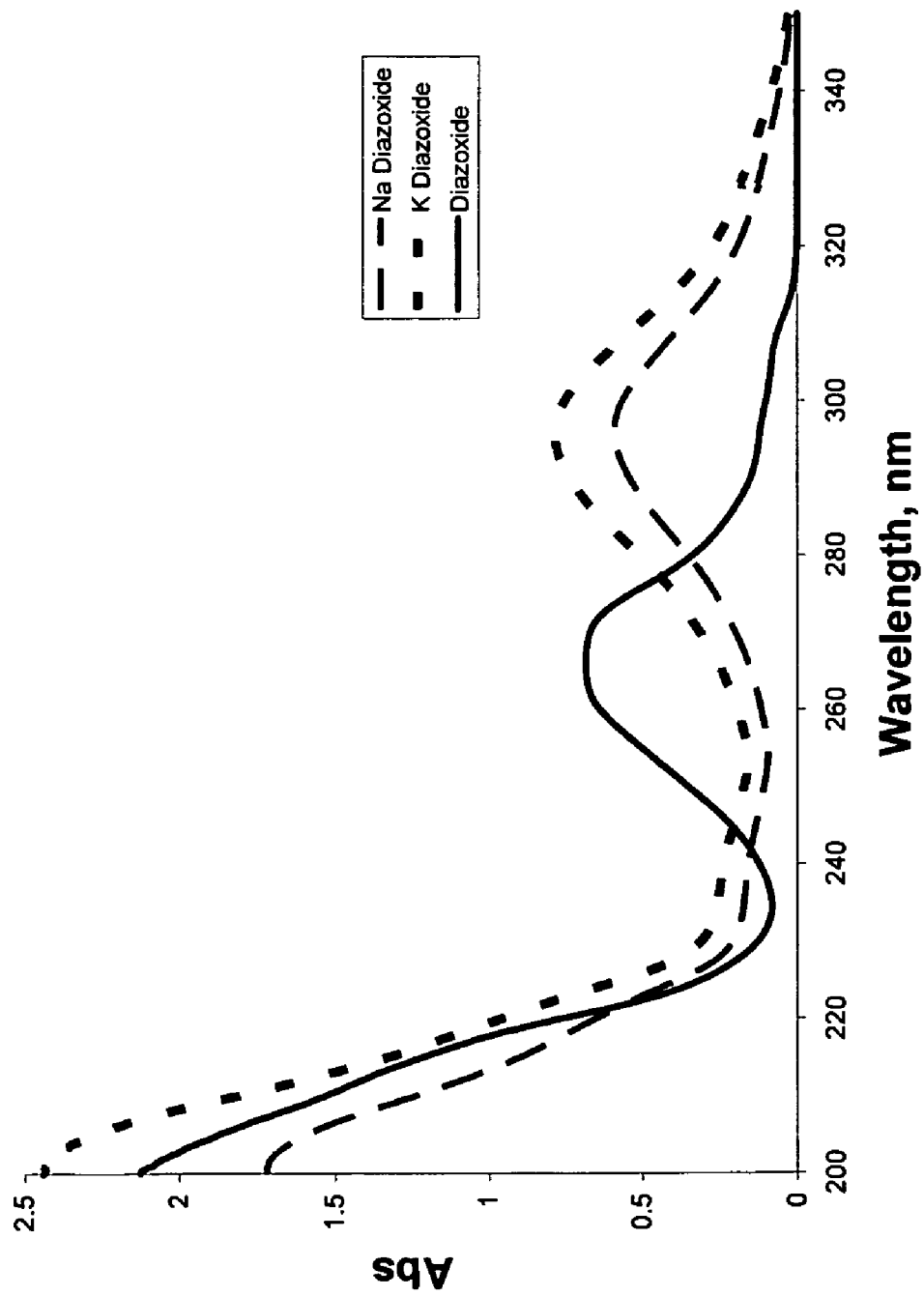
FIG. 1 shows UV spectra of the free form diazoxide and the sodium and potassium salts of diazoxide in acetonitrile.

The present invention provides salts of compounds of Formulae I-VIII and methods for their preparation. Salts of compounds of Formulae I-IV may be prepared using monovalent alkali metal cations and compounds which include one or more of a tertiary amine or quaternary ammonium moiety. In such salts, the compounds of Formulae I-IV exist in their anionic form. Furthermore, it has been discovered that the selection of a solvent for the preparation of these salts plays an important role in salt formation. Also described herein is the failure to obtain a salt of diazoxide from an alkali metal alkoxide using the method described in U.S. Pat. No. 2,986,573.

Compounds of Formulae V-VIII can form both anions and cations, and thus salts can be prepared using a variety of counter ions, including both anions and cations. Cations of the compounds of Formulae V-VIII can be formed at an amino group, and anions of the compounds of Formulae V-VIII can be formed at either an amino group or at the sulfonyl group. The formation of salts based on compounds of Formulae V-VIII can be done in a variety of solvents, preferably organic solvents.

As discussed herein, two polymorphic forms (i.e., Forms A and B) of the choline salt of diazoxide have been identified. In summary, both Forms A and B are anhydrous crystals of diazoxide choline salt. Diazoxide choline salt Form A can be formed using fast cooling procedures as provided herein, whereas slow cooling procedures generally favor formation of Form B. Slurry studies shows that Form A readily converts to Form B. Without wishing to be bound by theory, the slurry studies indicate that Form B of diazoxide choline salt is the thermodynamically more stable form.

Regarding the potassium salt of diazoxide, seven polymorphic forms have been identified (i.e., Forms A-G). Diazoxide potassium salt Forms C, D, and F were observed be an acetone solvent, a hemihydrate, and a dioxane solvent, respectively. Forms A, B, E, and G were not commonly observed during screening, and elemental analysis suggests that Forms A, B, E and G may be mixtures, have residual solvent present, and/or not be a potassium salt, at least in part. Without wishing to be bound by theory, slurry studies suggest that Form D is the thermodynamically most stable polymorph of the diazoxide potassium salt polymorphs.

Further provided are pharmaceutical formulations of particular $K_{ATP}$ channel openers of salts of compounds of Formulae I-VIII that when administered to subjects achieve novel pharmacodynamic, pharmacokinetic, therapeutic, physiological, and metabolic outcomes. Yet further provided are pharmaceutical formulations, methods of administration and dosing of particular $K_{ATP}$ channel openers selected from salts of the compounds defined by Formulae I-VIII that achieve therapeutic outcomes while reducing the incidence of adverse effects.

In particular, pharmaceutical formulations selected from salts of compounds defined by Formulae I-VIII and formulated for oral administration exhibit advantageous properties including: facilitating consistency of absorption, pharmacokinetic and pharmacodynamic responses across treated patients, contributing to patient compliance and improving the safety profile of the product, such as by reducing the frequency of serious adverse effects. Method of treatment of metabolic and other diseases of humans and animals by administering the formulations are also provided.

As shown below, diazoxide and derivatives thereof can exist as proton tautomers. Proton tautomers are isomers that differ from each other only in the location of a hydrogen atom and a double bond. The hydrogen atom and double bond switch locations between a carbon atom and a heteroatom, such as for example N. Thus, when the substituent on the nitrogen is hydrogen, the two isomeric chemical structures may be used interchangeably.

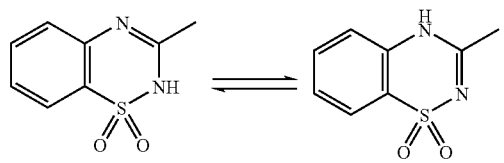

The particular $K_{ATP}$ channel openers that can be used in the invention formulations include salts of any of the compounds within Formulae I to VIII. Exemplary compounds which have been previously reported include diazoxide, BPDZ 62, BPDZ 73, NN414 and BPDZ 154 (see, for example, Schou et al., Bioorg. Med. Chem., 13, 141-155 (2005)). Compound BPDZ 154 also is an effective $K_{ATP}$ channel activator in patients with hyperinsulinism and in patients with pancreatic insulinoma. The synthesis of BPDZ compound is provided in Cosgrove et al., J. Clin. Endocrinol. Metab., 87, 4860-4868 (2002).

Channel openers demonstrating decreased activity in the inhibition of insulin release and increased activity in vascular smooth muscle tissue have been previously reported and include analogs of diazoxide such as, for example, 3-isopropylamino-7-methoxy-4H-1,2,4,-benzothiadiazine 1,1-dioxide, (a selective Kir6.2/SUR1 channel opener; see Dabrowski et al., Diabetes, 51, 1896-1906 (2002), and 2-alkyl substituted diazoxides (see, for example, Ouedraogo et al., Biol. Chem., 383, 1759-1768 (2002)). The 2-alkyl substituted diazoxides generally do not function as traditional potassium channel activators, but instead show potential as $Ca^{2+}$ blockers.

Other diazoxide analogs which have been previously reported include described in Schou et al., Bioorg. Med. Chem., 13, 141-155 (2005), are shown below.

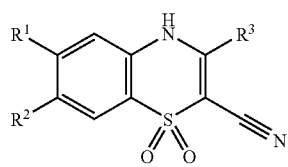

$R^1$, $R^2$ and $R^3$ are:
a) H, Cl, NHCH(CH$_3$)$_2$
b) CF$_3$, H, NHCH(CH$_3$)$_2$
c) H, Cl, NHCH$_2$CH$_2$CH(CH$_3$)$_2$
d) H, Cl, NH-cyclobutyl Diazoxide analogs having different alkyl substituents at the 3 position of the molecule (identified as $R^3$ shown below) are described in Bertolino et al., Receptors and Channels, 1, 267-278 (1993).

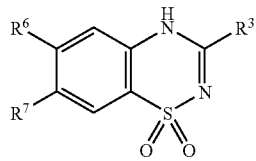

R³, R⁶ and R⁷ are:
a) H, H, CH₃
b) H, H, Cl
c) CH₃, Cl, H
d) CH₂Cl, H, Cl
e) NH₂, H, H
f) CH₂CH₂Cl, H, Cl
g) nC₄H₉, H, Cl
h) nC₅H₁₁, H, Cl
i) nC₇H₁₅, H, Cl
j) nC₃H₇, Cl, H
k) nC₄H₉, Cl, H
l) nC₅H₁₁, Cl, H
m) nC₇H₁₅, Cl, H
n) nC₃H₇, Cl, Cl
o) nC₄H₉, Cl, Cl
p) nC₅H₁₁, Cl, Cl
q) nC₇H₁₅, Cl, Cl
r) H, Cl, H $K_{ATP}$ channel activity of salts of the compounds of Formulae I-VIII and related compounds can be measured by membrane potential studies as described in Schou et al., *Bioorg. Med. Chem.*, 13, 141-155 (2005) and Dabrowski, et al., *Diabetes*, 51, 1896-1906 (2002).

Measurement of the inhibition of glucose-stimulated insulin release from βTC6 cells is described in Schou et al., *Bioorg. Med. Chem.*, 13, 141-155 (2005). The ability of particular $K_{ATP}$ channel openers to inhibit release of insulin from incubated rat pancreatic islets can be performed as described by Ouedraogo et al., *Biol. Chem.*, 383, 1759-1768 (2002).

Activation of recombinant $K_{ATP}$ channels by $K_{ATP}$ channel openers can be examined by monitoring macroscopic currents of inside-out membrane patches from *Xenopus* oocytes co-expressing Kir6.2 and either SUR1, SUR2A or SUR2B. SUR expressing membranes can be prepared by known methods. See, for example, Dabrowski et al., Diabetes, 51, 1896-1906 (2002).

Binding experiments can be used to determine the ability of $K_{ATP}$ channel openers to bind SUR1, SUR2A and SUR2B. See, for example, Schwanstecher et al., EMBO J., 17, 5529-5535 (1998).

Preparation of SUR1 and SUR2A chimeras, as described by Babenko et al., allows for comparison of pharmacologic profiles (i.e. sulfonyl sensitivity and responsiveness to diazoxide or other potassium channel openers) of the SUR1/Kir6.2 and SUR2A/Kir6.2 potassium channels. See Babenko et al., J. Biol. Chem., 275(2), 717-720 (2000). The cloning of a sulfonylurea receptor and an inwardly rectifying K⁺ channel is described by Isomoto et al., J. Biol. Chem., 271 (40), 24321-24324 (1996); D'hahan et al., PNAS, 96(21), 12162-12167 (1999).

Differences between the human SUR1 and human SUR2 genes are described and shown in Aguilar-Bryan et al., Physiological Review, 78(1):227-245 (1998).

"Halo" and "halogen" refer to all halogens, that is, chloro (Cl), fluoro (F), bromo (Br), or iodo (I).

"Hydroxyl" and "hydroxy" refer to the group —OH.

"Substituted oxy" refers to the group —OR$^{aa}$, where R$^{aa}$ can be alkyl, substituted alkyl, acyl, substituted acyl, aryl, substituted aryl, heteroaryl, substituted heteroaryl, aralkyl, substituted aralkyl, cycloalkyl, substituted cycloalkyl, heterocyclyl, or substituted heterocyclyl.

"Substituted thiol" refers to the group —SR$^{bb}$, where R$^{bb}$ can be alkyl, substituted alkyl, acyl, substituted acyl, aryl, substituted aryl, heteroaryl, substituted heteroaryl, aralkyl, substituted aralkyl, cycloalkyl, substituted cycloalkyl, heterocyclyl, or substituted heterocyclyl.

"Alkyl" refers to an alkane-derived radical containing from 1 to 10, preferably 1 to 6, more preferably 1-4, yet more preferably 1-2, carbon atoms. Alkyl includes straight chain alkyl, branched alkyl and cycloalkyl, such as methyl, ethyl, propyl, isopropyl, butyl, t-butyl, and the like. The alkyl group can be attached at any available point to produce a stable compound. An "alkylene" is a divalent alkyl.

A "substituted alkyl" is an alkyl group independently substituted with 1 or more, e.g., 1, 2, or 3, groups or substituents such as halo, hydroxy, optionally substituted alkoxy, optionally substituted alkylthio, alkylsulfinyl, alkylsulfonyl, optionally substituted amino, optionally substituted amido, amidino, urea optionally substituted with alkyl, aminosulfonyl optionally N-mono- or N,N-di-substituted with alkyl, alkylsulfonylamino, carboxyl, heterocycle, substituted heterocycle, nitro, cyano, thiol, sulfonylamino or the like attached at any available point to produce a stable compound. In particular, "fluoro substituted" refers to substitution by 1 or more, e.g., 1, 2, or 3 fluorine atoms. "Optionally fluoro substituted" means that substitution, if present, is fluoro. The term "optionally substituted" as used herein means that substitution may, but need not, be present.

"Lower alkyl" refers to an alkyl group having 1-6 carbon atoms.

A "substituted lower alkyl" is a lower alkyl which is substituted with 1 or more, e.g., 1, 2, or 3, groups or substituents, as defined above, attached at any available point to produce a stable compound.

"Cycloalkyl" refers to saturated or unsaturated, non-aromatic monocyclic, bicyclic or tricyclic carbon ring systems of 3-8, more preferably 3-6, ring members per ring, such as cyclopropyl, cyclopentyl, cyclohexyl, adamantyl, and the like. "Cycloalkylene" is a divalent cycloalkyl.

"Substituted cycloalkyl" refers to saturated or unsaturated, non-aromatic monocyclic, bicyclic or tricyclic carbon ring systems of 3-8, more preferably 3-6, ring members per ring, such as cyclopropyl, cyclopentyl, cyclohexyl, adamantyl, and the like independently substituted with 1 or more, e.g., 1, 2, or 3, groups or substituents such as halo, hydroxy, optionally substituted alkoxy, optionally substituted alkylthio, alkylsulfinyl, alkylsulfonyl, optionally substituted amino, optionally substituted amido, amidino, urea optionally substituted with alkyl, aminosulfonyl optionally N-mono- or N,N-di-substituted with alkyl, alkylsulfonylamino, carboxyl, heterocycle, substituted heterocycle, nitro, cyano, thiol, sulfonylamino or the like attached at any available point to produce a stable compound.

"Aryl" alone or in combination means phenyl or naphthyl optionally carbocyclic fused with a cycloalkyl of preferably 5-7, more preferably 5-6, ring members.

"Substituted aryl" refers to an aryl group as defined above independently substituted with 1 or more, e.g., 1, 2, or 3, groups or substituents such as halo, hydroxy, optionally substituted alkoxy, optionally substituted alkylthio, alkylsulfinyl, alkylsulfonyl, optionally substituted amino, optionally substituted amido, amidino, urea optionally substituted with alkyl, aminosulfonyl optionally N-mono- or N,N-di-substituted with alkyl, alkylsulfonylamino, carboxyl, heterocycle, substituted heterocycle, nitro, cyano, thiol, sulfonylamino or the like attached at any available point to produce a stable compound.

"Alkoxy" denotes the group —OR$^{cc}$, where R$^{cc}$ is alkyl. "Lower alkoxy" denotes the group —OR$^{ccc}$, where R$^{ccc}$ is lower alkyl "Substituted alkoxy" denotes the group —OR$^{dd}$, where R$^{dd}$ is substituted alkyl. "Substituted lower alkoxy" denotes the group —OR$^{ddd}$, where R$^{ddd}$ is substituted lower alkyl.

"Alkylthio" or "thioalkoxy" refers to the group —S—$R^{ee}$, where $R^{ee}$ is alkyl.

"Substituted alkylthio" or "substituted thioalkoxy" refers to the group —S—R, where R is substituted alkyl.

"Sulfinyl" denotes the group —S(O)—.

"Sulfonyl" denotes the group —S(O)$_2$—.

"Substituted sulfinyl" denotes the group —S(O)—$R^{ff}$, where $R^{ff}$ is alkyl, substituted alkyl, cycloalkyl, substituted cycloalkyl, cycloalkylalkyl, substituted cycloalkylalkyl, heterocyclyl, substituted heterocyclyl, heterocyclylalkyl, substituted hetereocyclylalkyl, aryl, substituted aryl, heteroaryl, substituted heteroaryl, heteroaralkyl, substituted heteroaralkyl, aralkyl or substituted aralkyl.

"Substituted sulfonyl" denotes the group —S(O)$_2$$R^{gg}$, where $R^{gg}$ is alkyl, substituted alkyl, cycloalkyl, substituted cycloalkyl, cycloalkylalkyl, substituted cycloalkylalkyl, heterocyclyl, substituted heterocyclyl, heterocyclylalkyl, substituted hetereocyclylalkyl, aryl, substituted aryl, heteroaryl, substituted heteroaryl, heteroaralkyl, substituted heteroaralkyl, aralkyl or substituted aralkyl.

"Sulfonylamino" denotes the group —S(O)$_2$NR$^{hh}$— where $R^{hh}$ is hydrogen or alkyl.

"Substituted sulfonylamino" denotes the group —S(O)$_2$$R^{ii}$—$R^{jj}$, where $R^{ii}$ is hydrogen or optionally substituted alkyl, and $R^{jj}$ is alkyl, substituted alkyl, cycloalkyl, substituted cycloalkyl, heterocyclyl, substituted heterocyclyl, aryl, substituted aryl, heteroaryl, substituted heteroaryl, heteroaralkyl, substituted heteroaralkyl, aralkyl or substituted aralkyl.

"Amino" or "amine" denotes the group —NH$_2$. A "divalent amine" denotes the group —NH—. A "substituted divalent amine" denotes the group —NR$^{kk}$— wherein $R^{kk}$ is alkyl, substituted alkyl, aryl, substituted aryl, heteroaryl, substituted heteroaryl, acyl, substituted acyl, sulfonyl or substituted sulfonyl.

"Substituted amino" or "substituted amine" denotes the group —NR$^{mm}$R$^{nn}$, wherein $R^{mm}$ and $R^{nn}$ are independently hydrogen, alkyl, substituted alkyl, aryl, substituted aryl, heteroaryl, substituted heteroaryl, acyl, substituted acyl, sulfonyl, substituted sulfonyl, or cycloalkyl provided, however, that at least one of $R^{mm}$ and $R^{nn}$ is not hydrogen. $R^{mm}R^{nn}$ in combination with the nitrogen may form an optionally substituted heterocyclic or heteroaryl ring.

"Alkylsulfinyl" denotes the group —S(O)$R^{oo}$, wherein $R^{oo}$ is optionally substituted alkyl.

"Alkylsulfonyl" denotes the group —S(O)$_2$$R^{pp}$, wherein $R^{pp}$ is optionally substituted alkyl.

"Alkylsulfonylamino" denotes the group —NR$^{qq}$S(O)$_2$ $^{rr}$, wherein $R^{rr}$ is optionally substituted alkyl, and $R^{qq}$ is hydrogen or alkyl.

A "primary amino substituent" denotes the group —NH$_2$.

A "secondary amino substituent" denotes the group —NHR$^{ss}$, wherein $R^{ss}$ is alkyl, substituted alkyl, aryl, substituted aryl, heteroaryl, substituted heteroaryl, acyl, substituted acyl, sulfonyl, substituted sulfonyl, or cycloalkyl.

A "tertiary amino substituent" denotes the group —NR$^{ss}$-$R^{tt}$, wherein $R^{ss}$ and $R^{tt}$ are independently alkyl, substituted alkyl, aryl, substituted aryl, heteroaryl, substituted heteroaryl, acyl, substituted acyl, sulfonyl, substituted sulfonyl, or cycloalkyl.

"Quaternary ammonium substituent" denotes the group —N$^+$R$^{ss}$R$^{tt}$R$^{uu}$, wherein $R^{ss}$, $R^{tt}$ and $R^{uu}$ are independently alkyl, substituted alkyl, aryl, substituted aryl, heteroaryl, substituted heteroaryl, acyl, substituted acyl, sulfonyl, substituted sulfonyl, or cycloalkyl.

"Heteroaryl" means a monocyclic aromatic ring structure containing 5 or 6 ring atoms, or a bicyclic aromatic group having 8 to 10 atoms, containing one or more, preferably 1-4, more preferably 1-3, even more preferably 1-2, heteroatoms independently selected from the group consisting of O, S, and N. Heteroaryl is also intended to include oxidized S or N, such as sulfinyl, sulfonyl and N-oxide of a tertiary ring nitrogen. A carbon or nitrogen atom is the point of attachment of the heteroaryl ring structure such that a stable aromatic ring is retained. Examples of heteroaryl groups are pyridinyl, pyridazinyl, pyrazinyl, quinaoxalyl, indolizinyl, benzo[b]thienyl, quinazolinyl, purinyl, indolyl, quinolinyl, pyrimidinyl, pyrrolyl, oxazolyl, thiazolyl, thienyl, isoxazolyl, oxathiadiazolyl, isothiazolyl, tetrazolyl, imidazolyl, triazinyl, furanyl, benzofuryl, indolyl, and the like. "Heteroarylene" means a divalent heteroaryl.

"Heterocycle" or "heterocyclyl" means a saturated or unsaturated, non-aromatic carbocyclic group having a single ring or multiple condensed rings, e.g. a cycloalkyl group having from 5 to 10 atoms in which from 1 to 3 carbon atoms in a ring are replaced by heteroatoms, such as O, S, N, and are optionally fused with benzo or heteroaryl of 5-6 ring members and/or are optionally substituted. Heterocyclyl is intended to include oxidized S or N, such as sulfinyl, sulfonyl and N-oxide of a tertiary ring nitrogen. Examples of heterocycle or heterocyclyl groups are morpholino, tetrahydrofuranyl, dihydropyridinyl, piperidinyl, pyrrolidinyl, piperazinyl, dihydrobenzofuryl, dihydroindolyl, and the like.

"Heterocyclylalkyl" refers to the group —R-Het where Het is a heterocycle group and R is an alkylene group.

A "substituted heteroaryl," "substituted heterocyclyl," or "substituted heterocyclylalkyl" is a heteroaryl, heterocyclyl, or heterocyclylalkyl, respectively, independently substituted with 1 or more, e.g., 1, 2, or 3, groups or substituents such as halogen, hydroxy, optionally substituted alkoxy, optionally substituted alkylthio, alkylsulfinyl, alkylsulfonyl, acyloxy, optionally substituted aryl, optionally substituted aryloxy, optionally substituted heteroaryloxy, optionally substituted amino, optionally substituted amido, amidino, urea optionally substituted with alkyl, aryl, heteroaryl or heterocyclyl groups, aminosulfonyl optionally N-mono- or N,N-di-substituted with alkyl, aryl or heteroaryl groups, alkylsulfonylamino, arylsulfonylamino, heteroarylsulfonylamino, alkylcarbonylamino, arylcarbonylamino, heteroarylcarbonylamino, carboxyl, heterocycle, substituted heterocycle, heteroaryl, substituted heteroaryl, nitro, cyano, thiol, sulfonylamino, optionally substituted alkyl, optionally substituted alkenyl, or optionally substituted alkynyl, attached at any available point to produce a stable compound.

"Amido" denotes the group —C(O)NH$_2$. "Substituted amido" denotes the group —C(O)NR$^k$R$^l$, wherein $R^k$ and $R^l$ are independently hydrogen, lower alkyl, substituted lower alkyl, aryl, substituted aryl, heteroaryl, or substituted heteroaryl, provided, however, that at least one of $R^k$ and $R^l$ is not hydrogen. $R^kR^l$ in combination with the nitrogen may form an optionally substituted heterocyclic or heteroaryl ring.

"Amidino" denotes the group —C(=NR$^m$)NR$^n$R$^o$, wherein $R^m$, $R^n$, and $R^o$ are independently hydrogen or optionally substituted lower alkyl.

"Acyloxy" denotes the group —OC(O)$R^h$, where $R^h$ is hydrogen, alkyl, substituted alkyl, cycloalkyl, substituted cycloalkyl, heterocyclyl, substituted heterocyclyl, aryl, substituted aryl, heteroaryl, substituted heteroaryl and the like.

"Aryloxy" denotes the group —OAr, where Ar is an aryl, or substituted aryl, group. "Heteroaryloxy" denotes groups —OHet, wherein Het is an optionally substituted heteroaryl group.

"Arylsulfonylamino" denotes the group —NR$^q$S(O)$_2$$R^s$, wherein $R^s$ is optionally substituted aryl, and $R^q$ is hydrogen or lower alkyl. "Heteroarylsulfonylamino" denotes the group —NR$^q$S(O)$_2$R$^t$, wherein R$^t$ is optionally substituted heteroaryl, and R$^q$ is hydrogen or lower alkyl.

"Alkylcarbonylamino" denotes the group —NR$^q$C(O)R$^P$, wherein R$^P$ is optionally substituted alkyl, and R$^q$ is hydrogen or lower alkyl.

"Arylcarbonylamino" denotes the group —NR$^q$C(O)R$^s$, wherein R$^s$ is optionally substituted aryl, and R$^q$ is hydrogen or lower alkyl.

"Heteroarylcarbonylamino" denotes the group —NR$^q$C(O)R$^t$, wherein R$^t$ is optionally substituted aryl, and R$^q$ is hydrogen or lower alkyl.

Pharmaceutical formulations containing K$_{ATP}$ channel openers can include the free base of a compound defined by any of Formulae I-VIII, or a salt thereof. Salts of the compounds of Formulae I-VIII as provided herein may have one or more of the following characteristics: (1) stability in solution during synthesis and formulation, (2) stability in a solid state, (3) compatibility with excipients used in the manufacture of tablet formulations, (4) quantitatively yield the K$_{ATP}$ channel opener upon exposure to simulated or actual gastric and duodenal conditions, (5) release K$_{ATP}$ channel opener from sufficiently small particles that are readily dissolved and absorbed, (6) provide, when incorporated into a pharmaceutical formulation, for absorption of greater than 80% of the administered dose, (7) present no elevated toxicological risk as compared to the free base of the K$_{ATP}$ channel opener, (8) can be formulated into acceptable pharmaceutical formulations to treat obesity and other diseases of humans, (9) are acceptable to the FDA as the basis of a drug product, (10) can be recrystallized to improve purity, (11) can be used to form co-crystals of two or more salts of the K$_{ATP}$ channel opener, (12) have limited hygroscopicity to improve stability, (13) synthetic and crystallization conditions under which the salt is formed can be varied resulting in different crystal structures (polymorphs) can be controlled in the synthesis of the salt, or (14) have improved solubility as compared to the free base in aqueous systems at physiological pH values.

The K$_{ATP}$ channel openers provided in Formulae I-VIII are preferably formulated as pharmaceutically acceptable salts. Pharmaceutically acceptable salts are non-toxic salts in the amounts and concentrations at which they are administered. The preparation of such salts can facilitate the pharmacological use by altering the physical characteristics of a compound without preventing it from exerting its physiological effect. Useful alterations in physical properties include lowering the melting point to facilitate transmucosal administration and increasing the solubility to facilitate administering lower effective doses of the drug.

Salts of the compounds of Formulae I-IV can include metal cations, preferably alkali metal cations, such as for example, sodium or potassium. Cations can be selected from any group I alkali metal. Divalent metals cations, such as alkaline earth metals (e.g., magnesium, calcium and the like), have not been found to be useful for salt formation with the compounds of Formulae I-IV.

Salts of the compounds of Formulae I-IV which include alkali metal cations can be prepared by reacting the compounds of Formulae I-IV with an alkali metal hydroxide or alkali metal alkoxide, such as for example, NaOH, KOH or NaOCH3, in a variety of solvents which may be selected from low molecular weight ketones (e.g., acetone, methyl ethyl ketone), tetrahydrofuran (THF), dimethylformamide (DMF), and n-methylpyrrolidinone, and the like. Surprisingly, salt formation with an alkali metal hydroxide or alkoxide is not observed when an alcohol, particularly a lower alcohol such as for example methanol or ethanol, is used as the solvent. This result was confirmed by both X-Ray Powder Diffraction and NMR, and is contrary to the disclosure of U.S. Pat. No. 2,986,573, which purports to describe formation of diazoxide salts in alcohol.

The compounds of Formulae I-IV can also form salts with organic cations that include at least one tertiary amine or ammonium cation. Organic cation compounds can be monovalent, divalent, trivalent and tetravalent by inclusion of one, two, three or four tertiary amine or ammonium ions within the compound, respectively. When a multivalent compound is used, the tertiary amine or quaternary ammonium moieties are preferably separated by a chain of at least 4 atoms, more preferably by a chain of at least 6 atoms, such as for example, hexamethyl hexamethylene diammonium dihydroxide, wherein the quaternary ammonium moieties are separated by —(CH$_2$)$_6$—. Primary and secondary amines do not to effectively form salts with the compounds of Formulae I-IV.

Salts of the compounds of Formulae I-IV can be prepared by reacting the compounds of Formulae I-IV with compounds that include at least one tertiary amine or quaternary ammonium ion (e.g., choline hydroxide, hexamethylhexamethylene diammonium dihydroxide) in a solvent selected from low molecular weight ketones (e.g., acetone, methyl ethyl ketone), tetrahydrofuran, dimethylformamide, and n-methyl pyrrolidinone. As with the preparation of salts from alkali metal hydroxides, amine and ammonium containing compounds do not form salts when the solvent is an alcohol.

Pharmaceutically acceptable salts of the compounds of Formulae I-IV can also include basic addition salts such as those containing benzathine, chloroprocaine, choline, diethylamino-ethanol, hydroxyethyl pyrrolidine, ammonium, tetrapropylammonium, tetrabutylphosphonium, hexamethyl diammonium, methyldiethanamine, triethylamine, meglumine, and procaine, and can be prepared using the appropriate corresponding bases.

Preferred basic addition salts of the compounds of Formulae I-IV can include those containing hexamethyl hexamethylene diammonium, choline, sodium, potassium, methyldiethyl amine, triethylamine, diethylamino-ethanol, hydroxyethyl pyrrolidine, tetrapropylammonium and tetrabutylphosphonium ions.

Preferred basic addition salts of the compounds of Formulae I-IV can be prepared using hexamethyl hexamethylene diammonium dihydroxide, choline hydroxide, sodium hydroxide, sodium methoxide, potassium hydroxide, potassium methoxide, ammonium hydroxide, tetrapropylammonium hydroxide, and tetrabutylphosphonium hydroxide. The basic addition salts can be separated into inorganic salts (e.g., sodium, potassium and the like) and organic salts (e.g., choline, hexamethyl hexamethylene diammonium hydroxide, and the like).

The compounds of Formulae V-VIII have the unique property of being able to form both anions and cations. In basic media, the compounds of Formulae V-VIII typically form anions. Anions can be formed at either an amino or substituted amino substituent, or at the sulfonyl group. In acidic media, the compounds of Formulae V-VIII generally form cations by protonation of an amino group, thereby forming an ammonium moiety.

Salts of the anions of compounds of Formulae V-VIII can include metal cations, including monovalent metal cations of any group I alkali metal (e.g., sodium, potassium, and the like), divalent metal cations of any group II alkaline earth metal (e.g., calcium, magnesium, and the like), and aluminum cations.

Salts of the compounds of Formulae V-VIII which include metal cations can be prepared by reacting the compounds of Formulae V-VIII with a alkali or alkaline earth metal hydroxides or alkoxides, such as for example, sodium hydroxide or sodium methoxide, in an organic solvent, such as for example lower alcohols, low molecular weight ketones (e.g., acetone, methyl ethyl ketone, and the like), tetrahydrofuran, dimethylformamide, and n-methylpyrrolidinone, and the like.

Salts of the compounds of Formulae V-VIII, may include organic or inorganic counter ions, including but not limited to, acetate, acetonide, acetyl, adipate, aspartate, besylate, biacetate, bitartrate, bromide, butoxide, butyrate, calcium, camsylate, caproate, carbonate, citrate, cyprionate, decaroate, diacetate, dimegulumine, dinitrate, dipotassium, dipropionate, disodium, disulfide, edisylate, enanthate, estolate, etabonate, ethylsuccinate, fumarate, furoate, gluceptate, gluconate, hexacetonide, hippurate, hyclate, hydrobromide, hydrochloride, isethionate, lactobionate, malate, maleate, meglumine, methylbromide, methylsulfate, metrizoate, nafate, napsylate, nitrate, oleate, palmitate, pamoate, phenpropionate, phosphate, pivalate, polistirex, polygalacturonate, probutate, propionate, saccharate, sodium glycinate, sodium phosphate, sodium succinate, stearate, succinate, sulfate, sulfonate, sulfosalicylate, tartrate, tebutate, terephalate, terephthalate, tosylate, triflutate, trihydrate, trisilicate, tromethamine, valerate, or xinafolate. Preferred organic cations include compounds having tertiary amines or quaternary ammonium groups.

Other, pharmaceutically acceptable salts of the compounds of Formulae V-VIII include acid addition salts such as those containing sulfate, chloride, hydrochloride, fumarate, maleate, phosphate, sulfamate, acetate, citrate, lactate, tartrate, methanesulfonate, ethanesulfonate, benzenesulfonate, p-toluene sulfonate, cyclohexylsulfamate and quinate. Pharmaceutically acceptable salts of the compounds of Formulae V-VIII can be obtained from acids such as hydrochloric acid, maleic acid, sulfuric acid, phosphoric acid, sulfamic acid, acetic acid, citric acid, lactic acid, tartaric acid, malonic acid, methanesulfonic acid, ethanesulfonic acid, benzenesulfonic acid, p-toluenesulfonic acid, cyclohexylsulfamic acid, fumaric acid, and quinic acid.

Pharmaceutically acceptable salts of the compounds of Formulae V-VIII also include basic addition salts such as those containing benzathine, chloroprocaine, choline, diethanolamine, ethylenediamine, meglumine, procaine, aluminum, calcium, lithium, magnesium, potassium, sodium, ammonium, alkylamine, and zinc, when acidic functional groups, such as carboxylic acid or phenol are present. For example, see *Remington's Pharmaceutical Sciences*, 19th ed., Mack Publishing Co., Easton, Pa., Vol. 2, p. 1457, 1995. Such salts of the compounds of Formulae V-VIII can be prepared using the appropriate corresponding bases.

Salts of the compounds of Formulae V-VIII can be prepared, for example, by dissolving the free-base form of a compound in a suitable solvent, such as an aqueous or aqueous-alcohol in solution containing the appropriate acid and then isolated by evaporating the solution. In another example, a salt is prepared by reacting the free base and acid in an organic solvent.

The salts of the compounds of Formulae V-VIII may be present as a complex. Examples of complexes include 8-chlorotheophylline complex (analogous to, e.g., dimenhydrinate: diphenhydramine 8-chlorotheophylline (1:1) complex; Dramamine) and various cyclodextrin inclusion complexes.

Solvents useful in the preparation of pharmaceutically acceptable salts of the compounds of Formulae V-VIII include organic solvents, such as for example, acetonitrile, acetone, alcohols (e.g., methanol, ethanol and isopropanol), tetrahydrofuran, methyl ethyl ketone (MEK), ethers (e.g., diethyl ether), benzene, toluene, xylenes, dimethylformamide (DMF), and N-methylpyrrolidinone (NMP), and the like. Preferably, the solvents are selected from acetonitrile and MEK.

The salts of compounds of Formulae V-VIII may be present as a complex. Examples of complexes include 8-chlorotheophylline complex (analogous to, e.g., dimenhydrinate: diphenhydramine 8-chlorotheophylline (1:1) complex; Dramamine) and various cyclodextrin inclusion complexes.

Formulations of salts of the compounds of Formulae I-VIII provided herein exhibit at least one, or preferably some or even more preferably, all the following characteristics: (1) they are stable at ambient temperatures for a minimum of one year; (2) they provide for ease of oral administration; (3) they facilitate patient compliance with dosing; (4) upon administration, they consistently facilitate high levels of absorption of the pharmaceutical active; (5) upon once or twice daily oral administration they allow release of the $K_{ATP}$ channel opener over a sustained time frame such that the circulating concentration of the $K_{ATP}$ channel opener or its metabolically active metabolites does not fall below a therapeutically effective concentration; (6) they achieve these results independent of the pH of the gastrointestinal tract of treated subjects, and (7) they delay release until gastric transit is complete or nearly complete.

Formulations designed for oral administration of the salts of the compounds of Formulae I-VIII can be provided, for example, as capsules, tablets, or as quick dissolve tablets or films. Capsule or tablet formulations include a number of distinguishing components. One is a component to improve absorption of the $K_{ATP}$ channel opener. Another sustains release of the drug over more than 2 hours. A third delays substantial release of the drug until gastric transit is completed.

Oral administration formulations of the salts of the compounds of Formulae I-VIII can also be provided, for example, as oral suspensions, oral solutions, encapsulated oral suspensions, and encapsulated oral solutions. Formulations can be designed for immediate release or controlled release. Preferably, such oral formulations are not produced from a liquid form of the sodium salt of diazoxide.

Formulations of the salts of the compounds of Formulae I-VIII can also be prepared for transdermal, intranasal and intravenous (I.V.) administration, provided that when the anion is diazoxide and the cation is sodium, the formulation is not for intravenous use.

In another embodiment, formulations of the salts of the compounds of Formulae I-VIII are prepared for transdermal or intranasal administration, provided that when the anion is diazoxide and the cation is sodium, the formulation is not produced using a liquid form of the salt of the compounds of Formulae I-VIII.

In another embodiment, formulations of the salts of the compounds of Formulae I-VIII are prepared for transdermal, intranasal and intravenous (I.V.) administration excluding the sodium salt of diazoxide.

Formulations of $K_{ATP}$ channel openers prepared using salts of the compounds selected from Formulae I-VIII exhibit improved solubility and absorption compared to previous formulations of these drugs. These advantageous properties are achieved by any one or more of the following approaches: (1) reducing particle size of the formulation by comminution, spray drying, or other micronising techniques, (2) using an ion exchange resin in the formulation, (3) using inclusion complexes, for example using a cyclodextrin, (4) compaction of the salt of $K_{ATP}$ channel opener with a solubilizing agent including low viscosity hypromellose, low viscosity methylcellulose or similarly functioning excipient and combinations thereof, (5) associating the salt of the $K_{ATP}$ channel opener with a distinct salt prior to formulation, (6) using a solid dispersion of the salt of the $K_{ATP}$ channel opener, (7) using a self emulsifying system, (8) adding one or more surfactants to the formulation, (9) using nanoparticles in the formulation, or (10) combinations of these approaches.

Release of $K_{ATP}$ channel opener selected from salts of the compounds of Formulae I-VIII over a sustained period of time (e.g., 2-30 hours) can be achieved by the use of one or more approaches including, but not limited to: (1) the use of pH sensitive polymeric coatings, (2) the use of a hydrogel, (3) the use of a film coating that controls the rate of diffusion of the drug from a coated matrix, (4) the use of an erodable matrix that controls rate of drug release, (5) the use of polymer coated pellets, granules, or microparticles which can be further encapsulated or compressed into a tablet, (6) the use of an osmotic pump system, (7) the use of a compression coated tablet, or (8) combinations of these approaches.

Delay of release of $K_{ATP}$ channel openers selected from the salts of the compounds of Formulae I-VIII from the formulation until gastric transit is complete can be achieved in the formulations provided herein by any of several mechanisms. For example, pH sensitive polymer or co-polymer can be used which when applied around the drug matrix functions as an effective barrier to release of active at pH 3.0 or lower and is unstable at pH 5.5 and above. This provides for control of release of the active compound in the stomach but rapidly allows release once the dosage form has passed into the small intestine. An alternative to a pH sensitive polymer or co-polymer is a polymer or co-polymer that is non-aqueous-soluble. The extent of resistance to release in the gastric environment can be controlled by coating with a blend of the non-aqueous-soluble and a aqueous soluble polymer. In this approach neither of the blended polymers or co-polymers are pH sensitive. One example of a pH sensitive co-polymer is the Eudragit® methacrylic co-polymers, including Eudragit® L 100, S 100 or L 100-55 solids, L 30 D-55 or FS 30D dispersions, or the L 12.5 or S 12.5 organic solutions.

Polymers that delay release can be applied to a tablet either by spray coating (as a thin film) or by compression coating. If a capsule is used, then the polymer(s) may be applied over the surface of the capsule or applied to microparticles of the drug, which may then be encapsulated such as in a capsule or gel. If the capsule is coated, then it will resist disintegration until after gastric transit. If microparticles are coated, then the capsule may disintegrate in the stomach but little to no drug will be released until after the free microparticles complete gastric transit. Finally, an osmotic pump system that uses e.g., a swellable hydrogel can be used to delay drug release in the stomach. The swellable hydrogel takes up moisture after administration. Swelling of the gel results in displacement of the drug from the system for absorption. The timing and rate of release of the drug depend on the gel used, and the rate at which moisture reaches the gel, which can be controlled by the size of the opening in the system through which fluid enters. See Drug Delivery Technologies online article Dong et al., "L-OROS® SOFTCAP™ for Controlled Release of Non-Aqueous Liquid Formulations."

Accordingly, delay of release of formulations of $K_{ATP}$ channel openers prepared as salts of the compounds of Formulae I-VIII until after gastric transit is complete can be achieved by any of several mechanisms, including, but not limited to:

(a) a pH sensitive polymer or co-polymer applied as a compression coating on a tablet;

(b) a pH sensitive polymer or co-polymer applied as a thin film on a tablet; (c) a pH sensitive polymer or co-polymer applied as a thin film to an encapsulation system; (d) a pH sensitive polymer or co-polymer applied to encapsulated microparticles, (e) a non-aqueous-soluble polymer or copolymer applied as a compression coating on a tablet; (f) a non-aqueous-soluble polymer or co-polymer applied as a thin film on a tablet; (g) a non-aqueous soluble polymer applied as a thin film to an encapsulation system; (h) a non-aqueous soluble polymer applied to microparticles; (i) incorporation of the formulation in an osmotic pump system, or (j) use of systems controlled by ion exchange resins, or (k) combinations of these approaches, wherein the pH sensitive polymer or co-polymer is resistant to degradation under acid conditions.

Formulations are provided that are designed for administration once daily (i.e., once per 24 hours). These formulations can contain between 25 and 500 mg of $K_{ATP}$ channel openers selected from salts of the compounds of Formulae I-VIII. Formulations intended for administration twice daily (per 24 hours) may also be provided. These can contain between 25 and 250 mg of $K_{ATP}$ channel openers.

The formulations provided herein exhibit improved safety of the administered drug product. This improvement in safety occurs by at least two mechanisms. First, delay of release of active drug until gastric transit is complete can reduce the incidence of a range of gastrointestinal adverse side effects including nausea, vomiting, dyspepsia, abdominal pain, diarrhea and ileus. Second, by sustaining release of the active drug over 2 or more hours up to as long as 24 hours, peak drug levels are reduced relative to the peak drug levels observed for the same administered dose using any oral formulation that does not have sustained or controlled release. This reduction in peak drug levels can contribute to reductions in adverse effects that are partially or completely determined by peak drug levels. These adverse effects include: fluid retention with the associated reduced rates of excretion of sodium, chloride and uric acid, edema, hyperglycemia and the associated potential for progression to ketoacidosis, cataracts and non-ketotic hyperosmolar coma, headaches, tachycardia and palpitations.

Also provided herein are controlled release formulations of $K_{ATP}$ channel openers prepared from salts of compounds of Formulae I-VIII, which have one feature from each of A-D as shown in Table 1.

TABLE 1

Controlled Release Formulation Characteristics and Properties

| | |
|---|---|
| A. Unit Form: | Tablet or Capsule |
| B. Dosage/unit: | 10-100 mg |
| | 100-200 mg |
| | 200-300 mg |
| | 300-500 mg |
| | 500-2000 mg |
| C. Dosing | Once daily (24 hours) |
| | Twice daily (24 hours) |
| D. Release time: | 2-4 hrs |
| | 4-8 hrs |
| | 8-24 hours |

For example, a controlled release composition can be a tablet containing 25-100 mg of a salt of a compound of Formulae I-VIII, wherein such tablet administered once daily to achieve a controlled release time of 2-4 hours. All of these formulations can further include the feature of substantially delaying pharmaceutical active release until after gastric transit is complete.

In addition, any of the above formulations from Table 1 can include at least one feature that improves the solubility or absorption of the $K_{ATP}$ channel opener.

Exemplary controlled release formulations provided herein include the active compound (i.e., a $K_{ATP}$ channel opener selected from a salt of a compound of any of Formulae I-VIII) and a matrix which includes a gelling agent that swells upon contact with aqueous fluid. The active compound entrapped within the gel is slowly released into the body upon dissolution of the gel. The active compound can be evenly dispersed within the matrix or can be present as pockets of drug in the matrix. For example, the drug can be formulated into small granules which are dispersed within the matrix. In addition, the granules of drug also can include a matrix, thus, providing a primary and a secondary matrix as described in U.S. Pat. No. 4,880,830 to Rhodes.

The gelling agent preferably is a polymeric material, which can include, for example, any pharmaceutically acceptable water soluble or water insoluble slow releasing polymer such as xantham gum, gelatin, cellulose ethers, gum arabic, locust bean gum, guar gum, carboxyvinyl polymer, agar, acacia gum, tragacanth, veegum, sodium alginate or alginic acid, polyvinylpyrrolidone, polyvinyl alcohol, or film forming polymers such as methyl cellulose (MC), carboxymethyl cellulose (CMC), hydroxypropyl methylcellulose, hydroxypropyl methyl cellulose (HPMC), hydroxypropyl cellulose (HPC), hydroxyethyl cellulose (HEC), ethylcellulose (EC), acrylic resins or mixtures of the above (see e.g., U.S. Pat. No. 5,415,871).

The gelling agent of the matrix also can be a heterodisperse gum comprising a heteropolysaccharide component and a homopolysaccharide component which produces a fast-forming and rigid gel as described in U.S. Pat. No. 5,399,359. The matrix also can include a cross-linking agent such as a monovalent or multivalent metal cations to further add rigidity and decrease dissolution of the matrix, thus further slowing release of drug. The amount of crosslinking agent to add can be determined using methods routine to the ordinary skilled artisan.

The matrix of the controlled release composition also can include one or more pharmaceutically acceptable excipients recognized by those skilled in the art, i.e. formulation excipients. Such excipients include, for example, binders: polyvinylpyrrolidone, gelatin, starch paste, microcrystalline cellulose; diluents (or fillers): starch, sucrose, dextrose, lactose, fructose, xylitol, sorbitol, sodium chloride, dextrins, calcium phosphate, calcium sulphate; and lubricants: stearic acid, magnesium stearate, calcium stearate, Precirol® and flow aids for example talc or colloidal silicon dioxide.

The matrix of the controlled release composition can further include a hydrophobic material which slows the hydration of the gelling agent without disrupting the hydrophilic nature of the matrix, as described in U.S. Pat. No. 5,399,359. The hydrophobic polymer can include, for example, alkylcellulose such as ethylcellulose, other hydrophobic cellulosic materials, polymers or copolymers derived from acrylic or methacrylic acid esters, copolymers of acrylic and methacrylic acid esters, zein, waxes, shellac, hydrogenated vegetable oils, waxes and waxy substances such as carnauba wax, spermaceti wax, candellila wax, cocoa butter, cetosteryl alcohol, beeswax, ceresin, paraffin, myristyl alcohol, stearyl alcohol, cetylalcohol and stearic acid, and any other pharmaceutically acceptable hydrophobic material known to those skilled in the art.

The amount of hydrophobic material incorporated into the controlled release composition is that which is effective to slow the hydration of the gelling agent without disrupting the hydrophilic matrix formed upon exposure to an environmental fluid. In certain preferred embodiments, the hydrophobic material is included in the matrix in an amount from about 1 to about 20 percent by weight and replaces a corresponding amount of the formulation excipient. A solvent for the hydrophobic material may be an aqueous or organic solvent, or mixtures thereof.

Examples of commercially available alkylcelluloses are Aquacoat® (aqueous dispersion of ethylcellulose available from FMC) and Surelease® (aqueous dispersion of ethylcellulose available from Colorcon). Examples of commercially available acrylic polymers suitable for use as the hydrophobic material include Eudragit® RS and RL (copolymers of acrylic and methacrylic acid esters having a low content (e.g., 1:20 or 1:40) of quaternary ammonium compounds).

The controlled release composition also can be coated to retard access of liquids to the active compound and/or retard release of the active compound through the film-coating. The film-coating can provide characteristics of gastroresistance and enterosolubility by resisting rapid dissolution of the composition in the digestive tract. The film-coating generally represents about 5-15% by weight of the controlled release composition. Preferably, the core by weight represents about 90% of the composition with the remaining 10% provided by the coating. Such coating can be a film-coating as is well known in the art and include gels, waxes, fats, emulsifiers, combination of fats and emulsifiers, polymers, starch, and the like.

Polymers and co-polymers are useful as thin film coatings. Solution coatings and dispersion coatings can be used to coat the active compound, either alone or combined with a matrix. The coating is preferably applied to the drug or drug and matrix combination as a solid core of material as is well known in the art.

A solution for coating can include polymers in both organic solvent and aqueous solvent systems, and typically further including one or more compounds that act as a plasticizer. Polymers useful for coating compositions include, for example, methylcellulose (Methocel® A; Dow Chemical Co.), hydroxypropylmethylcellulose with a molecular weight between 1,000 and 4,000,000 (Methocel® E; Dow Chemical Co. or Pharmacoat®; Shin Etsu), hydroxypropyl cellulose with a molecular weight between 2,000 and 2,000,000, ethyl cellulose, cellulose acetate, cellulose triacetate, cellulose acetate butyrate, cellulose acetate phthalate, cellulose acetate trimellitate (Eastman Kodak), carboxymethylethyl cellulose (Duodcel®), hydroxypropyl methylcellulose phthalate, ethylcellulose, methylcellulose and, in general, cellulosic derivatives, olymethacrylic acid-methacrylic acid copolymer (Type A 1:1 Eudragit L100; Type B1:2 Eudragit S100; and Type C 1:1 Eudragit L100-55, aqueous dispersion 30% solids, Eudragit L30D), poly(meth)acryl ester: poly(ethyl acrylate, methyl methacrylate 2:1), Eudragit NE30D aqueous dispersion 30% solids, polyaminomethacrylate Eudragit EL 00, poly(trimethylammonioethyl methacrylate chloride) ammoniomethacrylate copolymer, Eudragit RL30D and Eudragit RS30D, carboxyvinyl polymers, polyvinylalcohols, glucans scleroglucans, mannans, and xanthans.

Aqueous polymeric dispersions include Eudragit L30D and RS/RL30D, and NE30D, AQUACOAT® brand ethyl cellulose, Surelease brand ethyl cellulose, EC brand N-10F ethyl cellulose, Aquateric brand cellulose acetate phthalate, Coateric brand Poly(vinyl acetate phthalate), and Aqacoat brand hydroxypropyl methylcellulose acetate succinate. Most of these dispersions are latex, pseudolatex powder or micronized powder mediums.

A plasticizing agent may be included in the coating to improve the elasticity and the stability of the polymer film and to prevent changes in the polymer permeability over prolonged storage. Such changes may affect the drug release rate. Suitable conventional plasticizing agents include, for example, diethyl phthalate, glycerol triacetate, acetylated monoglycerides, acetyltributylcitrate, acetyltriethyl citrate, castor oil, citric acid esters, dibutyl phthalate, dibutyl sebacate, diethyloxalate, diethyl malate, diethylfumarate, diethylphthalate, diethylsuccinate, diethylmalonate, diethyltartarate, dimethylphthalate, glycerin, glycerol, glyceryl triacetate, glyceryltributyrate, mineral oil and lanolin alcohols, petrolatum and lanolin alcohols, phthalic acid esters, polyethylene glycols, propylene glycol, rape oil, sesame oil, triacetin, tributyl citrate, triethyl citrate, and triethyl acetyl citrate, or a mixture of any two or more of the foregoing. Plasticizers which can be used for aqueous coatings include, for example, propylene glycol, polyethylene glycol (PEG 400), triacetin, polysorbate 80, triethyl citrate, and diethyl d-tartrate.

A coating solution comprising a mixture of hydroxypropylmethylcellulose and aqueous ethylcellulose (e.g. Aquacoat brand) as the polymer and dibutyl sebacate as plasticizer can be used for coating microparticles. (Aquacoat is an aqueous polymeric dispersion of ethylcellulose and contains sodium lauryl sulfate and cetyl alcohol). Preferably, the plasticizer represents about 1-2% of the composition.

In addition to the polymers, the coating layer can include an excipient to assist in formulation of the coating solution. Such excipients may include a lubricant or a wetting agent. Suitable lubricants as excipients for the film coating include, for example, talc, calcium stearate, colloidal silicon dioxide, glycerin, magnesium stearate, mineral oil, polyethylene glycol, and zinc stearate, aluminum stearate or a mixture of any two or more of the foregoing. Suitable wetting agents include, for example, sodium lauryl sulfate, acacia, benzalkonium chloride, cetomacrogol emulsifying wax, cetostearyl alcohol, cetyl alcohol, cholesterol, diethanolamine, docusate sodium, sodium stearate, emulsifying wax, glyceryl monostearate, hydroxypropyl cellulose, lanolin alcohols, lecithin, mineral oil, onoethanolamine, poloxamer, polyoxyethylene alkyl ethers, polyoxyethylene castor oil derivatives, polyoxyethylene sorbitan fatty acid esters, polyoxyethylene stearates, propylene glycol alginate, sorbitan esters, stearyl alcohol and triethanolamine, or a mixture of any two or more of the foregoing.

The specified tablet or capsule formulations of Table 1 may include co-formulation with an obesity treating drug (in addition to a $K_{ATP}$ channel opener selected from a salt of a compound of Formulae I-VIII). Obesity treating drugs that may be used include, but are not limited to, sibutramine hydrochloride (5-30 mg/unit), orlistat (50-360 mg/unit), phentermine hydrochloride or resin complex (15 to 40 mg/unit), zonisamide (100 to 600 mg/unit), topiramate (64 to 400 mg/unit), naltrexone hydrochloride (50 to 600 mg/unit), rimonabant (5 to 20 mg/unit), ADP356 (5 to 25 mg/unit), ATL962 (20 to 400 mg/unit), or AOD9604 (1 to 10 mg/unit). These formulations are preferably used once daily. For a twice daily dosing, the amount of $K_{ATP}$ channel opener selected from a salt of a compound of Formulae I-VIII is one half the amount included in the once daily formulation and the co-formulated obesity treating drug is half of the amount specified. Alternative obesity treating drugs may include, but are not limited to: selective serotonin 2c receptor agonists, dopamine antagonists, cannabinoid-1 receptor antagonists, leptin analogues, leptin transport and/or leptin receptor promoters, neuropeptide Y and agouti-related peptide antagonists, proopiomelanocortin and cocaine and amphetamine regulated transcript promoters, melanocyte-stimulating hormone analogues, melanocortin-4 receptor agonists, and agents that affect insulin metabolism/activity, which can include protein-tyrosine phosphatase-1B inhibitors, peroxisome proliferator activated receptor antagonists, short-acting bromocriptine (ergoset), somatostatin agonists (octreotide), and adiponectin, gastrointestinal-neural pathway agents, including those that increase cholecystokinin activity, increase glucagon-like peptide-1 activity (e.g., extendin 4, liraglutide, dipeptidyl peptidase IV inhibitors), and increase protein YY3-36 activity and those that decrease ghrelin activity, as well as amylin analogues, agents that may increase resting metabolic rate ("selective" β-3 stimulators/agonist, uncoupling protein homologues, and thyroid receptor agonists), melanin concentrating hormone antagonists, phytostanol analogues, amylase inhibitors, growth hormone fragments, synthetic analogues of dehydroepiandrosterone sulfate, antagonists of adipocyte 11Bhydroxysteroid dehydrogenase type 1 activity, corticotropin releasing hormone agonists, inhibitors of fatty acid synthesis, carboxypeptidase inhibitors, indanones/indanols, aminosterols, and other gastrointestinal lipase inhibitors.

The specified tablet or capsule formulations of Table 1 may include co-formulation with a diabetes treating drug (in addition to a $K_{ATP}$ channel opener selected from a salt of a compound of Formulae I-VIII). Diabetes treating drugs that may be used include, but are not limited to, acarbose (50 to 300 mg/unit), miglitol (25 to 300 mg/unit), metformin hydrochloride (300 to 2000 mg/unit), repaglinide (1-16 mg/unit), nateglinide (200 to 400 mg/unit), rosiglitizone (5 to 50 mg/unit), metaglidasen (100 to 400 mg/unit) or any drug that improves insulin sensitivity, or improves glucose utilization and uptake. These formulations are preferably used once daily. For a twice daily dosing, the amount of the $K_{ATP}$ channel opener selected from a salt of a compound of Formulae I-VIII is half the amount included in the once daily formulation and the co-formulated diabetes treating drug is half of the amount specified.

The specified tablet or capsule formulations of Table 1 may include co-formulation with a cholesterol lowering drug. Cholesterol lowering drugs that may be used include, but are not limited to, pravastatin, simvastatin, atorvastatin, fluvastatin, rosuvastatin, or lovastatin (all at 10 to 80 mg/unit). These formulations are preferably used once daily. For a twice daily dosing, the amount of $K_{ATP}$ channel opener selected from a salt of a compound of Formulae I-VIII is preferably 25 to 200 mg/unit and the co-formulated cholesterol lowering drug is half of the amount specified.

The specified tablet or capsule formulations of Table 1 may include co-formulation with a depression treating drug. Depression treating drugs that may be used include, but are not limited to, citalopram hydrobromide (10 to 80 mg/unit), escitalopram hydrobromide (5 to 40 mg/unit), fluvoxamine maleate (25 to 300 mg/unit), paroxetine hydrochloride (12.5 to 75 mg/unit), fluoxetine hydrochloride (30 to 100 mg/unit), setraline hydrochloride (25 to 200 mg/unit), amitriptyline hydrochloride (10 to 200 mg/unit), desipramine hydrochloride (10 to 300 mg/unit), nortriptyline hydrochloride (10 to 150 mg/unit), duloxetine hydrochloride (20 to 210 mg/unit), venlafaxine hydrochloride (37.5 to 150 mg/unit), phenelzine sulfate (10 to 30 mg/unit), bupropion hydrochloride (200 to 400 mg/unit), or mirtazapine (7.5 to 90 mg/unit). These formulations are preferably used once daily. For a twice daily dosing, the amount of $K_{ATP}$ channel opener selected from a salt of a compound of Formulae I-VIII is preferably half the amount included in the once daily formulation and the co-formulated depression treating drug is half of the amount specified.

The specified tablet or capsule formulations of Table 1 may include co-formulation with a hypertension treating drug. Hypertension treating drugs that may be used include, but are not limited, to enalapril maleate (2.5 to 40 mg/unit), captopril (2.5 to 150 mg/unit), lisinopril (10 to 40 mg/unit), benzaepril hydrochloride (10 to 80 mg/unit), quinapril hydrochloride (10 to 80 mg/unit), peridopril erbumine (4 to 8 mg/unit), ramipril (1.25 to 20 mg/unit), trandolapril (1 to 8 mg/unit), fosinopril sodium (10 to 80 mg/unit), moexipril hydrochloride (5 to 20 mg/unit), losartan potassium (25 to 200 mg/unit), irbesartan (75 to 600 mg/unit), valsartan (40 to 600 mg/unit), candesartan cilexetil (4 to 64 mg/unit), olmesartan medoxamil (5 to 80 mg/unit), telmisartan (20 to 160 mg/unit), eprosartan mesylate (75 to 600 mg/unit), atenolol (25 to 200 mg/unit), propranolol hydrochloride (10 to 180 mg/unit), metoprolol tartrate, succinate or fumarate (each at 25 to 400 mg/unit), nadolol (20 to 160 mg/unit), betaxolol hydrochloride (10 to 40 mg/unit), acebutolol hydrochloride (200 to 800 mg/unit), pindolol (5 to 20 mg/unit), bisoprolol fumarate (5 to 20 mg/unit), nifedipine (15 to 100 mg/unit), felodipine (2.5 to 20 mg/unit), amlodipine besylate (2.5 to 20 mg/unit), nicardipine (10 to 40 mg/unit), nisoldipine (10 to 80 mg/unit), terazosin hydrochloride (1 to 20 mg/unit), doxasoxin mesylate (4 to 16 mg/unit), prazosin hydrochloride (2.5 to 10 mg/unit), or alfuzosin hydrochloride (10 to 20 mg/unit). These formulations are preferably used once daily. For a twice daily dosing, the amount of $K_{ATP}$ channel opener is preferably half the amount included in the once daily formulation and the co-formulated hypertension treating drug is half of the amount specified.

The specified tablet or capsule formulations of Table 1 may include co-formulation with a diuretic to treat edema. Diuretics that may be used include, but are not limited to amiloride hydrochloride (1 to 10 mg/unit), spironolactone (10 to 100 mg/unit), triamterene (25 to 200 mg/unit), bumetanide (0.5 to 4 mg/unit), furosemide (10 to 160 mg/unit), ethacrynic acid or ethacrynate sodium (each at 10 to 50 mg/unit), tosemide (5 to 100 mg/unit), chlorthalidone (10 to 200 mg/unit), indapamide (1 to 5 mg/unit), hydrochlorothiazide (10 to 100 mg/unit), chlorothiazide (50 to 500 mg/unit), bendroflumethiazide (5 to 25 mg/unit), hydroflumethiazide (10 to 50 mg/unit), mythyclothiazide (1 to 5 mg/unit), or polythiazide (1 to 10 mg/unit). These formulations are preferably used once daily. For a twice daily dosing, the amount of $K_{ATP}$ channel opener selected from a salt of a compound of Formulae I-VIII is preferably half the amount included in the once daily formulation and the co-formulated diuretic is half of the amount specified.

The specified tablet or capsule formulations of Table 1 may include co-formulation with a drug to treat inflammation or pain. Drugs for treating inflammation or pain that may be used include, but are not limited to aspirin (100 to 1000 mg/unit), tramadol hydrochloride (25 to 150 mg/unit), gabapentin (100 to 800 mg/unit), acetaminophen (100 to 1000 mg/unit), carbamazepine (100 to 400 mg/unit), ibuprofen (100 to 1600 mg/unit), ketoprofen (12 to 200 mg/unit), fenprofen sodium (100 to 600 mg/unit), flurbiprofen sodium or flurbiprofen (both at 50 to 200 mg/unit), or combinations of any of these with a steroid or aspirin. These formulations are preferably used once daily. For a twice daily dosing, the amount of $K_{ATP}$ channel opener selected from a salt of a compound of Formulae I-VIII is preferably half the amount included in the once daily formulation and the co-formulated diuretic is half of the amount specified.

The specified tablet or capsule formulations of Table 1 may include co-formulation with a drug to treat obesity associated co-morbidities include those specified above for treating diabetes, cholesterol, depression, hypertension and edema, or drugs to treat atherosclerosis, osteoarthritis, disc herniation, degeneration of knees and hips, breast, endometrial, cervical, colon, leukemia and prostate cancers, hyperlipidemia, asthma/reactive airway disease, gallstones, GERD, obstructive sleep apnea, obesity hypoventilation syndrome, recurrent ventral hernias, menstrual irregularity and infertility.

The specified tablet or capsule formulations of Table 1 may include co-formulation with an anti-psychotic drug the combination used to treat the psychotic condition and to treat or prevent weight gain, dyslipidemia or impaired glucose tolerance in the treated subject. Drugs for treating various psychotic conditions that may be used include, but are not limited to, lithium or a salt thereof (250 to 2500 mg/unit), carbamazepine or a salt thereof (50 to 1200 mg/unit), valproate, valproic acid, or divalproex (125 to 2500 mg/unit), lamotrigine (12.5 to 200 mg/unit), olanzapine (5 to 20 mg/unit), clozapine (12.5 to 450 mg/unit), or risperidone (0.25 to 4 mg/unit). These coformulations are preferably intended for once per day administration. For a twice daily dosing, the amount of $K_{ATP}$ channel opener selected from a salt of a compound of Formulae I-VIII is preferably half the amount included in the once daily formulation and the co-formulated anti-psychotic is half of the amount specified.

The specified tablet or capsule formulations of Table 1 may include co-formulation with a drug to treat or prevent ischemic or reperfusion injury. Drugs for treating or preventing ischemic or reperfusion injury that may be used include, but are not limited to: low molecular weight heparins (e.g., dalteparin, enoxaparin, nadroparin, tinzaparin or danaparoid), ancrd, pentoxifylline, nimodipine, flunarizine, ebselen, tirilazad, clomethiazole, an AMPA agonist (e.g., GYKI 52466, NBQX, YM90K, zonampanel, or MPQX), SYM 2081, selfotel, Cerestat, CP-101,606, dextrophan, dextromethorphan, MK-801, NPS 1502, remacemide, ACEA 1021, GV150526, eliprodil ifenprodil, lubeluzole, naloxone, nalfemene citicoline, acetyl-1-carnitine, nifedipine, resveratrol, a nitrone derivative, clopidogrel, dabigatram, prasugrel, troxoprodil, AGY-94806, or KAI-9803.

Provided are formulations administered once or twice daily to an obese or overweight subject continuously result in a circulating concentration of $K_{ATP}$ channel opener selected from a salt of a compound of Formulae I-VIII sufficient to induce weight loss. Weight loss occurs by the preferential loss of body fat. Additional weight loss can occur when the formulation is administered in combination with a reduced calorie diet.

Provided are formulations of $K_{ATP}$ channel openers selected from a salt of a compound of Formulae I-VIII administered as a single dose to an obese, overweight or obesity-prone subject that result in the inhibition of fasting or glucose stimulated insulin secretion for about 24 hours or for about 18 hours.

Provided are formulations of $K_{ATP}$ channel openers selected from a salt of a compound of Formulae I-VIII administered as a single dose to an obese, overweight or obesity-prone subject that result in the elevation of energy expenditure for about 24 hours or for about 18 hours.

Provided are formulations of $K_{ATP}$ channel openers selected from a salt of a compound of Formulae I-VIII administered as a single dose to an obese, overweight or obesity-prone subject that result in the elevation of beta oxidation of fat for about 24 hours or for about 18 hours.

Provided are formulations of $K_{ATP}$ channel openers selected from a salt of a compound of Formulae I-VIII administered as a single dose to an obese, overweight or obesity-prone hyperphagic subject that result in the inhibition of hyperphagia for about 24 hours or for about 18 hours.

Provided are formulations suitable for continuous administration once or twice daily (per 24 hours) to a subject, resulting in a circulating concentration of $K_{ATP}$ channel openers selected from a salt of a compound of Formulae I-VIII sufficient to induce either beta-cell rest or improved insulin sensitivity or both. Such beta-cell rest and improvements in insulin sensitivity can contribute to effective treatment of type I diabetes, type II diabetes and prediabetes. Such beta-cell rest and improvements in insulin sensitivity can contribute to effective restoration of normal glucose tolerance in type II diabetic and prediabetic subjects.

The various pharmaceutical $K_{ATP}$ channel opener formulations selected from a salt of a compound of Formulae I-VIII have a variety of applications, including, but not limited to: (1) treatment of obesity; (2) prevention of weight gain in subjects who are predisposed to obesity; (3) treatment of hyperinsulinemia or hyperinsulinism; (4) treatment of hypoglycemia; (5) treatment of hyperlipidemia, (6) treatment of type II diabetes, (7) preservation of pancreatic function in type I diabetics; (8) treatment of metabolic syndrome (or syndrome X); (9) prevention of the transition from prediabetes to diabetes, (10) correction of the defects in insulin secretion and insulin sensitivity contributing to prediabetes and type II diabetes, (11) treatment of polycystic ovary syndrome, (12) prevention of ischemic or reperfusion injury, (13) treat weight gain, dyslipidemia, or impairment of glucose tolerance in subjects treated with antipsychotics drugs, (14) prevent weight gain, dyslipidemia, or impairment of glucose tolerance in subjects treated with antipsychotics drugs and (15) treatment of any disease where hyperlipidemia, hyperinsulinemia, hyperinsulinism, hyperlipidemia, hyperphagia or obesity are contributing factors to the severity or progression of the disease, including but not limited to, Prader Willi Syndrome, Froelich's syndrome, Cohen syndrome, Summit Syndrome, Alstrom Syndrome, Borjesen Syndrome, Bardet-Biedl Syndrome, or hyperlipoproteinemia type I, II, III, and IV.

In one embodiment, a $K_{ATP}$ channel opener selected from a salt of a compound of Formulae I-VIII is administered to an overweight or obese subject as an oral dosage once per 24 hours to induce weight loss. In further embodiments, the subject (a) is not a type I diabetic, (b) is not a type II diabetic, (c) is not experiencing chronic, recurrent or drug-induced hypoglycemia, (d) does not have metabolic syndrome, or (e) is not experiencing malignant hypertension.

In one embodiment, a $K_{ATP}$ channel opener selected from a salt of a compound of Formulae I-VIII is administered to an overweight or obese subject as an oral dosage twice per 24 hours to induce weight loss. This treatment can be the sole treatment to induce weight loss. In further embodiments, the overweight or obese subject (a) does not have an insulin secreting tumor, (b) is not suffering from Poly Cystic Ovary Syndrome, (c) is not a type I diabetic, (d) is not a type II diabetic, (e) does not have metabolic syndrome, (f) is not experiencing chronic recurrent or drug-induced hypoglycemia, (g) has not been treated for schizophrenia with haloperidol, or (h) is not experiencing malignant hypertension. In further embodiments, the overweight or obese adolescent (a) has not been diagnosed as being type I or type II diabetic, (b) is not experiencing chronic, recurrent or drug-induced hypoglycemia, or (c) has not been diagnosed as having metabolic syndrome.

In another embodiment, a $K_{ATP}$ channel opener selected from a salt of a compound of Formulae I-VIII is administered to an overweight or obese subject as an oral dosage form three times per 24 hours to induce weight loss. This treatment can be the sole treatment to induce weight loss. In further embodiments, the overweight or obese subject (a) does not have an insulin-secreting tumor, (b) is not suffering from Poly Cystic Ovary Syndrome, (c) is not a type I diabetic, (d) is not a type II diabetic, (e) does not have metabolic syndrome, or (f) is not experiencing chronic, recurrent or drug-induced hypoglycemia.

In another embodiment, a $K_{ATP}$ channel opener selected from a salt of a compound of Formulae I-VIII is administered to an overweight or obese adolescent as an oral dosage form three times per 24 hours to induce weight loss. This treatment can be the sole treatment to induce weight loss. In further embodiments, the overweight or obese adolescent is (a) is not a type I or type II diabetic, (b) is not experiencing chronic, recurrent or drug-induced hypoglycemia or (c) does not have metabolic syndrome.

In another embodiment, a $K_{ATP}$ channel opener selected from a salt of a compound of Formulae I-VIII is administered as an oral dosage form three times per 24 hours to induce weight loss to an overweight or obese adult who (a) is not simultaneously receiving glucagon injections, triiodothyroxin or furosemide, (b) is not being treated for schizophrenia with haloperidol, or (c) is not experiencing malignant hypertension.

In another embodiment, a $K_{ATP}$ channel opener selected from a salt of a compound of Formulae I-VIII is administered to an overweight or obese subject as an oral dosage form four times per 24 hours to induce weight loss.

In another embodiment, a $K_{ATP}$ channel opener selected from a salt of a compound of Formulae I-VIII is administered to an overweight or obese subject as an oral dosage form administered from one, two, three or four times per 24 hours to induce weight loss at a daily dose of 50 to 700 mg. In a further embodiment, the overweight or obese subject (a) is not type I diabetic, (b) is not type II diabetic, (c) is not suffering chronic, recurrent or drug-induced hypoglycemia, or (d) does not have metabolic syndrome.

In another embodiment, a $K_{ATP}$ channel opener selected from a salt of a compound of Formulae I-VIII is administered to an overweight or obese subject as an oral dosage form administered from one, two, three or four times per 24 hours to induce weight loss at a daily dose of 130 to 400 mg. In a further embodiment, the overweight or obese subject (a) is not type I diabetic, (b) is not type II diabetic, (c) is not suffering chronic, recurrent or drug-induced hypoglycemia, or (d) does not have metabolic syndrome.

In other embodiments, a $K_{ATP}$ channel opener selected from a salt of a compound of Formulae I-VIII is administered to an overweight or obesity prone subject as an oral dosage form one, two, three or four times per 24 hours to maintain a weight loss, as it is preferable to maintain weight in an obese subject once some weight loss has occurred when the alternative is to regain weight. In a further embodiment, the administered daily dose of the $K_{ATP}$ channel opener is 50 to 275 mg.

In other embodiments, a $K_{ATP}$ channel opener selected from a salt of a compound of Formulae I-VIII is administered as an oral dosage form to an overweight, obese, or obesity prone subject to (a) elevate energy expenditure, (b) elevate beta oxidation of fat, or (c) reduce circulating triglyceride concentrations.

In other embodiments, an oral dosage of a $K_{ATP}$ channel opener selected from a salt of a compound of Formulae I-VIII is administered to an subject in need thereof to induce the loss of 25%, 50%, or 75% of initial body fat.

In another embodiment, an oral dosage of a $K_{ATP}$ channel opener selected from a salt of a compound of Formulae I-VIII is administered to an subject in need thereof to induce (a) the preferential loss of body fat or (b) the preferential loss of visceral body fat.

In additional embodiments, an oral dosage of a $K_{ATP}$ channel opener selected from a salt of a compound of Formulae I-VIII is administered one, two or three times per 24 hours at daily doses of 50 to 700 mg to an subject to (a) induce the loss of 25%, 50% or 75% of initial body fat, (b) induce the preferential loss of body fat, or (c) induce the preferential loss of visceral fat.

In another embodiment, an oral dosage of a $K_{ATP}$ channel opener selected from a salt of a compound of Formulae I-VIII is administered to an subject to induce the preferential loss of body fat and to induce reduction in circulating triglycerides.

In another embodiment, an oral dosage of a $K_{ATP}$ channel opener selected from a salt of a compound of Formulae I-VIII is co-administered with sibutramine, orlistat, rimonabant, an appetite suppressant, an anti-depressant, an anti-epileptic, a diuretic, a drug that induces weight loss by a mechanism that is distinct from a $K_{ATP}$ channel opener, or a drug that lowers blood pressure, to induce weight loss and/or treat obesity associated co-morbidities in an overweight, obese, or obesity prone subject. In further embodiments, the overweight, obese, or obesity prone subject (a) is a type I diabetic, (b) is not a type II diabetic, (c) is not suffering from chronic, recurrent or drug-induced hypoglycemia, or (d) does not have metabolic syndrome.

In another embodiment an oral dosage of a $K_{ATP}$ channel opener selected from a salt of a compound of Formulae I-VIII is co-administered with an anti-depressant, a drug that lowers blood pressure, a drug that lowers cholesterol, a drug that raises HDL, an anti-inflammatory that is not a Cox-2 inhibitor, a drug that lowers circulating triglycerides, to an overweight, obese, or obesity prone subject to induce weight loss and/or treat obesity associated co-morbidities. In further embodiments, the overweight, obese, or obesity prone subject (a) is not a type I diabetic, (b) is not a type II diabetic, (c) is not suffering from chronic, recurrent or drug-induced hypoglycemia, or (d) does not have metabolic syndrome.

In another embodiment, an oral dosage of a $K_{ATP}$ channel opener selected from a salt of a compound of Formulae I-VIII is co-administered with a drug that lowers blood pressure, a drug that lowers cholesterol, a drug that raises HDL, an anti-inflammatory that is not a Cox-2 inhibitor, a drug that lowers circulating triglycerides, to maintain weight and/or treat obesity associated co-morbidities in an overweight, obese, or obesity prone subject, as it is preferable to maintain weight in an obese subject once some weight loss has occurred when the alternative is to regain weight. In further embodiments, the overweight, obese, or obesity prone subject (a) is not a type I diabetic, (b) is not a type II diabetic, (c) is not suffering from chronic, recurrent or drug-induced hypoglycemia, or (d) does not have metabolic syndrome.

In additional embodiments, an oral dosage form of a $K_{ATP}$ channel opener selected from a salt of a compound of Formulae I-VIII is used to administer a therapeutically effective dose of a $K_{ATP}$ channel opener to an obese, overweight or obesity prone subject in need thereof to treat obesity, to (a) provide beta cell rest, (b) treat type I or type II diabetes, or (c) prevent the occurrence of diabetes.

In additional embodiments, an oral dosage form of a $K_{ATP}$ channel opener selected from a salt of a compound of Formulae I-VIII is co-administered with Phentermine or a derivative thereof to an obese adult or adolescent to induce weight loss and/or treat obesity and obesity-associated co-morbidities. In further embodiments, a solid oral dosage form or tablet formulation of a $K_{ATP}$ channel opener is co-administered with Phentermine or a derivative thereof to an obese adult or adolescent to treat metabolic syndrome in a patient in need thereof.

In further embodiments, a pharmaceutically acceptable formulation of a $K_{ATP}$ channel opener selected from a salt of a compound of Formulae I-VIII at doses of 50 to 700 mg/day is co-administered with Phentermine or a derivative thereof at daily doses of 15 to 37.5 mg to an overweight or obese subject to induce weight loss, to treat metabolic syndrome, or to induce weight loss and treat obesity-associated co-morbidities.

In another embodiment, a quick dissolving formulation of a $K_{ATP}$ channel opener selected from a salt of a compound of Formulae I-VIII is used to provide a therapeutically effective dose to a patient in need thereof.

In further embodiments, a $K_{ATP}$ channel opener selected from a salt of a compound of Formulae I-VIII is administered once per 24 hours at doses of 50 mg to 700 mg to an overweight or obese subject.

In further embodiments, a $K_{ATP}$ channel opener selected from a salt of a compound of Formulae I-VIII is formulated as a tablet or capsule for oral administration. The tablet or capsule may be co-formulated with metformin. In another embodiment, a $K_{ATP}$ channel opener selected from a salt of a compound of Formulae I-VIII is formulated as an oral suspension or solution, and the oral suspension or solution may be further encapsulated in another embodiment.

In another embodiment, a pharmaceutical salt of a $K_{ATP}$ channel opener selected from a salt of a compound of Formulae I-VIII is formulated as a tablet or capsule for oral administration, or as an oral suspension or as an oral solution, or as an oral suspension or solution that is encapsulated.

In another embodiment a $K_{ATP}$ channel opener selected from a salt of a compound of Formulae I-VIII is co-formulated with hydro-chlorothiazide, chlorothiazide, cyclothiazide, benzthiazide, metyclothiazide, bendro-flumethiazide, hydroflumethiazide, trichlormethiazide, or polythiazide in a pharmaceutical formulation suitable for oral administration.

Upon administration of formulations which include a salt of a compound of Formulae I-VIII provided herein to humans or animals, some or all of the following effects are observed: (1) the production of lipoprotein lipase by adipocytes is reduced; (2) enhanced lipolysis by adipocytes; (3) expression of fatty acid synthase by adipocytes is reduced; (4) glyceraldehydes phosphate dehydrogenase activity of adipocytes is reduced; (5) little or no new triglycerides are synthesized and stored by adipocytes; (6) enhanced expression of β3 Adrenergic Receptor (β3AR) an improvement in the adrenergic function in adipocytes; (7) reduced glucose stimulated secretion of insulin by pancreatic B-cells; (8) decreased insulinemia; (9) enhanced blood glucose levels; (10) increased expression of Uncoupling Protein 1 in adipocytes; (11) enhanced thermogenesis in white and brown adipose tissue; (12) reduction of plasma triglyceride concentration; (13) decrease in circulating leptin concentrations; (14) up-regulation of insulin receptors; (15) enhanced glucose uptake; (16) reduced adipocyte hyperplasia; (17) reduced adipocyte hypertrophy; (18) reduced rates of conversion of preadipocytes to adipocytes; (19) reduced rates of hyperphagia; (20) increased protection of CNS, cardiac and other tissues from ischemic or reperfusion injury; (21) improved insulin sensitivity; (22) elevated CSF insulin concentrations; (23) elevated circulating adiponectin concentrations; (25) reduced circulating triglyceride concentrations; (26) enhancement of beta-cell rest.

Threshold concentrations of the current invention include those circulating concentrations of $K_{ATP}$ channel openers resulting from the administration of the selected from salts of compounds of Formulae I-VIII as an i.v. formulation, an immediate release oral formulation, a controlled release formulation, a transdermal formulation, or an intranasal formulation to an overweight or obese subject which results in (1) measurable suppression of fasting insulin levels, (2) suppression of fasting insulin levels by at least 20% from the baseline measurement in the same subject prior to treatment with a $K_{ATP}$ channel opener selected from a salt of a compound of Formulae I-VIII, (3) suppression of fasting insulin levels by at least 30% from the baseline measurement in the same subject prior to treatment with a $K_{ATP}$ channel opener selected from a salt of a compound of Formulae I-VIII, (4) suppression of fasting insulin levels by at least 40% from the baseline measurement in the same subject prior to treatment with a $K_{ATP}$ channel opener selected from a salt of a compound of Formulae I-VIII, (5) suppression of fasting insulin levels by at least 50% from the baseline measurement in the same subject prior to treatment with a $K_{ATP}$ channel opener selected from a salt of a compound of Formulae I-VIII, (6) suppression of fasting insulin levels by at least 60% from the baseline measurement in the same subject prior to treatment with a $K_{ATP}$ channel opener selected from a salt of a compound of Formulae I-VIII, (7) suppression of fasting insulin levels by at least 70% from the baseline measurement in the same subject prior to treatment with a $K_{ATP}$ channel opener selected from a salt of a compound of Formulae I-VIII, (8) suppression of fasting insulin levels by at least 80% from the baseline measurement in the same subject prior to treatment with a $K_{ATP}$ channel opener selected from a salt of a compound of Formulae I-VIII, (9) loss of weight, (10) elevation of resting energy expenditure, or (11) elevation of the oxidation of fat or fatty acids. Threshold effects of the current invention include those circulating concentrations of $K_{ATP}$ channel openers selected from salts of compounds of Formulae I-VIII resulting from the administration of an i.v. formulation of the drug, or an immediate release oral formulation of the drug, or a controlled release formulation of the drug, or a sustained release formulation, or a transdermal formulation, or an intranasal formulation of the drug to an obesity prone subject which result in (1) the loss of weight, and (2) the maintenance of weight. Threshold effects of the current invention include those circulating concentrations of $K_{ATP}$ channel openers selected from salts of compounds of Formulae I-VIII resulting from the administration of an i.v. formulation of the drug, or an immediate release oral formulation of the drug, or a controlled release formulation of the drug, or a sustained release formulation, or a transdermal formulation, or an intranasal formulation of the drug to a prediabetic subject which result in prevention of the transition to diabetes. Threshold effects of the current invention include those circulating concentrations of $K_{ATP}$ channel openers resulting from the administration of selected from salts of compounds of Formulae I-VIII as an i.v. formulation, or an immediate release oral formulation, or a controlled release formulation, or a sustained release formulation, or a transdermal formulation, or an intranasal formulation to a subject with type 1 diabetes which result in beta cell rest.

The mode of action by which weight is maintained or lost resulting from the prolonged administration of $K_{ATP}$ channel openers selected from salts of compounds of Formulae I-VIII to overweight, obese or obesity prone subjects as provided herein includes, but is not limited to, one or more of (1) enhanced energy expenditure, (2) enhanced oxidation of fat and fatty acids, (3) enhancement of lipolysis in adipose tissue, (4) enhanced glucose uptake by tissues and enhanced insulin sensitivity, and (5) improved beta adrenergic response. The mode of action by which weight is maintained or lost resulting from the prolonged administration of $K_{ATP}$ channel openers selected from salts of compounds of Formulae I-VIII to obese or obesity prone subjects as provided herein may also include the suppression of appetite.

Prolonged administration of pharmaceutical formulations of $K_{ATP}$ channel openers selected from salts of compounds of Formulae I-VIII to overweight or obese humans or animals results in substantial and sustained weight loss including some or all of the following effects: (1) preferential loss of body fat; (2) loss of greater than 25% of initial body fat mass; (3) loss of greater than 50% of initial body fat mass; (4) loss of greater than 75% of initial body fat mass; (5) significant increase in resting energy expenditure; (6) increase in the oxidation of fat and fatty acids; (7) reduction in blood pressure; (8) production of lipoprotein lipase by adipocytes is reduced; (9) enhanced lipolysis by adipocytes; (10) expression of fatty acid synthase by adipocytes is reduced; (11) glyceraldehydes phosphate dehydrogenase activity of adipocytes is reduced; (12) little or no new triglycerides are synthesized and stored by adipocytes; (13) enhanced expression of $\beta_3$ Adrenergic Receptor ($\beta_3 AR$) and an improvement in the adrenergic function in adipocytes; (14) reduced glucose stimulated secretion of insulin by pancreatic B-cells; (15) decreased insulinemia; (16) enhanced blood glucose levels; (17) increased expression of Uncoupling Protein 1 in adipocytes; (18) enhanced thermogenesis in white and brown adipose tissue; (19) reduction of plasma triglyceride concentration; (20) decrease in circulating leptin concentrations; (21) up-regulation of insulin receptors; (22) enhanced glucose uptake; (23) reduced adipocyte hyperplasia; (24) reduced adipocyte hypertrophy; (25) reduced rates of conversion of preadipocytes to adipocytes; (26) reduced rates of hyperphagia; (27) the sequential loss first of the metabolically most active adipose tissue (visceral), followed by the loss of less metabolically active adipose tissue; (28) elevation of circulating adiponectin concentrations; (29) elevation of cerebrospinal fluid insulin levels; (30) enhanced islet insulin mRNA and insulin content; or (31) enhanced metabolic efficiency of insulin.

Prolonged administration of formulations of $K_{ATP}$ channel openers selected from salts of compounds of Formulae I-VIII to obesity prone humans or animals, including subjects who have undergone various types of bariatric surgery, results in sustained maintenance of weight including some or all of the following effects: (1) increased resting energy expenditure; (2) increase in the oxidation of fat and fatty acids; (3) reduction in blood pressure; (4) production of lipoprotein lipase by adipocytes is reduced; (5) enhanced lipolysis by adipocytes; (6) expression of fatty acid synthase by adipocytes is reduced; (7) glyceraldehyde phosphate dehydrogenase activity of adipocytes is reduced; (8) little or no new triglycerides are synthesized and stored by adipocytes; (9) enhanced expression of $\beta_3$ Adrenergic Receptor ($\beta_3 AR$) and improvement in the adrenergic function in adipocytes; (10) reduced glucose stimulated secretion of insulin by pancreatic B-cells; (11) decreased insulinemia; (12) enhanced blood glucose levels; (13) increased expression of Uncoupling Protein 1 in adipocytes; (14) enhanced thermogenesis in white and brown adipose tissue; (15) reduction of plasma triglyceride concentration; (16) decreased circulating leptin concentration; (17) up-regulation of insulin receptors; (18) enhanced glucose uptake; (19) reduced adipocyte hyperplasia; (20) reduced adipocyte hypertrophy; (21) reduced rates of conversion of preadipocytes to adipocytes; (22) reduced rates of hyperphagia; (23) elevated circulating adiponectin concentration; (24) elevated cerebrospinal fluid insulin levels; (25) enhanced islet insulin mRNA and insulin content; or (26) enhanced metabolic efficiency of insulin.

Immediate or prolonged administration of formulations of $K_{ATP}$ channel openers selected from salts of compounds of Formulae I-VIII to prediabetic or type I diabetic humans or animals results in the prevention of beta cell failure, improved glycemic control, and prevention of the transition from prediabetes to diabetes including some or all of the following effects: (1) increase in resting energy expenditure; (2) increase in the oxidation of fat and fatty acids; (3) reduction in blood pressure; (4) production of lipoprotein lipase by adipocytes is reduced; (5) enhanced lipolysis by adipocytes; (6) expression of fatty acid synthase by adipocytes is reduced; (7) glyceraldehyde phosphate dehydrogenase activity of adipocytes is reduced; (8) little or no new triglycerides are synthesized and stored by adipocytes; (9) enhanced expression of $\beta_3$ Adrenergic Receptor ($\beta_3$AR) and an improvement in the adrenergic function in adipocytes; (10) reduced glucose stimulated secretion of insulin by pancreatic B-cells; (11) decreased insulinemia; (12) enhanced blood glucose levels; (13) increased expression of Uncoupling Protein 1 in adipocytes; (14) enhanced thermogenesis in white and brown adipose tissue; (15) reduction of plasma triglyceride concentration; (16) decreased circulating leptin concentrations; (17) up-regulation of insulin receptors; (18) enhanced glucose uptake; (19) reduced adipocyte hyperplasia; (20) reduced adipocyte hypertrophy; (21) reduced rates of conversion of preadipocytes to adipocytes; (22) reduced rates of hyperphagia; (23) elevated circulating adiponectin concentrations; (24) elevated cerebrospinal fluid insulin levels; (25) enhanced islet insulin mRNA and insulin content; or (26) enhanced metabolic efficiency of insulin.

Immediate or prolonged administration of formulations of $K_{ATP}$ channel openers selected from salts of compounds of Formulae I-VIII to humans or animals that are at risk for myocardial infarct, or stroke, or undergoing surgical procedure that restores blood flow to heart or brain results in improved therapeutic outcomes post-surgically, or following the occurrence of myocardial infarct or stroke by improving the survival of tissue after blood flow is restored, reduced stunning of tissue, and altering the nature of the inflammatory responses.

Pharmaceutical formulations as provided herein are designed to be used in the treatment of obesity, hyperlipidemia, hypertension, weight maintenance, type I diabetes, prediabetes, type II diabetes, metabolic syndrome or any condition where weight loss, reduction in circulating triglycerides or beta cell rest contributes to therapeutic outcomes provide for a range of critical changes in pharmacodynamic and pharmacokinetic responses to administered doses of $K_{ATP}$ channel openers selected from salts of compounds of Formulae I-VIII which changes include one or more of the following: (1) extending the pharmacodynamic effect of an administered dose to 24 hours or longer as measured by the suppression of insulin secretion; (2) providing for substantial uptake of the active pharmaceutical ingredient in the small intestine; (3) providing for substantial uptake of the active pharmaceutical ingredient in the large intestine; (4) result in lowered Cmax versus current oral suspension or capsule products for the same administered dose of active pharmaceutical ingredient; (5) provide for circulating concentrations of unbound active pharmaceutical ingredient above threshold concentrations for 24 or more hours from a single administered dose; and (6) provide for more consistent drug absorption by treated subjects as compared to existing capsule formulations.

Pharmaceutical co-formulations of the current invention designed to treat a range of conditions in humans and animals include the combination of $K_{ATP}$ channel openers selected from salts of compounds of Formulae I-VIII with: (1) a diuretic, (2) a drug that lowers blood pressure, (3) a drug that suppresses appetite, (4) a cannabinoid receptor antagonist, (5) a drug that suppresses that action of gastric lipases, (6) any drug that is used to induce weight loss, (7) a drug that lowers cholesterol, (8) a drug that lowers LDL bound cholesterol, (9) a drug that improves insulin sensitivity, (10) a drug that improves glucose utilization or uptake, (11) a drug that reduces incidence of atherosclerotic plaque, (12) a drug that reduces inflammation, (13) a drug that is antidepressant, (14) a drug that is an anti-epileptic, or (15) a drug that is an anti-psychotic.

Treatment of humans or animals using pharmaceutical formulations (which include $K_{ATP}$ channel openers selected from salts of compounds of Formulae I-VIII) result in reduced incidence of adverse side effects including but not limited to edema, fluid retention, reduced rates of excretion of sodium, chloride, and uric acid, hyperglycemia, ketoacidosis, nausea, vomiting, dyspepsia, ileus and headaches. These reductions in frequency of adverse side effects are achieved by: (1) initiating dosing of subjects at subtherapeutic doses and in a step wise manner increasing the dose daily until the therapeutic dose is achieved where the number of days over which the step up in dose is effected is 2 to 10, (2) use of the lowest effective dose to achieve the desired therapeutic effect, (3) use of a pharmaceutical formulation that delays release of active until gastric transit is complete, (4) use of a pharmaceutical formulation that delays release of active until gastric transit is complete, (5) use of a pharmaceutical formulation that results in lower circulating peak drug levels as compared to an immediate release oral suspension or capsule formulation for the same administered dose, and (6) optimizing the timing of administration of dose within the day and relative to meals.

Treatment of patients suffering from Prader Willi Syndrome, Froelich's Syndrome, Cohen Syndrome, Summit Syndrome, Alstrom Syndrome, Borjesen Syndrome, Bardet-Biedl Syndrome, and hyperlipoproteinemia type I, II, III, and IV with the current invention using pharmaceutical formulations of $K_{ATP}$ channel openers selected from salts of compounds of Formulae I-VIII result in some or all of the following therapeutic outcomes: (1) weight loss, (2) reduced rates of weight gain, (3) inhibition of hyperphagia, (4) reduced incidence of impaired glucose tolerance, prediabetes or diabetes, (5) reduced incidence of congestive heart failure, (6) reduced hypertension, and (7) reduced rates of all cause mortality.

Treatment of prediabetic subjects using invention pharmaceutical formulations of $K_{ATP}$ channel openers selected from salts of compounds of Formulae I-VIII result in some or all of the following therapeutic outcomes: (1) weight loss, (2) restoration of normal glucose tolerance, (3) delayed rates of progression to diabetes, (4) reduced hypertension, and (5) reduced rates of all cause mortality.

Treatment of diabetic subjects using invention pharmaceutical formulations of $K_{ATP}$ channel openers selected from salts of compounds of Formulae I-VIII result in some or all of the following therapeutic outcomes: (1) weight loss, (2) restoration of normal glucose tolerance, (3) delayed rates of progression of diabetes, (4) improvements in glucose tolerance, (5) reduced hypertension, and (6) reduced rates of all cause mortality.

Co-administration of drugs with formulations of $K_{ATP}$ channel openers selected from salts of compounds of Formulae I-VIII in the treatment of diseases of overweight, obese or obesity prone human and animal subjects involves the co-administration of a pharmaceutically acceptable formulation of $K_{ATP}$ channel openers with an acceptable formulation of: (1) sibutramine, (2) orlistat, (3) rimonabant, (4) a drug that is an appetite suppressant, (5) any drug used to induce weight loss in an obese or overweight subject, (6) a non-thiazide diuretic, (7) a drug that lowers cholesterol, (8) a drug that raises HDL cholesterol, (9) a drug that lowers LDL cholesterol, (10) a drug that lowers blood pressure, (11) a drug that is an anti-depressant, (12) a drug that improves insulin sensitivity, (13) a drug that improves glucose utilization and uptake (14) a drug that is an anti-epileptic, (15) a drug that is an anti-inflammatory, or (16) a drug that lowers circulating triglycerides.

Co-administration of drugs with formulations of $K_{ATP}$ channel openers selected from salts of compounds of Formulae I-VIII in the treatment or prevention of weight gain, dyslipidemia, impaired glucose tolerance or diabetes in subjects treated with antipsychotics drugs involve the co-administration of a pharmaceutically acceptable formulation of $K_{ATP}$ channel openers with an acceptable formulation of: lithium, carbamazepine, valproic acid and divalproex, and lamotrigine; antidepressants generally classified as monoamine oxidase inhibitors including isocarboxazid, phenelzine sulfate and tranylcypromine sulfate; tricyclic antidepressants including doxepin, clomipramine, amitriptyline, maproiline, desipromine, nortryptyline, desipramine, doxepin, trimipramine, imipramine and protryptyline; tetracyclic antidepressants including mianserin, mirtazapine, maprotiline, oxaprotline, delequamine, levoprotline, triflucarbine, setiptiline, lortalaline, azipramine, aptazapine maleate and pirlindole; and major tranquilizers and atypical antipsychotics including paloproxidol, perphenazine, thioridazine, risperidone, clozapine, olanzapine and chlorpromazine.

In one embodiment, a $K_{ATP}$ channel opener selected from a salt of a compound of Formulae I-VIII is administered to an overweight or obese subject as an oral, transdermal or intranasal formulation to reach and maintain the threshold concentration required to measurably reduce fasting insulin levels for a prolonged period. Preferably the $K_{ATP}$ channel opener formulation reduces fasting insulin levels by at least 20%, more preferably by at least 30%, more preferably by at least by 40%, more preferably by at least 50%, more preferably by at least by 60%, more preferably by at least by 70%, and more preferably by at least 80%. Fasting insulin levels are commonly measured using the glucose tolerance test (OGTT). After an overnight fast, a patient ingests a known amount of glucose. Initial glucose levels are determined by measuring pre-test glucose levels in blood and urine. Blood insulin levels are measured by a blood is draw every hour after the glucose is consumed for up to three hours. In a fasting glucose assay, subjects with plasma glucose values greater than 200 mg/dl at 2 hours post-glucose load indicate an impaired glucose tolerance.

In another embodiment, a $K_{ATP}$ channel opener selected from a salt of a compound of Formulae I-VIII is administered to an overweight or obese subject as an oral, transdermal or intranasal formulation to reach and maintain the threshold concentration required to induce weight loss for a prolonged period.

In another embodiment, a $K_{ATP}$ channel opener selected from a salt of a compound of Formulae I-VIII is administered to an overweight or obese subject as an oral, transdermal or intranasal formulation to reach and maintain the threshold concentration required to elevate resting energy expenditure for a prolonged period.

In another embodiment, a $K_{ATP}$ channel opener selected from a salt of a compound of Formulae I-VIII is administered to an overweight or obese subject as an oral, transdermal or intranasal formulation to reach and maintain the threshold concentration required to elevate fat and fatty acid oxidation for a prolonged period.

In another embodiment, a $K_{ATP}$ channel opener selected from a salt of a compound of Formulae I-VIII is administered to an obesity prone subject as an oral, transdermal or intranasal formulation to reach and maintain the threshold concentration required to induce weight loss for a prolonged period.

In another embodiment, a $K_{ATP}$ channel opener selected from a salt of a compound of Formulae I-VIII is administered to an obesity prone subject as an oral, transdermal or intranasal formulation to reach and maintain the threshold concentration required to maintain weight for a prolonged period.

In another embodiment, a $K_{ATP}$ channel opener selected from a salt of a compound of Formulae I-VIII is administered to an overweight or obese subject as an oral, transdermal or intranasal formulation to reach and maintain a drug concentration above the threshold concentration required to induce weight loss for a prolonged period.

In another embodiment, a $K_{ATP}$ channel opener selected from a salt of a compound of Formulae I-VIII is administered to an overweight or obese subject as an oral, transdermal or intranasal formulation for a prolonged period of time to reduce body fat by more than 25%, more preferably by at least 50%, and more preferably by at least 75%.

In another embodiment, a $K_{ATP}$ channel opener selected from a salt of a compound of Formulae I-VIII is administered to an overweight or obese subject as an oral, transdermal or intranasal formulation for a prolonged period of time to preferentially reduce visceral fat deposits.

In another embodiment, a $K_{ATP}$ channel opener selected from a salt of a compound of Formulae I-VIII is administered to an overweight or obese subject as an oral, transdermal or intranasal formulation for a prolonged period of time to reduce visceral fat depots and other fat deposits.

In another embodiment, a $K_{ATP}$ channel opener selected from a salt of a compound of Formulae I-VIII is administered to a normoinsulinemic overweight or obese subject as an oral, transdermal or intranasal formulation to reach and maintain a drug concentration above the threshold concentration required to induce weight loss for a prolonged period.

In another embodiment, a $K_{ATP}$ channel opener selected from a salt of a compound of Formulae I-VIII is administered to a prediabetic subject as an oral, transdermal or intranasal formulation to reach and maintain a drug concentration above the threshold concentration required to prevent the transition to diabetes for a prolonged period.

In another embodiment, a $K_{ATP}$ channel opener selected from a salt of a compound of Formulae I-VIII is administered to a type 1 diabetic subject as an oral, transdermal or intranasal formulation to reach and maintain a drug concentration above the threshold concentration required to induce beta cell rest for a prolonged period.

In another embodiment, a single dose of a pharmaceutically acceptable formulation of a $K_{ATP}$ channel opener selected from a salt of a compound of Formulae I-VIII is administered to an subject in need thereof that results in circulating concentration of active drug sufficient to diminish the secretion of insulin for 24 or more hours.

In another embodiment, a pharmaceutically acceptable formulation of a $K_{ATP}$ channel opener selected from a salt of a compound of Formulae I-VIII is administered over a prolonged basis to an subject in need thereof no more than once per 24 hours that results in circulating concentration of active drug sufficient to diminish the secretion of insulin on a continuous basis.

In another embodiment, a single dose of a pharmaceutically acceptable formulation of a $K_{ATP}$ channel opener selected from a salt of a compound of Formulae I-VIII is administered to an subject in need thereof that results in circulating concentration of active drug sufficient to elevate non-esterified fatty acids in circulation for 24 or more hours.

In another embodiment, a pharmaceutically acceptable formulation of a $K_{ATP}$ channel opener selected from a salt of a compound of Formulae I-VIII is administered over a prolonged basis to an subject in need thereof no more than once per 24 hours that results in circulating concentration of active drug sufficient to elevate non-esterified fatty acids in circulation on a continuous basis.

In another embodiment, a single dose of a pharmaceutically acceptable formulation of a $K_{ATP}$ channel opener selected from a salt of a compound of Formulae I-VIII is administered to an subject in need thereof that results in circulating concentration of active drug sufficient to treat hypoglycemia in circulation for 24 or more hours.

In another embodiment, a pharmaceutically acceptable formulation of a $K_{ATP}$ channel opener selected from a salt of a compound of Formulae I-VIII is administered over a prolonged basis to an subject in need thereof no more than once per 24 hours that results in circulating concentration of active drug sufficient to treat hypoglycemia on a continuous basis.

In another embodiment, a pharmaceutically acceptable formulation of a $K_{ATP}$ channel opener selected from a salt of a compound of Formulae I-VIII is administered over a prolonged basis to an subject in need thereof no more than once per 24 hours that results in circulating concentration of active drug sufficient to induce weight loss on a continuous basis.

In another embodiment, a pharmaceutically acceptable formulation of a $K_{ATP}$ channel opener selected from a salt of a compound of Formulae I-VIII is administered over a prolonged basis to an subject in need thereof no more than once per 24 hours that results in circulating concentration of active drug sufficient to maintain weight on a continuous basis, as it is preferable to maintain weight in an obese subject once some weight loss has occurred when the alternative is to regain weight.

In another embodiment, a pharmaceutically acceptable formulation of a $K_{ATP}$ channel opener selected from a salt of a compound of Formulae I-VIII is administered over a prolonged basis to an subject in need thereof no more than once per 24 hours that results in circulating concentration of active drug sufficient to reduce circulating triglyceride levels on a continuous basis.

In another embodiment, a single dose of a pharmaceutically acceptable formulation of a $K_{ATP}$ channel opener selected from a salt of a compound of Formulae I-VIII is administered to an subject in need thereof that results in circulating concentration of active drug sufficient to reduce or prevent ischemic or reperfusion injury in circulation for 24 or more hours.

In another embodiment, a pharmaceutically acceptable formulation of a $K_{ATP}$ channel opener selected from a salt of a compound of Formulae I-VIII is administered over a prolonged basis to an subject in need thereof no more than once per 24 hours that results in circulating concentration of active drug sufficient reduce or prevent ischemic or reperfusion injury on a continuous basis.

In another embodiment, the frequency of adverse effects caused by treatment with a $K_{ATP}$ channel opener selected from a salt of a compound of Formulae I-VIII is reduced using a pharmaceutically acceptable formulation of diazoxide or its derivatives that is administered to an subject in need thereof on a daily basis in which the first dose is known to be subtherapeutic and daily dose is subsequently increased stepwise until the therapeutic dose is reached.

In another embodiment, the frequency of adverse effects caused by treatment with a $K_{ATP}$ channel opener selected from a salt of a compound of Formulae I-VIII is reduced using a pharmaceutically acceptable formulation that is administered to an subject in need thereof on a daily basis in which the active ingredient is not released from the formulation until gastric transit is complete.

In another embodiment, the frequency of adverse effects caused by treatment with a $K_{ATP}$ channel opener selected from a salt of a compound of Formulae I-VIII is reduced using a pharmaceutically acceptable formulation that is administered to an subject in need thereof on a daily basis in which the maximum circulating concentration of active ingredient is lower than what would be realized by the administration of the same dose using an oral suspension or capsule formulation of Proglycem®.

In another embodiment, the frequency of adverse effects caused by treatment with a $K_{ATP}$ channel opener selected from a salt of a compound of Formulae I-VIII is reduced using a pharmaceutically acceptable formulation that is administered to an subject in need thereof on a daily basis in which the first dose is known to be subtherapeutic and daily dose is subsequently increased stepwise until the therapeutic dose is reached, the active ingredient is not release from the formulation until gastric transit is complete and in which the maximum circulating concentration of active ingredient is lower than what would be realized by the administration of the same dose using an oral suspension or capsule formulation of Proglycem®.

In another embodiment, the frequency of adverse effects caused by treatment with a $K_{ATP}$ channel opener selected from a salt of a compound of Formulae I-VIII is reduced using a pharmaceutically acceptable formulation that is administered to an overweight or obese subject in need thereof on a daily basis in which the first dose is known to be subtherapeutic and daily dose is subsequently increased stepwise until the therapeutic dose is reached, the active ingredient is not release from the formulation until gastric transit is complete, in which the maximum circulating concentration of active ingredient is lower than what would be realized by the administration of the same dose using an oral suspension or capsule formulation of Proglycem®, and in which the maximum dose is less than 5 mg/kg/day.

In another embodiment, the frequency of adverse effects caused by treatment with a $K_{ATP}$ channel opener selected from a salt of a compound of Formulae I-VIII is reduced using a pharmaceutically acceptable formulation that is administered to an overweight or obese subject in need thereof on a daily basis in which the first dose is known to be subtherapeutic and daily dose is subsequently increased stepwise until the therapeutic dose is reached, the active ingredient is not release from the formulation until gastric transit is complete, in which the maximum circulating concentration of active ingredient is lower than what would be realized by the administration of the same dose using an oral suspension or capsule formulation, and in which the maximum dose is less than 2.5 mg/kg/day.

In another embodiment, the treatment of an overweight or obese subject is optimized for weight loss by administration of a pharmaceutically acceptable formulation of a $K_{ATP}$ channel opener selected from a salt of a compound of Formulae I-VIII once per 24 hours in which the release of the active ingredient from the formulation has been modified to provide continuous release for at least 6 hours.

In another embodiment, the treatment of an overweight or obese subject is optimized for weight loss by administration of a pharmaceutically acceptable formulation of a $K_{ATP}$ channel opener selected from a salt of a compound of Formulae I-VIII once per 24 hours in which the release of the active ingredient from the formulation has been modified to provide continuous release for at least 12 hours.

In another embodiment, the treatment of an overweight or obese subject is optimized for weight loss by administration of a pharmaceutically acceptable formulation of a $K_{ATP}$ channel opener selected from a salt of a compound of Formulae I-VIII once per 24 hours in which the release of the active ingredient from the formulation has been modified to provide a rising drug concentration in circulation for at least 8 hours.

In another embodiment, the treatment of an overweight or obese subject is optimized for weight loss by administration of a pharmaceutically acceptable formulation of a $K_{ATP}$ channel opener selected from a salt of a compound of Formulae I-VIII once per 24 hours in which the release of the active ingredient from the formulation has been modified to provide a rising drug concentration in circulation for at least 12 hours.

In another embodiment, the treatment of an overweight or obese subject is optimized for weight loss by administration of a pharmaceutically acceptable formulation of a $K_{ATP}$ channel opener selected from a salt of a compound of Formulae I-VIII once per 24 hours in which the release of the active ingredient from the formulation has been modified to match the pattern of basal insulin secretion.

In another embodiment, the frequency of adverse effects caused by treatment with a $K_{ATP}$ channel opener selected from a salt of a compound of Formulae I-VIII is reduced using a pharmaceutically acceptable formulation that is administered to an obesity prone subject in need thereof on a daily basis in which the first dose is known to be subtherapeutic and daily dose is subsequently increased stepwise until the therapeutic dose is reached, the active ingredient is not release from the formulation until gastric transit is complete, in which the maximum circulating concentration of active ingredient is lower than what would be realized by the administration of the same dose using an oral suspension or capsule formulation, and in which the maximum dose is less than 5 mg/kg/day.

In another embodiment, the frequency of adverse effects caused by treatment with a $K_{ATP}$ channel opener selected from a salt of a compound of Formulae I-VIII is reduced using a pharmaceutically acceptable formulation that is administered to an obesity prone subject in need thereof on a daily basis in which the first dose is known to be subtherapeutic and daily dose is subsequently increased stepwise until the therapeutic dose is reached, the active ingredient is not release from the formulation until gastric transit is complete, in which the maximum circulating concentration of active ingredient is lower than what would be realized by the administration of the same dose using an oral suspension or capsule formulation, and in which the maximum dose is less than 2.5 mg/kg/day.

In another embodiment, the treatment of an obesity prone subject is optimized for weight maintenance by administration of a pharmaceutically acceptable formulation of a $K_{ATP}$ channel opener selected from a salt of a compound of Formulae I-VIII once per 24 hours in which the release of the active ingredient from the formulation has been modified to provide continuous release for at least 6 hours.

In another embodiment, the treatment of an obesity prone subject is optimized for weight maintenance by administration of a pharmaceutically acceptable formulation of a $K_{ATP}$ channel opener selected from a salt of a compound of Formulae I-VIII once per 24 hours in which the release of the active ingredient from the formulation has been modified to provide continuous release for at least 12 hours.

In another embodiment, the treatment of an obesity prone subject is optimized for weight maintenance by administration of a pharmaceutically acceptable formulation of a $K_{ATP}$ channel opener selected from a salt of a compound of Formulae I-VIII once per 24 hours in which the release of the active ingredient from the formulation has been modified to provide a rising drug concentration in circulation for at least 8 hours.

In another embodiment, the treatment of an obesity prone subject is optimized for weight maintenance by administration of a pharmaceutically acceptable formulation of a $K_{ATP}$ channel opener selected from a salt of a compound of Formulae I-VIII once per 24 hours in which the release of the active ingredient from the formulation has been modified to provide a rising drug concentration in circulation for at least 12 hours.

In another embodiment, the treatment of an obesity prone subject is optimized for weight maintenance by administration of a pharmaceutically acceptable formulation of a $K_{ATP}$ channel opener selected from a salt of a compound of Formulae I-VIII once per 24 hours in which the release of the active ingredient from the formulation has been modified to match the pattern of basal insulin secretion.

In another embodiment, a pharmaceutically acceptable formulation of a $K_{ATP}$ channel opener selected from a salt of a compound of Formulae I-VIII is co-administered with sibutramine to an overweight or obese subject to induce weight loss.

In another embodiment, a pharmaceutically acceptable formulation of a $K_{ATP}$ channel opener selected from a salt of a compound of Formulae I-VIII is co-administered with orlistat to an overweight or obese subject to induce weight loss.

In another embodiment, a pharmaceutically acceptable formulation of a $K_{ATP}$ channel opener selected from a salt of a compound of Formulae I-VIII is co-administered with rimonabant to an overweight or obese subject to induce weight loss.

In another embodiment, a pharmaceutically acceptable formulation of a $K_{ATP}$ channel opener selected from a salt of a compound of Formulae I-VIII is co-administered with an appetite suppressant to an overweight or obese subject to induce weight loss.

In another embodiment, a pharmaceutically acceptable formulation of a $K_{ATP}$ channel opener selected from a salt of a compound of Formulae I-VIII is co-administered with an anti-depressant to an overweight or obese subject to induce weight loss.

In another embodiment, a pharmaceutically acceptable formulation of a $K_{ATP}$ channel opener selected from a salt of a compound of Formulae I-VIII is co-administered with anti-epileptic to an overweight or obese subject to induce weight loss.

In another embodiment, a pharmaceutically acceptable formulation of a $K_{ATP}$ channel opener is selected from a salt of a compound of Formulae I-VIII is co-administered with a non-thiazide diuretic to an overweight or obese subject to induce weight loss.

In another embodiment, a pharmaceutically acceptable formulation of a $K_{ATP}$ channel opener selected from a salt of a compound of Formulae I-VIII is co-administered with a drug that induces weight loss by a mechanism that is distinct from diazoxide to an overweight or obese subject to induce weight loss.

In another embodiment, a pharmaceutically acceptable formulation of a $K_{ATP}$ channel opener selected from a salt of a compound of Formulae I-VIII is co-administered with a drug that lowers blood pressure to an overweight, obesity prone or obese subject to induce weight loss and treat obesity associated co-morbidities.

In another embodiment, a pharmaceutically acceptable formulation of a $K_{ATP}$ channel opener selected from a salt of a compound of Formulae I-VIII is co-administered with a drug that lowers cholesterol to an overweight, obesity prone or obese subject to induce weight loss and treat obesity associated co-morbidities.

In another embodiment, a pharmaceutically acceptable formulation of a $K_{ATP}$ channel opener selected from a salt of a compound of Formulae I-VIII is co-administered with a drug that raises HDL associated cholesterol to an overweight, obesity prone or obese subject to induce weight loss and treat obesity associated co-morbidities.

In another embodiment, a pharmaceutically acceptable formulation of a $K_{ATP}$ channel opener selected from a salt of a compound of Formulae I-VIII is co-administered with a drug that improves insulin sensitivity to an overweight, obesity prone or obese subject to induce weight loss and treat obesity associated co-morbidities.

In another embodiment, a pharmaceutically acceptable formulation of a $K_{ATP}$ channel opener selected from a salt of a compound of Formulae I-VIII is co-administered with a an anti-inflammatory to an overweight, obesity prone or obese subject to induce weight loss and treat obesity associated co-morbidities.

In another embodiment, a pharmaceutically acceptable formulation of a $K_{ATP}$ channel opener selected from a salt of a compound of Formulae I-VIII is co-administered with a drug that lowers circulating triglycerides to an overweight, obesity prone or obese subject to induce weight loss and treat obesity associated co-morbidities.

In another embodiment, $K_{ATP}$ channel openers selected from salts of compounds of Formulae I-VIII are co-formulated with sibutramine in a pharmaceutically acceptable formulation that is administered to an overweight, obesity prone or obese subject to induce weight loss and treat obesity-associated co-morbidities.

In another embodiment, $K_{ATP}$ channel openers selected from salts of compounds of Formulae I-VIII are co-formulated with orlistat or other active that suppresses the action of gastric lipases in a pharmaceutically acceptable formulation that is administered to an overweight, obesity prone or obese subject to induce weight loss and treat obesity-associated co-morbidities.

In another embodiment, $K_{ATP}$ channel openers selected from salts of compounds of Formulae I-VIII are co-formulated with a non-thiazide diuretic in a pharmaceutically acceptable formulation that is administered to an overweight, obesity prone or obese subject to induce weight loss and treat obesity-associated co-morbidities.

In another embodiment, $K_{ATP}$ channel openers selected from salts of compounds of Formulae I-VIII are co-formulated with an appetite suppressant in a pharmaceutically acceptable formulation that is administered to an overweight, obesity prone or obese subject to induce weight loss and treat obesity-associated co-morbidities.

In another embodiment, $K_{ATP}$ channel openers selected from salts of compounds of Formulae I-VIII are co-formulated with a cannabinoid receptor antagonist in a pharmaceutically acceptable formulation that is administered to an overweight, obesity prone or obese subject to induce weight loss and treat obesity-associated co-morbidities.

In another embodiment, $K_{ATP}$ channel openers selected from salts of compounds of Formulae I-VIII are co-formulated with an anti-cholesteremic active in a pharmaceutically acceptable formulation that is administered to an overweight, obesity prone or obese subject to induce weight loss and treat obesity-associated co-morbidities.

In another embodiment, $K_{ATP}$ channel openers selected from salts of compounds of Formulae I-VIII are co-formulated with an antihypertensive active in a pharmaceutically acceptable formulation that is administered to an overweight, obesity prone or obese subject to induce weight loss and treat obesity-associated co-morbidities.

In another embodiment, $K_{ATP}$ channel openers selected from salts of compounds of Formulae I-VIII are co-formulated with an insulin sensitizing active in a pharmaceutically acceptable formulation that is administered to an overweight, obesity prone or obese subject to induce weight loss and treat obesity-associated co-morbidities.

In another embodiment, $K_{ATP}$ channel openers selected from salts of compounds of Formulae I-VIII are co-formulated with an anti-inflammatory active in a pharmaceutically acceptable formulation that is administered to an overweight, obesity prone or obese subject to induce weight loss and treat obesity-associated co-morbidities.

In another embodiment, $K_{ATP}$ channel openers selected from salts of compounds of Formulae I-VIII are co-formulated with an anti-depressant active in a pharmaceutically acceptable formulation that is administered to an overweight, obesity prone or obese subject to induce weight loss and treat obesity-associated co-morbidities.

In another embodiment, $K_{ATP}$ channel openers selected from salts of compounds of Formulae I-VIII are co-formulated with an anti-epileptic active in a pharmaceutically acceptable formulation that is administered to an overweight, obesity prone or obese subject to induce weight loss and treat obesity-associated co-morbidities.

In another embodiment, $K_{ATP}$ channel openers selected from salts of compounds of Formulae I-VIII are co-formulated with an active that reduces the incidence of atherosclerotic plaque in a pharmaceutically acceptable formulation that is administered to an overweight, obesity prone or obese subject to induce weight loss and treat obesity-associated co-morbidities.

In another embodiment, $K_{ATP}$ channel openers selected from salts of compounds of Formulae I-VIII are co-formulated with an active that lowers circulating concentrations of triglycerides in a pharmaceutically acceptable formulation that is administered to an overweight, obesity prone or obese subject to induce weight loss and treat obesity-associated co-morbidities.

The reduction of circulating triglycerides in an overweight, obese or obesity prone subject is achieved by the administration of an effective amount of an oral dosage form of a $K_{ATP}$ channel opener. selected from a salt of a compound of Formulae I-VIII.

An oral dosage form of $K_{ATP}$ channel opener selected from a salt of a compound of Formulae I-VIII can be used to administer a therapeutically effective dose of $K_{ATP}$ channel opener to an overweight or obesity prone subject in need thereof to maintain weight, as it is preferable to maintain weight in an obese subject once some weight loss has occurred when the alternative is to regain weight.

In another embodiment of the invention, $K_{ATP}$ channel openers selected from salts of compounds of Formulae I-VIII are co-formulated with a drug to treat obesity. Such co-formulations can be formulated for oral administration once per 24 hours, for delayed release of the active until gastric transit is complete, and for sustained release of the active over a period of 2 to 24 hours. Such obesity treatment drugs include, but are not limited to: sibutramine hydrochloride (5-30 mg), orlistat (50-360 mg), phentermine hydrochloride or resin complex (15 to 40 mg), zonisamide (100 to 600 mg), topiramate (64 to 400 mg), naltrexone hydrochloride (50 to 600 mg), or rimonabant (5 to 20 mg).

A further embodiment of the co-formulation contains $K_{ATP}$ channel openers selected from salts of compounds of Formulae I-VIII and a drug to treat obesity. Such co-formulations can be formulated for oral administration twice per 24 hours, for delayed release of the active until gastric transit is complete, and for sustained release of the active over a period of 2 to 12 hours. Such obesity treatment drugs include, but are not limited to: sibutramine hydrochloride (2.5 to 15 mg), orlistat (25 to 180 mg), phentermine hydrochloride or resin complex (7.5 to 20 mg), zonisamide (50 to 300 mg), topiramate (32 to 200 mg), naltrexone hydrochloride (25 to 300 mg), or rimonabant (2.5 to 10 mg).

In another embodiment of the invention $K_{ATP}$ channel openers selected from salts of compounds of Formulas I-VIII are co-formulated with a drug to treat obesity, diabetes, metabolic syndrome or an obesity related comorbidity. Such drugs to treat these conditions include drugs that: agonizes the α1-noradrenergic receptor; agonizes the β2 noradrenergic receptor; stimulates noradrenalin release; blocks noradrenalin uptake; stimulates 5-HT release; blocks 5-HT uptake; is a serotonin (5-hydroxytryptamine) 2C receptor agonist; antagonizes acetyl-CoA carboxylase 2; agonizes the DI-receptor; antagonizes the H3-receptor; is a leptin analogue; agonizes the leptin receptor, sensitizes CNS tissue to the action of leptin; agonizes the MC4 receptor; agonizes NPY-Y1; agonizes NPY-Y2; agonizes NPY-Y4; agonizes NPY-Y5; antagonizes the MCH receptor; blocks CRH-BP; agonizes the CRH receptor; agonizes the urocortin receptor; antagonizes the galanin receptor; antagonizes the orexin receptor; agonizes the CART receptor; agonizes the Amylin receptor; agonizes the Apo($A^{IV}$) receptor; antagonizes the CB-1 receptor; is an αMSH analogue; inhibits PTP-1B; antagonizes PPARγ receptor; is a short acting bromocriptine; agonizes somatostatin; increases adiponectin; increases CCK activity; increases PYY activity; increases GLP-1 activity; decreases ghrelin activity; is a selective B3 stimulator or agonist; agonizes thyroid receptor; inhibits gastrointestinal lipases or other digestive enzymes; blocks absorption of dietary fat; or block de-novo fatty acid synthesis. Additionally, such drugs to treat obesity may include, but are not limited to those that antagonize or agonize the function or expression of 11B hydroxysteroid dehydrogenase type 1; acetyl-CoA carboxylase 1; ADAM 12, member 12 of a disintegrin and metalloprotease family or its shorter secreted form; agouti related protein; angiotensinogen; adipocyte lipid binding protein; adipocyte fatty acid binding protein; adrenergic receptors; acylation-stimulating protein; bombesin receptor subtype-3; C/EBP, CCAAT/enhancer binding protein; cocaine- and amphetamine-regulated transcript; cholecystokinin; cholecystokinin A receptor; CD36, fatty acid translocase; corticotropin-releasing hormone; diacylglycerol acyltransferases; E2F transcription factor; eukaryotic translation initiation factor 4e binding protein 1; estrogen receptor; fatty acid synthase; fibroblast growth factor; forkhead box C2; glucose-dependent insulinotropic peptide; GIP receptor; inhibitory G protein alpha-subunit; glucagon-like peptide-1; GLP-1 receptor; glycerol-3-phosphate acyltransferase; glycerol 3-phosphate dehydrogenase; stimulatory G protein alpha-subunit; high-mobility group phosphoprotein isoform I-C; hormone sensitive lipase; inducible nitric oxide synthase; Janus kinases; lipoprotein lipase; melanocortin-3 receptor; melanocortin-4 receptor; mitochondrial GPAT; metallothionein-I and -II; nescient helix-loop-helix 2; neuropeptide Y; neuropeptide Y-1 receptor; neuropeptide Y-2 receptor; neuropeptide Y-4 receptor; neuropeptide Y-5 receptor; plasminogen activator inhibitor-1; PPARgamma co-activator 1; pro-opiomelanocortin; peroxisome proliferator-activated receptor; protein tyrosine phosphatase 1B; regulatory subunit IIbeta of protein kinase A; retinoid X receptor; steroidogenic factor 1; single-minded 1; sterol regulatory element binding protein; tyrosine hydroxylase; thyroid hormone receptor a2; uncoupling protein; nerve growth factor induced protein; leucine zipper transcription factor; a-melanocyte-stimulating hormone.

In another embodiment of the invention, $K_{ATP}$ channel openers selected from salts of compounds of Formulae I-VIII are co-formulated with a drug to treat diabetes. Such co-formulations can be formulated for oral administration once per 24 hours, for delayed release of the active until gastric transit is complete, and for sustained release of the active over a period of 2 to 24 hours. Such diabetes treatment drugs include, but are not limited to: acarbose (50 to 300 mg), miglitol (25 to 300 mg), metformin hydrochloride (300 to 2000 mg), repaglinide (1-16 mg), nateglinide (200 to 400 mg), or rosiglitizone (5 to 50 mg).

In a further embodiment, the co-formulation can be formulated for oral administration twice per 24 hours, for delayed release of the active until gastric transit is complete, and for sustained release of the active over a period of 2 to 12 hours. Such drugs to treat diabetes include, but are not limited to: acarbose (25 to 150 mg), miglitol (12.5 to 150 mg), metformin hydrochloride (150 to 1000 mg), repaglinide (0.5 to 8 mg), nateglinide (100 to 200 mg), or rosiglitizone (2.5 to 25 mg).

In another embodiment of the invention, $K_{ATP}$ channel openers selected from salts of compounds of Formulae I-VIII are co-formulated with a drug to treat elevated cholesterol. Such co-formulations can be formulated for oral administration once per 24 hours, for delayed release of the active until gastric transit is complete, and for sustained release of the active over a period of 2 to 24 hours. Such drugs to treat elevated cholesterol include, but are not limited to: pravastatin, simvastatin, atorvastatin, fluvastatin, rosuvastatin or lovastatin (10 to 80 mg).

In a further embodiment, the co-formulation can be formulated for oral administration twice per 24 hours, for delayed release of the active until gastric transit is complete, and for sustained release of the active over a period of 2 to 12 hours. Such drugs to treat elevated cholesterol include, but are not limited to: pravastatin, simvastatin, atorvastatin, fluvastatin, rosuvastatin or lovastatin (5 to 40 mg).

In another embodiment of the invention, $K_{ATP}$ channel openers selected from salts of compounds of Formulae I-VIII are co-formulated with a drug to treat depression. Such coformulations can be formulated for oral administration once per 24 hours, for delayed release of the active until gastric transit is complete, and for sustained release of the active over a period of 2 to 24 hours. Such drugs to treat depression include, but are not limited to: citalopram hydrobromide (10 to 80 mg), escitalopram hydrobromide (5 to 40 mg), fluvoxamine maleate (25 to 300 mg), paroxetine hydrochloride (12.5 to 75 mg), fluoxetine hydrochloride (30 to 100 mg), setraline hydrochloride (25 to 200 mg), amitriptyline hydrochloride (10 to 200 mg), desipramine hydrochloride (10 to 300 mg), nortriptyline hydrochloride (10 to 150 mg), duloxetine hydrochloride (20 to 210 mg), venlafaxine hydrochloride (37.5 to 150 mg), phenelzine sulfate (10 to 30 mg), bupropion hydrochloride (200 to 400 mg), or mirtazapine (7.5 to 90 mg).

In a further embodiment, the co-formulation can be formulated for oral administration twice per 24 hours, for delayed release of the active until gastric transit is complete, and for sustained release of the active for 2 to 12 hours. Such drugs to treat depression include, but are not limited to: citalopram hydrobromide (5 to 40 mg), escitalopram hydrobromide (2.5 to 20 mg), fluvoxamine maleate (12.5 to 150 mg), paroxetine hydrochloride (6.25 to 37.5 mg), fluoxetine hydrochloride (15 to 50 mg), setraline hydrochloride (12.5 to 100 mg), amitriptyline hydrochloride (5 to 100 mg), desipramine hydrochloride (5 to 150 mg), nortriptyline hydrochloride (5 to 75 mg), duloxetine hydrochloride (10 to 100 mg), venlafaxine hydrochloride (18 to 75 mg), phenelzine sulfate (5 to 15 mg), bupropion hydrochloride (100 to 200 mg), or mirtazapine (4 to 45 mg).

In another embodiment of the invention, $K_{ATP}$ channel openers selected from salts of compounds of Formulae I-VIII are co-formulated with a drug to treat hypertension. Such co-formulations can be formulated for oral administration once per 24 hours, for delayed release of the active until gastric transit is complete, and for sustained release of the active over a period of 2 to 24 hours. Such drugs to treat hypertension include, but are not limited to: enalapril maleate (2.5 to 40 mg), captopril (2.5 to 150 mg), lisinopril (10 to 40 mg), benzaepril hydrochloride (10 to 80 mg), quinapril hydrochloride (10 to 80 mg), peridopril erbumine (4 to 8 mg), ramipril (1.25 to 20 mg), trandolapril (1 to 8 mg), fosinopril sodium (10 to 80 mg), moexipril hydrochloride (5 to 20 mg), losartan potassium (25 to 200 mg), irbesartan (75 to 600 mg), valsartan (40 to 600 mg), candesartan cilexetil (4 to 64 mg), olmesartan medoxamil (5 to 80 mg), telmisartan (20 to 160 mg), eprosartan mesylate (75 to 600 mg), atenolol (25 to 200 mg), propranolol hydrochloride (10 to 180 mg), metoprolol tartrate, succinate or fumarate (25 to 400 mg), nadolol (20 to 160 mg), betaxolol hydrochloride (10 to 40 mg), acebutolol hydrochloride (200 to 800 mg), pindolol (5 to 20 mg), bisoprolol fumarate (5 to 20 mg), nifedipine (15 to 100 mg), felodipine (2.5 to 20 mg), amlodipine besylate (2.5 to 20 mg), nicardipine (10 to 40 mg), nisoldipine (10 to 80 mg), terazosin hydrochloride (1 to 20 mg), doxasoxin mesylate (4 to 16 mg), prazosin hydrochloride (2.5 to 10 mg), or alfuzosin hydrochloride (10 to 20 mg).

In a further embodiment, the co-formulation can be formulated for oral administration twice per 24 hours, for delayed release of the active until gastric transit is complete, and for sustained release of active over a period of 2 to 12 hours. Such drugs to treat hypertension include, but are not limited to: enalapril maleate (1.25 to 20 mg), captopril (2 to 75 mg), lisinopril (5 to 20 mg), benzaepril hydrochloride (5 to 40 mg), quinapril hydrochloride (5 to 40 mg), peridopril erbumine (2 to 4 mg), ramipril (1 to 10 mg), trandolapril (1 to 4 mg), fosinopril sodium (5 to 40 mg), moexipril hydrochloride (2.5 to 10 mg), losartan potassium (12.5 to 100 mg), irbesartan (37.5 to 300 mg), valsartan (20 to 300 mg), candesartan cilexetil (2 to 32 mg), olmesartan medoxamil (2.5 to 40 mg), telmisartan (10 to 80 mg), eprosartan mesylate (37.5 to 300 mg), atenolol (12.5 to 100 mg), propranolol hydrochloride (5 to 90 mg), metoprolol tartrate, succinate or fumarate (12.5 to 200 mg), nadolol (10 to 80 mg), betaxolol hydrochloride (5 to 20 mg), acebutolol hydrochloride (100 to 400 mg), pindolol (2.5 to 10 mg), bisoprolol fumarate (2.5 to 10 mg), nifedipine (7.5 to 50 mg), felodipine (1 to 10 mg), amlodipine besylate (1 to 10 mg), nicardipine (5 to 20 mg), nisoldipine (5 to 40 mg), terazosin hydrochloride (1 to 10 mg), doxasoxin mesylate (2 to 8 mg), prazosin hydrochloride (1 to 5 mg), or alfuzosin hydrochloride (5 to 10 mg).

In another embodiment of the invention, $K_{ATP}$ channel openers selected from salts of compounds of Formulae I-VIII are co-formulated with a diuretic. Such co-formulations can be formulated for oral administration once per 24 hours, for delayed release of the active until gastric transit is complete, and for sustained release of the active over a period of 2 to 24 hours. Such diuretics can include, but are not limited to: amiloride hydrochloride (1 to 10 mg), spironolactone (10 to 100 mg), triamterene (25 to 200 mg), bumetanide (0.5 to 4 mg), furosemide (10 to 160 mg), ethacrynic acid or ethacrynate sodium (10 to 50 mg), tosemide (5 to 100 mg), chlorthalidone (10 to 200 mg), indapamide (1 to 5 mg), hydrochlorothiazide (10 to 100 mg), chlorothiazide (50 to 500 mg), bendroflumethiazide (5 to 25 mg), hydroflumethiazide (10 to 50 mg), mythyclothiazide (1 to 5 mg), and polythiazide (1 to 10 mg).

In a further embodiment, the co-formulation can be formulated for oral administration twice per 24 hours, for delayed release of the active until gastric transit is complete, and for sustained release of the active over a period of 2 to 12 hours. Such diuretics include, but are not limited to: amiloride hydrochloride (0.5 to 5 mg), spironolactone (5 to 50 mg), triamterene (12 to 100 mg), bumetanide (0.2 to 2 mg), furosemide (5 to 80 mg), ethacrynic acid or ethacrynate sodium (5 to 25 mg), tosemide (2 to 50 mg), chlorthalidone (5 to 100 mg), indapamide (0.5 to 2.5 mg), hydrochlorothiazide (5 to 50 mg), chlorothiazide (25 to 250 mg), bendroflumethiazide (2 to 12.5 mg), hydroflumethiazide (5 to 25 mg), mythyclothiazide (0.5 to 2.5 mg), and polythiazide (0.5 to 5 mg).

In another embodiment of the invention, $K_{ATP}$ channel openers selected from salts of compounds of Formulae I-VIII are co-formulated with a drug to treat inflammation or pain. Such co-formulations can be formulated for oral administration once per 24 hours, for delayed release of the active until gastric transit is complete, and for sustained release of the active over a period of 2 to 24 hours. Such drugs to treat inflammation or pain include, but are not limited to: aspirin (100 to 1000 mg), tramadol hydrochloride (25 to 150 mg), gabapentin (100 to 800 mg), acetominophen (100 to 1000 mg), carbamazepine (100 to 400 mg), ibuprofen (100 to 1600 mg), ketoprofen (12 to 200 mg), fenprofen sodium (100 to 600 mg), flurbiprofen sodium or flurbiprofen (50 to 200 mg), or combinations of these with a steroid or aspirin.

In a further embodiment, the co-formulation can be formulated for oral administration twice per 24 hours, for delayed release of the active until gastric transit is complete, and for sustained release of the active over a period of 2 to 12 hours. Such drugs to treat inflammation or pain include, but are not limited to: aspirin (100 to 650 mg), tramadol hydrochloride (12 to 75 mg), gabapentin (50 to 400 mg), acetominophen (50 to 500 mg), carbamazepine (50 to 200 mg), ibuprofen (50 to 800 mg), ketoprofen (6 to 100 mg), fenprofen sodium (50 to 300 mg), flurbiprofen sodium or flurbiprofen (25 to 100 mg), or combinations of these with a steroid or aspirin.

A method of inducing loss of greater than 25% of initial body fat in an overweight or obese subject can be achieved by the prolonged administration of an oral dosage form of a $K_{ATP}$ channel opener. selected from a salt of a compound of Formulae I-VIII.

A method of inducing loss of greater than 50% of initial body fat in an overweight or obese subject can be achieved by the prolonged administration of an oral dosage form of a $K_{ATP}$ channel opener selected from a salt of a compound of Formulae I-VIII.

A method of inducing loss of greater than 75% of initial body fat in an overweight or obese subject can be achieved by the prolonged administration of an oral dosage form of a $K_{ATP}$ channel opener. selected from a salt of a compound of Formulae I-VIII.

A method of inducing preferential loss of visceral fat in an overweight or obese subject can be achieved by the prolonged administration of an oral dosage form of a $K_{ATP}$ channel opener. selected from a salt of a compound of Formulae I-VIII.

A method of inducing loss of body fat and reductions in circulating triglycerides in an overweight or obese subject can be achieved by the prolonged administration of an oral dosage form of a $K_{ATP}$ channel opener. selected from a salt of a compound of Formulae I-VIII.

In some embodiments, the invention provides a polymorph of a salt, which salt includes diazoxide and a cation selected from the group consisting of an alkali metal and a compound comprising a tertiary amine or quaternary ammonium group. In some embodiments, the cation is choline.

In some embodiments, the polymorph of diazoxide choline salt is of Form A having characteristic peaks in the XRPD pattern at values of two-theta (Cu Kα, 40 kV, 40 mA) at approximately 9.8, 10.5, 14.9, 17.8, 17.9, 18.5, 19.5, 22.1, 22.6, 26.2, 29.6, and 31.2 degrees.

In some embodiments, the polymorph of diazoxide choline salt is of Form B having characteristic peaks in the XRPD pattern at values of two-theta (Cu Kα, 40 kV, 40 mA) at approximately 8.9, 10.3, 12.0, 18.3, 20.6, 24.1, 24.5, 26.3, 27.1, and 28.9 degrees.

In some embodiments, the polymorph of diazoxide choline salt is of Form A having characteristic infrared absorbances at 2926, 2654, 1592, 1449, and 1248 cm$^{-1}$.

In some embodiments, the polymorph of diazoxide choline salt is of Form B having characteristic infrared absorbances at 3256, 2174, 2890, 1605, 1463, and 1235 cm$^{-1}$.

In some embodiments, the polymorph of diazoxide includes potassium as the cation.

In some embodiments, the polymorph of diazoxide potassium salt is of Form A having characteristic peaks in the XRPD pattern at values of two-theta (Cu Kα, 40 kV, 40 mA) at approximately 6.0, 8.1, 16.3, 17.7, 18.6, 19.1, 22.9, 23.3, 23.7, 24.7, 25.4, 26.1, 28.2, 29.6, and 30.2 degrees.

In some embodiments, the polymorph of diazoxide potassium salt is of Form B having characteristic peaks in the XRPD pattern at values of two-theta (Cu Kα, 40 kV, 40 mA) at approximately 8.5, 10.8, 16.9, 18.2, 21.6, 25.5, 26.1, and 28.9 degrees.

In some embodiments, the polymorph of diazoxide potassium salt is of Form C having characteristic peaks in the XRPD pattern at values of two-theta (Cu Kα, 40 kV, 40 mA) at approximately 5.7, 6.1, 17.9, 23.9, 25.1, and 37.3 degrees.

In some embodiments, the polymorph of diazoxide potassium salt is of Form D having characteristic peaks in the XRPD pattern at values of two-theta (Cu Kα, 40 kV, 40 mA) at approximately 5.7, 6.2, 8.1, 8.5, 8.8, 16.9, 18.6, 23.2, 24.5, 25.8, and 26.1 degrees.

In some embodiments, the polymorph of diazoxide potassium salt is of Form E having characteristic peaks in the XRPD pattern at values of two-theta (Cu Kα, 40 kV, 40 mA) at approximately 6.7, 7.1, 14.1, and 21.2 degrees.

In some embodiments, the polymorph of diazoxide potassium salt is of Form F having characteristic peaks in the XRPD pattern at values of two-theta (Cu Kα, 40 kV, 40 mA) at approximately 8.5, 9.0, 18.7, 20.6, 23.5, 27.5, and 36.3 degrees.

In some embodiments, the polymorph of diazoxide potassium salt is of Form G having characteristic peaks in the XRPD pattern at values of two-theta (Cu Kα, 40 kV, 40 mA) at approximately 5.2, 5.5, 13.1, 16.5, 19.3, 22.8, 24.8, 26.4, 28.7, and 34.1 degrees.

In some embodiments, the polymorph of diazoxide potassium salt is of Form A having characteristic infrared absorbances at 1503, 1374, 1339, 1207, 1131, 1056, and 771 cm$^{-1}$.

In some embodiments, the polymorph of diazoxide potassium salt is of Form B having characteristic infrared absorbances at 1509, 1464, 1378, and 1347 cm$^{-1}$.

In some embodiments, the polymorph of diazoxide potassium salt is of Form C having characteristic infrared absorbances at 1706, 1208, 1146, and 746 cm$^{-1}$.

In some embodiments, the polymorph of diazoxide potassium salt is of Form D having characteristic infrared absorbances at 1595, 1258, 1219, and 890 cm$^{-1}$.

In some embodiments, the polymorph of diazoxide potassium salt is of Form E having characteristic infrared absorbances at 1550, 1508, 1268, 1101, and 1006 cm$^{-1}$.

In some embodiments, the polymorph of diazoxide potassium salt is of Form F having characteristic infrared absorbances at 1643, 1595, 1234, 1145, and 810 cm$^{-1}$.

In some embodiments, the polymorph of diazoxide potassium salt is of Form G having characteristic infrared absorbances at 1675, 1591, 1504, 1458, 1432, 1266, 999, 958, 905, and 872 cm$^{-1}$.

Figure 16A:
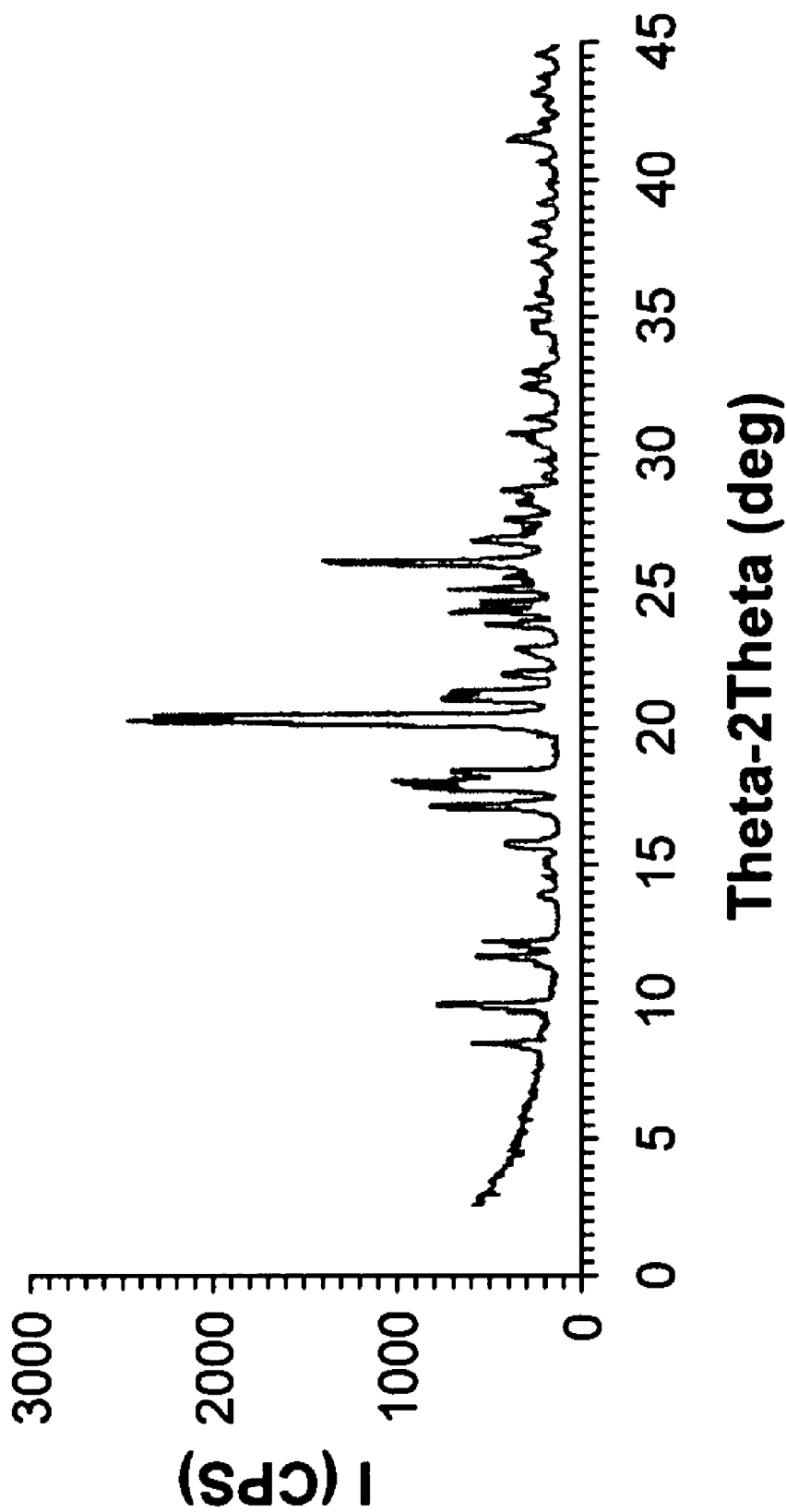
FIG. 16A and FIG. 16B show XRPD patterns of (A) polymorphic Form A of the choline salt of diazoxide, and (B) a mixture of polymorphic forms A and B of the choline salt of diazoxide, respectively.
Figure 16B:
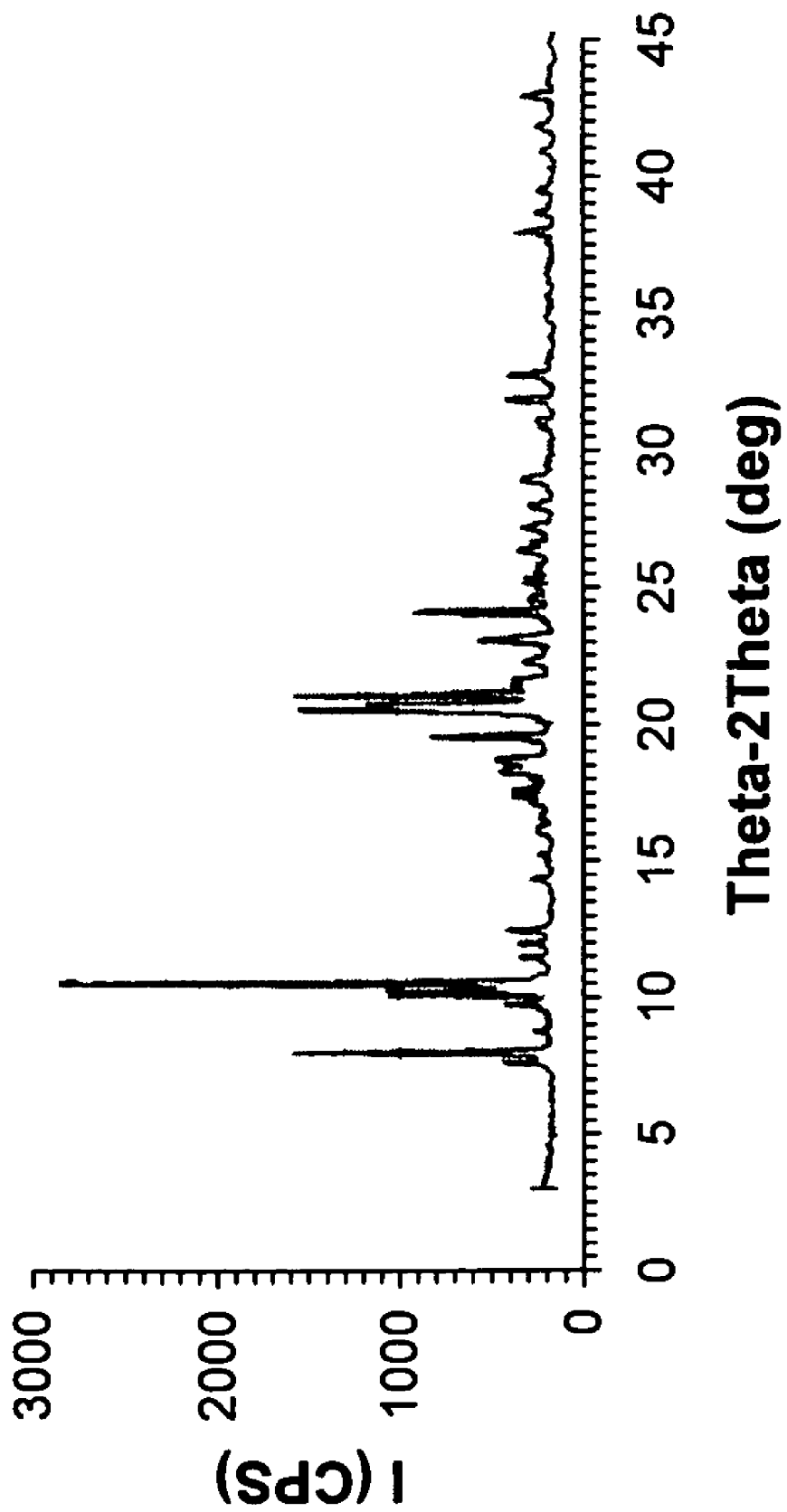
Figure 17A:
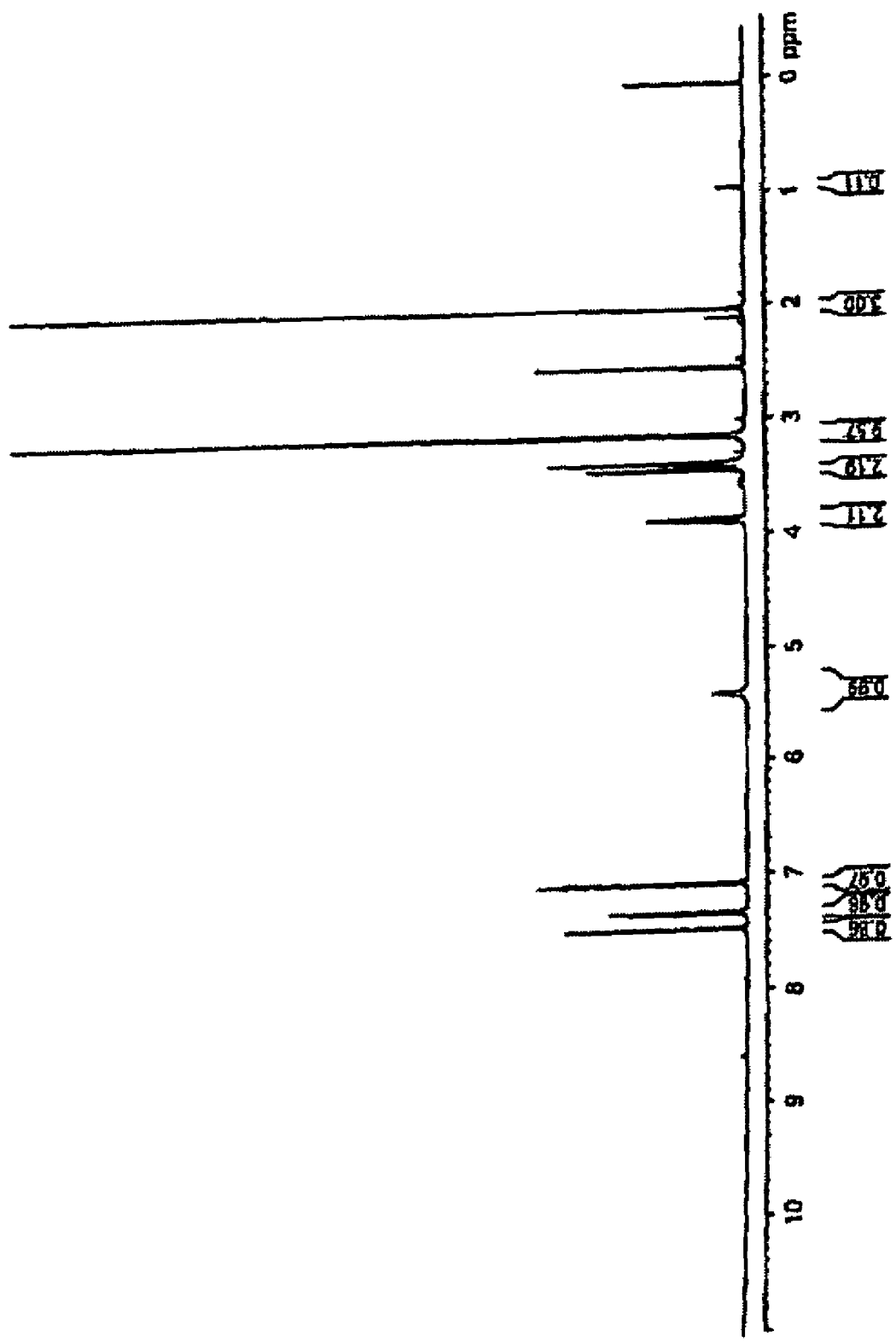
FIG. 17A and FIG. 17B show the NMR spectra (DMSO-d6 solvent) for (A) polymorphic Form A of the choline salt of diazoxide, and (B) polymorphic Form B of the choline salt of diazoxide, respectively.
Figure 17B:
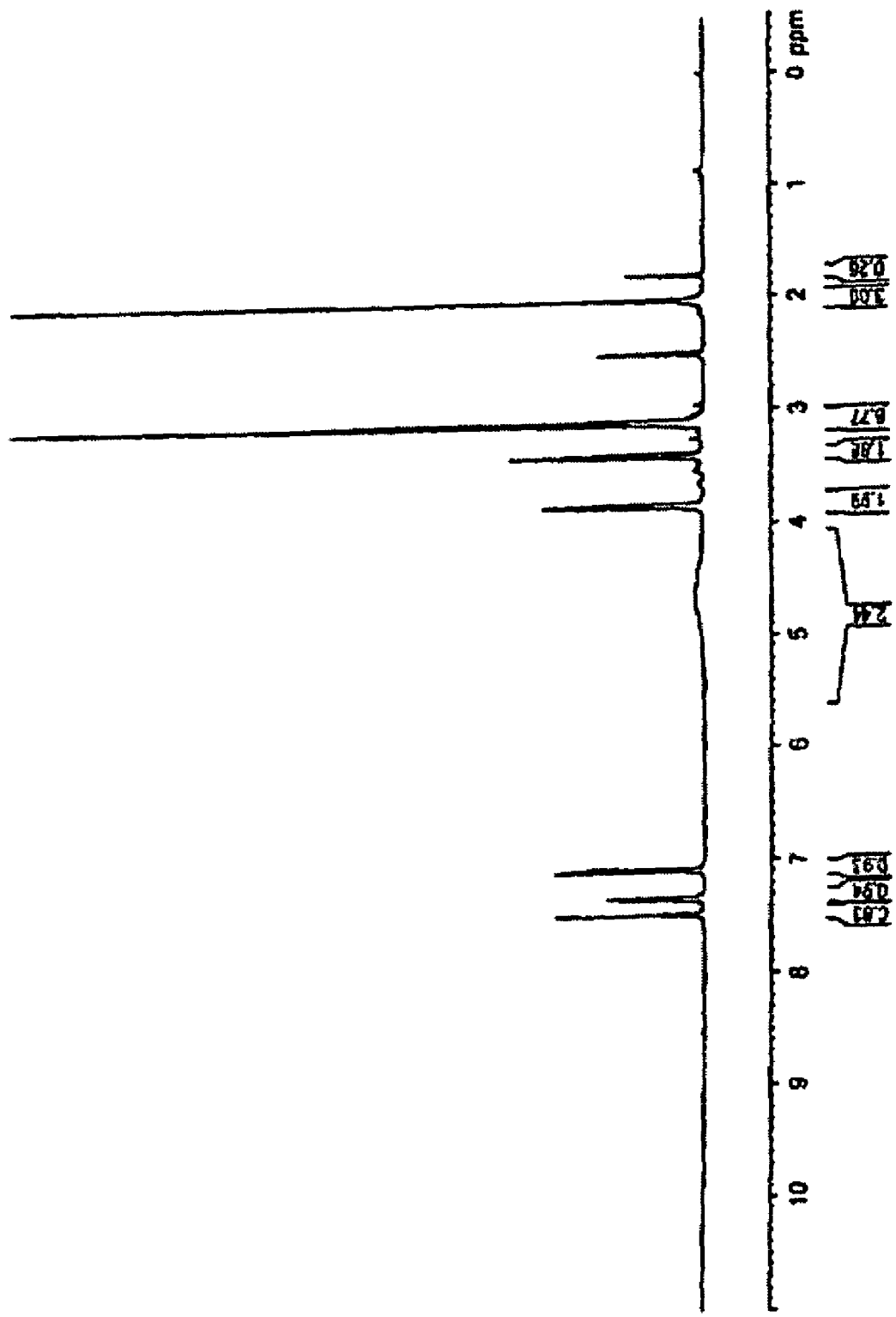

In some embodiments, the polymorph of diazoxide choline salt is of Form A having characteristic peaks in the XRPD pattern substantially as shown in FIG. 16(*a*), and an NMR spectrum substantially as shown in FIG. 17(*a*).

In some embodiments, the polymorph of diazoxide choline salt is of Form B having characteristic peaks in the XRPD pattern substantially as shown in FIG. 16(*c*) and an NMR spectrum substantially as shown in FIG. 17(*b*).

Figure 18A:
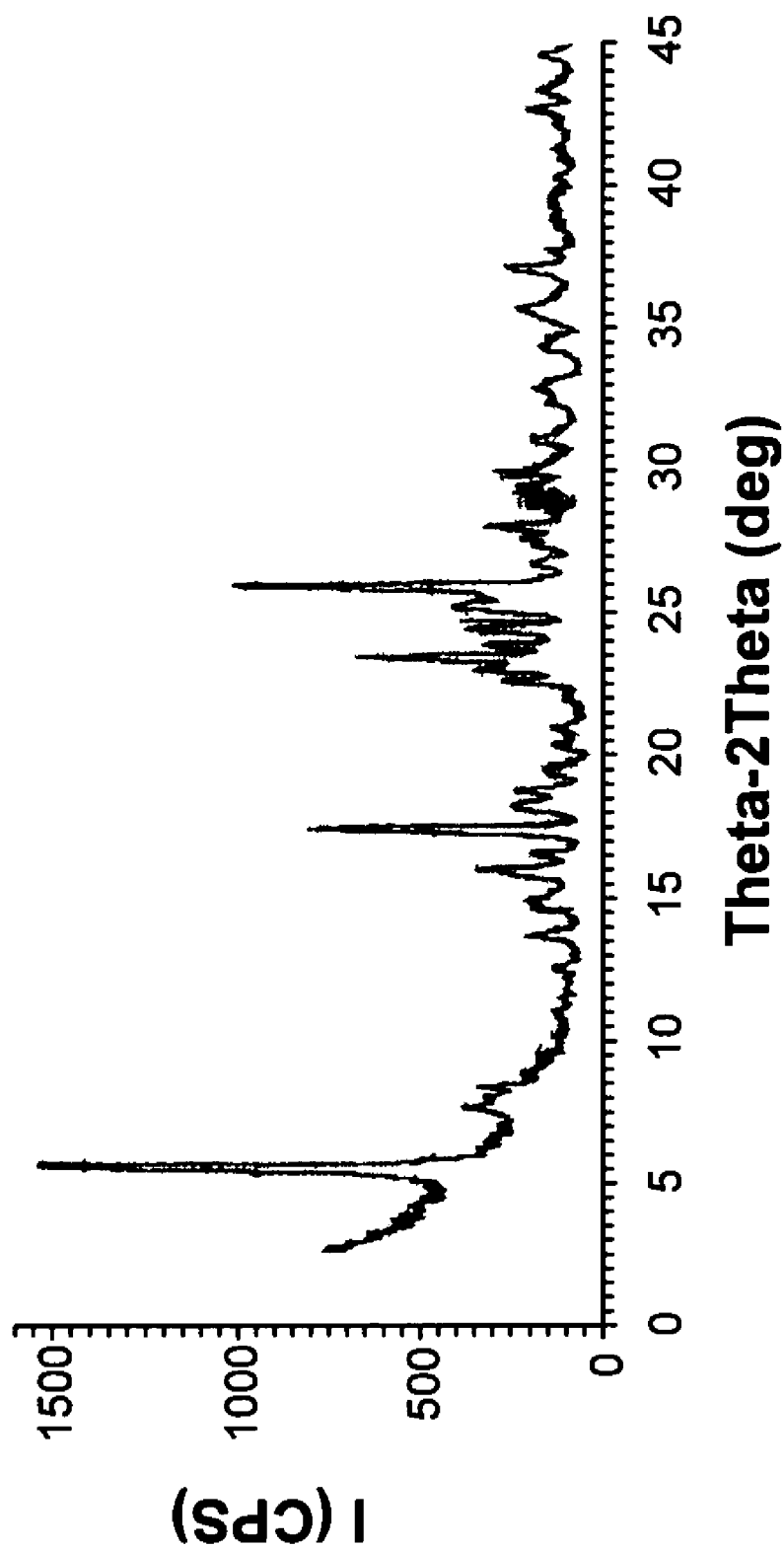
FIG. 18A, FIG. 18B and FIG. 18C show XRPD patterns of (A) polymorphic Form A of the potassium salt of diazoxide, (B) polymorphic Form B of the potassium salt of diazoxide, and (C) polymorphic Form C of the potassium salt of diazoxide, respectively.
Figure 18B:
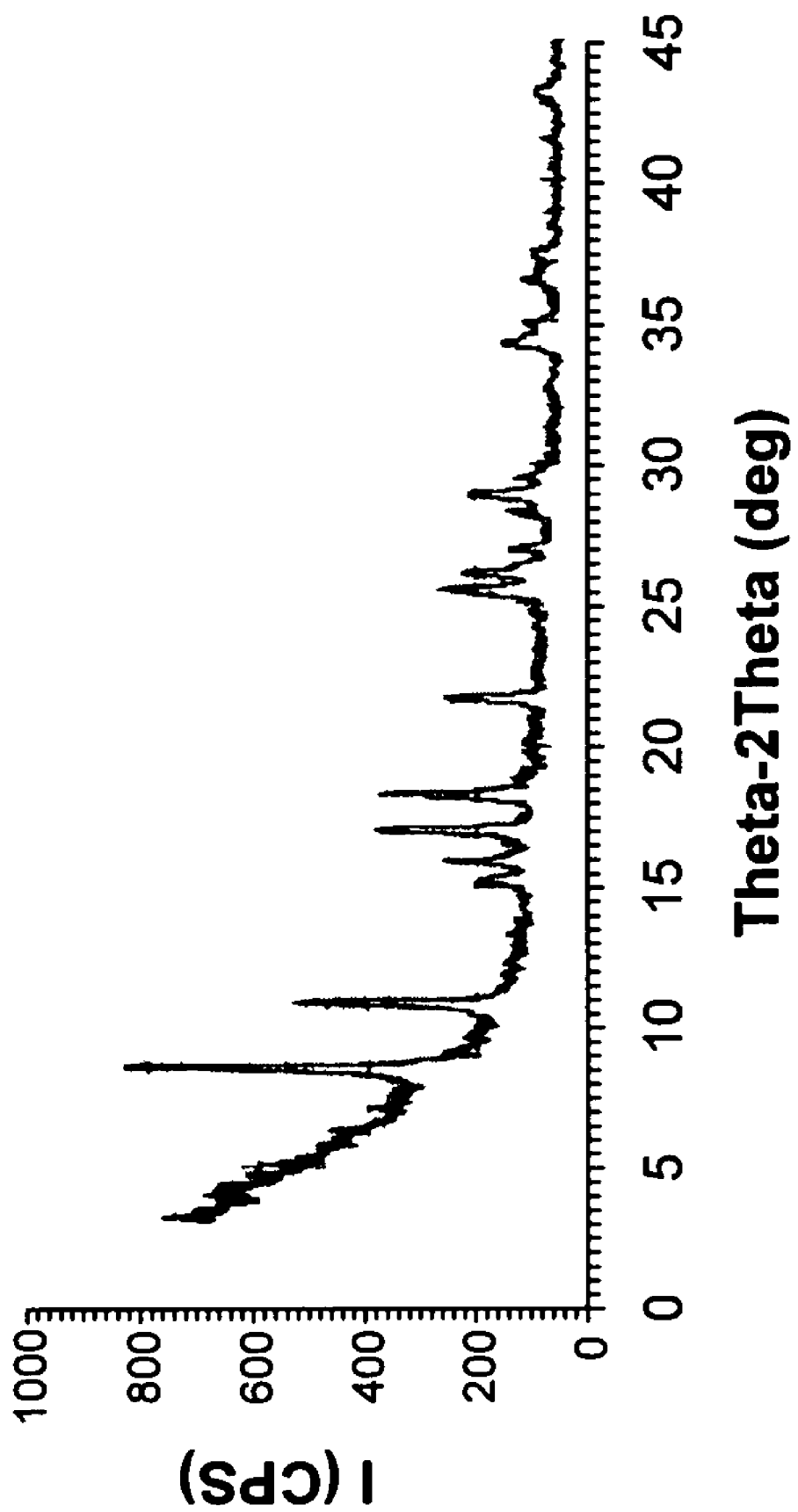
Figure 18C:
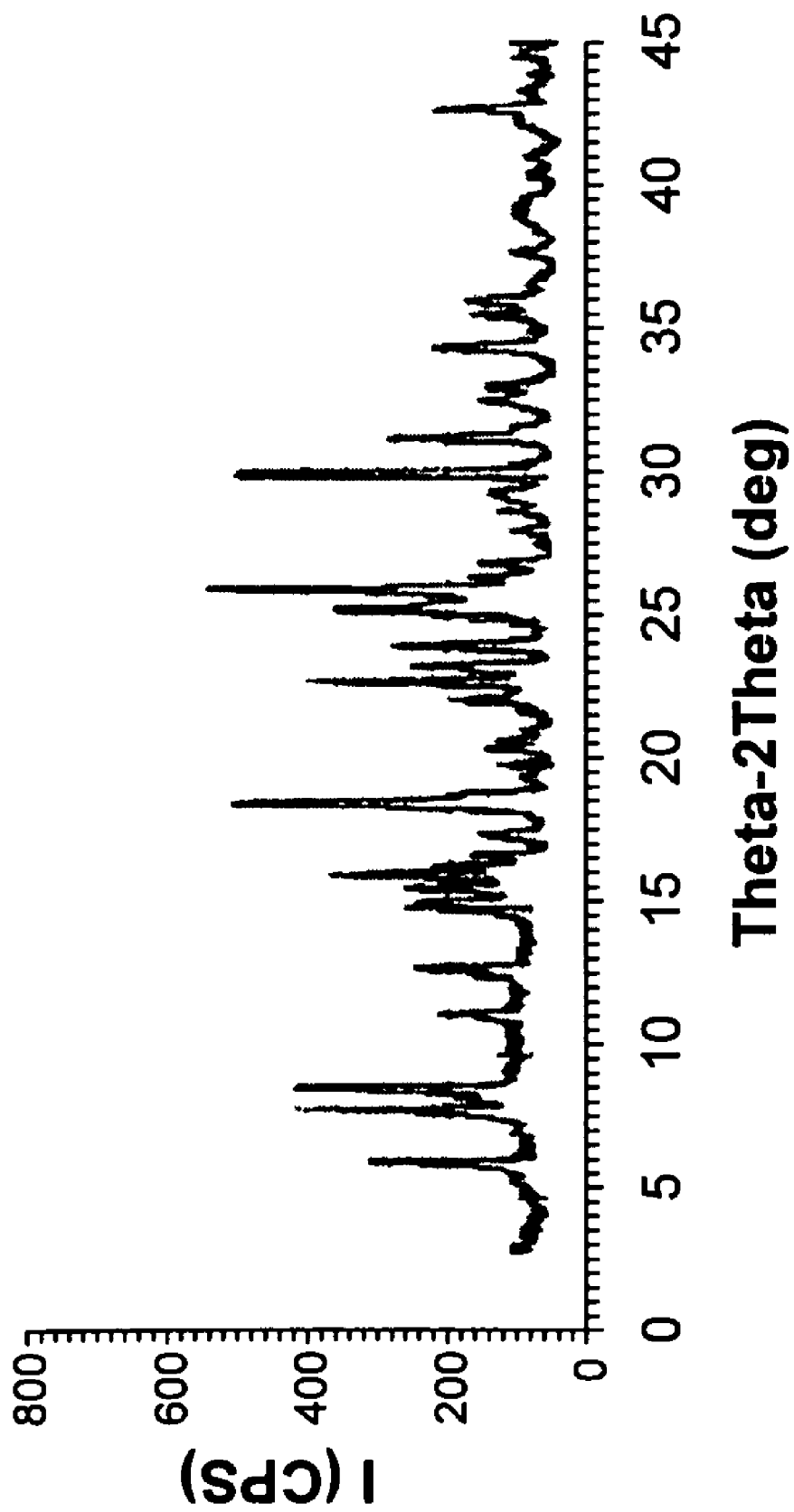
Figure 19A:
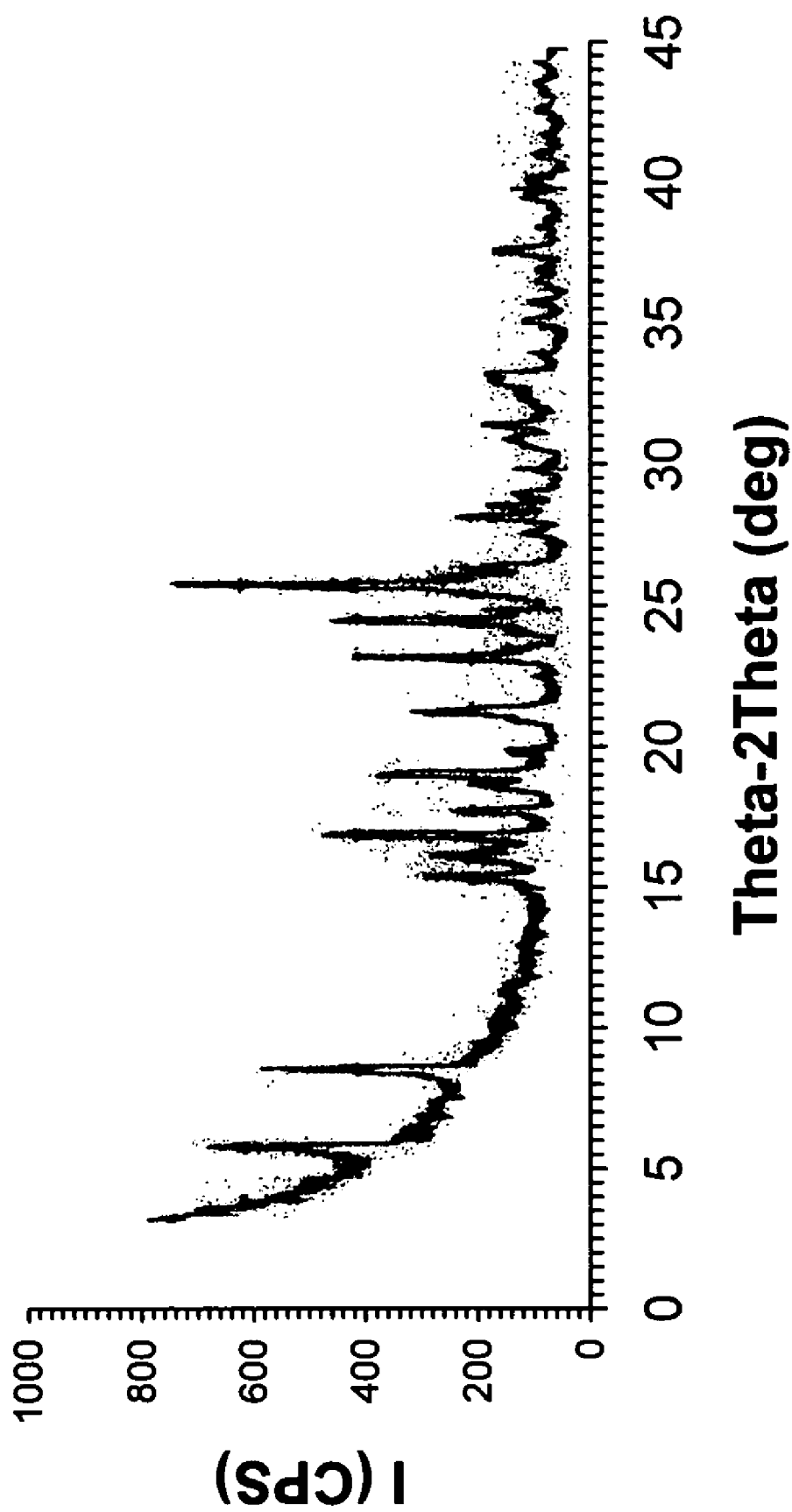
FIG. 19A, FIG. 19B, FIG. 19C and FIG. 19D show XRPD patterns of (A) polymorphic Form D of the potassium salt of diazoxide, (B) polymorphic Form E of the potassium salt of diazoxide, (C) polymorphic Form F of the potassium salt of diazoxide, and (D) polymorphic Form G of the potassium salt of diazoxide, respectively.
Figure 19B:
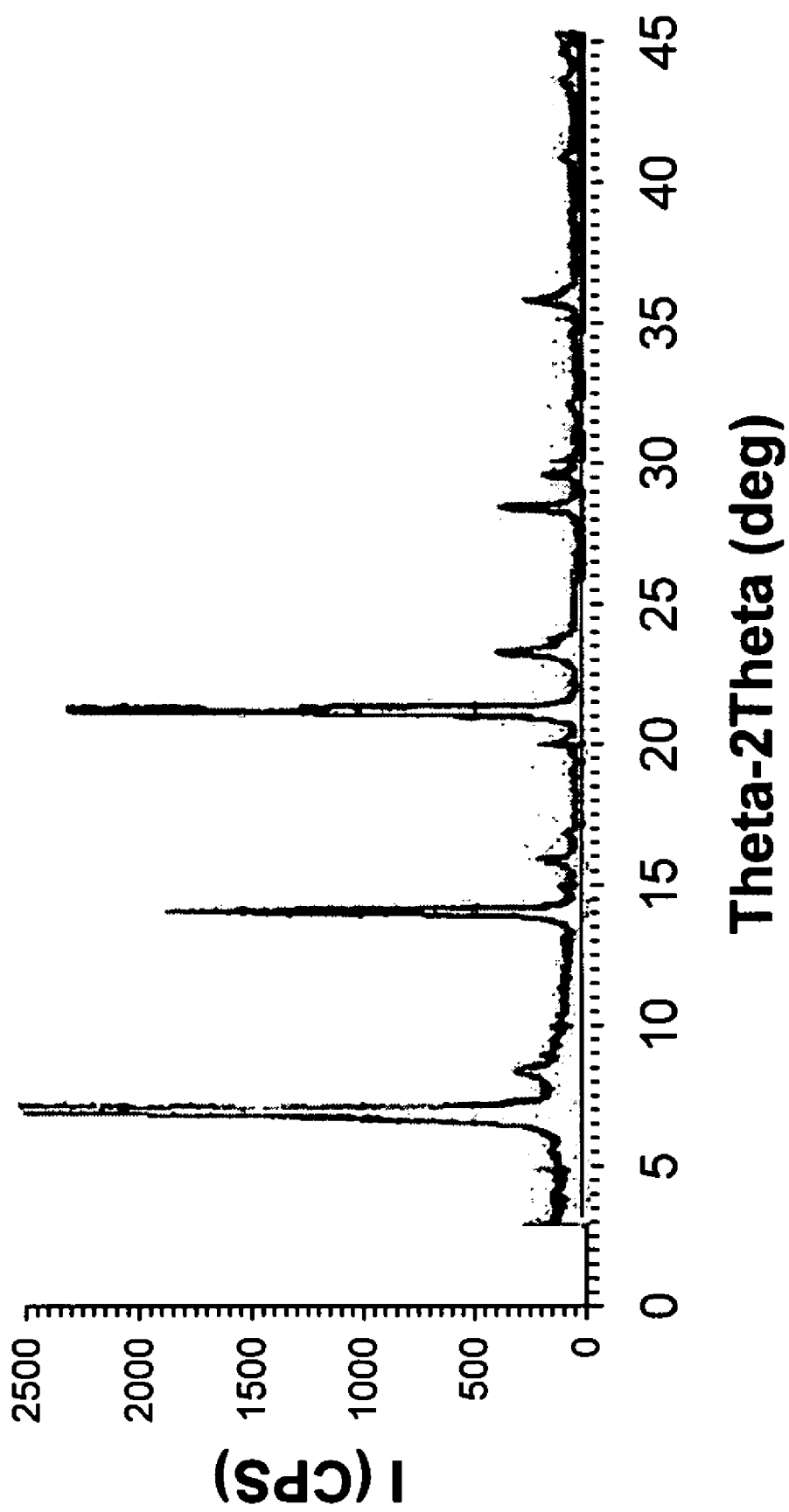
Figure 19C:
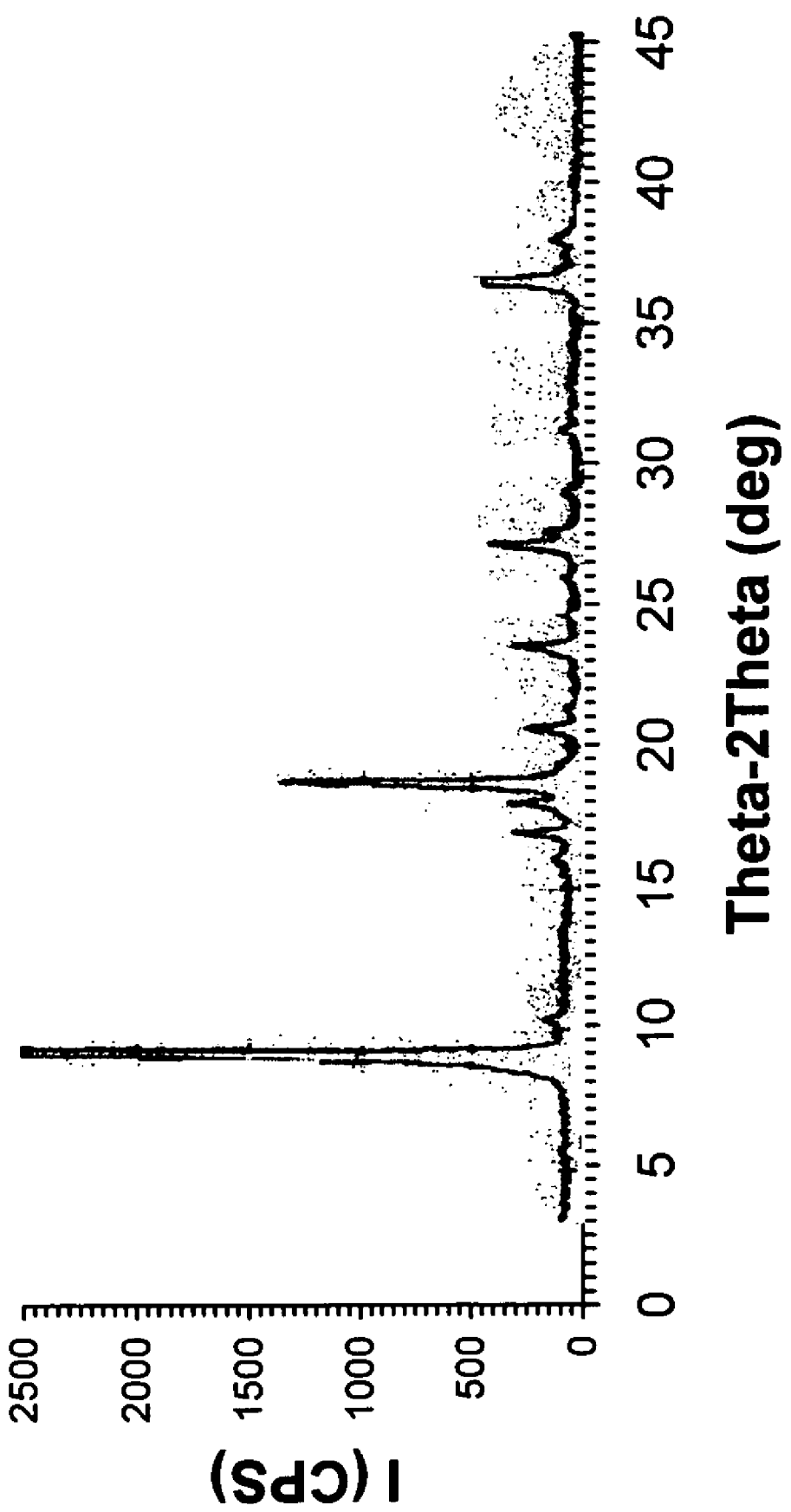
Figure 19D:
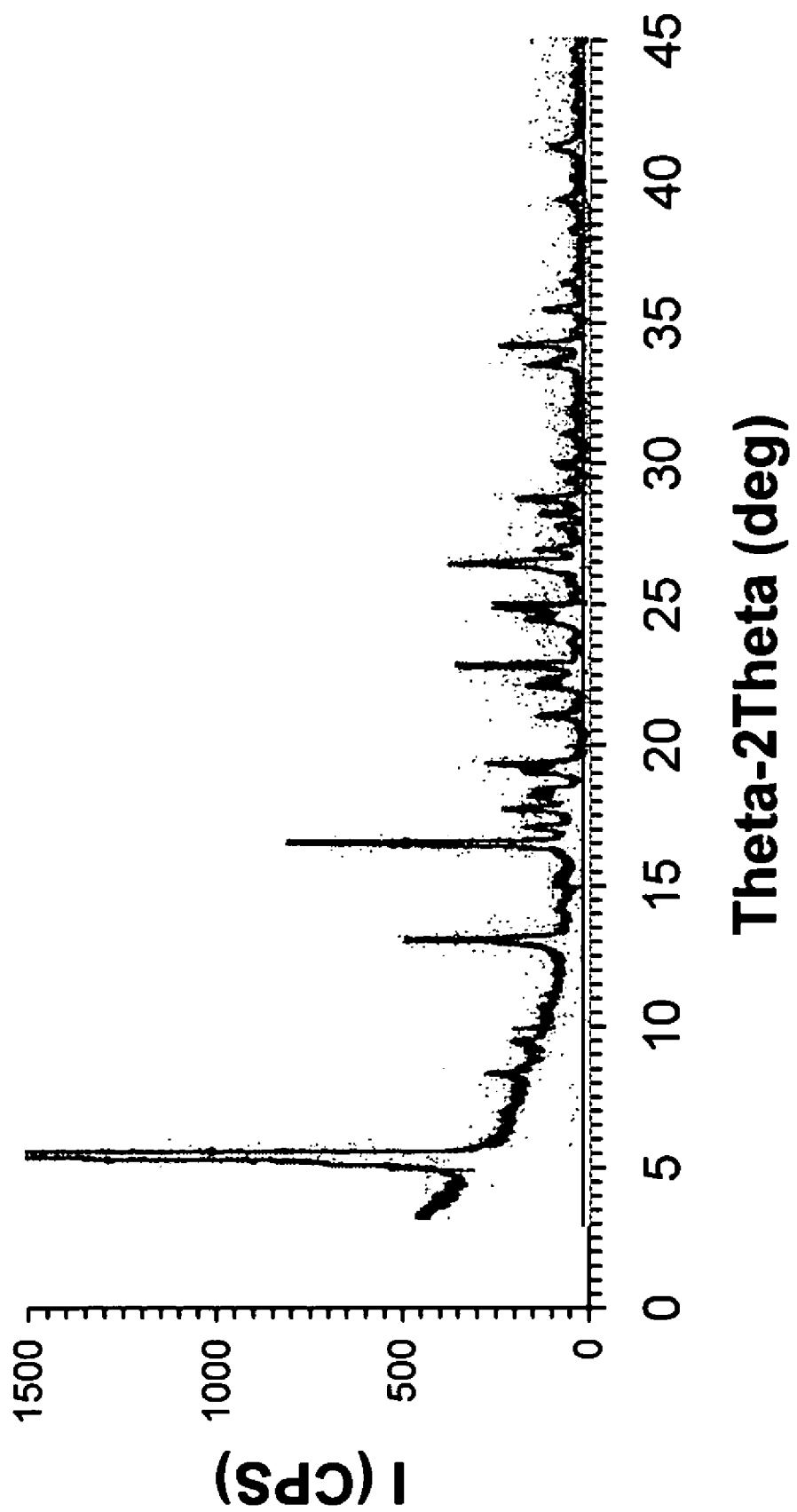

In some embodiments, the polymorph of diazoxide potassium salt includes one or more of Forms A-G, wherein each of the Forms A-G has characteristic peaks in the XRPD pattern substantially as shown in FIG. 18-19.

In some embodiments of the invention there are provided methods for producing a diazoxide choline salt, which methods include suspending diazoxide in a solvent (e.g., alcohols such as methanol, i-BuOH, i-AmOH, t-BuOH, and the like, ketones, tetrahydrofuran, dimethylformamide, n-methylpyrrolidinone, and the like) and mixing with a choline salt (e.g., choline hydroxide), adding a co-solvent (e.g., MTBE, EtOA, IPA, c-Hexane, heptane, toluene, $CH_2CL_2$, dioxane, and the like) to the suspension under conditions sufficient to cause formation and precipitation of said diazoxide choline salt, and harvesting the precipitate to provide the diazoxide choline salt.

In some embodiments, the solvent is tetrahydrofuran. In some embodiments, the solvent is 2-methyltetrahydrofuran (2-MeTHF).

In some embodiments, the diazoxide and the solvent are present at a ratio of about 1 g diazoxide per 1 mL solvent to about 1 g diazoxide per 5 mL solvent. In some embodiments, the diazoxide and the solvent are present at a ratio of about 1 g diazoxide per 3 mL solvent.

In some embodiments, the choline salt is a solution in MeOH. In some embodiments, the choline salt is choline hydroxide in about a 45% solution (e.g., 40%, 41%, 42%, 43%, 44%, 45%, 46%, 47%, 48%, 49%, 50%) in MeOH.

In some embodiments, the choline salt is added as 1 equivalent of diazoxide.

In some embodiments, the co-solvent is MTBE.

In some embodiments, the amount of co-solvent added is in a ratio to the amount of the solvent of about 3:14 (solvent:co-solvent) (e.g., 3:12, 3:13, 3:14, 3:15, 3:16).

In some embodiments, the process of making polymorphs of diazoxide choline salt includes the step of seeding with crystals of diazoxide choline salt polymorph Form B prior to the harvesting step.

In some embodiments for the method for producing a diazoxide choline salt the salt includes polymorph Form B substantially free of polymorph Form A, the polymorph Form B having characteristic peaks in the XRPD pattern at values of two-theta (Cu Kα, 40 kV, 40 mA) at approximately 8.5, 10.8, 16.9, 18.2, 21.6, 25.5, 26.1, and 28.9 degrees.

In some embodiments for the method of treating obesity or obesity-related morbidity in an obese subject, the compound is a compound of Formula V.

In some embodiments for the method of treating obesity or obesity-related morbidity in an obese subject, the compound is a compound of Formula VI.

In some embodiments for the method of treating obesity or obesity-related morbidity in an obese subject, the compound is a compound of Formula VII.

In some embodiments for the method of treating obesity or obesity-related morbidity in an obese subject, the compound is a compound of Formula VIII.

In some embodiments for the method of treating obesity or obesity-related morbidity in an obese subject, the method further comprises administering a drug selected from the group consisting of Sibutramine, Orlistat, Rimonabant, an appetite suppressant, a non-thiazide diuretic, a drug that lowers cholesterol, a drug that raises HDL cholesterol, a drug that lowers LDL cholesterol, a drug that lowers blood pressure, a drug that is an anti-depressant, a drug that is an anti-epileptic, a drug that is an anti-inflammatory, a drug that is an appetite suppressant, a drug that lowers circulating triglycerides, and a drug that is used to induce weight loss in an overweight or obese individual.

In some embodiments for the method of treating obesity or obesity-related morbidity in an obese subject, the method further comprises administering a pharmaceutically active agent other than the $K_{ATP}$ channel opener. In some embodiments, the other pharmaceutically active agent is an agent useful for the treatment of a condition selected from the group consisting of obesity, prediabetes, diabetes, hypertension, depression, elevated cholesterol, fluid retention, obesity associated co-morbidities, ischemic and reperfusion injury, epilepsy, cognitive impairment, schizophrenia, mania, and other psychotic condition.

In some embodiments for the method for treating a subject suffering from or at risk for Alzheimer's disease (AD), the method includes administration to a subject a therapeutically effective amount of a salt of diazoxide including salts provided herein. In some embodiments for the method for treating a subject suffering from or at risk for AD, the method includes administration to a subject a therapeutically effective amount of a compound according to any of Formulae I-VIII. In some embodiments, the compound is diazoxide or a salt thereof.

AD is a neurodegenerative disorder neuropathologically characterized by abnormal accumulations of intracellular neurofibrilary tangles and extracellular amyloid plaques throughout cortical and limbic brain regions and the loss of synapses and neurons. AD is further characterized by significant cognitive and memory impairment. β amyloid plaques form from the β amyloid peptide, either 1-40 or 1-42 peptide, which is released from amyloid precursor protein following cleavage by gamma secretase. In addition to forming plaques, the β amyloid peptides are cytotoxic either as the monomer or as a short-lived oligomeric intermediate. β amyloid peptides (monomers, dimers or oligomers) can be identified both in CSF (cerebrospinal fluid) and in serum. Amyloid angiopathy is characterized by Aβ deposition and may contribute to the cerebrovascular abnormalities that precede the onset of AD.

The invention will now be described with reference to the following non-limiting examples.

EXAMPLES

A. Potassium ATP Channel Activator Containing Formulations

1. Compressed Tablet Formulations of Diazoxide Salt or Derivative

Diazoxide salt or a derivative thereof at about 15-30% by weight is mixed with hydroxypropyl methylcellulose at about 55-80% by weight, ethylcellulose at about 3-10 wt/vol % and magnesium stearate (as lubricant) and talc (as glidant) each at less than 3% by weight. The mixture is used to produce a compressed tablet as described in Reddy et al., *AAPS Pharm Sci Tech* 4(4):1-9 (2003). The tablet may be coated with a thin film as discussed below for microparticles.

A tablet containing 100 mg of diazoxide salt or a derivative thereof will also contain approximately 400 mg of hydroxypropyl cellulose and 10 mg of ethylcellulose. A tablet containing 50 mg of diazoxide salt or a derivative thereof will also contain approximately 200 mg of hydroxypropyl cellulose and 5 mg of ethylcellulose. A tablet containing 25 mg of diazoxide salt or a derivative thereof will also contain approximately 100 mg of hydroxypropyl cellulose and 2.5 mg of ethylcellulose.

2. Encapsulated Coated Microparticle Formulation of Diazoxide Salt or Derivative Diazoxide salt or a derivative thereof is encapsulated into microparticles in accordance with well known methods (see, e.g. U.S. Pat. No. 6,022,562). Microparticles of between 100 and 500 microns in diameter containing diazoxide salt or a derivative thereof, alone or in combination with one or more suitable excipient, is formed with the assistance of a granulator and then sieved to separate microparticles having the appropriate size. Microparticles are coated with a thin film by spray drying using commercial instrumentation (e.g. Uniglatt Spray Coating Machine). The thin film comprises ethylcellulose, cellulose acetate, polyvinylpyrrolidone and/or polyacrylamide. The coating solution for the thin film may include a plasticizer which may be castor oil, diethyl phthalate, triethyl citrate and salicylic acid. The coating solution may also include a lubricating agent which may be magnesium stearate, sodium oleate, or polyoxyethylenated sorbitan laurate. The coating solution may further include an excipient such as talc, colloidal silica or of a mixture of the two added at 1.5 to 3% by weight to prevent caking of the film coated particles.

3. Formulations for Controlled Release of Diazoxide or Derivative 3.1. Formulation of a Tableted Form of Diazoxide or a Derivative for Controlled Release Prior to mixing, both the active ingredient and hydroxypropyl methylcellulose (Dow Methocel K4M P) are passed through an ASTM 80 mesh sieve. A mixture is formed from 1 part diazoxide salt or a derivative thereof to 4 parts hydroxypropyl methylcellulose. After thorough mixing, a sufficient volume of an ethanolic solution of ethylcellulose as a granulating agent is added slowly. The quantity of ethylcellulose per tablet in the final formulation is about 1/10th part. The mass resulting from mixing the granulating agent is sieved through 22/44 mesh. Resulting granules are dried at 40° C. for 12 hours and thereafter kept in a desiccator for 12 hours at room temperature. Once dry the granules retained on 44 mesh are mixed with 15% fines (granules that passed through 44 mesh). Talc and magnesium stearate are added as glidant and lubricant at 2% of weight each. A colorant is also added. The tablets are compressed using a single punch tablet compression machine.

3.2. Formulation of a Compression Tableted Form of Diazoxide or a Derivative Thereof that Provides for Controlled Release.

Diazoxide salt or a derivative thereof at 20-40% weight is mixed with 30% weight hydroxypropyl methylcellulose (Dow Methocel K100LV P) and 20-40% weight impalpable lactose. The mixture is granulated with the addition of water. The granulated mixture is wet milled and then dried 12 hours at 110° C. The dried mixture is dry milled. Following milling, 25% weight ethylcellulose resin is added (Dow Ethocel 10FP or Ethocel 100FP) followed by 0.5% weight magnesium stearate. A colorant may also be added. The tablets are compressed using a single punch tablet compression machine (Dasbach et al., Poster at AAPS Annual Meeting Nov. 10-14 (2002)).

3.3. Formulation of a Compression Coated Tableted Form of Diazoxide or a Derivative Thereof that Provides for Controlled Release.

The core tablet is formulated by mixing either 100 mg of diazoxide salt or a derivative thereof with 10 mg of ethylcellulose (Dow Ethocel 10FP), or by mixing 75 mg of diazoxide or a derivative thereof with 25 mg lactose and 10 mg of ethylcellulose (Dow Ethocel 10FP), or by mixing 50 mg of diazoxide or a derivative thereof with 50 mg of lactose and 10 mg of ethylcellulose (Dow Ethocel 10FP). The core tablets are formed on an automated press with concave tooling. The compression coating consisting of 400 mg of polyethylene oxide (Union Carbide POLYOX WSR Coagulant) is applied and compressed to 3000 psi (Dasbach et al., Poster at AAPS Annual Meeting Oct. 26-30 (2003)).

3.4. Formulation of a Controlled Release Tableted Form of Diazoxide Choline Salt 3.4.1 Controlled Release Formulations Controlled release tableted formulations of diazoxide choline salt were developed and investigated with respect to a variety of properties known by those of skill in the pharmaceutical art relating to the manufacture of tableted formulations including, for example, ease and consistency of manufacture, appearance (e.g., sheen, compressibility, microscopic appearance), and dissolution properties (e.g., rate, order and extent of dissolution). Tablets were produced individually on a press, where the final blend of diazoxide choline salt and excipient was weighed out to the desired total tablet weight prior to compression. As shown in Table 2, Formulations A-H, J, and L contained 50.0 mg diazoxide as the choline salt (i.e., 72.5 mg total diazoxide choline salt present), and Formulations I and K contained 200.0 mg diazoxide as the choline salt (i.e., 290.0 mg total diazoxide choline salt present). The manufacture of formulation L is exemplary of the manufacturing methods available to the skilled artisan. For formulation L, diazoxide choline salt, talc, and approximately half of the colloidal silicon dioxide (Cab-o-sil) were mixed in a KG-5 mixer bowl with an impeller speed of about 300 rpm and a chopper speed of about 3000 rpm for about 4 min. The mixture was passed through a co-mil equipped with a 024R screen, square-edged paddle, and 0.175" spacer. To this milled mixture in a 8-qt V-shell blender was added Emcompress through a #20 mesh hand screen with blending for about 10 min. To this mixture was added PEO N750 and PEO 303, which had been passed through a #20 mesh hand screen, with blending for about 10 min. To this mixture was added Pruv and the remainder of the Cab-o-sil, having been passed through a #20 mesh hand screen, with blending for about 5 min. The mixture was subjected to pressing (Manesty Beta Press) using 0.2220"×0.5720" caplet shaped tooling (Set #21.)

TABLE 2

Exemplary Formulations for Diazoxide Choline salt.

| Formulation | INGREDIENT | Amount per tablet (mg) |
|---|---|---|
| A. | Diazoxide Choline | 72.50 |
|  | Kollidon SR | 100.0 |
|  | PEO N303 | 25.00 |
|  | Emcompress | 50.50 |
|  | Pruv | 2.00 |
|  | TOTAL WEIGHT | 250.0 |
| B. | Diazoxide Choline | 72.50 |
|  | Methocel K100M | 237.3 |
|  | Emcompress | 35.00 |
|  | Magnesium Stearate | 3.50 |
|  | Cab-o-sil | 1.75 |
|  | TOTAL WEIGHT | 350.0 |
| C. | Diazoxide Choline | 72.50 |
|  | Kollidon SR | 105.0 |
|  | PEO N303 | 35.0 |
|  | Emcompress | 134.1 |
|  | Pruv | 3.50 |
|  | TOTAL WEIGHT | 350.1 |
| D. | Diazoxide Choline | 72.50 |
|  | Methocel K100M | 175.1 |
|  | Emcompress | 97.30 |
|  | Magnesium Stearate | 3.50 |
|  | Cab-o-sil | 1.75 |
|  | TOTAL WEIGHT | 350.2 |
| E. | Diazoxide Choline | 72.50 |
|  | PEO N750 NF | 105.0 |
|  | PEO N303 NF | 52.50 |
|  | Emcompress | 116.6 |
|  | Pruv | 3.50 |
|  | TOTAL WEIGHT | 350.1 |
| F. | Diazoxide Choline | 72.50 |
|  | Kollidon SR | 105.0 |
|  | PEO N303 | 7.00 |
|  | Emcompress | 162.1 |
|  | Pruv | 3.50 |
|  | TOTAL WEIGHT | 350.1 |
| G. | Diazoxide Choline | 72.50 |
|  | Methocel K100M | 175.1 |
|  | Emcompress | 105.1 |
|  | Magnesium Stearate | 3.50 |
|  | Cab-o-sil | 1.75 |
|  | TOTAL WEIGHT | 358.0 |

TABLE 2-continued

Exemplary Formulations for Diazoxide Choline salt.

| Formulation | INGREDIENT | Amount per tablet (mg) |
|---|---|---|
| H. | Diazoxide Choline | 72.50 |
|  | PEO N750 NF | 105.0 |
|  | PEO N303 NF | 35.01 |
|  | Emcompress | 134.1 |
|  | Pruv | 3.50 |
|  | TOTAL WEIGHT | 350.1 |
| I. | Diazoxide Choline | 290.0 |
|  | Methocel K100M | 240.0 |
|  | Emcompress | 258.0 |
|  | Magnesium Stearate | 8.00 |
|  | Cab-o-sil | 4.00 |
|  | TOTAL WEIGHT | 800.0 |
| J. | Diazoxide Choline | 72.50 |
|  | PEO N750 NF | 105.0 |
|  | PEO N303 NF | 52.50 |
|  | Emcompress | 116.6 |
|  | Pruv | 3.50 |
|  | Talc | 3.50 |
|  | Cab-o-sil | 1.75 |
|  | TOTAL WEIGHT | 355.4 |
| K. | Diazoxide Choline | 290.0 |
|  | PEO N750 NF | 249.0 |
|  | PEO N303 NF | 124.5 |
|  | Emcompress | 145.3 |
|  | Pruv | 8.30 |
|  | Talc | 8.30 |
|  | Cab-o-sil | 4.15 |
|  | TOTAL WEIGHT | 829.6 |
| L. | Diazoxide Choline | 72.51 |
|  | PEO N750 NF | 105.1 |
|  | PEO N303 NF | 52.54 |
|  | Emcompress | 111.4 |
|  | Pruv | 3.50 |
|  | Talc | 3.50 |
|  | Cab-o-sil | 1.75 |
|  | TOTAL WEIGHT | 350.3 |

Microscopic observation of the tablets having Formulation A revealed a grainy texture of the diazoxide choline salt, and at the 29% loading of diazoxide choline salt in Formulation A the blend had poor flow characteristics. Accordingly, the loading of diazoxide choline was reduced in Formulation B. A caplet shaped tooling, approximately 6 mm×15 mm was found to result in acceptable tablet appearance, sheen, and ease of compressibility. However, Formulation B also exhibited poor blend flow.

Subsequent formulations (e.g., Formulations C-L) incorporated a milling step of the diazoxide choline salt prior to incorporation into the tablet blend. A milling study was conducted using a test mill equipped with different screen sizes to evaluate and determine a suitable milling process. Particle size was determined by visual comparison with 40 μm reference beads. As shown in Table 3, use of the 024R screen resulted in the best recovery of API (i.e., "active pharmaceutical ingredient"=diazoxide as the diazoxide choline salt) providing the broadest range of particle sizes. Accordingly, material milled through a 024R screen was selected for subsequent formulation.

TABLE 3

Milling study for diazoxide choline salt prior to formulation

| Screen/Paddle/Spacer/Speed | API loaded/API recovered (g) | Particle size (μm) |
|---|---|---|
| 018R/square/0.200"/80% | 50.0/36.5 | ~100-200 |
| 024R/square/0.200"/80% | 50.0/42.0 | ~100-250 |
| 039R/square/0.200"/80% | 50.0/42.0 | ~150-250 |

3.4.2. Dissolution Studies

Dissolution of tablets with formulation as set forth in Table 4 was investigated. One or more tablets (e.g., 1 or 2) of the indicated tableted formulation were placed into a volume of buffer (e.g., 900 mL) with known buffer salt concentration (e.g., 0.05 M potassium phosphate, pH 8.6; 0.05 M potassium phosphate, pH 7.5), with or without surfactant (e.g., 0.05% CTAB), at a known temperature (e.g., 37° C.). Stirring conditions employed paddles at, for example, 50 RPM. Aliquots (e.g, 10 mL) removed as a function of time were filtered (e.g., 0.45 μm GMF Filter) prior to analysis.

TABLE 4

Dissolution study for formulations of diazoxide choline salt
(entries are % dissolved diazoxide)

| | | Time (hr) | | | | | | | | |
|---|---|---|---|---|---|---|---|---|---|---|
| Entry | Protocol | 0 | 1 | 2 | 3 | 6 | 9 | 12 | 18 | 24 |
| C | a | 0.0 | 2.9 | 4.5 | 5.7 | 9.4 | 13.0 | 16.6 | | |
| D | a | 0.0 | 4.5 | 7.8 | 11.0 | 19.1 | 25.6 | 31.3 | | |
| F | b | | | | 29 | 36 | | 44 | | 54 |
| G | b | | | | 30 | 39 | | 50 | | 67 |
| H | b | | | | 50 | 75 | | 91 | | 101 |
| I | b | | | | 25 | 37 | | 48 | | 57 |
| J | b | | | | 34 | 53 | | 76 | | 104 |
| K | b | | | | 25 | 43 | | 64 | | 94 |
| | | | | | 24 | 41 | | 62 | | 92 |

Column 1: Entry from Table 2.
Column 2: Protocol a) 0.05 M potassium phosphate, pH 8.6, 37° C.; Protocol b) 0.05 M potassium phosphate, pH 7.5, 0.05% CTAB, 37° C.

The dissolution profile (i.e., % dissolved with time) of Proglycem® capsules (100 mg) and controlled-release tablet formulations of diazoxide as provided herein is shown in Table 5. The 50 mg tablet entry of Table 5 refers to Formulation J (Table 2) wherein talc and cab-o-sil was present at 2% and 1%, respectively. The 200 mg tablet entry of Table 5 refers to Formulation K (Table 2) wherein talc and cab-o-sil are present at 2% and 1%, respectively

TABLE 5

Dissolution profile of 100 mg Proglycem ® (capsule)
and diazoxide choline salt (tablet)

| Time (hr) | 100 mg capsule Proglycem ® | 200 mg tablet diazoxide choline salt | 50 mg tablet diazoxide choline salt |
|---|---|---|---|
| 0 | 0 | 0 | 0 |
| 3 | 79 | 22 | 25 |
| 6 | 85 | 36 | 39 |
| 12 | 92 | 54 | 70 |
| 24 | 98 | 88 | 99 |

As evidenced by Table 5, the 100-mg Proglycem® capsule provides for faster dissolution of diazoxide relative to tablets described herein. Approximately 79% diazoxide component of Proglycem® is recovered in dissolution buffer after 3-hr. In contrast, the 50 and 200-mg tablets described in Table 5 dissolved at levels of 25% and 22%, respectively, at 3-hr. At 12-hr, 100-mg Proglycem® capsule dissolved at 92%, whereas the 50 and 200-mg tablets dissolved at 70% and 54%, respectively. Approximately total dissolution is observed with 100-nmg Proglycem® capsule and 50-mg tablet at 24 hrs.

3.4.3. Excipient Compatibility Studies

Studies to determine the compatibility of diazoxide choline salt for various excipients are summarized in Table 6. Each mixture of excipient (100 mg) and diazoxide choline salt (100 mg) was made in acetonitrile to 10 mL Samples were assayed immediately (i.e., "Initial" column of Table 6) and at one-month storage under conditions a) 40° C./75% RH (relative humidity), and b) 50° C.

TABLE 6

Excipient compatibility study for diazoxide choline salt.

| Excipient | Initial % (w/w) | 1 Month 40° C./ 75% RH % (w/w) | 1 Month 50° C. % (w/w) |
|---|---|---|---|
| Hydroxyrpropylmethyl cellulose (HMPC) | 98.8 | 101.4 | 96.6 |
| Hydroxypropylcellulose (HPC) | 103.1 | 97.4 | 100.8 |
| Ethylcellulose (EC) | 90.6 99.5* | 102.0 | 99.7 |
| Methylcellulose (MC) | 102.3 | 100.3 | 99.1 |
| Carboxymethyl cellulose Na (CMC Na) | 96.8 | 101.6 | 99.5 |
| Starch 1500 | 103.3 | 90.6 | 95.2 |
| Kollidon SR | 81.2 100.2* | 99.8 | 100.9 |
| Polyethyleneoxide N3 03 (PEO) | 81.0 99.1* | 99.2 | 99.0 |
| Dibasic Calcium Phosphate | 98.4 | 102.9 | 102.2 |
| Sodium Stearyl Fumarate | 98.9 | 101.1 | 103.7 |
| Magnesium Stearate | 100.1 | 101.4 | 99.3 |
| Colloidal Silicon Dioxide (Cab-o-sil) | 99.0 | 99.4 | 104.5 |
| Microcrystalline Cellulose | 96.8 | 98.6 | 107.0 |
| Lactose Monohydrate | 94.5 | 99.2 | 103.0 |
| Mannitol | 111.7 | 98.1 | 81.3 |
| Diazoxide Control | N/A | 99.0 | 99.4 |

*Re-assayed

Initial low results for ethylcellulose, Kollidon SR, and polyethyleneoxide were investigated by re-preparing samples of diazoxide choline salt and excipient. As shown in Table 6, initial sample recovery (i.e., column "Recovery") of the re-prepared samples indicates method accuracy.

No reportable impurities were detected in any sample, and no degradation was observed in the samples stored for one-month with the exception of mannitol wherein 81.3% of diazoxide was recovered after 1-month at 50° C.

3.4.3. Stability Studies for Diazoxide Choline Controlled Release Tablets

Studies to determine the stability of formulations of diazoxide choline salt as the controlled release tablet were conducted on sample formulations as described in Table 2, results of which are shown in Table 7. In these studies, storage conditions were the following: a) 25° C./60% RH, and b) 40° C./75% RH. In Table 7, the term "Appearance" refers to the physical appearance of the tablets of the study. The term "Assay (%)" refers to the percentage of diazoxide choline salt assayed with respect to nominal (i.e., 50 mg or 200 mg) content of the sample The term "Dissolution (%)" refers to the amount, expressed as a percentage, of diazoxide choline salt assayed by method described herein.

TABLE 7

Stability Study for Formulations of Diazoxide Choline Salt.

| | Time point | | |
|---|---|---|---|
| Test | Initial | 1 month | 2 months |
| 50 mg tablet, Formulation J, 25° C./60% RH, | | | |
| Appearance | White tablets | White tablets | White tablets |
| Assay (%) | 95.8 | 102.9 | 99.3 |
| Dissolution (%): | | | |
| 3 hr | 24 | 19 | 15 |
| 6 hr | 41 | 30 | 27 |
| 12 hr | 62 | 48 | 52 |
| 24 hr | 92 | 90 | 94 |
| 50 mg tablet, Formulation J, 40° C./75% RH, | | | |
| Appearance | White tablets | White tablets | White tablets |
| Assay (%) | 95.8 | 103.2 | 99.4 |
| Dissolution (%): | | | |
| 3 hr | 24 | 10 | 10 |
| 6 hr | 41 | 22 | 21 |
| 12 hr | 62 | 50 | 46 |
| 24 hr | 92 | 90 | 84 |
| 200 mg tablet, Formulation K, 25° C./60% RH | | | |
| Appearance | White tablets | White tablets | White tablets |
| Assay (%) | 95.9 | 100.9 | 100.3 |
| Dissolution (%): | | | |
| 3 hr | 34 | 15 | 13 |
| 6 hr | 53 | 31 | 30 |
| 12 hr | 76 | 69 | 68 |
| 24 hr | 104 | 101 | 96 |
| 200 mg tablet, Formulation K, 40° C./75% RH | | | |
| Appearance | White tablets | White tablets | White tablets |
| Assay (%) | 95.9 | 99.6 | 100.0 |
| Dissolution (%): | | | |
| 3 hr | 34 | 10 | 10 |
| 6 hr | 53 | 26 | 28 |
| 12 hr | 76 | 60 | 61 |
| 24 hr | 104 | 90 | 90 |

3.5. A Controlled Release Dosage Form of Diazoxide or a Derivative Thereof Using an Osmotically Controlled Release System.

Diazoxide salt or a derivative thereof is formulated as an osmotically regulated release system. In general, two components, and an expandable hydrogel that drives release of the active drug is assembled with diazoxide salt or a derivative thereof into a semipermeable bilaminate shell. Upon assembly a hole is drilled in the shell to facilitate release of active upon hydration of the hydrogel.

A dosage form adapted, designed and shaped as an osmotic delivery system is manufactured as follows: first, a diazoxide salt or a derivative thereof composition is provided by blending together into a homogeneous blend of polyethylene oxide, diazoxide salt or a derivative thereof and hydroxypropyl methylcellulose. Then, a volume of denatured anhydrous ethanol weighing 70% of the dry mass is added slowly with continuous mixing over 5 minutes. The freshly prepared wet granulation is screened through a 20 mesh screen through a 20 mesh screen, dried at room temperature for 16 hours, and again screened through a 20 mesh screen. Finally, the screened granulation is mixed with 0.5% weight of magnesium stearate for 5 minutes.

A hydrogel composition is prepared as follows: first, 69% weight of polyethylene oxide weight, 25% weight of sodium chloride and 1% weight ferric oxide are separately screened through a 40 mesh screen. Then, all the screened ingredients are mixed with 5% weight of hydroxypropyl methylcellulose to produce a homogeneous blend. Next, a volume of denatured anhydrous alcohol equal to 50% of the dry mass is added slowly to the blend with continuous mixing for 5 minutes. The freshly prepared wet granulation is passed through a 20 mesh screen, allowed to dry at room temperature for 16 hours, and again passed through a 20 mesh screen. The screened granulation is mixed with 0.5% weight of magnesium stearate for 5 minutes (see U.S. Pat. No. 6,361,795 by Kuczynski, et al.).

The diazoxide salt composition, or a derivative thereof, and the hydrogel composition, are compressed into bilaminate tablets. First the diazoxide salt or a derivative thereof composition is added and tamped. The hydrogel composition is then added and the laminae are pressed under a pressure head of 2 tons into a contacting laminated arrangement.

The bilaminate arrangements are coated with a semipermeable wall (i.e. thin film). The wall forming composition comprises 93% cellulose acetate having a 39.8% acetyl content, and 7% polyethylene glycol. The wall forming composition is sprayed onto and around the bilaminate.

Finally, an exit passageway can be drilled through the semipermeable wall to connect the diazoxide salt or a derivative thereof drug lamina with the exterior of the dosage system. Residual solvent is removed by drying at 500 C and 50% humidity. The osmotic systems are dried at 500 C to remove excess moisture (see U.S. Pat. No. 6,361,795 by Kuczynski, et al.).

4. Preparation of Diazoxide Salts
4.1. Preparation of the Sodium Salt

The sodium salt of diazoxide was prepared by dissolving 300 mg of diazoxide in approximately 45 mL methyl ethyl ketone (MEK). The diazoxide/MEK solution was heated at 75° C. on an orbital shaker to ensure dissolution. To the solution was added 1.3 mL of 1M NaOH (1 molar equivalent). The combined solutions were heated at 75° C. for approximately 30 minutes and allowed to cool to room temperature. The mixture was concentrated under reduced pressure, and dried in vacuo at 55° C. and 30 in. Hg. Elemental analysis: Calculated, 38.03% C, 2.39% H, 11.09% N and 9.1% Na; Found, 38.40% C, 2.25% H, 10.83% N and 7.4% Na.

A sodium salt of diazoxide was also prepared by dissolving 300 mg of diazoxide in approximately 45 mL acetonitrile. The diazoxide/acetonitrile solution was heated at 75° C. on an orbital shaker to ensure dissolution. To the solution was added 1.3 mL of 1M NaOH (approximately 1 molar equivalent). The combined solutions were heated at 75° C. for approximately 30 minutes and allowed to cool to room temperature. The mixture was concentrated under reduced pressure, and dried in vacuo at 55° C. and 30 in. Hg.

4.2. Preparation of the Potassium Salt

The potassium salt of diazoxide was prepared by dissolving 300 mg of diazoxide in approximately 45 mL methyl ethyl ketone (MEK). The diazoxide/MEK solution was heated at 75° C. on an orbital shaker to ensure dissolution. To the solution was added approximately 1.3 mL of 1 M KOH (1 molar equivalent) and the solution was returned to the orbital shaker, heated at 75° C. for approximately 30 minutes and allowed to cool to room temperature. The solvent was removed under reduced pressure and the solid was dried in vacuo at 55° C. and 30 in. Hg. Elemental analysis: Calculated, 33.59% C, 2.81% H, 9.77% N and 13.63% K; Found, 34.71% C, 2.62% H, 9.60% N and 10.60% K.

The potassium salt of diazoxide was also prepared by dissolving 300 mg of diazoxide in approximately 45 mL tetrahydrofuran (THF). The diazoxide/THF solution was heated at 75° C. on an orbital shaker to ensure dissolution. To the solution was added approximately 1.3 mL of 1 M KOH (1 molar equivalent) and the resulting solution was returned to the orbital shaker, heated at 75° C. for approximately 30 minutes and allowed to cool to room temperature. THF was removed under reduced pressure and the solid was dried in vacuo at 55° C. and 30 in. Hg.

4.3. Preparation of Choline Salt
4.3.1. Preparation of the Choline Salt: Proof of Concept The choline salt of diazoxide was prepared by dissolving 300 mg of diazoxide in approximately 45 mL methyl ethyl ketone (MEK). The diazoxide/MEK solution was heated at 75° C. on an orbital shaker to ensure dissolution. To the solution was added approximately 315 mg of 50 wt. % of choline hydroxide (1 molar equivalent) and the solution was returned to the orbital shaker and stirred at 75° C. for approximately 30 minutes. The solvent was removed under reduced pressure, and the solid was dried in vacuo at 55° C. and 30 in. Hg. Elemental analysis: Calculated, 46.77% C, 5.86% H, and 12.00% N; Found, 46.25% C, 6.04% H, and 12.59% N.

4.3.2. Process of Preparation of the Choline Salt

An investigation of the minimum solvent volumes required to optimize the formation of the diazoxide choline salt was performed in MeCN, THF, MEK, and 2-MeTHF on small scale in the presence and absence of MTBE. Analyses by $^1$H NMR and XRPD of all reactions were consistent with the assigned structure and Form B of diazoxide choline salt.

4.3.2.1. Solvent Efficiency Study with Single Solvent System.

Investigation of single solvent system synthesis of diazoxide choline salt using solvents THF, MEK, and 2-MeTHF were conducted, results of which are shown in Table 8. These results suggest that precipitation can be achieved with a single solvent system in THF or 2-MeTHF. The best results, (i.e., Table 8 entries 14-17) obtained with 2-MeTHF. However, it was observed that in 2-MeTHF at 3-volumes and above, complete dissolution was not achieved after addition of choline hydroxide.

TABLE 8

Solvent Efficiency of a Single Solvent System

| Entry | Solvent | Solvent volume | Yield (%) | Polymorphic Form |
|---|---|---|---|---|
| 1 | THF | 1.0 | 7 | B |
| 2 | THF | 2.0 | n/a | n/a |
| 3 | THF | 3.0 | 20 | B |
| 4 | THF | 4.0 | 28 | B |
| 5 | THF | 5.0 | 32 | B |
| 6 | THF | 6.0 | 42 | B |
| 7 | THF | 7.0 | 53 | B |
| 8 | THF | 8.0 | 50 | B |
| 9 | MEK | 4.0 | n/a | n/a |
| 10 | 2-MeTHF | 1.0 | n/a | n/a |
| 11 | 2-MeTHF | 2.0 | 48 | B |
| 12 | 2-MeTHF | 3.0 | 41 | B |
| 13 | 2-MeTHF | 4.0 | 48 | B |
| 14 | 2-MeTHF | 5.0 | 71 | B |
| 15 | 2-MeTHF | 6.0 | 71 | B |
| 16 | 2-MeTHF | 7.0 | 72 | B |
| 17 | 2-MeTHF | 8.0 | 67 | B | n/a: Samples were either seen to form a gum, or no precipitate was observed.

4.3.2.2. Solvent Efficiency Study with Binary Solvent Systems.

The addition of a second solvent at 1-20 volumes (i.e., 1-8, 9, 10, 11, 12, 13, 14, 15, 16, 17, 18, 19, 20) to the solvent volumes of Table 8 was envisaged to optimize diazoxide salt production yields. Results of investigation of methods to enhance precipitation and increase yield employing binary solvent system synthesis of diazoxide choline salt using solvents THF, MeCN, MEK, and 2-MeTHF and co-solvent MTBE are shown in Table 9. Optimum conditions for the preparation of the diazoxide choline salt obtained with 1-3 volumes of THF (see Table 8, entries 1-3), with 3 volumes being the ratio of choice to eliminate excessive drag during stirring of slurry in large scale production.

TABLE 9

Solvent Efficiency of a Binary Solvent System

| Entry | Solvent | Solvent Volume | Co-Solvent (12 Vol) | Yield (%) | Polymorphic Form |
|---|---|---|---|---|---|
| 1 | THF | 1.0 | MTBE | 96 | B |
| 2 | THF | 2.0 | MTBE | 96 | B |
| 3 | THF | 3.0 | MTBE | 91 | B |
| 4 | THF | 4.0 | MTBE | 90 | B |
| 5 | THF | 5.0 | MTBE | 84 | B |
| 6 | THF | 6.0 | MTBE | 90 | B |
| 7 | THF | 7.0 | MTBE | 94 | B |
| 8 | THF | 8.0 | MTBE | 94 | B |
| 9 | MeCN | 1.0 | MTBE | 92 | B |
| 10 | MeCN | 2.0 | MTBE | 90 | B |
| 11 | MeCN | 3.0 | MTBE | 87 | B |
| 12 | MeCN | 4.0 | MTBE | 79 | B |
| 13 | MeCN | 5.0 | MTBE | 79 | B |
| 14 | MeCN | 6.0 | MTBE | 75 | B |
| 15 | MeCN | 7.0 | MTBE | 70 | B |
| 16 | MeCN | 8.0 | MTBE | 74 | B |
| 17 | MEK | 4.0 | MTBE | 83 | B |
| 18 | 2-MeTHF | 1.0 | MTBE | 97 | B |
| 19 | 2-MeTHF | 2.0 | MTBE | 94 | B |
| 20 | 2-MeTHF | 3.0 | MTBE | 94 | B |
| 21 | 2-MeTHF | 4.0 | MTBE | 95 | B |
| 22 | 2-MeTHF | 5.0 | MTBE | 97 | B |
| 23 | 2-MeTHF | 6.0 | MTBE | 94 | B |
| 24 | 2-MeTHF | 7.0 | MTBE | 97 | B |
| 25 | 2-MeTHF | 8.0 | MTBE | >99 | B |

4.3.2.3. Co-Solvent Efficiency and Optimization with MTBE.

Results of optimization of co-solvent (MTBE) volume in the presence of 3 volumes of solvent are shown in Table 10.

TABLE 10

Co-Solvent Efficiency and Optimization with MTBE

| Entry | Solvent | MTBE Volume | Yield (%) | Form |
|---|---|---|---|---|
| 1 | MeCN | 8.0 | 76 | B |
| 2 | MeCN | 14.0 | 85 | B |
| 3 | THF | 6.0 | 93 | B |
| 4 | THF | 8.0 | 93 | B |
| 5 | THF | 14.0 | 98 | B |

Optimized conditions for the production of the choline salt of diazoxide in a binary solvent system obtained with 3:14 (i.e., 1:4.7) THF/MTBE (v/v).

4.3.2.4. Optimization of Cooling Profile.

Optimization for the controlled precipitation of diazoxide choline salt was conducted by varying the cooling temperatures and hold times. Reactions were carried out in MeCN, THF, and 2-MeTHF (3 vol) with MTBE (14 vol). The results are presented in Table 11. These results suggest that optimum crystal growth was achieved with cooling to 0-5° C. for eight hours in THF and 2-MeTHF (Entries 5-6) when compared to those in MeCN (Entries 1, 2, and 4). These results however did not indicate enhanced precipitation when compared to previous studies carried out in THF and 2-MeTHF when the slurries were allowed to stir for two hours. In addition no notable improvements were observed for the additional cooling to −15° C. or with the filtration at ambient temperature.

TABLE 11

Cooling Profile Optimization for Controlled Precipitation

| Entry | Solvent | Cooling Temp. (° C.) | Hold Time (hr) | Yield (%) | Form |
|---|---|---|---|---|---|
| 1 | MeCN | 0-5 | 2 | 89 | B |
| 2 | MeCN | −10 → −15 | 2 | 85 | B |
| 3 | THF | RT | 2 | 80 | B |
| 4 | MeCN | RT | 2 | 85 | B |
| 5 | THF | 0-5 | 8 | 94 | B |
| 6 | 2-MeTHF | 0-5 | 8 | 95 | B |

4.3.2.5. Optimization of Rate of Co-Solvent Addition.

The effect of rate and hold time of co-solvent addition on the precipitation of diazoxide choline salt was examined. The reactions were carried out on 500 mg scale in three volumes of primary solvent and 14 volumes of MTBE (THF and 2-MeTHF) or 1:3 volume ratio (MeCN). Addition of the co-solvent was made dropwise in one portion for Entry 1, and for Entries 2 and 3 the co-solvent was added at a rate of 1 mL/20 minutes for a total hold time of 140 minutes for the addition of 7 mL. The results, presented in Table 12, indicate that optimum precipitation of diazoxide choline salt was achieved by the addition of MTBE with 20 minute hold times in between additions in THF or 2-MeTHF (entries 2-3).

TABLE 12

Optimization of Rate of Co-solvent addition

| Entry | Solvent | Hold Time (min) | Addition Rate (mL/min) | Yield (%) | Form |
|---|---|---|---|---|---|
| 1 | MeCN | 60 | n/a | 87 | B |
| 2 | THF | 140 | 1.0/20 | 96 | B |
| 3 | 2-MeTHF | 140 | 1.0/20 | 96 | B |

4.3.2.6. Thermal Stability Study.

The stability of the isolated diazoxide choline salt was investigated to determine optimal drying conditions to minimize residual solvents without degradation. Samples of the diazoxide choline salt prepared in THF and MTBE (Entries 1-4) were dried under vacuum at 40° C. for various durations on small scale (100 mg). The study was then carried out on 5 g scale (Entry 5) at 30° C. for eight hours under vacuum to show reproducibility on large scale. The results are presented in Table 13. Analyses of the samples of Table 13 by $^1$H NMR, XRPD, and HPLC indicated that elevated temperatures and prolonged drying times did not degrade the compound or affect the form of the compound.

TABLE 13

Thermal Stability Study

| Entry | Drying Temp (C.) | Time (h) | OVI (THF/MTBE) (ppm) | Polymorphic Form |
|---|---|---|---|---|
| 1 | RT | 12 | 376/248 | B |
| 2 | 40 | 20 | 317/160 | B |
| 3 | 40 | 28 | 276/127 | B |
| 4 | 40 | 42 | 268/128 | B |
| 5 | 30 | 8 | 241/509 | B |

4.3.2.6. Demonstration of 50-g Scale synthesis of Diazoxide Choline Salt in THF.

The preparation of the diazoxide choline salt was carried out in a binary-solvent system of THF and MTBE with a ratio of 1:4.7 (solvent/co-solvent) volumes and cooling to 0-5° C. for two hours with stirring. A demonstration run for the large scale production utilizing the modified procedure was carried out on 50 g-scale. Diazoxide (50 g) as a hot (62° C.) suspension in THF (140 mL) was treated with choline hydroxide (45% solution in MeOH, 1.0 equiv) added (2 mL/min) over 30 minutes. The resulting solution was stirred for 30 minutes, followed by cooling to 52° C. for the addition of MTBE (14 vol) over 45 minutes. On addition of two volumes of co-solvent precipitation was observed. The resultant slurry was then allowed to cool naturally to ambient temperature followed by further cooling to 0-5° C. with an ice/water bath and an additional 2 hr stirring. The precipitate was isolated by vacuum filtration, and the filter cake rinsed with ice cold MTBE (~50 mL) and dried under vacuum at room temperature for 12 hours. OVI analysis indicated that THF levels were above the recommended ICH guidelines (799 ppm) and the material was returned to the oven at 30° C. for eight hours to give diazoxide choline salt [70.87 g, 97% yield, 97% purity AUC] as a white crystalline solid. Analyses by $^1$H NMR, XRPD, and HPLC were consistent with the assigned structure of Form B while maintaining a high purity with good yield.

4.3.2.7. Demonstration of 50-g Scale Synthesis of Diazoxide Choline Salt in 2-MeTHF.

A 50-g level synthesis was duplicated in 2-MeTHF/MTBE as an alternative to THF/MTBE for the large scale production of the diazoxide choline salt described above. No issues or concerns arose during the reaction other than complete dissolution was not achieved after addition of the choline hydroxide. A white precipitate formed after addition of the co-solvent, which was isolated via vacuum filtration and dried under vacuum at 30° C. for eight hours to give diazoxide choline salt [71.51 g, 97% yield] as a white crystalline solid. Analyses by $^1$H, XRPD, and HPLC were consistent with the assigned structure and Form B. OVI analysis showed 2-MeTHF and MTBE levels of 125 and 191 ppm, respectively, which were below the ICH guidelines.

4.3.2.8. 250-g Scale Synthesis of Diazoxide Choline Salt in THF.

Larger scale preparation of the diazoxide choline salt was carried out in a binary-solvent system of THF and MTBE with a ratio of 1:4.7 (v/v) volumes. Diazoxide as a hot (62° C.) suspension in THF (745 mL) was treated with choline hydroxide as a 45% solution in MeOH (1.0 equiv) added over 30 minutes. The resulting solution was stirred for 30 minutes, followed by cooling to 52° C. for the addition of MTBE (14 vol) over 45 minutes. On addition of two volumes of co-solvent, precipitation was observed. The resultant slurry was then allowed to cool naturally to ambient temperature followed by cooling to 0-5° C. with an ice/water bath. The precipitate was isolated by vacuum filtration, and the filter cake rinsed with ice cold MTBE (approximately 250 mL) and dried under vacuum at 30° C. for 38 hours to give diazoxide choline salt (350.28 g, 97.7% yield) as a white crystalline solid. Analyses by $^1$H NMR, XRPD, and HPLC were consistent with the assigned structure of Form B while maintaining a high purity with good yield.

4.3.2.9. 2-kg Scale Synthesis of Diazoxide Choline Salt in THF.

A 12-L reaction flash was charged with 2.0 kg diazoxide and 5.0-L THF with stirring and heating to 55° C. Choline hydroxide (45% solution in methanol, 2.32 L) was added dropwise to this reaction mixture over about 2.5 hr with stirring. The temperature was maintained at 60±5° C. After addition of choline hydroxide, stirring was continued for about 30 min. The reaction mixture was clarified by in-line 10 micron filtration upon transfer to a 22-L reaction flask pre-charged with 2-L pre-filtered THF, into which was added 10-L pre-filtered MTBE dropwise. This reaction mixture was transferred to another flask which was then charged with an additional 30-L pre-filtered MTBE dropwise, with adjustment of temperature to <5° C. and stirring for about 2 hr. Diazoxide choline salt was recovered by vacuum filtration to afford 2.724 kg (94%) diazoxide choline salt (99.8%, HPLC purity), confirmed by $^1$H NMR, IR, and UV/Visible analysis.

4.4. Preparation of the Hexamethyl Hexamethylene Diammonium Hydroxide Salt

The hexamethyl hexamethylene ammonium salt of diazoxide was prepared by dissolving 50 mg of diazoxide in approximately 7.5 mL methyl ethyl ketone (MEK). The diazoxide/MEK solution was heated at 75° C. on an orbital shaker to ensure dissolution. To the solution was added approximately 2.17 mL of 0.1M hexamethyl hexamethylene ammonium hydroxide solution (1 molar equivalent) and the solution was stirred at 75° C. for an additional 10 minutes and then cooled to room temperature at the rate of 30° C./h. The solvent was removed under reduced pressure, and the solid was dried in vacuo at 55° C. and 30 in. Hg.

4.5. Failure to Obtain Salts of Diazoxide and Derivatives

4.5.1. Failure to Obtain Salts from Alkali Metal Hydroxides

U.S. Pat. No. 2,986,573 ("the '573 patent") describes the synthesis of diazoxide metal salts in aqueous or non-aqueous solutions in the presence of an alkali metal alkoxide. According to the '573 patent, diazoxide can be dissolved in an alkali metal solution, and the salt obtained upon evaporation. Also described is a method for forming salts from non-aqueous media wherein diazoxide and sodium methoxide are dissolved in anhydrous methanol and the solvent is evaporated to obtain the sodium salt of diazoxide as a white solid.

Attempts were made to prepare a diazoxide salt from alkali metal hydroxides by the method described in the '573 patent. Salt preparation was carried out in aqueous media by dissolving diazoxide in a basic solution 1M NaOH, followed by evaporation of the solvent. A solid was obtained and analyzed by XRPD (X-Ray Powder Diffraction) and NMR. However, this analysis confirmed that the solid obtained was the diazoxide starting material and not a salt.

Salt preparation was carried out in non-aqueous media by dissolving diazoxide in anhydrous methanol in the presence of either sodium methoxide or potassium methoxide and stirring the mixture at 60° C. for 15 minutes. The mixture was then cooled to room temperature while stirred. After approximately two hours, a solid was recovered, isolated by filtration, and dried in vacuo. Analysis by XRPD confirmed that the solid obtained was the diazoxide starting material and not a salt.

Figure 15A:
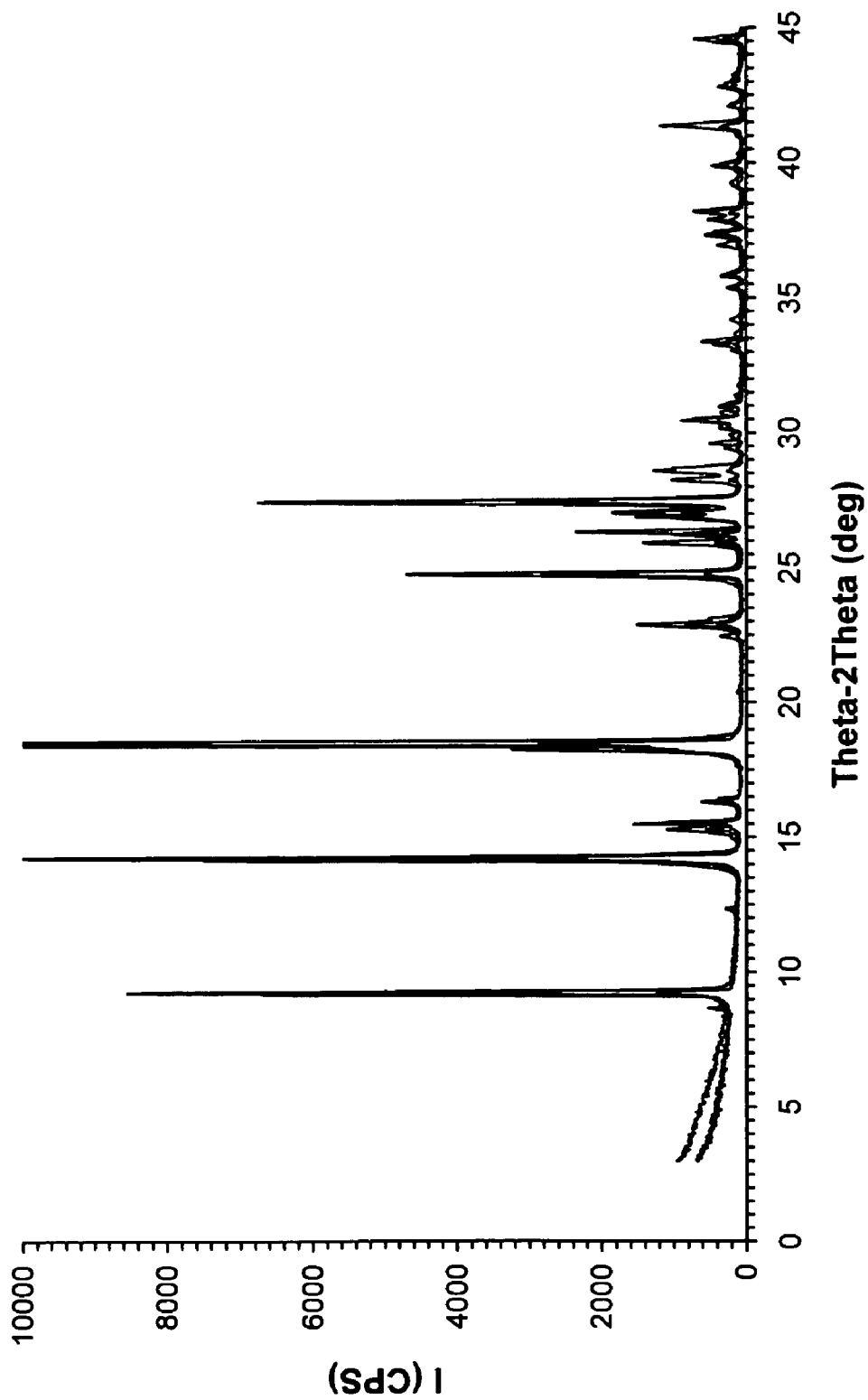
FIG. 15A shows overlay XRPD patterns of free form diazoxide, the product of potassium methoxide in methanol, and the product of sodium methoxide in methanol.
Figure 15B:
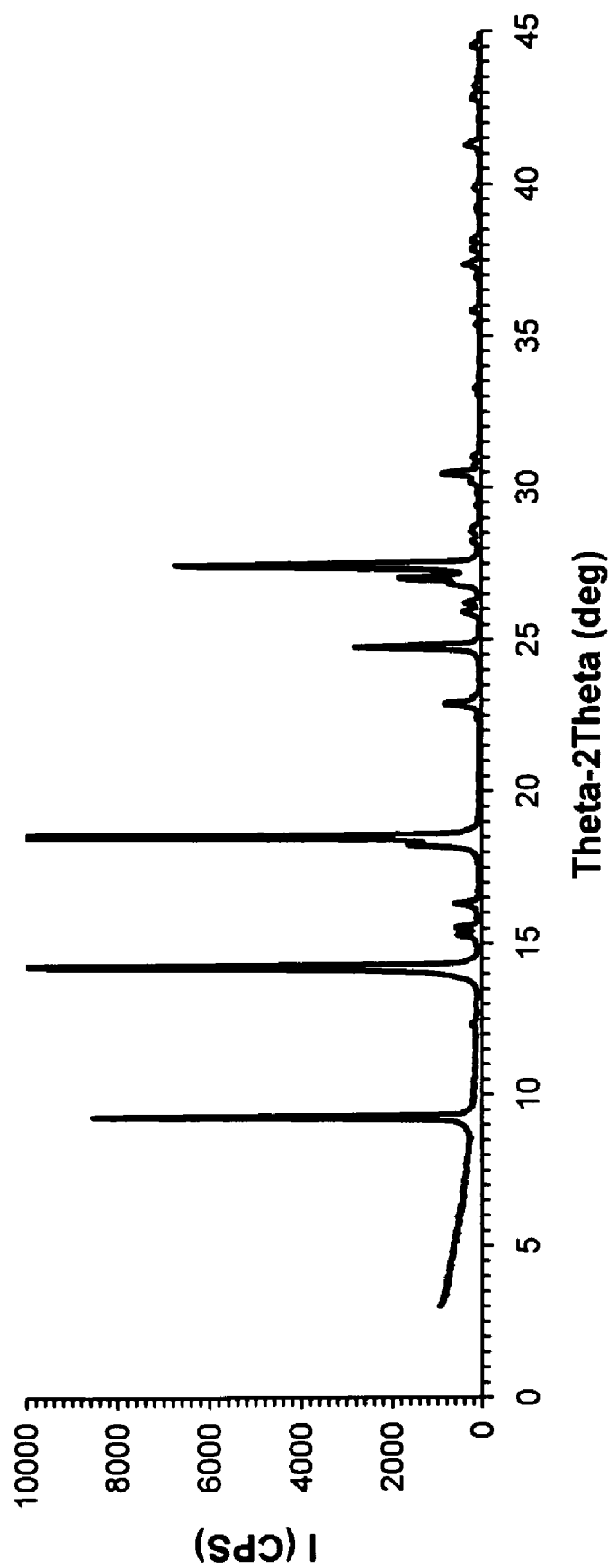
FIG. 15B, FIG. 15C and FIG. 15D show the XRPD patterns for product of potassium methoxide reaction with diazoxide in methanol, product of sodium methoxide reaction with diazoxide in methanol, and freeform diazoxide, respectively.
Figure 15C:
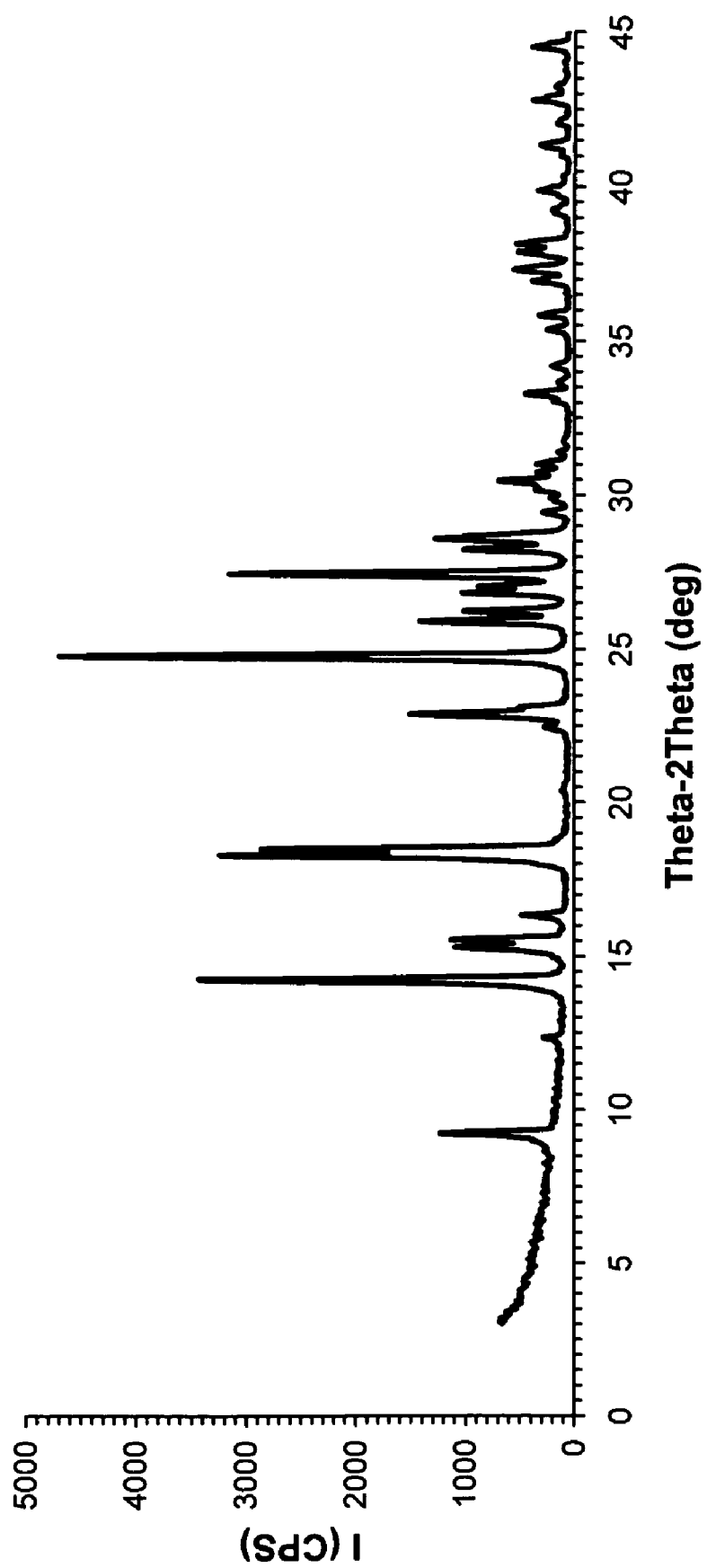
Figure 15D:
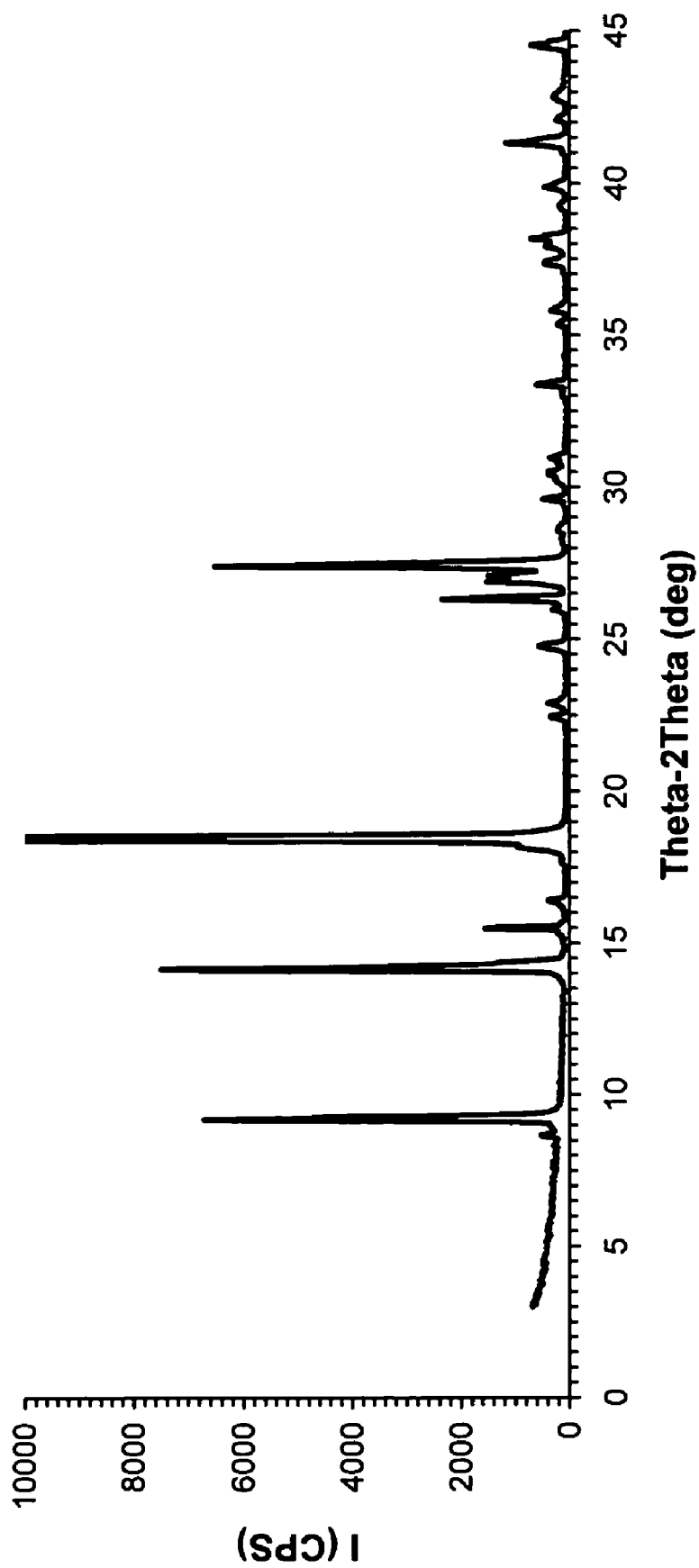

4.5.2. Preparation of Salts in Methanol or Ethanol According to the '573 Patent The preparation of diazoxide salts in methanol and ethanol was attempted using 22 different counter-ions according to the methods described by the '573 patent. For example, 20 mg of diazoxide was dissolved in 5 mL of ethanol and stirred and heated to ensure dissolution of the diazoxide. To the stirred solution was added approximately 1 molar equivalents of sodium methoxide. The solution was stirred for approximately 10-15 minutes at 60° C., and cooled to room temperature for approximately 2 hours. The resulting solid precipitate was concentrated under a nitrogen stream, and collected by filtration. The product was dried in vacuo and analyzed by XRPD. As shown in FIG. 15, XRPD of the solids collected from the sodium methoxide experiment, (as well as the solids collected from the potassium methoxide experiment, which was run under similar conditions), revealed that the solid was the diazoxide starting material and that no sodium or potassium salt was prepared. In FIG. 15D is the XRPD pattern of free form diazoxide; in FIG. 15B is the XRPD pattern of the product of potassium methoxide in methanol, and in FIG. 15C is the XRPD pattern of the product of sodium methoxide in methanol.

Although not wishing to be bound by any theory, it is believed that a possible explanation for the failure to prepare diazoxide salts by the methods of the '573 patent (i.e., in the presence of alcohols, e.g., methanol or ethanol), is that the alcohol may have an effect on the stability of the alkali salts of diazoxide. This was supported by UV spectroscopy analysis of alkali salts of diazoxide (sodium and potassium). Both the sodium and potassium salts of diazoxide were synthesized by reacting diazoxide with NaOH or KOH in MEK. Elemental analysis, NMR and XRPD confirmed that the salts were made.

Upon dissolution of the sodium or the potassium salt in acetonitrile, the UV spectrum shows a shift into the red region of the spectrum for the $\lambda_{max}$ from approximately 268 nm for the free form of diazoxide to approximately 298 nm for both the potassium and sodium salt (see FIG. 1). Similarly, these salts can be stabilized in aqueous solutions by elevating the pH to above 9.0. A similar shift in the absorption maximum at pH 9.0 is measured using UV spectroscopy. Subsequent adjustment of the pH from greater than 9.0 to less than 6.2 results in the hydrolysis of the salt as measured by the recovery of the UV absorption pattern of the diazoxide free base (see FIG. 2). In contrast, when the sodium or the potassium salt is dissolved in methanol, the UV-Vis spectrum of the salt was identical to that of the diazoxide starting material, (see FIG. 3).

These results demonstrate that using methanol as the solvent is incompatible with the synthesis of alkali salts of diazoxide. In addition, the results show that isolation of an alkali metal salt of diazoxide (or any other salt) in the presence of an alcohol, such as methanol, may not be possible.

4.5.3. Failure to Obtain Salts from Acidic Counter Ions

Salt formation with diazoxide was also attempted using acidic counter-ions, such as, for example, hydrochloric acid, maleic acid, sulfuric acid, phosphoric acid, sulfamic acid, acetic acid, citric acid, lactic acid, tartaric acid, malonic acid, methanesulfonic acid, ethanesulfonic acid, benzenesulfonic acid, p-toluenesulfonic acid, cyclohexylsulfamic acid, fumaric acid, benzoic acid, undecylenic acid, salicylic acid and quinic acid. However, no salt formation was observed for any acid in any solvent.

For example, 100 mg of diazoxide was dissolved in 50 mL of acetone and heated to 35° C. To a stirred solution was added approximately 4.65 molar equivalents of HCl. The reaction mixture was allowed to cool to room temperature for approximately 3 hours, with no precipitation observed. Solvent was removed in vacuo. The resulting solid was analyzed by XRPD, and the observed XRPD pattern was consistent with the free form diazoxide starting material. In all cases, the attempted synthesis of diazoxide salts from acids was unsuccessful in all solvents attempted.

4.6. Preparation of Salts of Compounds of Formulae V-VIII

The chloride salt of 3-amino-4-methyl-1,2,4-benzothiadiazine-1,1-dioxide is prepared dissolving approximately 300 mg (1.4 mmol) in 45 mL acetonitrile. The mixture is heated to approximately 75° C. and stirred for 30 min. To the stirred solution, approximately 1 molar equivalent of HCl is added dropwise, and stirred for approximately 30 min at 75° C. The mixture is cooled to room temperature and the solvent is removed under reduced pressure, affording the chloride salt as a solid.

The sodium salt of 3-amino-4-methyl-1,2,4-benzothiadiazine-1,1-dioxide is prepared dissolving approximately 300 mg (1.4 mmol) in 45 mL acetonitrile. The mixture is heated to approximately 75° C. and stirred for 30 min. To the stirred solution, approximately 1 molar equivalent of NaOH is added dropwise, and stirred for approximately 30 min at 75° C. The mixture is cooled to room temperature and the solvent is removed under reduced pressure, affording the sodium salt as a solid.

5. Characterization of Prepared Diazoxide Salts

Synthesis of the desired salts was confirmed by X-Ray Powder Diffraction (XRPD), UV-Vis spectroscopy, and NMR. All spectra were compared with the spectra of the free form diazoxide (i.e., not a salt). Differential scanning calorimetry (DSC), thermal gravimetric analysis (TGA), FTIR (Fourier transform infrared spectroscopy), NMR, UV-vis spectroscopy and moisture sorption analysis were also performed.

5.1. Experimental Procedures

DSC analysis were conducted with a Mettler 822 DSC, by measuring the amount of energy released by a sample, as the sample was heated from 30° C. to between 300-500° C. at a rate of 10° C./min. Typical applications of DSC analysis include determination of melting point temperature and the heat of melting; measurement of the glass transition temperature; curing and crystallization studies; and identification of phase transformations.

TGA measurements were conducted with a Mettler 851 SDTA/TGA, by measuring weight loss as a function of increasing temperature, as the samples were heated from 30° C. to 230° C. at a rate of 10° C./min. The TGA can be used to analyze deabsorption and decomposition behavior, characterize oxidation behavior, set burnout or conditioning parameters (temperature/ramp rate/time), and determine chemical composition.

XRPD samples were analyzed with a Shimadzu XRD-6000 system, using a Cu Kα, 40 kV, 40 mA X-ray tube. The divergence and scatter slits were 1.00 deg, and the receiving slit was 0.30 mm. Samples were continuously scanned at a range of 3.0-45.0 deg, with a step size of 0.04 deg., at a scan rate of 2 deg/min.

Fourier Transform Infrared Spectroscopy was measured with a Thermo-Nicolet Avatar 370 with a Smart Endurance Attenuated Total Reflection (ATR) attachment. Compressed samples were analyzed, with corrections for background noise being made. Using the IR spectrum, chemical bonds and the molecular structure of organic compounds can be identified. Attenuated total reflectance (ATR) allows for the analysis of thin films, organic and inorganic, in areas as small as 10-15 microns.

Nuclear Magnetic Resonance (NMR) was performed with a 400 MHz Bruker Avance with a 4 mm CPAMAS H—X probe. Acquisition of $^1$H NMR spectra were performed by taking between 5-10 mg of the sample, dissolved in approximately 0.78 mL of DMSO-$d_6$. Spectra were acquired with either 16 or 32 scans, using a pulse delay of 1.0 sec, with a 10 μsec (30°) pulse width.

UV spectroscopy was performed with a Perkin-Elmer Lambda 25 spectrometer. Samples were dissolved in acetonitrile, water and a buffer system having a pH between 5.6 and 10. Spectra were acquired between 340 and 190 nm, using a 1 cm path length with background correction.

Moisture Sorption Analysis was performed with a Hiden IGAsorp Moisture Sorption Instrument. Samples were first dried at 0% relative humidity at 25° C. until an equilibrium weight was reached, or for a maximum of 4 hours. Samples were then subjected to an isothermal (25° C.) scan from 10-90% relative humidity in steps of 10%. The samples were allowed to equilibrate to an asymptotic weight at each point for a maximum of 4 hours. Following absorption, a desorption scan from 85% relative humidity (at 25° C.) was run in steps of −10%, again allowing a maximum of 4 hours for the samples to equilibrate. The resulting samples after desorption were dried at 80° C. for two hours and analyzed by XRPD.

5.2. Free Form Diazoxide Characterization

The free form of diazoxide was characterized by XRPD, differential scanning calorimetry (DSC), thermal gravimetric analysis (TGA), moisture sorption, $^1$H NMR, FTIR and UV-vis spectroscopy to provide a baseline for comparison with the salts. Free form diazoxide is highly crystalline, as shown by the XRPD pattern. (See FIG. 4($a$)). The DSC shows a large endothermic event at 330° C., and TGA shows that the free form of diazoxide is anhydrous, where diazoxide shows no weight loss below 200° C., and a weight loss of only 0.2% below 230° C. Moisture absorption of the free form diazoxide shows the material to be non-hygroscopic. Absorption of water by diazoxide was tested at between 0-90% relative humidity (RH) at 25° C., showing absorption of approximately 0.04 wt % at 60% RH and 0.20 wt % at 90% RH. The molecule does not form a stable hydrate, as shown by the lack of hysteresis during desorption. Additionally, the XRPD pattern for the diazoxide before and after absorption of water indicate the same crystalline form.

Figure 2:
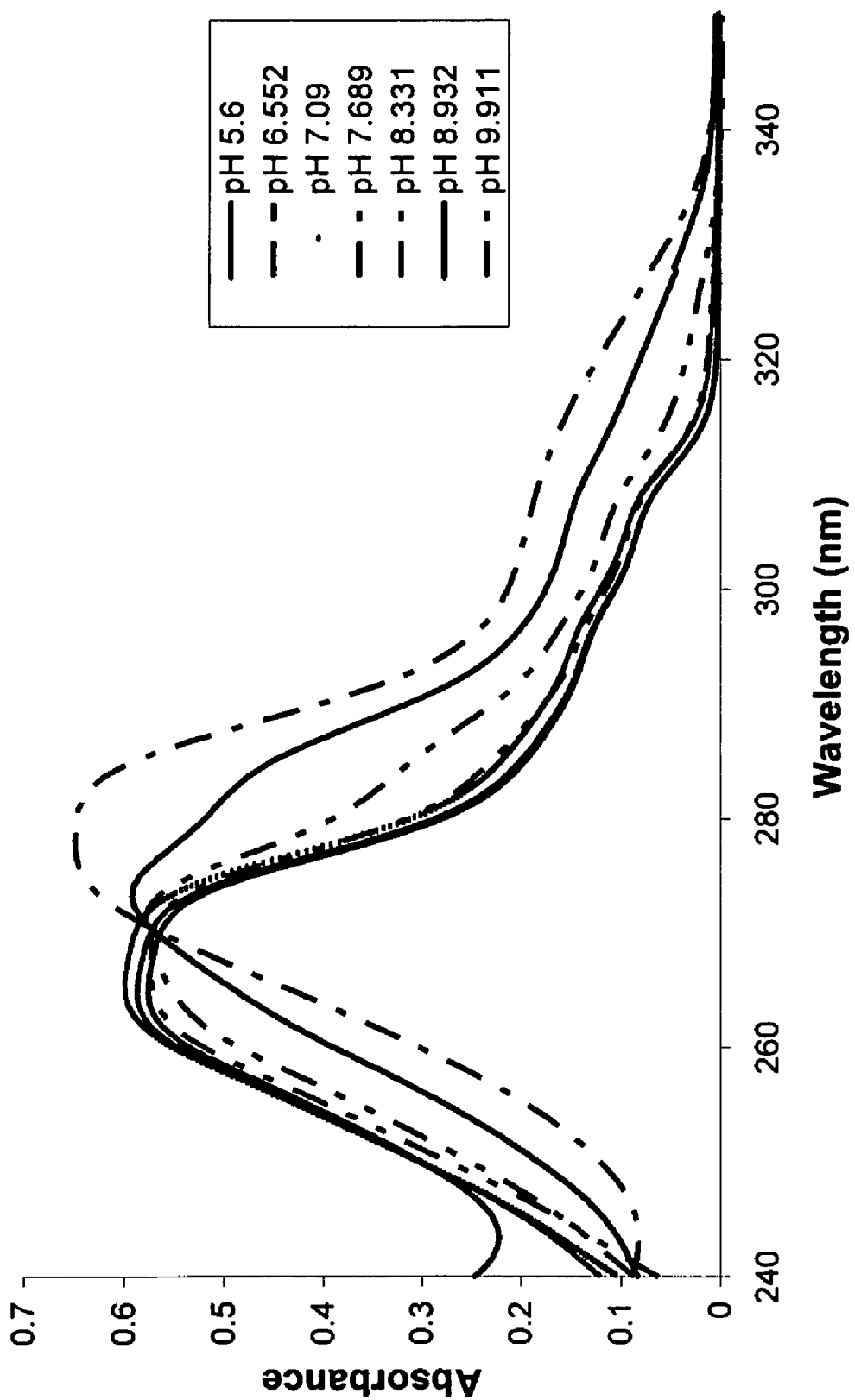
FIG. 2 shows UV spectra of the free form diazoxide at varying pH.
Figure 3:
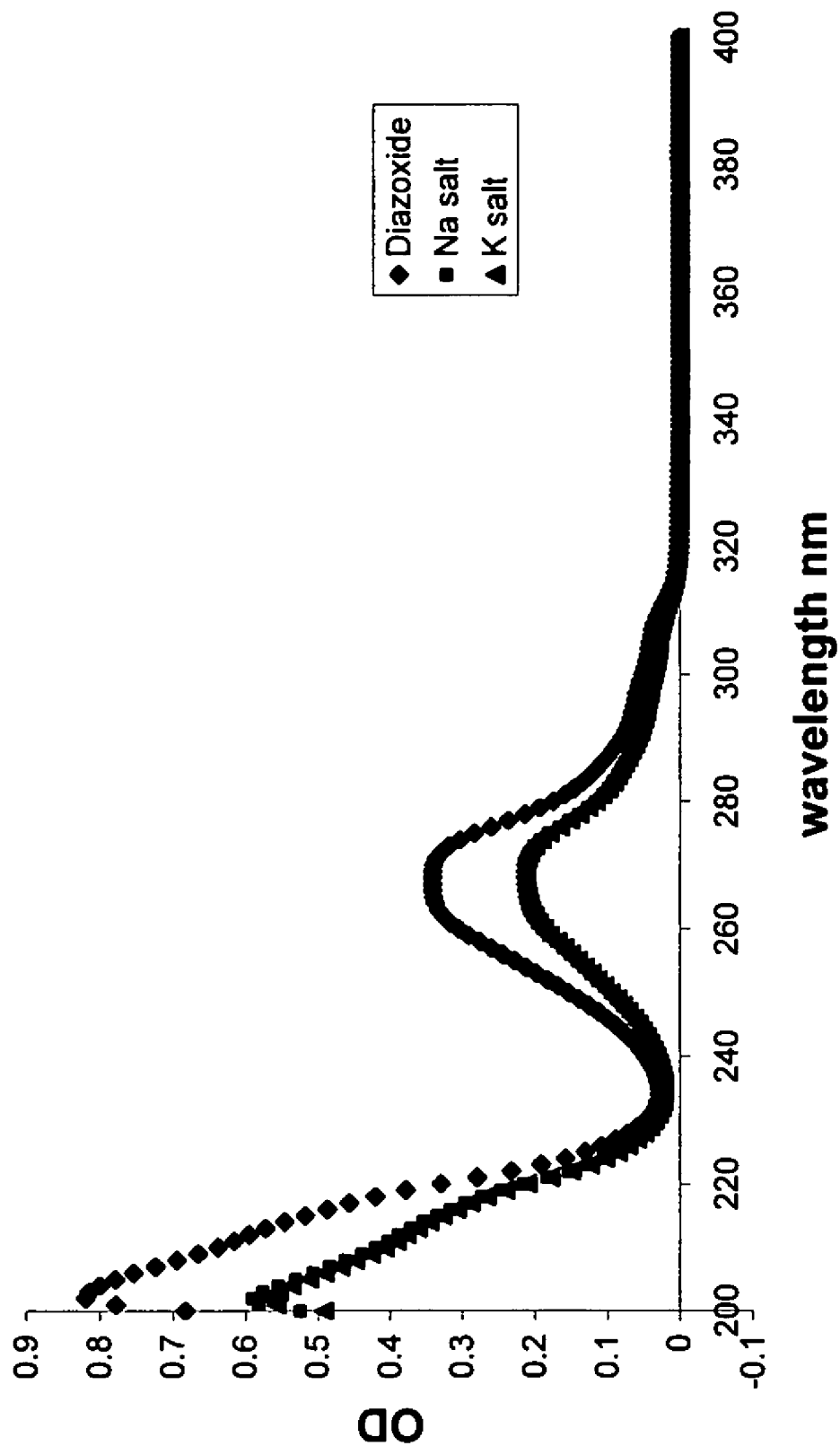
FIG. 3 shows UV spectra of the free form diazoxide and sodium and potassium salts of diazoxide in methanol.
Figure 4A:
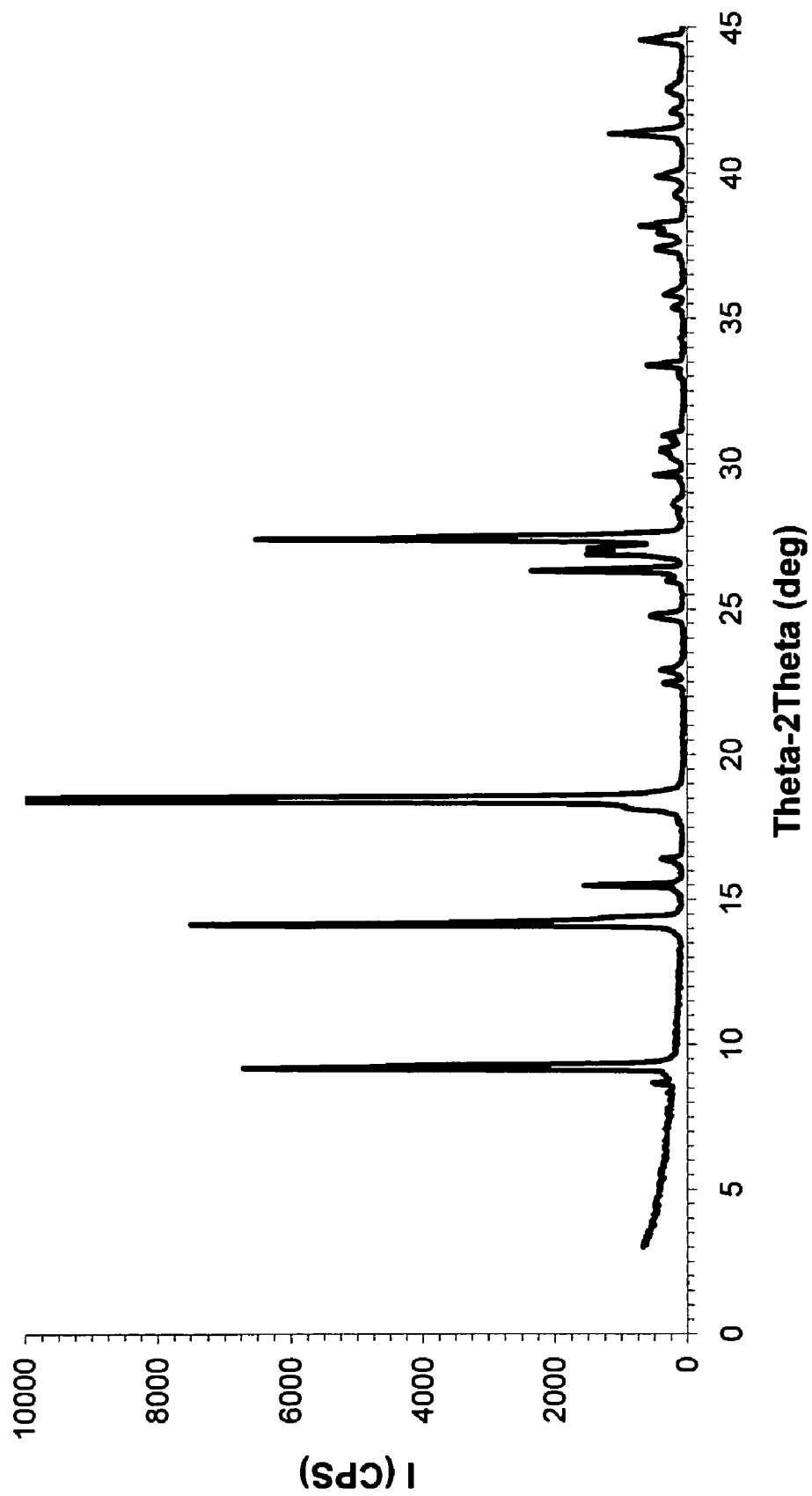
FIG. 4A, FIG. 4B, FIG. 4C, and FIG. 4D show an X-Ray Powder Diffraction patterns for (A) free form diazoxide, (B) potassium salt of diazoxide from THF, (C) lysine salt of diazoxide from MEK, and (D) sodium salt of diazoxide from acetonitrile, respectively.
Figure 4B:
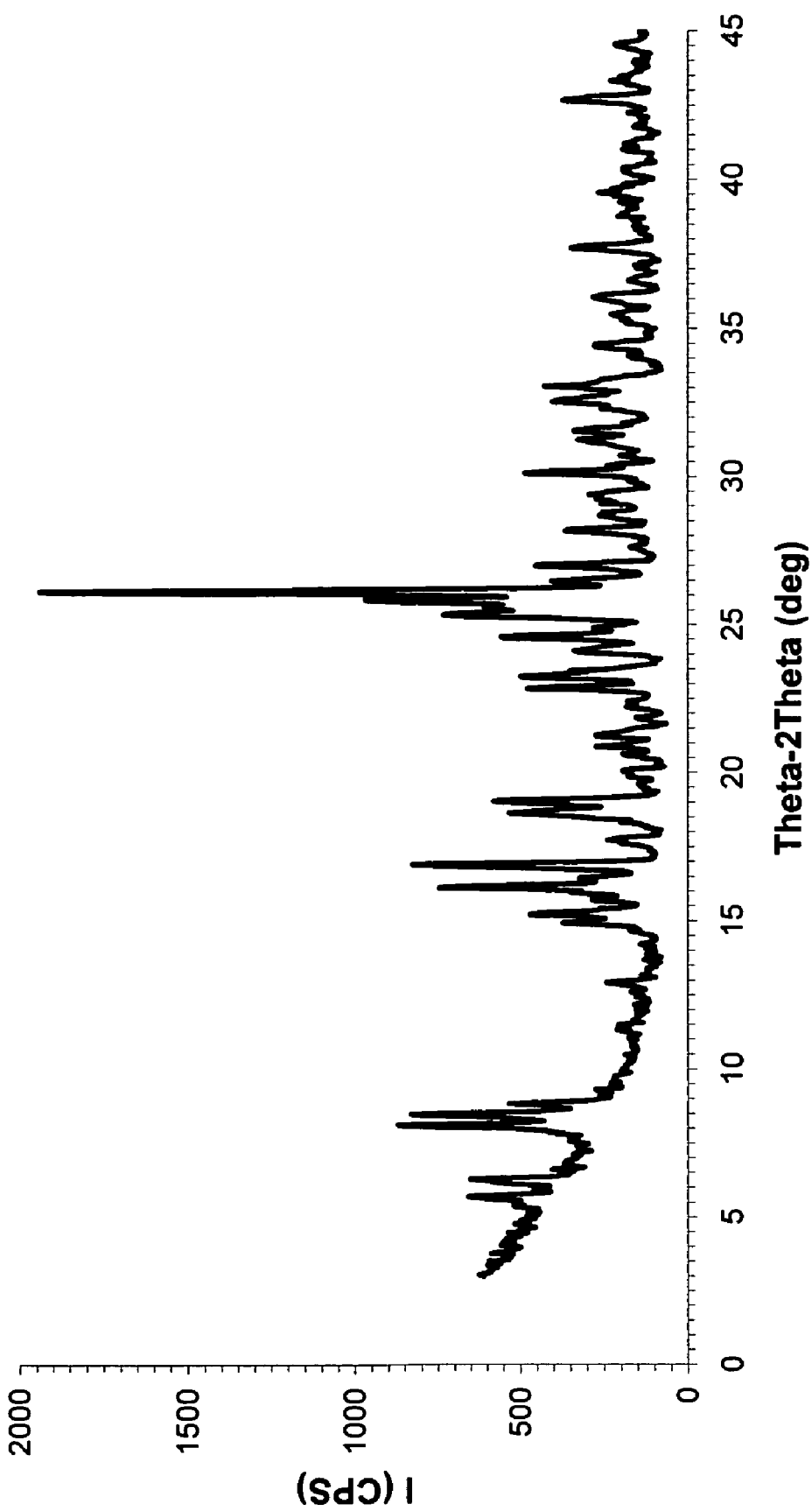
Figure 4C:
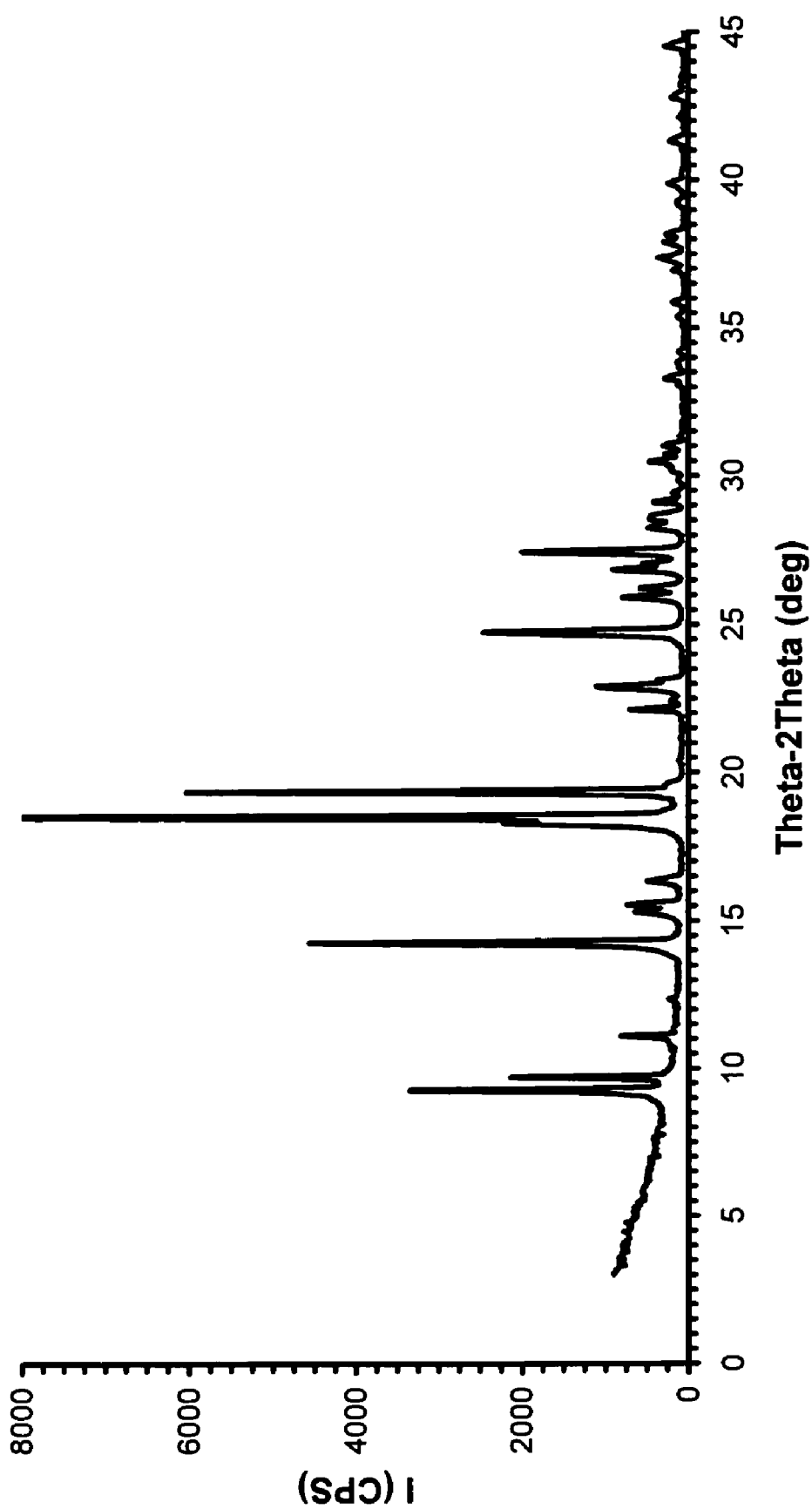
Figure 4D:
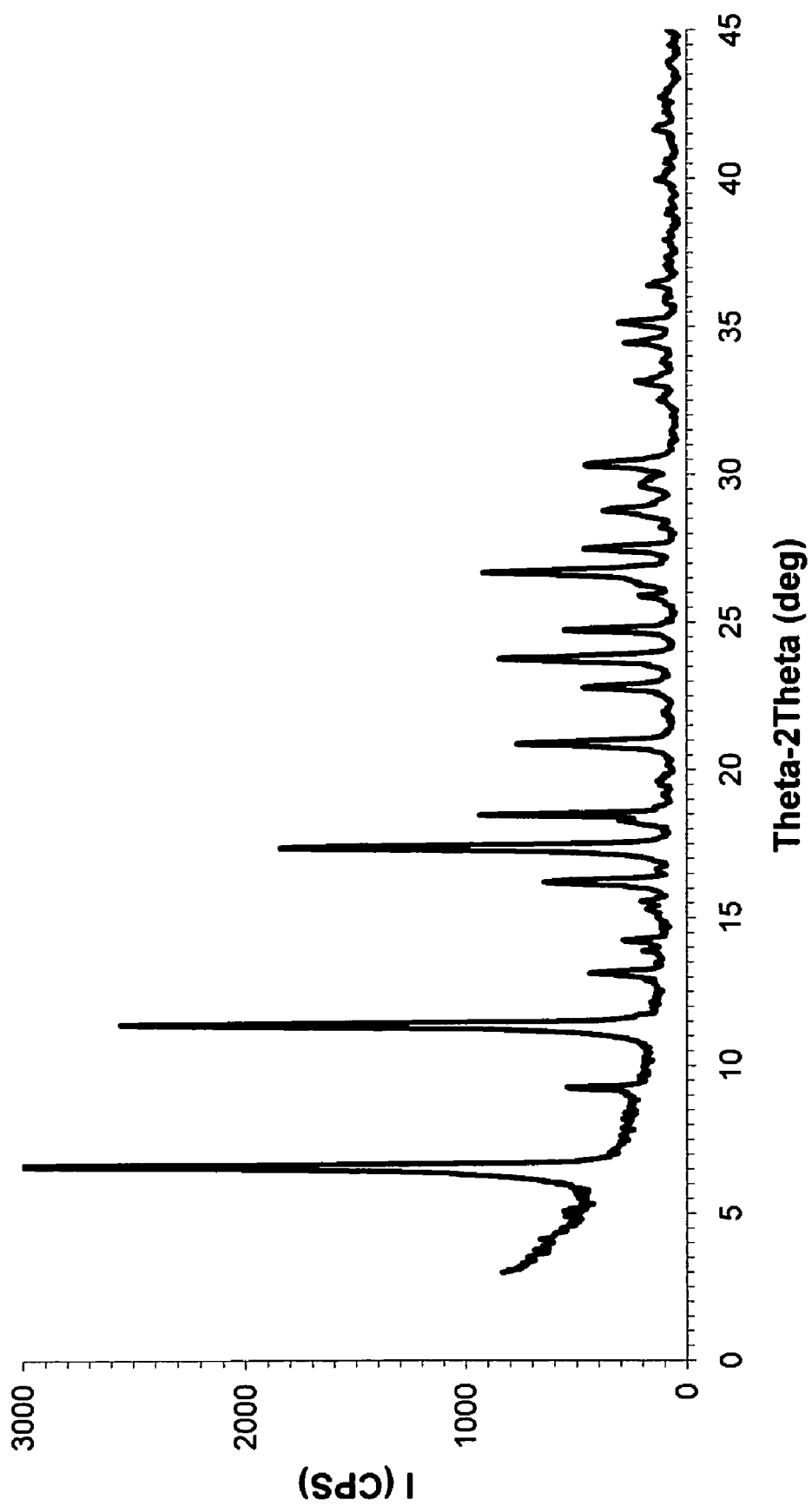

UV-vis spectroscopy measurements taken of the free form diazoxide in neutral aqueous solution show a λmax at approximately 268 nm. In acetonitrile, the λmax was 264 nm, demonstrating a small solvatochromic shift. As shown in FIG. 2, as pH increased the λmax also increased, from approximately 265 nm to approximately 280 nm, due to a change in the electronics of the molecule.

Studies were also conducted to evaluate the likelihood for conversion and degradation under thermal stress. Samples were heated in a closed environment, protected from light, at 60° C. for approximately 14 days. The diazoxide showed no conversion or degradation at 7 days or 14 days. Diazoxide samples were found to be consistent with the starting material with respect to XRPD and DSC.

Slurry studies to determine propensity of inter-conversion of the solid form were conducted on the free form diazoxide at room temperature, in the absence of light, using water, isopropyl alcohol, dichloromethane and toluene. Approximately 20 mg of the free form diazoxide was stirred for 14 days. Analysis by XRPD, DSC and HPLC were consistent with the starting material, indicating that the free form of diazoxide did not convert to alternate crystal forms.

5.3. Characterization of Sodium Diazoxide Salt

Figure 5A:
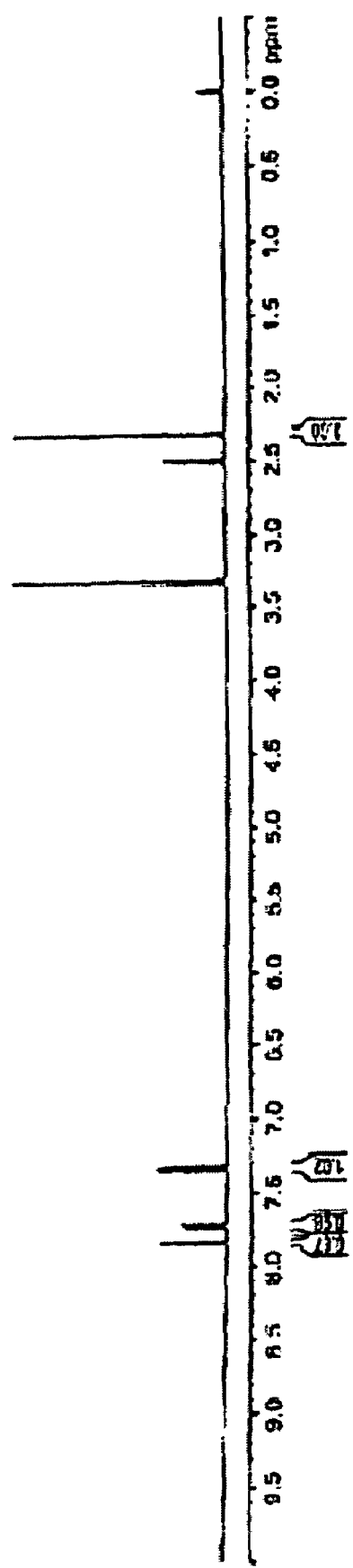
FIGS. 5A, 5B and 5C show NMR spectra (DMSO-d6 solvent) for (A) free form diazoxide, (B) potassium salt, and (C) sodium salt, respectively.
Figure 5B:
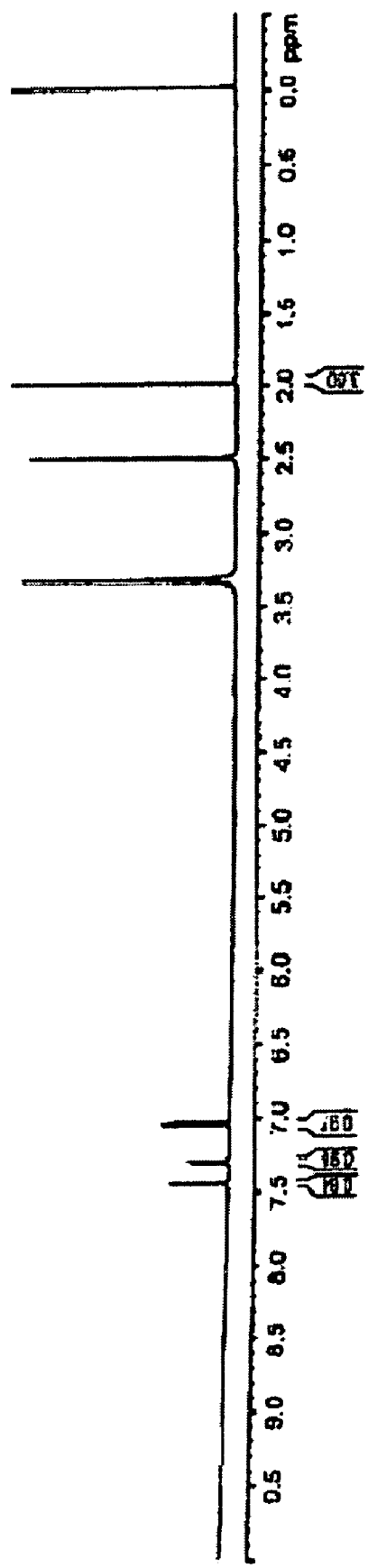
Figure 5C:
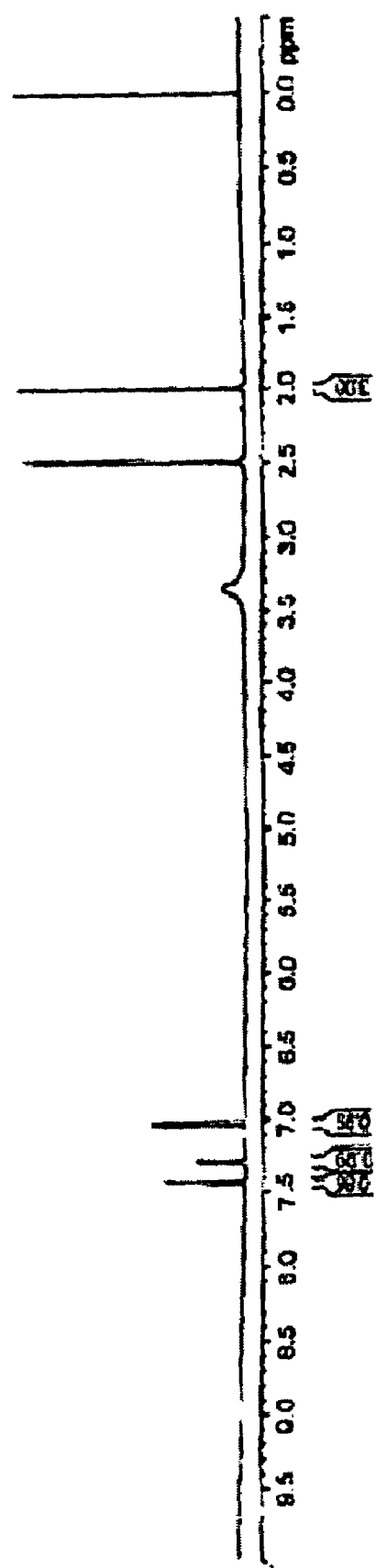

The XRPD pattern of the sodium salt of diazoxide was analyzed, showing the material to be crystalline. (See FIG. 4($d$)). The DSC analysis revealed a major exothermic event at 448° C. Small transitions below 400° C. are likely due to sample imperfections. TGA analysis showed weight loss of 0.2% and 0.03% below 120° C., which may be the result of bound solvent. Moisture absorption performed from 0-90% relative humidity at 25° C. showed the material to be hygroscopic as the sample deliquesced at 90% relative humidity. The sample absorbed 1.2 wt % of water at 60% RH, and 6.6 wt % water at 80% RH. Hysteresis was observed upon desorption at 65 and 55% RH, indicating possible hydrate formation. (Possible hydrate formation was noted, although the amount of water absorbed was less than 0.5 mole). $^1$H NMR showed a chemical shift in the aromatic and methyl resonances of the sodium salt, as expected due to changes to the aromatic system. See FIG. 5 showing NMR spectrum for the free form of diazoxide (a) and the sodium salt of diazoxide (c). FTIR showed expected changes for the sodium salt.

Elemental analysis of the salt indicated that the salt was formed in a ratio of approximately 1:1, with the percentage of sodium being slightly low (approximately 3.4%). This deficiency may be due to matrix effects, as NMR indicated the sample had a relatively high purity.

UV-vis measurements in neutral aqueous solution show a λmax of approximately 271 nm. (See FIG. 1). This value is slightly higher than free form diazoxide (265 nm). In acetonitrile, the λmax of the sodium salt exhibits a solvatochromic shift to approximately 296 nm. (See FIG. 3). An increase in the pH of the solution is expected to produce a bathochromic shift from approximately 265 nm to approximately 280 nm.

Solubility measurements performed at pH 2, 7, and 12 in 10 mM phosphate buffer at room temperature showed solubility of the sodium salt of diazoxide to be 13.0 mg/mL, 18.1 mg/mL and 48.6 mg/mL, respectively.

Figure 6A:
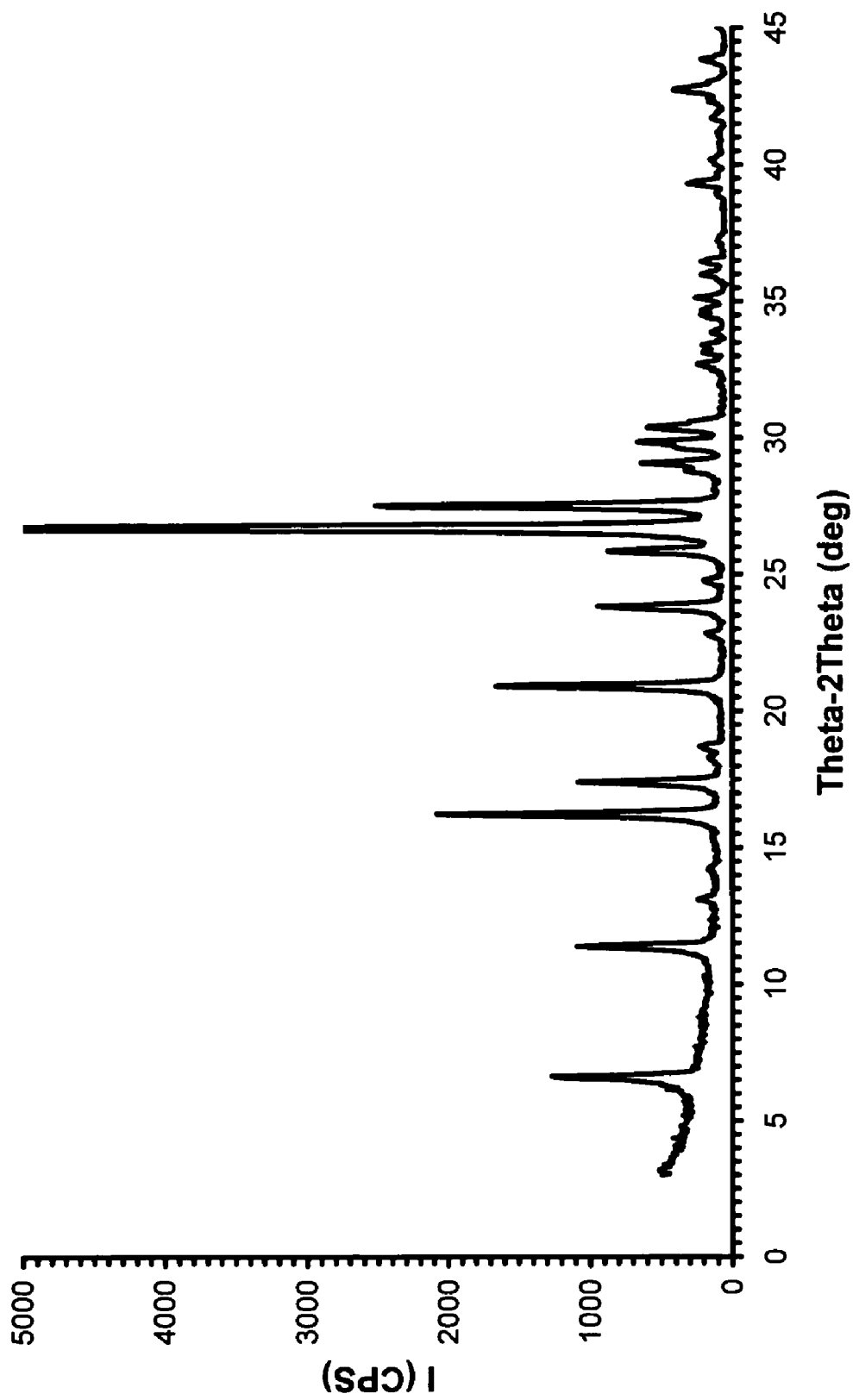
FIG. 6A, FIG. 6B and FIG. 6C show an X-Ray Powder Diffraction pattern for (A) sodium salt of diazoxide, (B) sodium salt of diazoxide after slurrying in water, and (C) free form diazoxide, respectively.
Figure 6B:
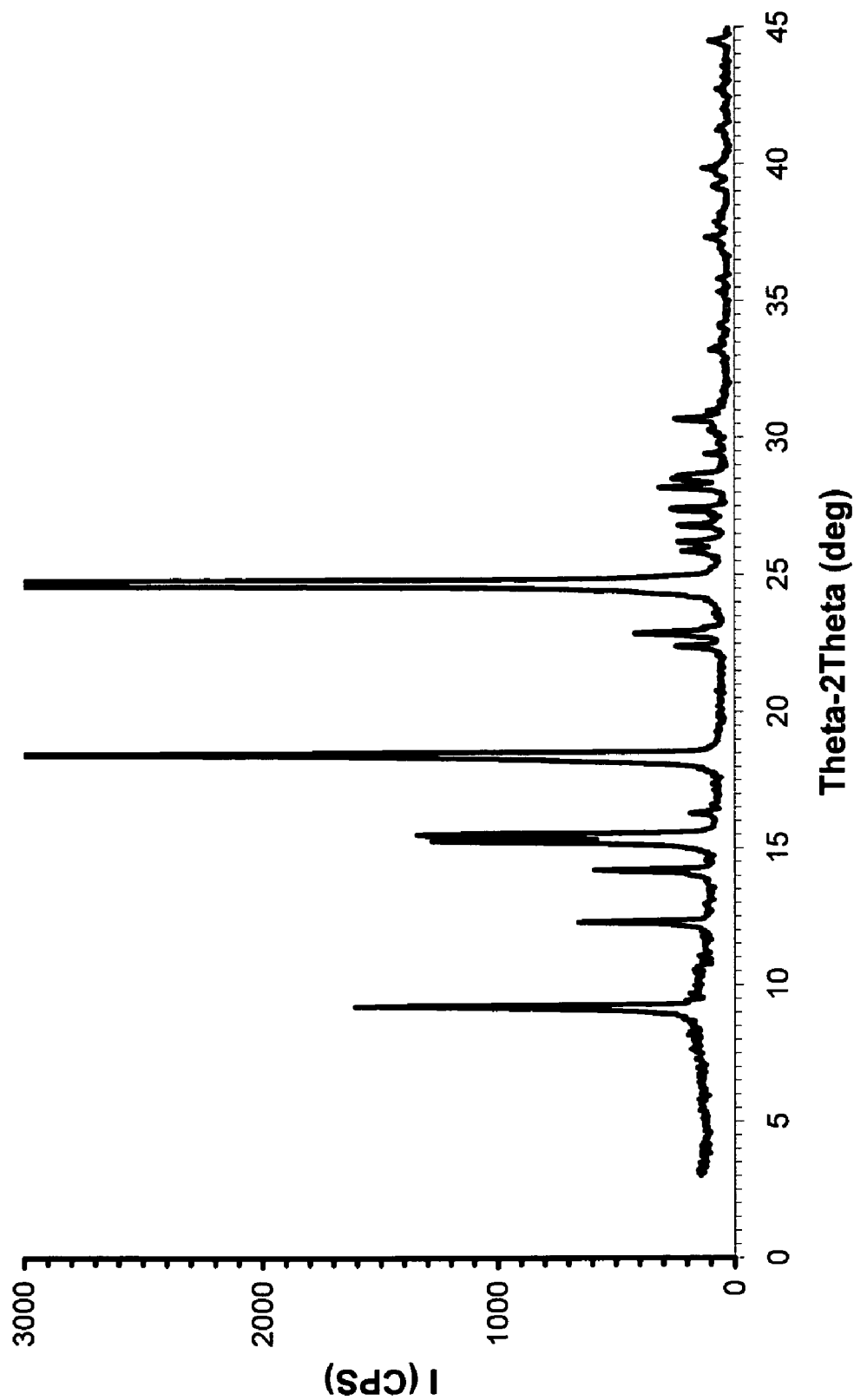
Figure 6C:
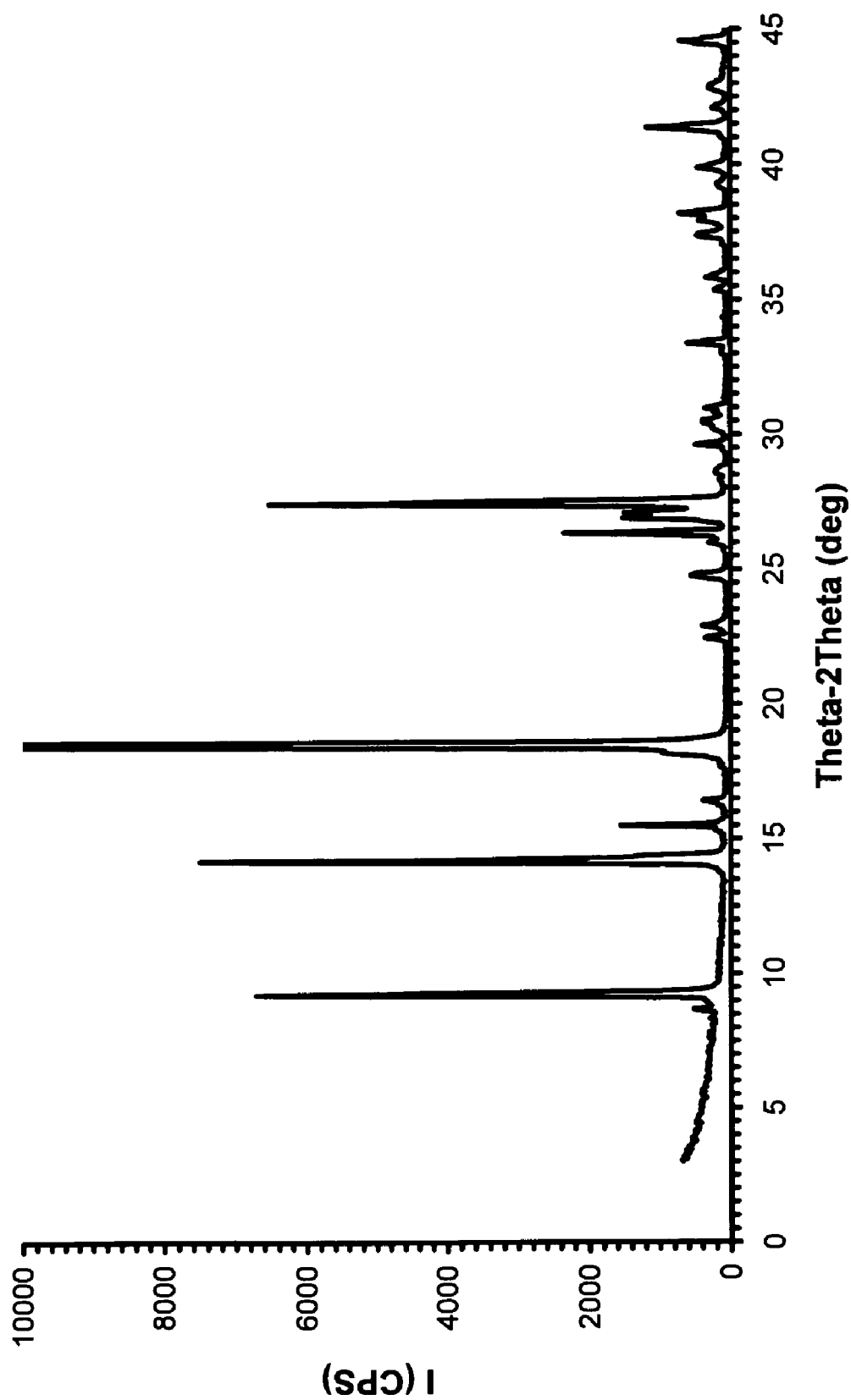

Form conversion and degradation under thermal stress were conducted as described for the free form diazoxide salt and showed the salt had little propensity to change form or degrade over a period of 14 days. Similarly, slurry studies were conducted as described for the free form diazoxide in n-heptane, dichloromethane and toluene showed no propensity of inter-conversion. See FIG. 6, wherein (a) is the XRPD pattern for the sodium salt of diazoxide, (b) is the XRPD pattern for the sodium salt after the slurry study, and (c) the XRPD of the free form of diazoxide.

5.4. Characterization of Potassium Diazoxide Salt

Figure 7:
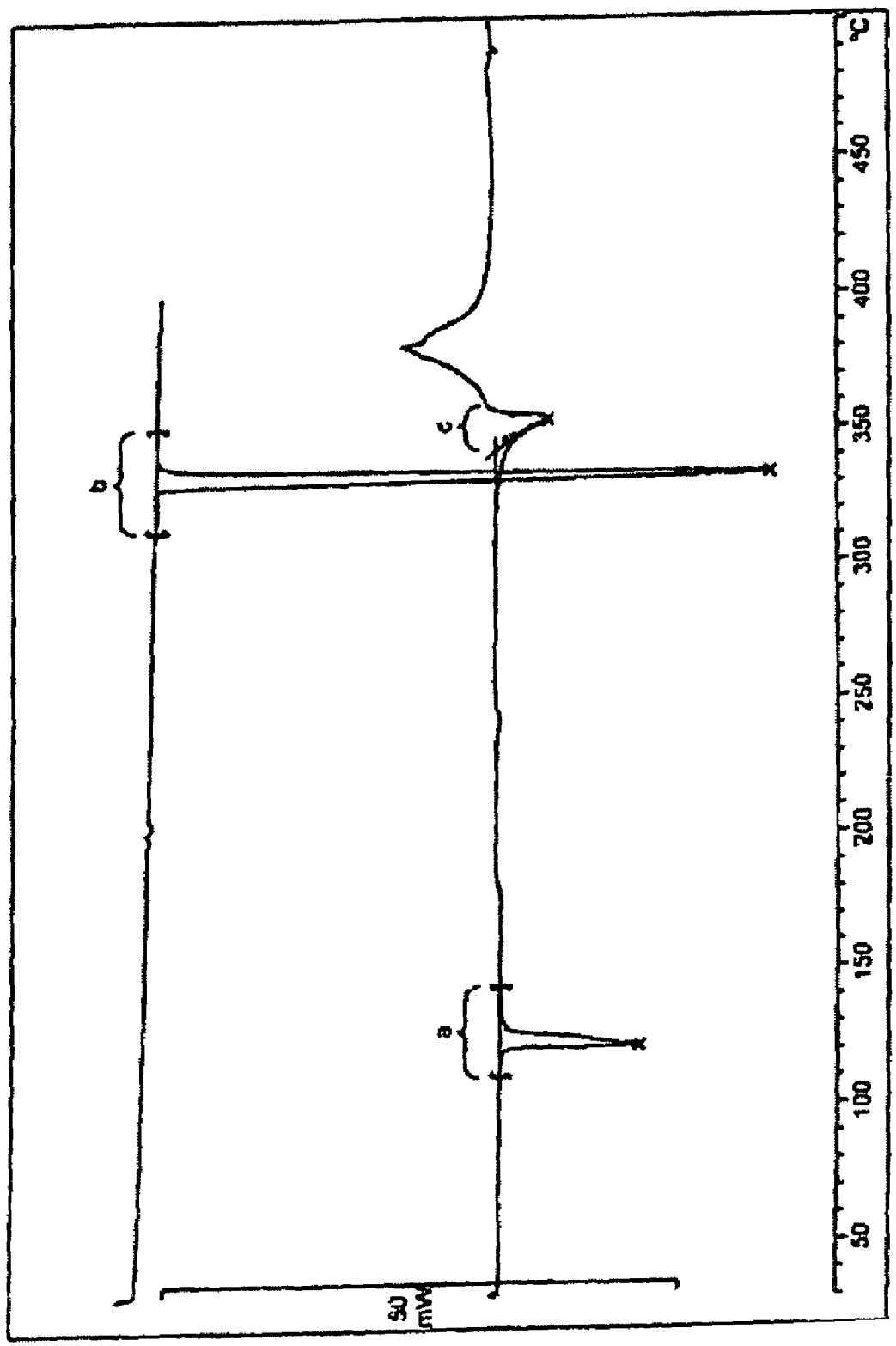
FIG. 7 shows DSC spectra for the free form diazoxide (top) and potassium salt of diazoxide (bottom). Description: "a" (Integral=−317.56 mJ; normalized=−84.82 Jg$^{-1}$; Onset=120.81° C.; Peak=121.29° C.); "b" (Integral=−1170.43 mJ; normalized=−154.64 Jg$^{-1}$; Onset=329.54° C.; Peak=329.21° C.); "c" (Extrap. Peak=355.01° C.; Peak Value=−4.58 mW; normalized=−1.22 Wg$^{-1}$; Peak=353.53° C.).
Figure 8:
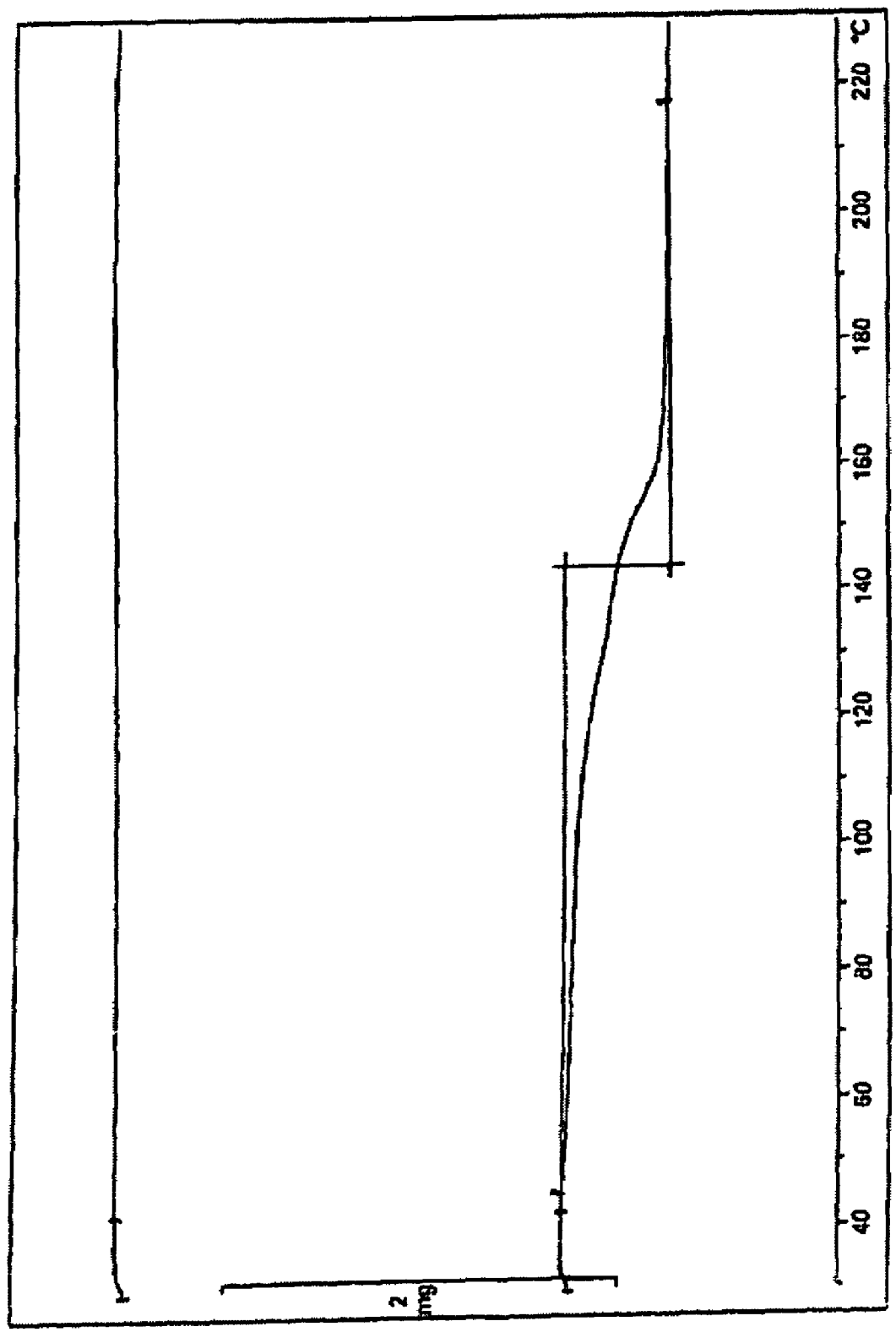
FIG. 8 shows TGA spectra for the free form diazoxide (top) and potassium salt of diazoxide (bottom).

The XRPD pattern for the potassium salt of diazoxide was analyzed, showing the material to be crystalline. (See FIG. 4($b$)). The DSC analysis revealed two major exothermic events at 128 and 354° C. (See FIG. 7). Small endotherms are likely due to sample impurities or the presence of solvent. TGA analysis showed weight loss of 7.7% below 220° C., which may be the result of moisture sorption. (See FIG. 8). Theoretical weight loss for a monohydrate of the diazoxide salt is 6.6%. Moisture absorption performed from 0-90% relative humidity at 25° C. showed the material to be hygroscopic as the sample deliquesced at 90% relative humidity, showing 38.3 wt % water. The sample absorbed 5.4 wt % of water at 60% RH. Hysteresis was observed upon desorption, however the material was determined to be a hemihydrate from 0-30% RH and a monohydrate from 35-75% RH. XRPD following the desorption analysis indicated that the sample had changed to an alternate crystalline form. $^1$H NMR showed a chemical shift in the aromatic and methyl resonances of the sodium salt, as expected due to changes to the aromatic system. (See FIG. 5 showing spectrum of the free form diazoxide (a) and the Potassium salt of diazoxide (b)). FTIR showed expected changes for the potassium salt.

Elemental analysis of the potassium salt indicated that the salt was formed in a ratio of approximately 1:1, with the percentage of potassium being slightly low (approximately 1.6%). This deficiency may be due to matrix effects, as NMR indicated the sample had a relatively high purity.

UV-vis measurements of the potassium diazoxide salt in neutral aqueous solution show a $\lambda_{max}$ of approximately 265 nm, which is equivalent to the diazoxide free form $\lambda_{max}$. (See FIG. 1. In acetonitrile, the $\lambda_{max}$ of the potassium salt exhibits a solvatochromic shift to approximately 296 nm. (See FIG. 3). The potassium salt was used in a pH dependency study and showed that increasing the pH of the solution resulted in a bathochromic shift of the $\lambda_{max}$ from approximately 265 nm to approximately 280 nm.

Solubility measurements performed at pH 2, 7, and 12 in 10 mM phosphate buffer at room temperature showed solubility of the sodium salt of diazoxide to be 9.9 mg/mL, 14.4 mg/mL and 43.0 mg/mL, respectively. The potassium salt displayed greater solubility than the free form diazoxide, and demonstrated similar solubility to the sodium diazoxide salt. The XRPD pattern of solids obtained after the solubility analysis indicated that the potassium salt had changed back to the free form diazoxide material.

Propensity for form conversion and degradation under thermal stress were conducted as described for the free form diazoxide salt. The XRPD pattern of the sample after 7 and 14 days showed unique peaks, as compared with the potassium salt starting material. Analysis by DSC after 14 days also showed unique peaks as well. Using a gradient area percent assay, HPLC did not show any significant degradation of the potassium salt.

Figure 9A:
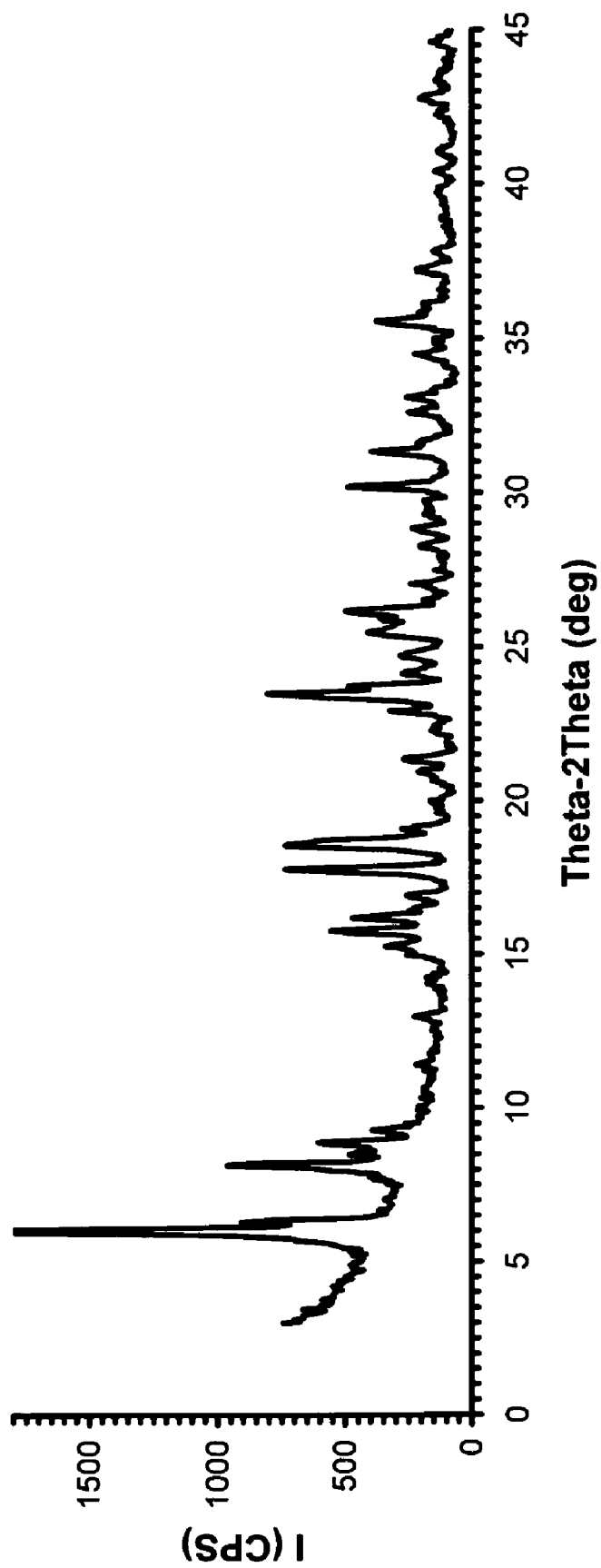
FIG. 9A, FIG. 9B and FIG. 9C show an X-Ray Powder Diffraction pattern for (A) potassium salt of diazoxide, (B) potassium salt of diazoxide after slurrying in toluene, and (C) potassium salt of diazoxide after slurrying in toluene for 14 days, respectively.
Figure 9B:
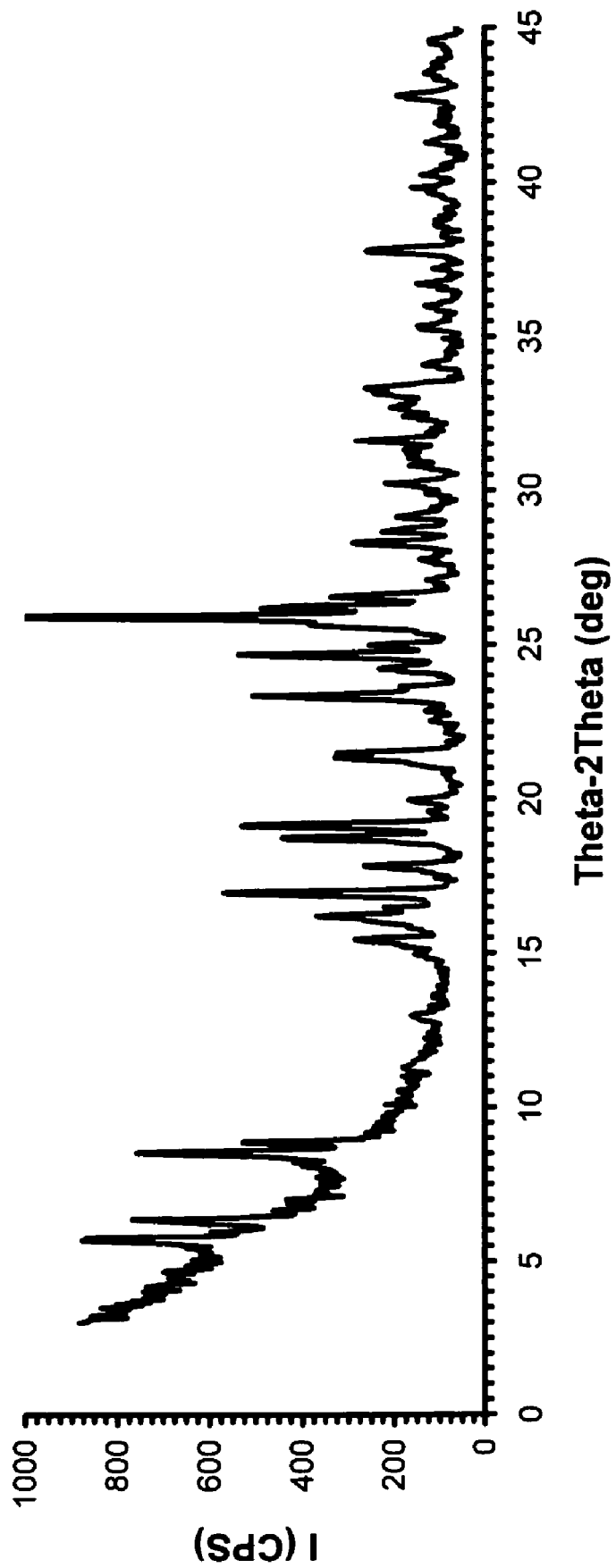
Figure 9C:
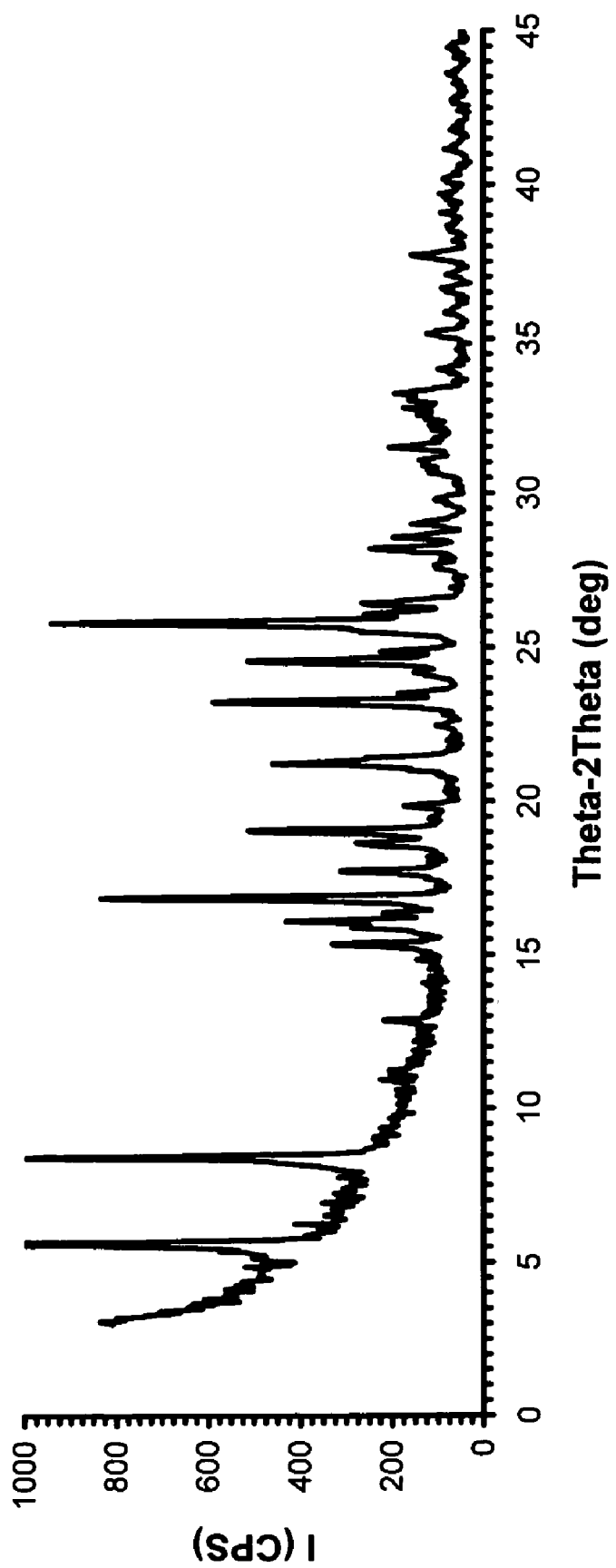

Slurry studies were conducted as described for the free form diazoxide in n-heptane, dichloromethane and toluene showed no propensity of inter-conversion. XRPD analysis of samples after 7 and 14 days showed unique peaks similar to those observed with the thermal stress study. See FIG. 9, wherein (a) is the XRPD pattern of the potassium salt of diazoxide, (b) is the XRPD pattern of the potassium salt of diazoxide after the slurry study in toluene, and (c) the XRPD pattern of the potassium salt after 14 days of the slurry study in toluene. Analysis by DSC after 14 days also showed unique peaks as compared with the starting material. HPLC using a gradient area percent assay did not show any significant degradation after the study.

5.5. Characterization of Choline Diazoxide Salt

Figure 10A:
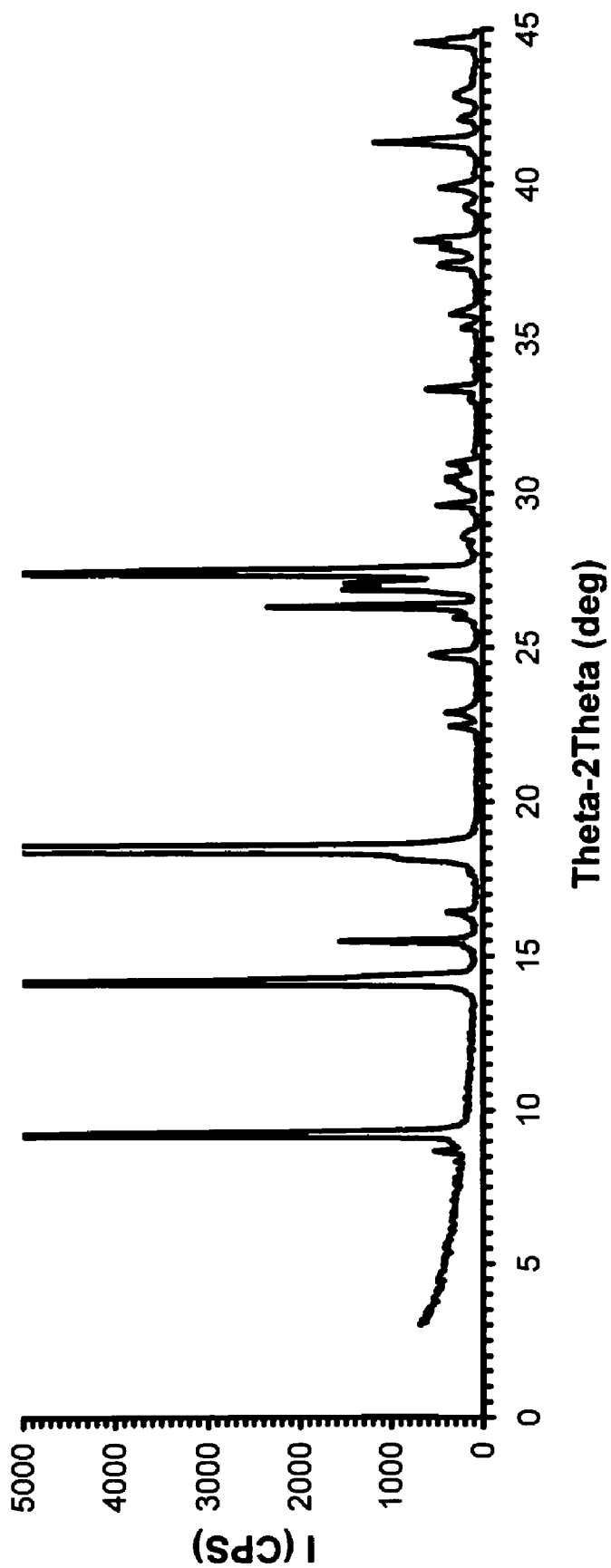
FIG. 10A, FIG. 10B and FIG. 10C show an X-Ray Powder Diffraction pattern for (A) free form diazoxide, (B) choline salt of diazoxide, and (C) hexamethyl hexamethylene diammonium hydroxide salt of diazoxide, respectively.
Figure 10B:
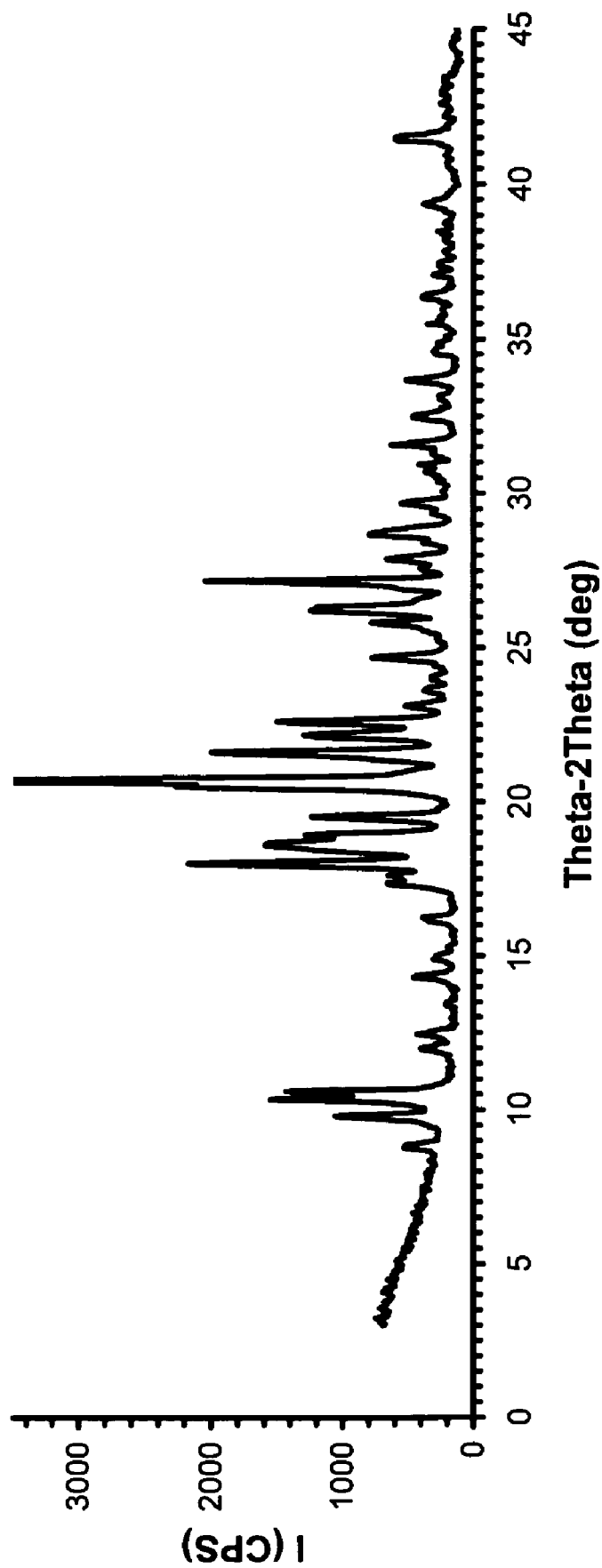
Figure 10C:
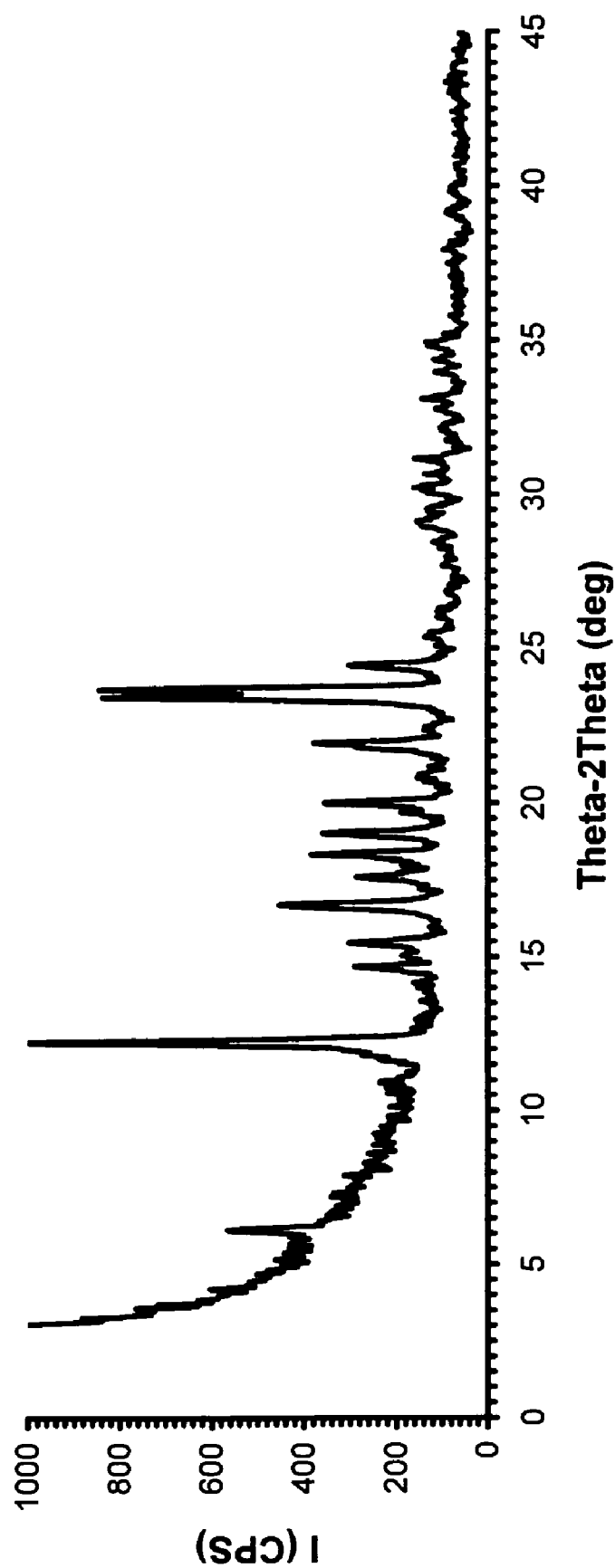
Figure 11:
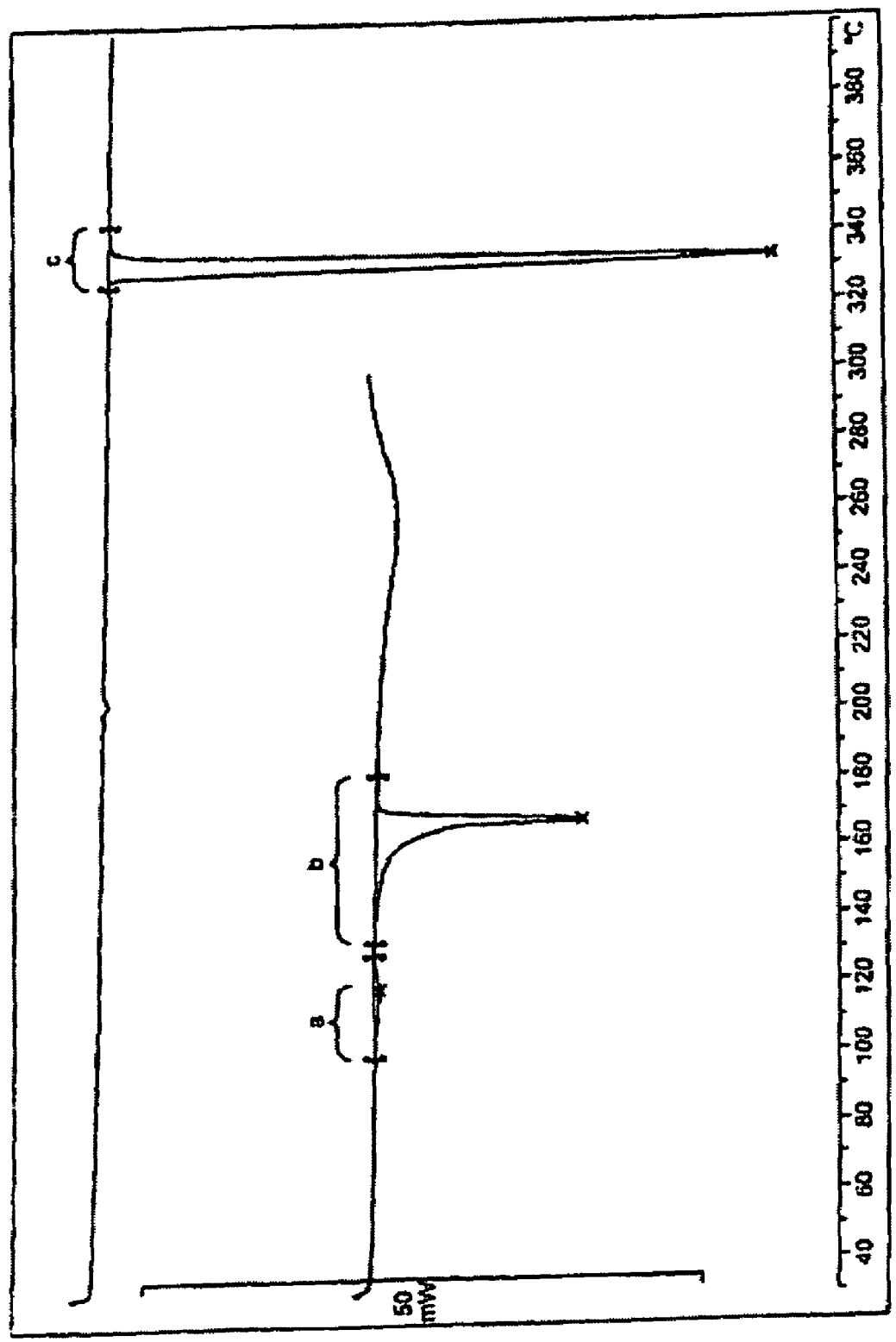
FIG. 11 shows DSC spectra for the free form diazoxide (top) and choline salt of diazoxide (bottom). Description: "a" (Integral=−41.24 mJ; normalized=−8.05 Jg$^{-1}$; Onset=101.23° C.; Peak=119.29° C.); "b" (Integral=−497.37 mJ; normalized=−97.10 Jg$^{-1}$; Onset=166.03° C.; Peak=167.27° C.); "c" (Integral=−1167.83 mJ; normalized=−154.29 Jg$^{-1}$; Onset=329.54° C.; Peak=329.21° C.).
Figure 12:
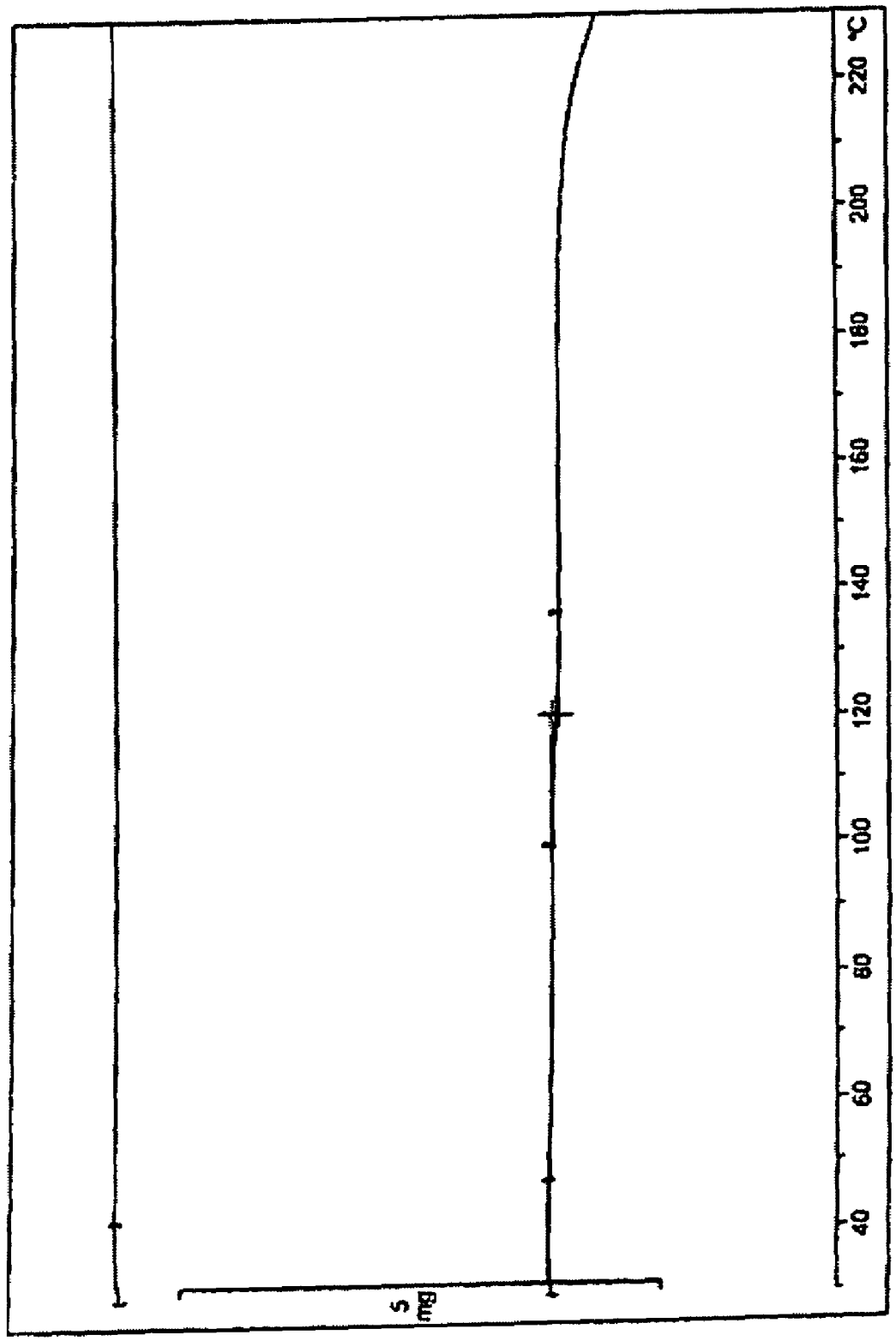
FIG. 12 shows TGA spectra for the free form diazoxide (top) and choline salt of diazoxide (bottom).
Figure 13A:
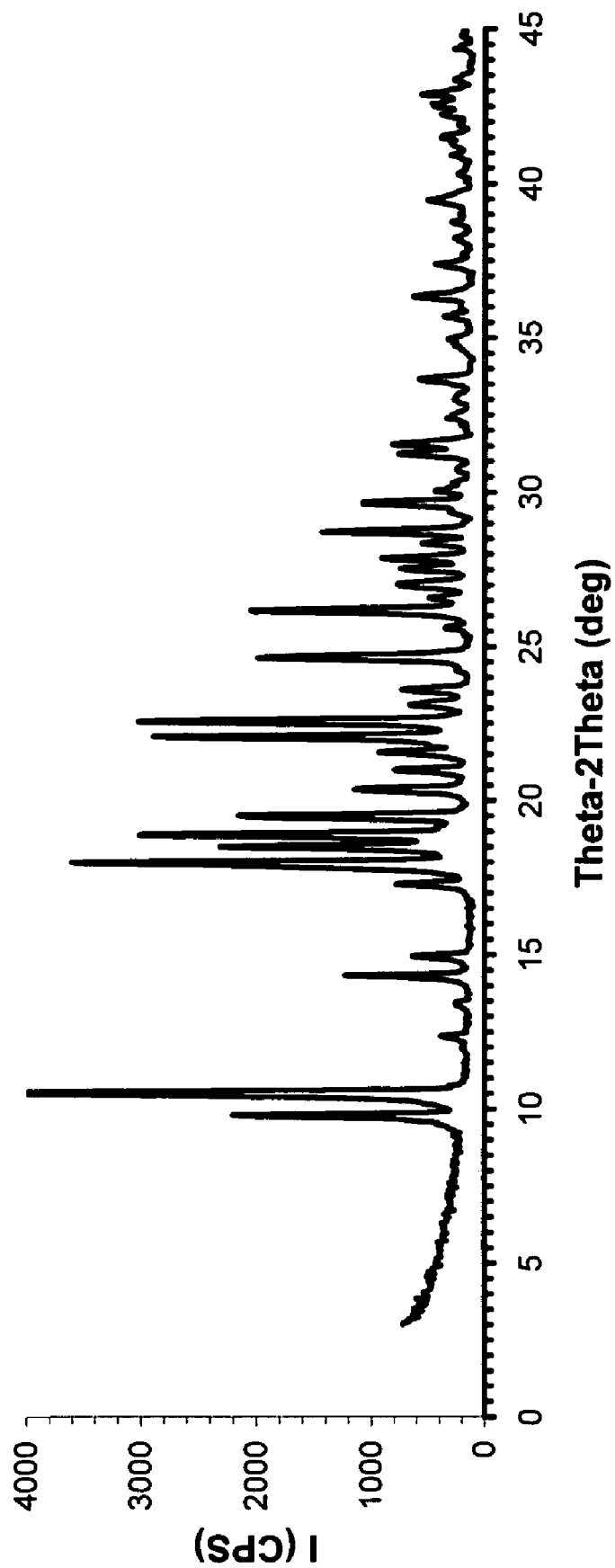
FIG. 13A, FIG. 13B and FIG. 13C show an X-Ray Powder Diffraction pattern for (A) choline salt of diazoxide, (B) choline salt of diazoxide after slurrying in dichloromethane for 7 days, and (C) choline salt of diazoxide after moisture sorption analysis, respectively.
Figure 13B:
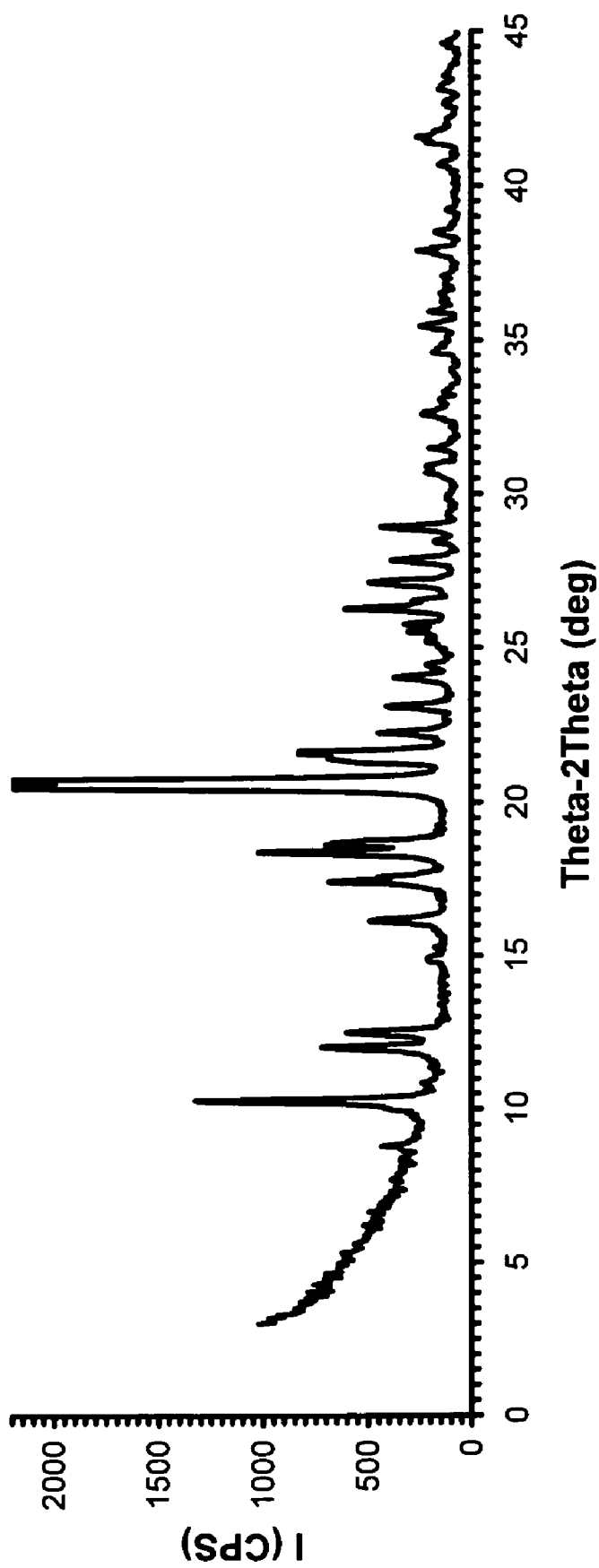
Figure 13C:
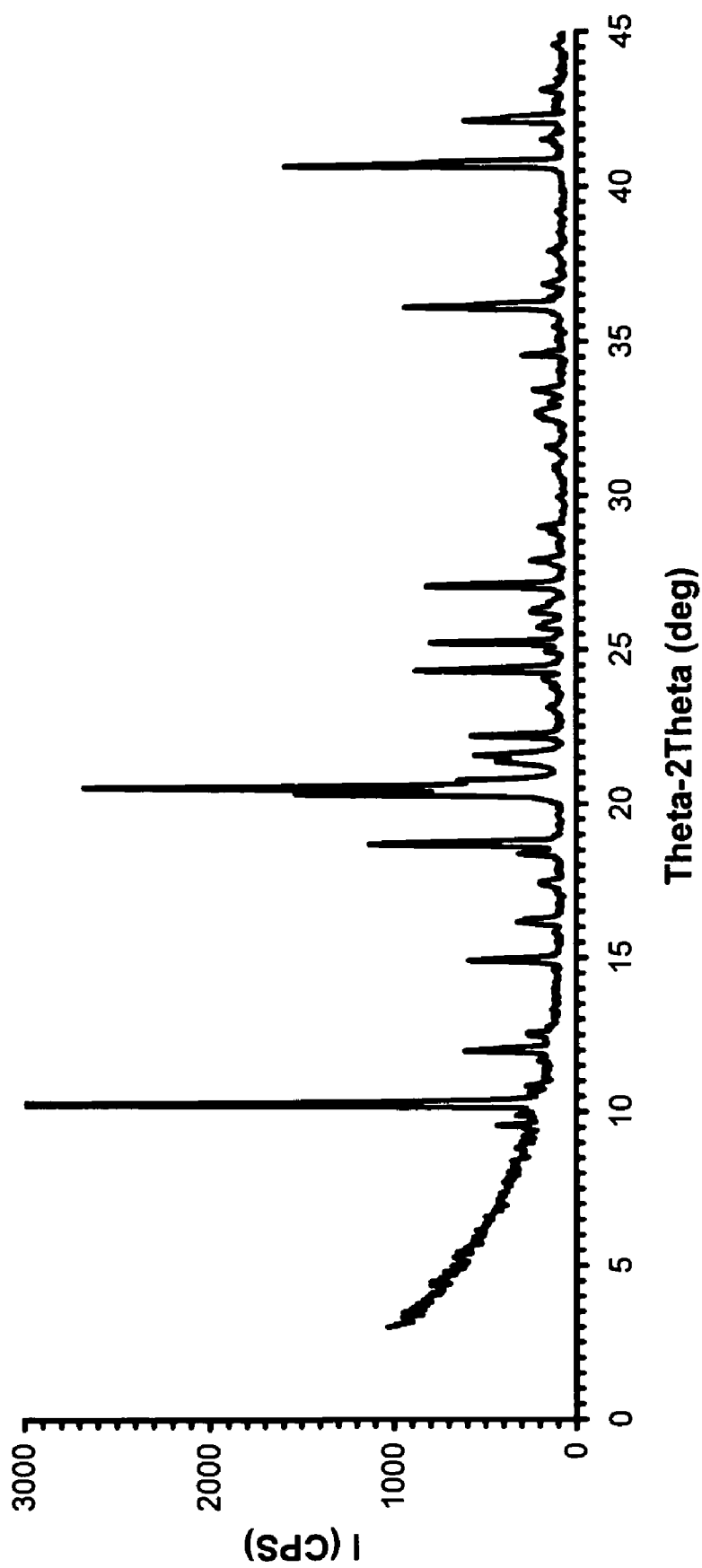
Figure 14A:
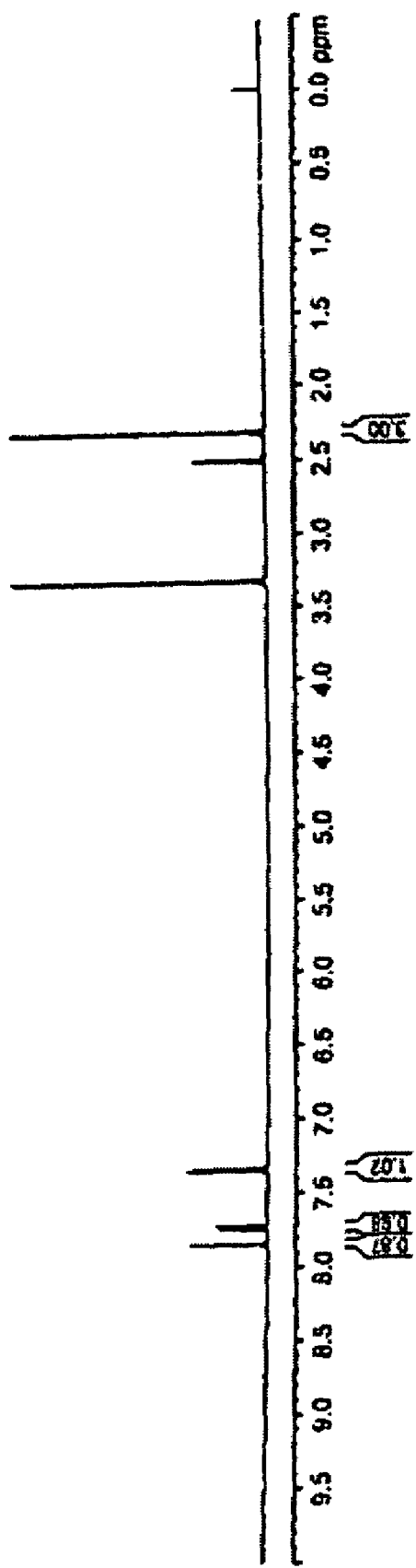
FIG. 14A, FIG. 14B and FIG. 14C show NMR spectra (DMSO-d6 solvent) for (A) free form diazoxide, (B) choline salt, and (C) hexamethyl hexamethylene diammonium hydroxide salt of diazoxide, respectively.
Figure 14B:
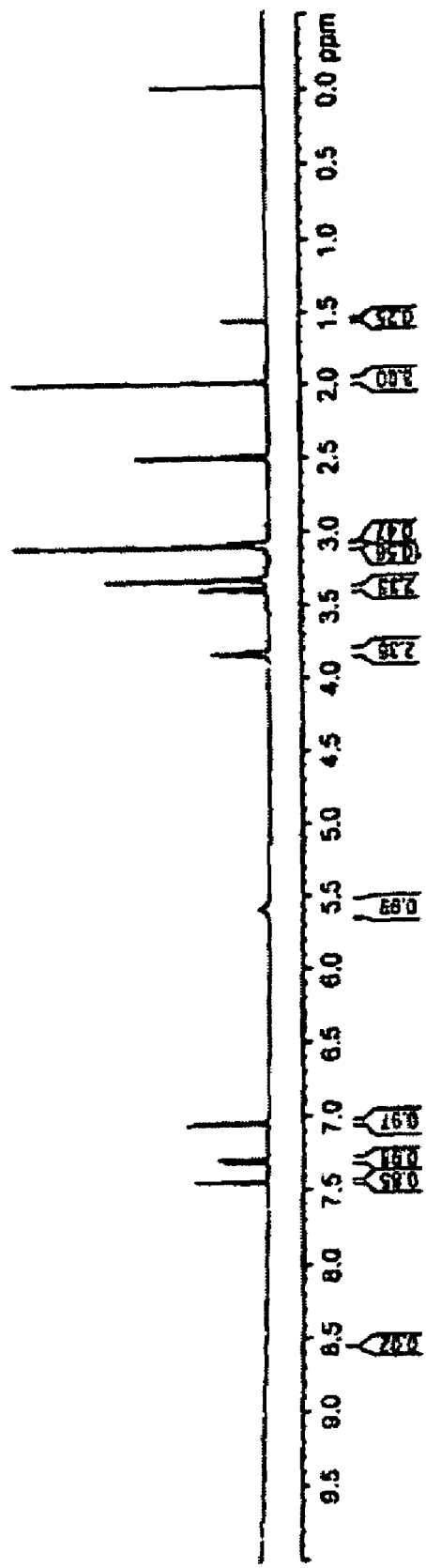
Figure 14C:
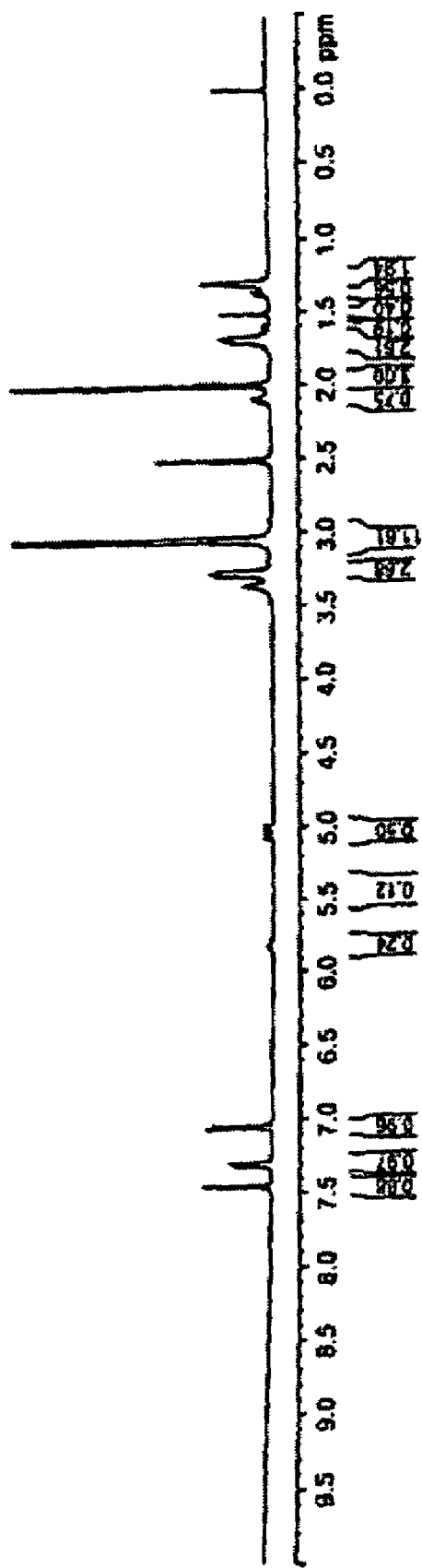

The XRPD pattern of the choline salt of diazoxide was analyzed, showing the material to be crystalline. (See FIG. 10 (b)). The DSC analysis revealed a major exothermic events at 167° C. (See FIG. 11). A smaller endothermic event was seen at 119° C. and is likely due to sample impurities or the presence of residual solvent. TGA analysis showed weight loss of 0.8% between 100 and 140° C., which may be the result of residual solvents. (See FIG. 12). Moisture absorption performed from 0-90% relative humidity at 25° C. showed the material to be hygroscopic as the sample absorbed over 28% at 80% relative humidity, and deliquesced at 90% RH. Hysteresis was not observed upon desorption, indicating the choline salt does not form a stable hydrate. The XRPD pattern following the desorption analysis indicated that the sample had changed to an alternate crystalline form during the hydration and subsequent desorption. (See FIG. 13 (c)) $^1$H NMR was consistent with a 1:1 molar ratio of diazoxide to counter-ion, and had the expected differences in the chemical shift of the aromatic and methyl resonances, as expected due to the change in the local environment of the aromatic system due to the presence of the choline counter-ion. (See FIG. 14 (b)). FTIR showed expected changes for the choline salt, similar to those seen with the sodium and potassium salts.

Elemental analysis of the choline salt indicated that the salt was formed in a ratio of approximately 1:1. This is consistent with the $^1$H NMR.

UV-vis measurements of the choline diazoxide salt in neutral aqueous solution show a $\lambda_{max}$ of approximately 268 nm, which is close to the $\lambda_{max}$ for the diazoxide free form of 265 nm. In acetonitrile, the $\lambda_{max}$ of the choline salt exhibits a solvatochromic shift to approximately 296 nm, which is consistent with the sodium and potassium diazoxide salts. The potassium salt was used in a pH dependency study and showed that increasing the pH of the solution resulted in a bathochromic shift of the $\lambda_{max}$ from approximately 265 nm to approximately 280 nm.

Solubility measurements performed at pH 2, 7, and 12 in 10 mM phosphate buffer at room temperature showed solubility of the sodium salt of diazoxide to be 28.2 mg/mL, 41.5 mg/mL and greater than 293 mg/mL, respectively. The choline salt displayed greater solubility than the free form diazoxide after being allowed to equilibrate for 12 hours. The XRPD pattern of the solids obtained after the solubility analysis (at pH 2 and 7 only) indicated that the choline salt had changed back to the free form diazoxide material.

Propensity of the choline salt for form conversion and degradation under thermal stress were conducted as described for the free form diazoxide salt. XRPD analysis of the sample after 7 and 14 days showed an XRPD pattern consistent with the starting material, as well as the presence of additional unique peaks. (More unique peaks were present after 14 days than after 7 days). Analysis by DSC after 14 days did not show any significant difference, with a small endotherm at 117° C. and a large endotherm at 168° C. (Initial DSC showed endotherms at 119° C. and a large endotherm at 167° C.). Using a gradient area percent assay, HPLC did not show any significant degradation of the choline salt.

Slurry studies were conducted as described for the free form diazoxide in n-heptane, dichloromethane and toluene showed no propensity of inter-conversion. XRPD analysis of samples after 7 and 14 days showed signal associated with the starting material, with additional unique peaks present. (See FIG. 13 (c)). The XRPD pattern of slurry study samples from n-heptane showed signals associated with the starting material, as well as other additional unique signals. The XRPD pattern of slurry samples from dichloromethane and toluene were consistent with spectra obtained after the thermal studies and the moisture sorption analysis. Analysis by DSC after 14 days revealed a small endotherm at 109° C., and a major endotherm at 167° C. HPLC using a gradient area percent assay did not show any significant degradation after the study.

5.6. Characterization of Diazoxide Salt of Hexamethyl Hexamethylene Diammonium Hydroxide (HHDADH)

The XRPD pattern of the HHDADH salt of diazoxide was analyzed, showing the material to be a crystalline solid. (See FIG. 10(c)). Integration of the $^1$H NMR spectra was consistent with a 2:1 molar ratio of diazoxide to counter-ion (wherein the HHDADH counter-ion is divalent), and had the expected differences in the chemical shift of the aromatic and methyl resonances due to the change in the local environment of the aromatic system due to the presence of the choline counter-ion. (See FIG. 14(c)). The $\lambda_{max}$ of the HHDADH diazoxide salt in acetonitrile measured by UV-vis is 296 nm, which is consistent with the sodium, potassium and choline diazoxide salts.

A summary of the characterization of the free form diazoxide and the potassium, sodium, choline and hexamethyl hexamethylene diammonium hydroxide salts of diazoxide are presented in Table 14.

TABLE 14

Summary of Characterization and Solubility for Diazoxide and Salts

| Test | Free form | Potassium diazoxide salt | Sodium diazoxide salt | Choline diazoxide salt | HHDADH |
|---|---|---|---|---|---|
| XRPD | crystalline | crystalline | crystalline | crystalline | crystalline |
| FTIR | consistent | consistent | consistent | consistent | N/A |
| DSC | single endotherm at 330° C. | multiple endotherms below 300° C. | Single exotherm above 400° C. | two endotherms below 200° C. | N/A |
| UV in aqueous acetonitrile | 268 nm 264 nm | 265 nm 296 nm | 271 nm 296 nm | 268 nm 296 nm | N/A 296 nm |
| TGA | <1% | 7.7 (monohydrate 6.7%) | <1% | <1% | N/A |
| Moisture Sorption | non-hygroscopic - no hysteresis | deliquescent - hemi/monohydrate | deliquescent - potential hemihydrate | deliquescent - no hysteresis | N/A |
| Solubility | | | | | N/A |
| pH 2.0 | 0.4 mg/mL | 9.9 mg/mL | 13.0 mg/mL | 28.2 mg/mL | |
| pH 7.0 | 0.04 mg/mL | 14.4 mg/mL | 18.1 mg/mL | 41.5 mg/mL | |
| pH 12.0 | 4.8 mg/mL | 43.0 mg/mL | 48.6 mg/mL | >293 mg/mL | |

Additional solubility studies were conducted for diazoxide free base form and diazoxide choline salt, as reported in Table 15. Each determination was carried out in duplicate, slurrying each sample in a 100 mM phosphate buffer solution, pH 7.00. Duplicate samples were then titrated to pH 7.0 and pH 8.8 using a 0.1 N phosphoric acid solution, followed by stirring for 18 h at ambient temperature. After this time all samples were centrifuged, and the supernatant was diluted with mobile phase (MeCN/Water.). Solubility was then obtained using a calibration curve for diazoxide by HPLC analysis. In Table 15, the term "Diazoxide, free from" refers to the free base of diazoxide; the term "Diazoxide, choline salt" is the choline salt of diazoxide as described herein; the term "Diazoxide, choline salt, milled" refers to the choline salt of diazoxide which has been milled by methods described herein. Table 15 shows that in 100 mM phosphate buffer, pH 7, and with titration with 0.1N phosphoric acid to a pH of about 6.8 to 8.8, solubility is notably suppressed compared to solubility at pH 10-11. Furthermore, the diazoxide choline salts were found to have increased solubility when compared to the parent free base.

TABLE 15

Summary of Solubility for Diazoxide and Diazoxide Choline Salt.

| Sample | Sample amount (mg) | Phosphate buffer amount (mL) | 1N $H_3PO_4$ (mL) | pH after titration with 0.1N $H_3PO_4$ | pH after 18 h slurry | Solubility [mg/mL] |
|---|---|---|---|---|---|---|
| Diazoxide, free form | 49.23 | 1 | 0.01 | 6.87 | 6.90 | 0.07 |
| Diazoxide, free form | 47.64 | 1 | — | 7.30 | 7.31 | 0.07 |
| Diazoxide, choline salt | 44.34 | 1 | 0.15 | 7.22 | 7.45 | 0.12 |
| Diazoxide, choline salt | 48.26 | 1 | 0.11 | 8.81 | 8.64 | 0.18 |
| Diazoxide, choline salt, milled | 45.35 | 1 | 0.14 | 7.32 | 7.36 | 0.12 |
| Diazoxide, choline salt, milled | 53.15 | 1 | 0.16 | 8.50 | 8.52 | 0.20 |
| Diazoxide, choline salt | 50.0 | 1 | — | — | 10.57 | 42.11 |
| Diazoxide, choline salt, milled | 50.0 | 3 | — | — | 10.52 | 32.88 |

"—" Indicates no titration was conducted.

6. Polymorphic Forms of Diazoxide Salts

Polymorphic forms of the salts of diazoxide, characterization, and preparation thereof are described.

6.1. Polymorphic Forms of the Choline Salt of Diazoxide 6.1.1. Demonstration of Preparation of Polymorphic Form B of the Choline Salt of Diazoxide A 1-L round bottom flask was charged with diazoxide (5 g), MEK (750 mL) and choline hydroxide (5.25 g of 50 wt % solution in water), and heated to 77° C. The mixture was allowed to cool to approximately 30° C., and filtered to remove insoluble brown residues. The filtrate was then concentrated under reduced pressure to afford yellow oil, which was dried in vacuo at 55° C. and 30 in. Hg to afford approximately 7.8 g as a waxy solid. The solids were dried in vacuo at 55° C. and 30 in. Hg to afford 7.13 g of the choline salt of diazoxide as a crystalline solid. Elemental analysis. Theoretical: C 46.77%, H 6.04% and N 12.59%. Measured: C 45.44%, H 5.98% and N 11.46%.

6.1.2. Characterization of the Polymorphic Form B of the Choline Salt of Diazoxide The polymorphic Form B of the choline salt of diazoxide was analyzed by XRPD, DSC, and $^1$H NMR. As shown in FIG. 16, the two identified polymorphic forms of the choline salt of diazoxide show different XRPD patterns. See FIG. 16A, wherein the polymorphic Form A of the choline salt of diazoxide is shown.

As shown in FIG. 17, $^1$H NMR of the polymorphic Form B of the choline salt of diazoxide shows no change from the polymorphic Form A.

Moisture absorption of the polymorphic Form B crystal structure of the choline salt of diazoxide performed from 0-80% relative humidity (RH) at 25° C. showed the material to be hygroscopic as the sample absorbed over 14.5% at 70% relative humidity, and deliquesced at 80% RH. The XRPD pattern following the desorption analysis indicated that the sample remained in the Form B crystal structure during the hydration and subsequent desorption.

Solubility measurements performed at pH 2, 7, and 12 in 10 mM phosphate buffer at room temperature showed solubility of the Form B crystal structure of the choline salt of diazoxide to be 32.8 mg/mL, 80.1 mg/mL and 216 mg/mL, respectively. The XRPD pattern of the solids obtained after the solubility analysis (at pH 2 and 7) indicated that Form B of the choline salt of diazoxide was still present.

Slurry experiments were performed on each form to determine the propensity for conversion and to search for possible new and/or unique forms. Upon slurrying Form B in CH2Cl2, n-heptane, and toluene, form conversion was not observed.

6.1.3. Demonstration of Preparation of the Polymorphic Form A of the Choline Salt of Diazoxide from the Polymorphic Form B of the Choline Salt of Diazoxide Approximately 20 mg of the Form B polymorph of the choline salt of diazoxide was added to approximately 1 mL of acetone and heated to approximately 55° C. The mixture was filtered while hot and placed in a refrigerator (4° C.) for 16 hours. No precipitate was observed. The solvent was evaporated down to dryness using a gentle stream of nitrogen. The resultant solids were also dried in vacuo at room temperature and 30 in. Hg. XRPD analysis showed the salt had converted from the Form B polymorph to the Form A polymorph.

Figure 20:
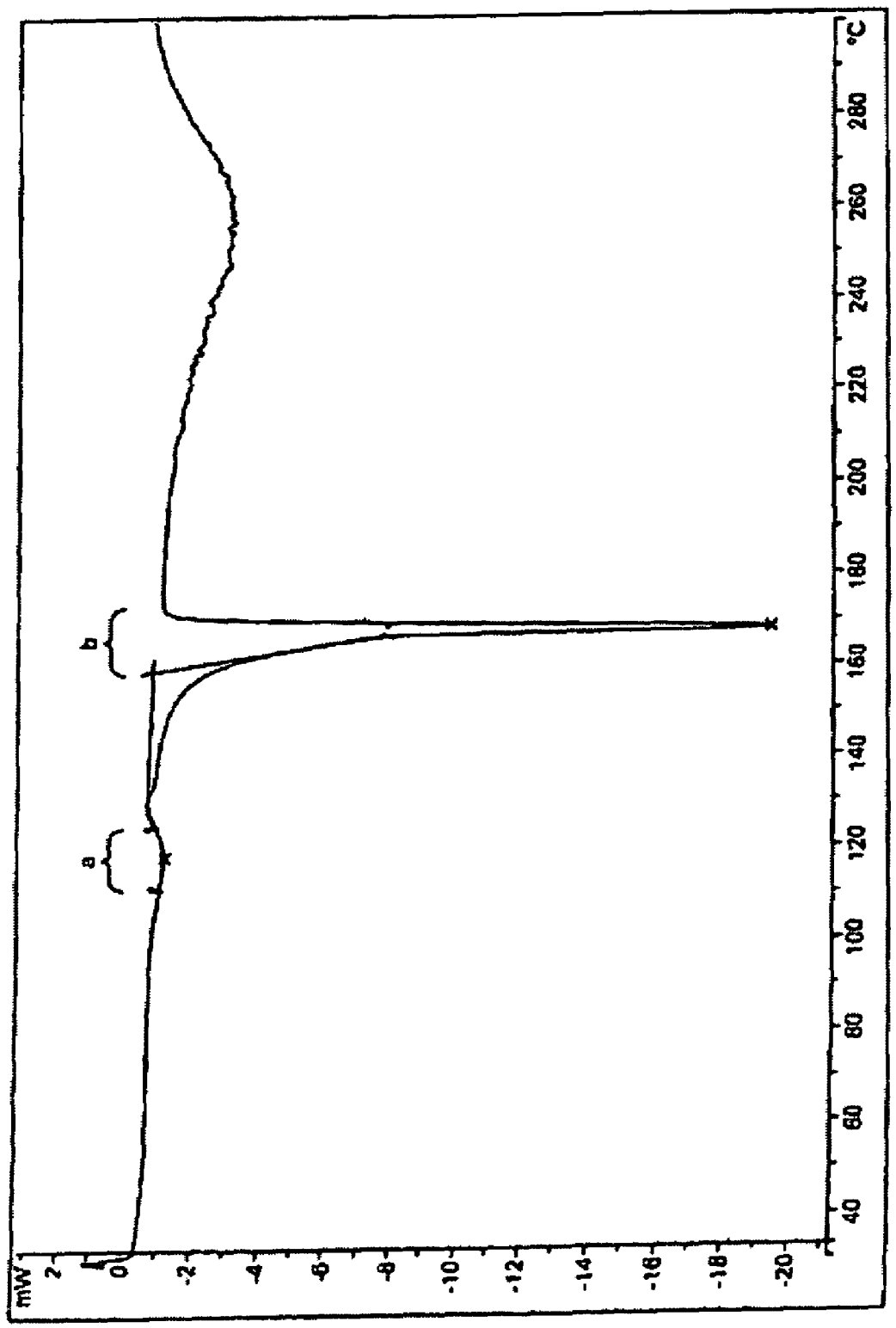
FIG. 20 shows the DSC spectra of diazoxide choline salt Form A. Description: "a" (Extrap. Peak=120.44° C.; Peak Value=−1.02 mW; normalized=−0.20 Wg$^{-1}$; Peak=118.63° C.); "b" (Extrap. Peak=167.94° C.; Peak Value=−19.39 mW; normalized=−3.79 Wg$^{-1}$; Peak=167.27° C.).
Figure 21:
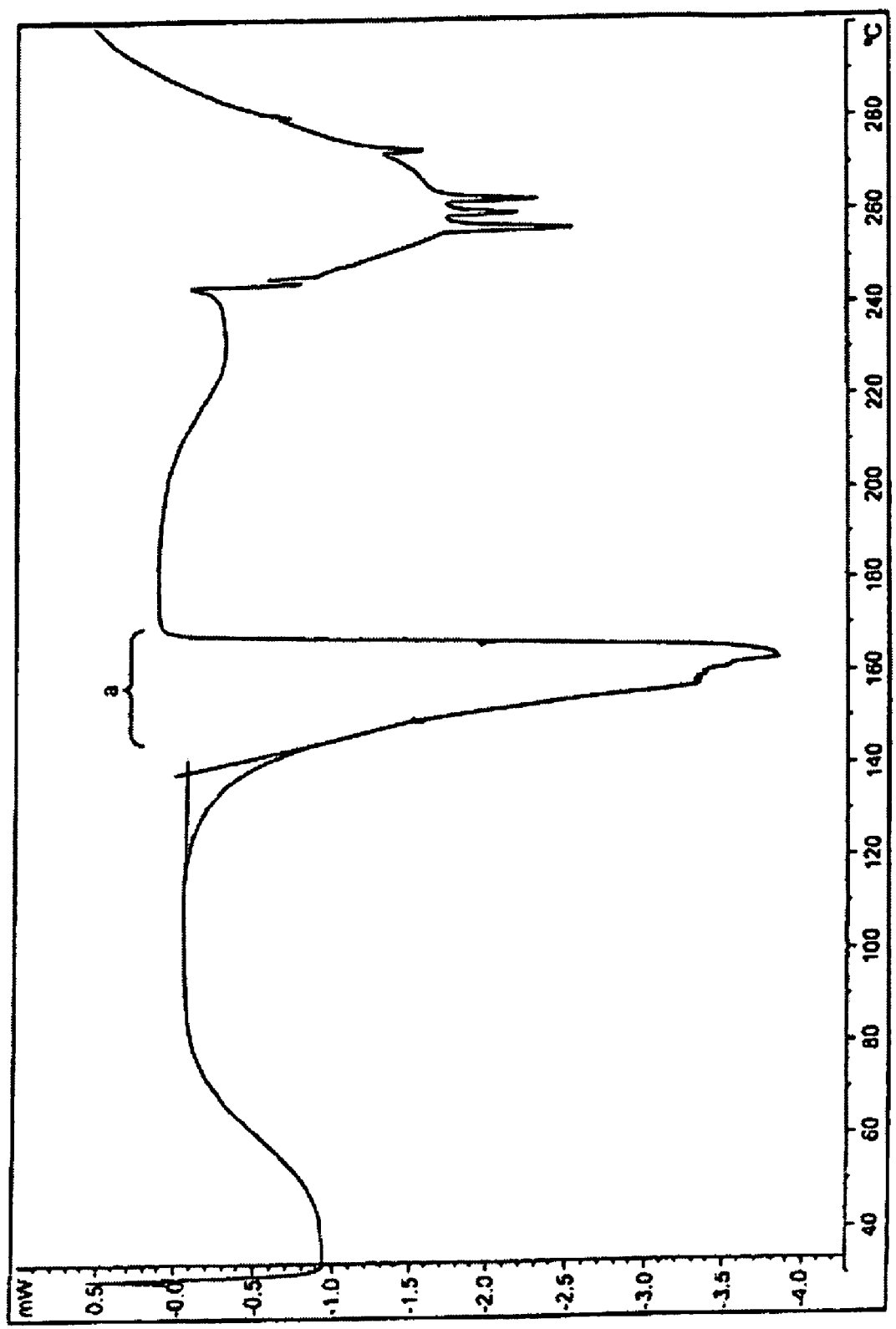
FIG. 21 shows the DSC spectra of diazoxide choline salt Form B. Description: "a" (Extrap. Peak=165.05° C.; Peak Value=−3.85 mW; normalized=−0.86 Wg$^{-1}$; Peak=162.66° C.).

6.1.4. Characterization of the Polymorphic Form A of the Choline Salt of Diazoxide Form A is an anhydrous crystalline form of diazoxide choline, with an endothermic event at approximately 165° C. in the DSC (see FIG. 20). The XRPD pattern for Form A is unique compared to that of Form B as shown in FIG. 21. FTIR (ATR) spectroscopy additionally indicates differences between the two forms. $^1$H NMR analysis affords a spectrum consistent with diazoxide and a 1:1 ratio of compound/counterion. NMR data also indicate that the magnetic environment of the diazoxide structure changes between free and polymorph forms, as evidenced by a movement in chemical shift of the aromatic and methyl proton resonances. In addition, the resonance due to the amine proton is not observed which suggests deprotonation in solution. Weight loss by TGA is less than 1% and may be due to residual solvent. The temperature of weight loss is above 100° C. which suggests that solvent may have been bound (i.e., solvate material). Moisture-sorption analysis conducted at 25° C. from 0 to 80% RH (adsorption) and 75 to 0% RH (desorption) shows Form A to be a hygroscopic solid, showing 2.4 wt % water at 60% RH. The sample was found to have deliquesced above 75% RH. In comparison, Form B is also hygroscopic and showed 7.4 wt % water at 60% RH and deliquesced at 80% RH. XRPD analysis following the moisture-sorption experiment affords a pattern consistent with Form A. Solubility studies conducted on both forms at pH 2, 7, and 12 in phosphate buffer showed differences, with Form A showing 28, 41, and >293 mg/mL respectively. Solubility concentrations were determined using area-percent calculations with HPLC calibration curves. Slurry experiments were performed on each form to determine propensity for conversion and to see if a unique form could be generated. Upon slurrying Form A in CH$_2$Cl$_2$, n-heptane, and toluene, conversion to Form B was observed after seven days. These results suggest that Form A is less thermodynamically stable under these conditions than Form B according to Ostwald's Rule of Stages.

6.1.5. Screening for Polymorphic Forms of Diazoxide Choline Salt.

A polymorph screening study of diazoxide choline salt was conducted with a series of crystallization and slurry conditions. As described herein, interconversion of diazoxide choline salt forms A and B was observed during this investigation. Each polymorphic form of diazoxide choline salt resulting from this study was characterized using the techniques and procedures described herein. A summary of characterization tests is listed in Table 16.

TABLE 16

Characterization of Forms A and B of Diazoxide Choline Salt In Screening Study

| Experiment | Form A | Form B |
|---|---|---|
| XRPD* | Crystalline | Crystalline |
| DSC | Endotherm ≈165° C. | Endotherm ≈160° C. |
| TGA | <1% | ≈1% |
| FTIR (ATR)** | Consistent w/ structure | Consistent w/ structure |
| $^1$H NMR | Consistent w/ 1:1 ratio | Consistent w/ 1:1 ratio |
| Moisture Sorption | Hygroscopic - deliquesced at 90% RH | Hygroscopic - deliquesced at 80% RH |
| Solubility | pH 2: 28 mg/mL<br>pH 7: 41 mg/mL<br>pH 12: >293 mg/mL | pH 2: 33 mg/mL<br>pH 7: 80 mg/mL<br>pH 12: 216 mg/mL |
| Thermal | Started to convert to Form B after 14 days at 60° C. | Stable after 14 days at 60° C. |
| Slurries | Converted to Form B after 7 days in n-heptane, toluene, and CH$_2$Cl$_2$ | Stable after 14 days in CH$_2$Cl$_2$, THF, and t-AmOH |

*Major peaks (2-θ):
Form A (9.8, 10.5, 14.9, 17.8, 17.9, 18.5, 19.5, 22.1, 22.6, 26.2, 29.6, 31.2);
Form B (8.9, 10.3, 12.0, 18.3, 20.6, 24.1, 24.5, 26.3, 27.1, 28.9).
**Unique FTIR (ATR) absorbances (cm$^{-1}$):
Form A (2926, 2654, 1592, 1449, 1248);
Form B (3256, 2174, 2890, 1605, 1463, 1235).

6.1.5.1. Solubility Screen in Organic Solvents.

Diazoxide choline, prepared in MEK using choline hydroxide as 50 wt % solution in water (see above) displayed some solubility in the following solvents: acetonitrile, acetone, ethanol, IPA, MEK, DMF, and methanol. These solvents were chosen due to differences in functionality, polarity, and boiling points and their ability to dissolve diazoxide. Other solvents which showed poor ability to dissolve salts were used as antisolvents and in slurry experiments where some solubility was observed: dioxane, MTBE, EtOAc, IPAc, THF, water, cyclohexane, heptane, CH$_2$Cl$_2$, and toluene.

Solvents for crystallizations during screening were chosen based on the solubility screen summarized in Table 17. Crystallizations of diazoxide choline from all conditions afforded a total of two forms, A and B. Forms A and B were found to be anhydrous polymorphs of diazoxide choline. Form B was observed to be generated from most solvents used. It was difficult to isolate pure Form A on large scales (>50 mg) as conditions observed to produce Form A on a smaller scale (approximately 50 mg or less) were found to result in Form B or mixtures of both forms on larger scales. Based on room-temperature slurry experiments, anhydrous Form B was found to be the most thermodynamically stable form in this study. Form A readily converted to Form B in all slurry solvents utilized.

TABLE 17

Solubility Screen for Diazoxide Choline Salt

| Solvent | Cmpd (mg) | Solvent (mL) | Conc. (mg/mL) | Temp. (° C.) | Soluble |
|---|---|---|---|---|---|
| MeCN | 1.7 | 0.25 | >6.80 | rt | Yes |
| Dioxane | 1.4 | 5.00 | 0.28 | 55 | No |
| Acetone | 1.9 | 0.25 | 7.60 | 55 | Yes |
| MTBE | 2.4 | 5.00 | 0.48 | 55 | No |
| EtOH | 1.5 | 0.25 | >6.00 | rt | Yes |
| EtOAc | 1.2 | 5.00 | 0.24 | 55 | No |
| IPAc | 1.4 | 5.00 | 0.28 | 55 | No |
| IPA | 1.8 | 0.25 | 7.20 | 55 | Yes |

TABLE 17-continued

Solubility Screen for Diazoxide Choline Salt

| Solvent | Cmpd (mg) | Solvent (mL) | Conc. (mg/mL) | Temp. (° C.) | Soluble |
|---|---|---|---|---|---|
| THF | 1.1 | 5.00 | 0.22 | 55 | No |
| MEK | 1.8 | 1.00 | 1.80 | 55 | Yes |
| DMF | 1.2 | 0.25 | >4.80 | rt | Yes |
| Water | 2.0 | 5.00 | 0.40 | 55 | No |
| MeOH | 1.9 | 0.25 | 7.60 | 55 | Yes |
| c-Hexane | 2.0 | 5.00 | 0.40 | 55 | No |
| Heptane | 1.9 | 5.00 | 0.38 | 55 | No |
| $CH_2Cl_2$ | 1.3 | 5.00 | 0.26 | 55 | Partially |
| Toluene | 1.4 | 5.00 | 0.28 | 55 | No |

6.1.5.2. Single-Solvent Crystallizations

Fast cooling procedure: Diazoxide (approximately 20 mg) was weighed out into vials and enough solvent (starting with 0.25 mL) was added until the material completely dissolved at elevated temperature. After hot filtration the vials were placed in a refrigerator (4° C.) for 16 hours. After the cooling-process the samples were observed for precipitates which were isolated by filtration. Vials not demonstrating precipitates were evaporated down to dryness using a gentle stream of nitrogen. All solids were dried in vacuo at ambient temperature and 30 in. Hg.

Slow cooling procedure: Diazoxide (approximately 30 mg of choline salt) was weighed out into vials and enough solvent was added until the material went into solution at elevated temperature. After hot filtration the vials were then slowly cooled to room temperature at the rate of 20° C./h and stirred at room temperature for 1-2 hours. All solids were dried in vacuo at ambient temperature and 30 in. Hg.

Based on the initial solubility study, seven solvents were selected for the fast-cooling crystallization: acetonitrile, acetone, ethanol, IPA, MEK, DMF, and methanol. Table 18 shows a list of the solvents that were used and the amount of solvent needed to dissolve the material. After the cooling-process precipitates were noticed in samples #2, 3, 5, and 6, the solids were isolated by filtration. The other samples (#1, 4, and 7) were evaporated down to dryness using a gentle stream of nitrogen. The diazoxide choline salts were found to be consistent with Form A by XRPD analysis for all solids with the exception of sample #2 (consistent with the freeform) and sample #5 (consistent with Form B with preferred orientation observed).

TABLE 18

Single-Solvent Crystallization of Diazoxide Choline Salt Using Fast-Cooling Procedure

| Entry | Solvent | BP (° C.) | Cmpd (mg) | Solvent Amt (mL) | Conc (mg/mL) | Temp. (° C.) | Precipitate | Form |
|---|---|---|---|---|---|---|---|---|
| 1 | Acetone | 56 | 21.0 | 1.00 | 21.00 | 55 | No/Evap | A |
| 2 | MeOH | 64 | 20.3 | 0.25 | 81.20 | 55 | Yes | FF* |
| 3 | EtOH | 78 | 21.3 | 0.25 | 85.20 | 62 | Yes | A |
| 4 | MEK | 80 | 19.6 | 1.25 | 15.68 | 75 | No/Evap | A |
| 5 | MeCN | 81 | 20.6 | 0.25 | 82.40 | 55 | Yes | Unique |
| 6 | IPA | 82 | 22.8 | 0.25 | 91.20 | 62 | Yes | A |
| 7 | DMF | 153 | 26.0 | 0.25 | 104.00 | 55 | No/Evap | A |

In accordance with the data obtained from fast-cooling experiments, four solvents which showed precipitation of solids were chosen for the slow-cooling experiments: MeOH, EtOH, MeCN, and IPA (Table 19). All obtained analyzable solids of the choline salt were found to be consistent with Form B by XRPD with the exception of Entry #1 which was consistent with diazoxide freeform and Entry #2 which was not analyzable. Mother liquor of Entry #2 was concentrated to dryness and the residual solids were analyzed by XRPD and found to be Form B material. As a result of obtaining freeform material from the single-solvent crystallizations in methanol, three more alcohols were tested for the single-solvent crystallizations using fast- and slow-cooling procedures. Tables 20 and 21 provide a list of the solvents that were used and the amount of solvent needed to dissolve the material. XRPD patterns of the fast-cooling procedure showed freeform of diazoxide from isobutanol, Form B from isoamyl alcohol, and Form A from tert-amyl alcohol compared to the slow-cooling procedure, which afforded Form B material from all three solvents.

TABLE 19

Single-Solvent Crystallization of Diazoxide Choline Salt Using Slow-Cooling Procedure

| Solvent | Boiling Point (° C.) | Material Amount (mg) | Solvent Amount (mL) | Conc. (mg/mL) | Temp. (° C.) | Precipitate | Form |
|---|---|---|---|---|---|---|---|
| MeOH | 64 | 32.1 | 0.3 | 107.00 | 62 | Yes | FF* |
| EtOH | 78 | 33.3 | 0.3 | 111.00 | 75 | Yes | NA** |
| MeCN | 81 | 30.9 | 0.3 | 103.00 | 62 | Yes | B |
| IPA | 82 | 33.7 | 0.3 | 112.33 | 80 | Yes | B |

TABLE 20

Single-Solvent Crystallization of Diazoxide Choline Salt Using Fast-Cooling Procedure

| Solvent | Boiling Point (° C.) | Material Amount (mg) | Solvent Amount (mL) | Conc. (mg/mL) | Temp. (° C.) | Precipitate | Form |
|---|---|---|---|---|---|---|---|
| i-BuOH | 108 | 29.7 | 0.3 | 99.00 | 78 | Yes | (sm)* |
| i-AmOH | 130 | 29.6 | 0.3 | 98.67 | 82 | Yes | B |
| t-AmOH | 102 | 29.5 | 0.3 | 98.33 | 95 | No/Evap | A |

TABLE 21

Single-Solvent Crystallization of Diazoxide Choline Salt Using Slow-Cooling Procedure

| Solvent | Boiling Point (° C.) | Material Amount (mg) | Solvent Amount (mL) | Conc. (mg/mL) | Temp. (° C.) | Precipitate | Form |
|---|---|---|---|---|---|---|---|
| i-BuOH | 108 | 33.0 | 0.3 | 110.00 | 92 | Yes | B |
| i-AmOH | 130 | 28.2 | 0.3 | 94.00 | 92 | Yes | B |
| t-AmOH | 102 | 29.0 | 0.4 | 72.50 | 92 | Yes | B |

The results of the choline salt single-solvent fast- and slow-cooling crystallizations (see Tables 19 to 21) indicated that Form A was more likely to be isolated with fast-cooling profiles and Form B with slow-cooling profiles.

6.1.5.3. Binary Solvent Crystallizations

Binary-solvent crystallizations of the choline salt were performed using four primary solvents (MeOH, EtOH, IPA, and MeCN) and nine cosolvents (MTBE, EtOAc, IPAc, THF, c-hexane, heptane, toluene, CH$_2$Cl$_2$, and dioxane) with a fast-cooling profile (supra). XRPD patterns showed that Form B was obtained from mixtures of MeOH with MTBE, EtOAc, IPAc, toluene, and dioxane. As shown in Table 22, Form A was obtained from mixtures of MeOH with THF and with CH$_2$Cl$_2$ after evaporating the solvent to dryness. The mixtures of MeOH with cyclohexane and heptane provided the freeform of diazoxide. All solids obtained from fast-cooling procedures with EtOH, IPA, and MeCN as primary solvents provided Form B material.

TABLE 22

Binary-Solvent Crystallizations of Choline Salt of Diazoxide Using Fast-Cooling Procedure and MeOH as a Primary Solvent

| Diazoxide Amt (mg) | MeOH* (mL) | Antisolvent | Amount (mL) | Precipitate | Form |
|---|---|---|---|---|---|
| 27.8 | 0.3 | MTBE | 1.4 | Yes | B |
| 30.7 | 0.3 | EtOAc | 6.0 | Yes | B |
| 32.0 | 0.3 | IPAc | 6.0 | Yes | B |
| 31.9 | 0.3 | THF | 6.0 | No/Evap to Dry | A |
| 29.5 | 0.3 | c-Hexane | 2.0 | Yes (small) | FF** |
| 30.2 | 0.3 | Heptane | 2.0 | Yes | FF** |
| 29.3 | 0.3 | Toluene | 6.0 | Yes | B |
| 32.0 | 0.3 | CH$_2$Cl$_2$ | 6.0 | No/Evap to Dry | A |
| 28.8 | 0.3 | Dioxane | 6.0 | Yes | B |

*Solids were dissolved at 62° C.
**Freeform of diazoxide.

Binary-solvent recrystallizations of the choline salt with the slow-cooling procedure were performed using two primary solvents (IPA and MeCN) and nine cosolvents (MTBE, EtOAc, IPAc, THF, c-hexane, heptane, toluene, CH$_2$Cl$_2$, and dioxane). All solids obtained from a slow-cooling procedure with IPA and MeCN as primary solvents provided Form B material based on XRPD analysis. The results of binary-solvent crystallizations indicated that Form B was the most thermodynamically stable form of diazoxide choline.

6.1.5.4. Binary Solvent Crystallizations Using Water as a Cosolvent

In an attempt to investigate the formation of hydrates of the choline salt, experiments was performed using fast- and slow-cooling procedures and water as a cosolvent.

The fast cooling procedure (supra) was used with the exception of using different primary solvents which were miscible with water: acetone, acetonitrile, DMF, IPA, i-BuOH, i-AmOH, and t-AmOH. Water was utilized in these crystallizations as a cosolvent. All solids obtained from the fast-cooling procedure with water as the cosolvent provided diazoxide freeform material by XRPD analysis.

To compare the results obtained from the fast-cooling procedure a set of experiments was performed using a slow-cooling procedure and water as a cosolvent. All obtained solids were analyzed by XRPD and afforded patterns consistent with diazoxide freeform. Without wishing to be bound by theory, these results suggest that the conditions used for crystallization caused dissociation of the choline salt. A small amount of a second crop was obtained in each sample, but only two samples were analyzable by XRPD and indicated that the samples were freeform material. All mother liquors were evaporated to dryness and the residual solids were also analyzed by XRPD to afford patterns consistent with Form B of the choline salt.

6.1.5.5. Metastable Zone Width Estimation

Form B: To produce a robust process, an understanding of the solubility profiles of the various solid forms under consideration is required. From a practical standpoint, this involves the measurement of the metastable zone width (MSZW) of pure forms, whereby the saturation and supersaturation curves of the different forms are generated over a well defined concentration and temperature range. This knowledge can then be used to design a crystallization protocol that should ideally favor a selective crystal growth of the desired form.

Form B of diazoxide choline salt showed moderate solubility in a solvent mixture made of MeCN/MeOH/MtBE (10:1:12, volume ratios). The wide width of the metastable zone as shown in Table 23 gives many seeding options. During the MSZW measurement, aliquots from the crystallizing material were withdrawn and analyzed by XRPD to ensure that no form conversion occurred during the experiment. Indeed, the material remained unchanged during the test.

TABLE 23

Meta-Stable Zone Width For Form B Diazoxide Choline Salt in MeCN/MeOH/MtBE (10:1:12) (v/v).

| Conc. (mg/mL) | Temp. In (° C.) | Temp. Out (° C.) | Temp. Range (° C.) |
|---|---|---|---|
| 30.8 | 53.2 | 35.0 | 18.2 |
| 28.5 | 49.0 | 33.6 | 15.4 |
| 26.5 | 47.0 | 32.0 | 15.0 |
| 24.7 | 43.8 | 29.1 | 14.7 |
| 23.2 | 40.5 | 28.5 | 12.0 |
| 21.9 | 38.0 | 26.0 | 12.0 |

Form A: The metastable zone width for Form could not be estimated because this polymorphic form converted during the experiment to Form B.

6.1.5.6. Crystallization of Form A of Diazoxide Choline Salt

The choline salt of diazoxide (160.3 mg) was dissolved in 1 mL of IPA at 55° C. which was then passed through a Millipore 0.45 µM filter into a clean vial. This vial was placed in freezer a –20° C. overnight. Solids were not noticed and the flask was scratched with a micro-spatula. The vial was placed back in the freezer and nucleation was noticed after ten minutes. The solids were collected by vacuum filtration and washed with 1 mL of MtBE. The solids were dried in vacuo at 40° C. and 30 in. Hg to afford 70 mg (43.6% recovery) of Form A as determined by XRPD.

6.1.5.7. 500-mg Scale Crystallization of Form B of Diazoxide Choline Salt

The choline salt of diazoxide (524.3 mg) was dissolved in 3 mL of IPA at 78° C. and this solution was then cooled to 55° C. for the addition of MtBE. The MtBE (4 mL) was added until nucleation was observed. After nucleation the batch was allowed to cool to room temperature at a rate of 20° C./h. The solids were collected by vacuum filtration and washed with 1 mL of MtBE. The solids were dried in vacuo at 40° C. and 30 in. of Hg to afford 426.7 mg (81.3% recovery) of Form B as determined by XRPD.

6.1.5.8. 2-g Scale Crystallization of Form B of Diazoxide Choline Salt

The choline salt of diazoxide (2.0015 g) was dissolved in 5.5 mL of IPA at 78° C. to afford a clear solution. This solution was passed through a Millipore Millex FH 0.45 µM filter. This solution was then cooled to 55° C. MtBE was added in 1 mL portions, with a two minute interval between portions. Nucleation was noted after the second addition of MtBE. This suspension was allowed to cool to room temperature at a rate of 20° C./h and stirred at this temperature for 16 hours. The solids were collected by vacuum filtration and washed with 1 mL of MtBE. The solids were dried in vacuo at 40° C. and 30 in. of Hg to afford 1.6091 g (80.4% recovery) of Form B as determined by XRPD.

6.1.5.9. Detection of Form Impurities

Mixtures of diazoxide choline Forms A and B were prepared by adding a minor amount of Form A to Form B. Samples were lightly ground by hands with a mortar and pestle for approximately one minute. Samples were then analyzed by XRPD analysis. XRPD analysis was found to be suitable for detecting 5% of Form A in Form B.

6.2. Polymorphic Forms of the Potassium Salt of Diazoxide

A summary of characterization tests for three common crystalline forms of diazoxide potassium salt are listed in Table 24. Solvents for crystallizations were chosen based on the solubility screen summarized below. Crystallizations of diazoxide potassium salt from all conditions provided herein afforded a total of seven unique crystalline forms, A through G. Forms C, D, and F were found to be the most common during the crystallization screen, and were therefore scaled up for further characterization.

TABLE 24

Results Summary of Characterization Tests for Salt of Diazoxide Potassium

| Experiment | Form C | Form D | Form F |
|---|---|---|---|
| XRPD* | Crystalline | Crystalline | Crystalline |
| DSC | 187, 360° C. | 130, 191, 352° C. | 191, 363° C. |
| TGA | 8.4%** | 4.5%** | 13.1%** |
| FTIR (ATR)* | Consistent w/ structure | Consistent w/ structure | Consistent w/ structure |
| $^1$H NMR | Consistent w/ structure** | Consistent w/ structure | Consistent w/ structure** |
| Moisture Sorption | Hygroscopic - deliquesced at 90% RH Hygroscopic - deliquesced at 90% RH | Hygroscopic - deliquesced at 90% RH | |
| Solubility | N/A | pH 2: 29 mg/mL pH 7: 33 mg/mL pH 12: 59 mg/mL | N/A |
| Thermal | Stable (7 days) | Stable (7 days) | Stable (7 days) |
| Slurries | Converted to Form D | Converted to Form D | Converted to Form D |

*XRPD Major peaks (2-θ):
Form A (6.0, 8.1, 16.3, 17.7, 18.6, 19.1, 22.9, 23.3, 23.7, 24.7, 25.4, 26.1, 28.2, 29.6, 30.2);
Form B (8.5, 10.8, 16.9, 18.2, 21.6, 25.5, 26.1, 28.9);
Form C (5.7, 6.1, 17.9, 23.9, 25.1, 37.3);
Form D (5.7, 6.2, 8.1, 8.5, 8.8, 16.9, 18.6, 23.2, 24.5, 25.8, 26.1);
Form E (6.7, 7.1, 14.1, 21.2);
Form F (8.5, 9.0, 18.7, 20.6, 23.5, 27.5, 36.3);
Form G (5.2, 5.5, 13.1, 16.5, 19.3, 22.8, 24.8, 26.4, 28.7, 34.1);
*Unique FTIR (ATR) absorbances (cm$^{-1}$):
Form A (1503, 1374, 1339, 1207, 1131, 1056, 771);
Form B (1509, 1464, 1378, 1347);
Form C (1706, 1208, 1146, 746);
Form D (1595, 1258, 1219, 890);
Form E (1550, 1508, 1268, 1101, 1006).
Form F (1643, 1595, 1234, 1145, 810).
Form G (1675, 1591, 1504, 1458, 1432, 1266, 999, 958, 905, 872).
**Data indicates a half-molar equivalent of acetone, water, or dioxane for Forms C, D, and F respectively.

Diazoxide potassium Forms C, D, and F were observed to be an acetone solvate, a hemihydrate, and a dioxane solvate of diazoxide potassium, respectively. Form C is an acetone solvate that was generated predominantly when acetone was used in the crystallization. Form D, a hemihydrate, was observed to be generated from most solvents used. Form F is a dioxane solvate generated when dioxane was used as an antisolvent. Forms A, B, E, and G were not commonly observed during the crystallization. Elemental analysis data indicated that the unique forms observed may be mixtures and/or have residual solvent(s) present.

Based on room-temperature slurry experiments presented, Form D was found to be the most thermodynamically stable form of those discovered in this study. Forms C and F readily converted to Form D in all slurry solvents utilized. Without wishing to be bound by theory, since nonaqueous solvents were used, the material may have converted to the hemihydrate, Form D, upon removal from the solvent.

6.2.1. Demonstration of Preparation of Polymorphic Form A of the Potassium Salt of Diazoxide The polymorphic Form A of the potassium salt of diazoxide was prepared as described above.

6.2.2. Demonstration of Preparation of the Polymorphic Form B of the Potassium Salt of Diazoxide Diazoxide (2.95 g) was combined with 450 mL of methyl ethyl ketone and heated to approximately 77° C. to dissolve the diazoxide. To the solution was added approximately 13 mL of 1M potassium hydroxide at a rate of approximately 20 mL/min, stirred and allowed to cool to room temperature. The solution was stirred at room temperature for ~16 h. The solvent was removed under reduced pressure, and the residual solids were dried in vacuo at 57° C. and 30 in. Hg to afford 3.7 g of the potassium salt.

6.2.3. Characterization of the Polymorphic Form B of the Potassium Salt of Diazoxide The Form B polymorph of the potassium salt of diazoxide was analyzed by XRPD, and $^1$H NMR. FIG. 18 shows the XRPD pattern of (a) the Form A polymorph of the potassium salt of diazoxide and (b) the Form B polymorph of the potassium salt of diazoxide.

The $^1$H NMR of the Form B polymorph of the potassium salt of diazoxide shows no change from the Form A polymorph.

6.2.4. Demonstration of Preparation of the Polymorphic Form A of the Potassium Salt of Diazoxide from Form B Approximately 20 mg of the Form B polymorph of the diazoxide potassium salt was added to 2 mL of acetone and heated until the material completely dissolved at 55° C. The solution was hot filtered and placed in a refrigerator (4° C.) for 16 hours. No precipitate was formed. The solvent was evaporated down to dryness using a gentle stream of nitrogen and the resultant solids were dried in vacuo at room temperature and 30 in. Hg. The solid was analyzed by XRPD to determine the physical form. See FIG. 18(a).

6.2.5. Preparation of the Polymorphic Form C of the Potassium Salt of Diazoxide from Form B Approximately 20 mg of the Form B polymorph of the diazoxide potassium salt was added to 6 mL of ethyl acetate and heated until the material completely dissolved at 75° C. The solution was hot filtered and placed in a refrigerator (4°

C.) for 16 hours. No precipitate was formed. The solvent was evaporated down to dryness using a gentle stream of nitrogen and the resultant solids were dried in vacuo at room temperature and 30 in. Hg. The solid was analyzed by XRPD to determine the physical form. See FIG. 18(c).

6.2.6. Preparation of the Polymorphic Form D of the Potassium Salt of Diazoxide from Form B Approximately 20 mg of the Form B polymorph of the diazoxide potassium salt was added to 0.3 mL of isopropyl alcohol and heated until the material completely dissolved at 62° C. The solution was hot filtered and placed in a refrigerator (4° C.) for 16 hours. No precipitate was formed. The solvent was evaporated down to dryness using a gentle stream of nitrogen and the resultant solids were dried in vacuo at room temperature and 30 in. Hg. The solid was analyzed by XRPD to determine the physical form. See FIG. 19(a).

6.2.7. Preparation of the Polymorphic Form E of the Potassium Salt of Diazoxide from Form B Approximately 20 mg of the Form B polymorph of the diazoxide potassium salt was added to 2.5 mL of tert-amyl alcohol and heated until the material completely dissolved at 95° C. The solution was hot filtered and placed in a refrigerator (4° C.) for 16 hours. No precipitate was formed. The solvent was evaporated down to dryness using a gentle stream of nitrogen and the resultant solids were dried in vacuo at room temperature and 30 in. Hg. The solid was analyzed by XRPD to determine the physical form. See FIG. 19(B).

6.2.8. Preparation of the Polymorphic Form F of the Potassium Salt of Diazoxide from Form B Approximately 20 mg of the Form B polymorph of the diazoxide potassium salt was added to 0.6 mL of acetonitrile and heated until the material completely dissolved at 80° C. The solution was hot filtered, 6 mL of dioxane was added, and the solution was placed in a refrigerator (4° C.) for 16 hours. No precipitate was formed. The solvent was evaporated down to dryness using a gentle stream of nitrogen and the resultant solids were dried in vacuo at room temperature and 30 in. Hg. The solid was analyzed by XRPD to determine the physical form. See FIG. 19(C).

6.2.9. Preparation of the Polymorphic Form G of the Potassium Salt of Diazoxide from Form B Approximately 22.3 mg of the Form B polymorph of the diazoxide potassium salt was added to 0.5 mL of isoamyl alcohol and heated until the material completely dissolved at 73° C. The solution was hot filtered, 6 mL of isopropyl acetate was added, and the solution was placed in a refrigerator (4° C.) for 16 hours. No precipitate was formed. The solvent was evaporated down to dryness using a gentle stream of nitrogen and the resultant solids were dried in vacuo at room temperature and 30 in. Hg. The solid was analyzed by XRPD to determine the physical form. See FIG. 19(D).

As shown in Tables 25 and 26, both the solvent used for recrystallization and the rate of cooling (i.e., fast cooling vs. slow cooling during the recrystallization) effect the crystal structure obtained once the product is isolated.

TABLE 25

Fast cooling of Potassium Salt of Diazoxide in Various Solvents

| Solvent | Cmpd (mg) | Solvent (mL) | Recovery (mg) | Form |
| --- | --- | --- | --- | --- |
| THF | 20.8 | 6.5 | 14.2 | B |
| EtOAc | 21.1 | 6.0 | 10.6 | C |
| MeCN | 21.2 | 0.5 | n/a | C + D |
| IPA | 22.7 | 0.3 | n/a | D |
| Water | 20.6 | 1.5 | n/a | Free form diazoxide |
| tAA | 21.9 | 2.5 | 16.7 | E |
| IAA | 19.7 | 0.3 | n/a | D |
| DMF | 21.6 | 0.3 | 15.9 | G |

TABLE 26

Slow cooling of Potassium Salt of Diazoxide in Various Solvents

| Solvent | Cmpd (mg) | Solvent (mL) | Recovery (mg) | Form |
| --- | --- | --- | --- | --- |
| EtOAc | 20.4 | 6.0 | 7.1 | D |
| MeCN | 22.8 | 0.5 | 13.8 | C |
| IPA | 21.5 | 0.3 | 13.2 | C |
| Water | 20.9 | 1.5 | 1.2 | Free form diazoxide |
| tAA | 21.5 | 2.5 | 15.4 | E |
| IAA | 20.6 | 0.3 | 6.6 | D |

6.2.10. Polymorphs Obtained by Recrystallization of the Potassium Salt of Diazoxide in Binary Solvents As shown in Tables 27 and 28, recrystallization of the potassium salt of diazoxide from a variety of binary solvent systems also demonstrated conversion of the potassium salt to an alternate form. Use of acetonitrile as the primary solvent is shown in Table 27 and use of acetone as the primary solvent is shown in Table 28. As shown in Table 27, recrystallization of the Form B polymorph of the potassium salt of diazoxide from acetonitrile using methyl tert-butyl ether, ethyl acetate, isopropyl acetate, tetrahydrofuran, c-hexane, heptane, toluene and dichloromethane as the secondary solvent all yielded the D Form polymorph of the potassium salt. Recrystallization from acetonitrile using dioxane as the secondary solvent yielded the F Form polymorph of the diazoxide salt of potassium.

TABLE 27

Recrystallization in Acetonitrile

| Acetonitrile (mL) | Secondary solvent | Cmpd (mg) | Recovery (mg) | Form |
| --- | --- | --- | --- | --- |
| 0.6 | MTBE | 20.7 | 13.7 | D |
| 0.6 | EtOAc | 23.4 | 9.5 | D |
| 0.6 | IPAc | 20.0 | 13.3 | D |
| 0.6 | THF | 20.3 | 6.4 | D |
| 0.6 | c-Hexane | 20.4 | 9.6 | D |
| 0.6 | Heptane | 20.3 | 10.8 | D |
| 0.6 | Toluene | 23.6 | 16.1 | D |
| 0.6 | Dichloromethane | 21.3 | 12.7 | D |
| 0.6 | Dioxane | 20.7 | 12.6 | F |

As shown in Table 28, recrystallization of the Form B polymorph of the potassium salt of diazoxide from acetone using methyl tert-butyl ether, tetrahydrofuran, and c-hexane as the secondary solvent all yielded the Form A polymorph of the potassium salt of diazoxide. Recrystallization from acetone using ethyl acetate, heptane, toluene and dichloromethane as the secondary solvent all yielded the C Form polymorph of the potassium salt. Recrystallization from acetone using isopropyl acetate as the secondary solvent yielded the D Form polymorph of the diazoxide salt of potassium. Recrystallization from acetone using dioxane as the secondary solvent yielded the F Form polymorph of the diazoxide salt of potassium.

TABLE 28

Recrystallization in Acetone

| Acetone (mL) | Other Solvent | Amt (mg) | Recovery (mg) | Form |
|---|---|---|---|---|
| 2.0 | MTBE | 20.2 | 13.9 | A |
| 2.0 | EtOAc | 21.6 | 4.8 | C |
| 2.0 | IPAc | 20.6 | 11.6 | D |
| 2.0 | THF | 20.9 | 12.0 | A |
| 2.0 | c-Hexane | 21.3 | 12.3 | A |
| 2.0 | Heptane | 20.6 | 12.7 | C |
| 2.0 | Toluene | 20.4 | 13.3 | C |
| 2.0 | Dichloromethane | 21.1 | 13.0 | C |
| 2.0 | Dioxane | 20.4 | 12.5 | F |

6.2.11. Screening for Polymorphic Forms of Diazoxide Potassium Salt.

A polymorphic screening study of diazoxide potassium salt was conducted with a series of crystallization conditions described below.

6.2.11.1. Solubility Screening for Polymorphic Forms of Diazoxide Potassium Salt.

Diazoxide potassium, prepared in MEK using 1 M potassium hydroxide solution in water, displayed some solubility in the following ten solvents: acetone, THF, EtOAc, MEK, MeCN, IPA, water, t-AmOH, i-AmOH, and DMF. These solvents were chosen due to differences in functionality, polarity, and boiling points and their ability to dissolve diazoxide. Solvents affording poor to fair solubility were used as antisolvents in binary/ternary crystallizations as well as slurry studies. Table 29 summarizes the results of the solubility screen.

TABLE 29

Solubility of Diazoxide Potassium Salt in Various Solvent

| Solvent | Cmpd Amt (mg) | Solvent (mL) | Conc. (mg/mL) | Temp. (° C.) | Soluble |
|---|---|---|---|---|---|
| MeCN | 1.7 | 2.00 | 0.85 | 55 | Yes |
| Dioxane | 1.4 | 5.00 | 0.28 | 55 | No |
| Acetone | 1.6 | 4.00 | 0.40 | 55 | Yes |
| MTBE | 1.8 | 5.00 | 0.36 | 55 | No |
| EtOH | 2.2 | 0.75 | 2.93 | 55 | Yes |
| EtOAc | 1.8 | 5.00 | 0.36 | 55 | No |
| IPAc | 1.7 | 5.00 | 0.34 | 55 | No |
| IPA | 2.1 | 1.00 | 2.10 | 55 | Yes |
| THF | 1.8 | 5.00 | 0.36 | 55 | Partially |
| MEK | 1.5 | 5.00 | 0.30 | 55 | Partially |
| DMF | 1.6 | 0.25 | >6.40 | rt | Yes |
| Water | 1.5 | 5.00 | 0.30 | 55 | No |
| MeOH | 1.5 | 0.25 | 6.00 | 55 | Yes |
| c-Hexane | 1.5 | 5.00 | 0.30 | 55 | No |
| Heptane | 1.2 | 5.00 | 0.24 | 55 | No |
| CH$_2$Cl$_2$ | 1.3 | 5.00 | 0.26 | 55 | No |
| Toluene | 1.4 | 5.00 | 0.28 | 55 | No |

6.2.11.2. Single-Solvent Screening for Polymorphic Forms of Diazoxide Potassium Salt.

Single-solvent crystallizations of potassium salt were performed using ten solvents: acetone, THF, EtOAc, MEK, MeCN, IPA, water, t-AmOH, i-AmOH, and DMF for the fast-cooling procedure and six solvents (EtOAc, MeCN, IPA, water, t-AmOH, and i-AmOH) for the slow-cooling procedures. The "fast" and "slow" cooling procedures were as described above. Four of the solvents were excluded from the slow-cooling experiments because they did not provide solids during fast-cooling experiments and needed to be evaporated to dryness. Tables 30 and 31 provide a list of the solvents that were used and the amount of solvent needed to dissolve the material. All solids were analyzed by XRPD to determine the physical form and six unique patterns (Forms A-E, G) were observed.

TABLE 30

Single-Solvent Crystallizations of Potassium Salt of Diazoxide Using Fast-Cooling

| Solvent | BP (° C.) | Cmpd Amt (mg) | Solvent Amt (mL) | Conc (mg/ mL) | Temp (° C.) | Precipitate | Form |
|---|---|---|---|---|---|---|---|
| Acetone | 56 | 20.7 | 2.0 | 10.35 | 55 | No/Evap | A |
| THF* | 65 | 20.8 | 6.5 | 3.20 | 63 | No/Evap | B |
| EtOAc | 76 | 21.1 | 6.0 | 3.52 | 75 | Yes | C |
| MEK | 80 | 20.2 | 4.0 | 5.05 | 75 | No/Evap | A |
| MeCN | 81 | 21.2 | 0.5 | 42.40 | 80 | Yes | C + D |
| IPA | 82 | 22.7 | 0.3 | 75.67 | 62 | Yes | D |
| Water | 100 | 20.6 | 1.5 | 13.73 | 95 | Yes | FF |
| t-AmOH | 103 | 21.9 | 2.5 | 8.76 | 95 | Yes | E |
| i-AmOH | 130 | 19.7 | 0.3 | 65.67 | 73 | Yes | D |
| DMF | 153 | 21.6 | 0.3 | 72.00 | RT | No/Evap | G |

*Solids were not completely dissolved.

TABLE 31

Single-Solvent Crystallizations of Potassium Salt of Diazoxide Using Slow-

| Solvent | BP (° C.) | Cmpd Amt (mg) | Solvent Amt (mL) | Conc (mg/ mL) | Temp (° C.) | Precipitate | Form |
|---|---|---|---|---|---|---|---|
| EtOAc | 76 | 20.4 | 6.0 | 3.40 | 75 | Yes | D |
| MeCN | 81 | 22.8 | 0.5 | 45.60 | 80 | Yes | C |
| IPA | 82 | 21.5 | 0.3 | 71.67 | 80 | No/Evap | C |
| Water | 100 | 20.9 | 1.5 | 13.93 | 95 | Yes | FF |
| t-AmOH | 103 | 21.5 | 2.5 | 8.60 | 95 | Yes | E |
| i-AmOH | 130 | 20.6 | 0.3 | 68.67 | 80 | Yes | D |

6.2.11.3. Binary-Solvent Screening for Polymorphic Forms of Diazoxide Potassium Salt.

Binary-solvent crystallizations of the potassium salt utilizing fast-cooling procedure were performed using MeCN, acetone, and isoamyl alcohol as primary solvents and the following nine cosolvents: MTBE, EtOAc, IPAc, THF, c-hexane, heptane, toluene, CH$_2$Cl$_2$, and dioxane. Table 32 is representative, employing acetonitrile as primary solvent. XRPD patterns from crystallizations using acetonitrile as a primary solvent were consistent with Form D with only one exception being the solids obtained from the mixture of MeCN/dioxane afforded a unique pattern (Form F) material.

TABLE 32

Binary-Solvent Crystallizations of Potassium Salt of Diazoxide Using Fast-cooling Procedure and McCN as a Primary Solvent

| Cmpd Amt (mg) | McCN* (mL) | Anti- solvent | Amt (mL) | Precipitate | Form |
|---|---|---|---|---|---|
| 20.7 | 0.6 | MTBE | 1.0 | Yes | D |
| 23.4 | 0.6 | EtOAc | 6.0 | Yes | D |
| 20.0 | 0.6 | IPAc | 3.0 | Yes | D |
| 20.3 | 0.6 | THF | 6.0 | No/Evap. To ppt | D |
| 20.4 | 0.6 | c-Hexane | 2.0 | Yes | D |

TABLE 32-continued

Binary-Solvent Crystallizations of Potassium Salt of Diazoxide Using Fast-cooling Procedure and McCN as a Primary Solvent

| Cmpd Amt (mg) | McCN* (mL) | Anti-solvent | Amt (mL) | Precipitate | Form |
|---|---|---|---|---|---|
| 20.3 | 0.6 | Heptane | 2.0 | Yes | D |
| 23.6 | 0.6 | Toluene | 1.0 | Yes | D |
| 21.3 | 0.6 | $CH_2Cl_2$ | 1.0 | Yes | D |
| 20.7 | 0.6 | Dioxane | 6.0 | Yes | F |

*Solids were dissolved at 80° C.

XRPD patterns from binary crystallizations with acetone as primary solvent employing a fast cooling procedure afforded four forms A, C, D, and F. Mixtures of acetone with MTBE, THF, and cyclohexane provided Form A material; Form C was obtained from the mixtures of acetone with EtOAc, heptane, toluene, and $CH_2Cl_2$. The mixture of acetone with IPAc afforded Form D, and the mixture of acetone with dioxane afforded Form F solids.

XRPD patterns from binary crystallizations with isoamyl alcohol as the primary solvent employing a fast cooling procedure afforded five forms: C, D, E, F, and G. Form C was obtained from crystallizations using MTBE and EtOAc as cosolvents; Form D was obtained from mixtures of isoamyl alcohol with heptane, toluene, and $CH_2Cl_2$; Form E was crystallized out of i-AmOH/THF and i-AmOH/cyclohexane; Form G was obtained from i-AmOH/IPAc and Form F was obtained from i-AmOH/dioxane. Form D was the most common form observed from the crystallizations, and Form F was observed only when dioxane was used as an antisolvent.

Binary solvent recrystallizations of the potassium salt with the slow-cooling procedure were performed using three primary solvents (MeCN, acetone, and i-AmOH) and eight cosolvents (MTBE, EtOAc, IPAc, c-hexane, heptane, toluene, $CH_2Cl_2$, and dioxane). All solids were analyzed by XRPD to determine the physical form. Two patterns were observed to be Forms C and D respectively with additional peaks present. Other crystallizations provided Forms D, C, or F. Form D was obtained from the following solvent mixtures: MeCN/MTBE, MeCN/IPAc, MeCN/toluene, MeCN/$CH_2Cl_2$ and also from the mixtures of i-AmOH with MTBE, IPAc, cyclohexane, heptane, and toluene. Form C was obtained from MeCN/heptane, i-AmOH/EtOAc, and mixtures of acetone with MTBE, EtOAc, IPAc, cyclohexane, heptane, toluene, and $CH_2Cl_2$. Form F was crystallized from the mixtures of MeCN/dioxane and i-AmOH/dioxane. The solvent mixture of MeCN/EtOH provided amorphous material. Elemental analysis results indicate that the forms observed may not be pure and/or have bound or residual solvents present. Forms C, D, and F were found to be the most common forms of the potassium salt isolated and based on the results, these forms were chosen for scale-up and further characterization. Differences were found in the XRPD patterns and FTIR spectra of the scale-up lots which were attributed to differences in impurity profiles, crystallinity, and form purity.

6.2.11.4. Characterization of Polymorphic Form C of Diazoxide Potassium Salt.

Form C of diazoxide potassium salt is an acetone solvate with a 2:1 ratio of diazoxide/solvent. It is a crystalline form of diazoxide potassium, with endothermic events at 187 and 360° C. in the DSC. The XRPD pattern for Form C is unique compared to all other forms observed. FTIR (ATR) spectroscopy showed differences between forms. $^1$H NMR spectra were found to be consistent with the structure of diazoxide with a half-molar equivalent of acetone present. NMR data also indicated that the magnetic environment of the diazoxide structure had changed evidenced by a movement in chemical shift of the aromatic and methyl proton resonances. In addition, the resonance due to the amine proton was not observed which suggested deprotonation in solution. Weight loss by TGA was 8.9%, consistent with a half-molar equivalent of acetone, and occurred near 180° C. consistent with the endotherm observed in the DSC experiment. Moisture-sorption analysis conducted at 25° C. from 0 to 90% RH (adsorption) and 85 to 0% RH (desorption) showed Form C to be a hygroscopic solid, showing approximately 47 wt % water at 90% RH which indicated the sample deliquesced. In comparison, Forms D and F (hemihydrate and dioxane solvate) showed approximately 26 and 22 wt % water at 90% RH respectively. XRPD analysis following the moisture-sorption experiment afforded a pattern consistent with Form D. Slurry experiments were performed on 50/50 mixtures of Forms C, D, and F to determine propensity for conversion and to see if a unique form could be generated. Upon slurrying Form C mixtures in ethyl acetate, acetonitrile, and isopropanol conversion to Form D was observed in all solvents. Without wishing to be bound by theory, these results as well as conversion of Form F to Form D in these conditions suggest that Form D is more thermodynamically stable than Form C and F according to Ostwald's Rule of Stages. A thermal-stability experiment on Form C at 60° C. found the form to be stable. Conversion to another form was not observed.

6.2.11.5. Characterization of Polymorphic Form D of Diazoxide Potassium Salt.

Form D of diazoxide potassium salt is a hemihydrate. It is a crystalline form of diazoxide potassium, with endothermic events at 130, 191, and 352° C. in the DSC. FTIR (ATR) spectroscopy showed differences between forms. $^1$H NMR spectra were found to be consistent with the structure of diazoxide. NMR data also indicated that the magnetic environment of the diazoxide structure had changed evidenced by a movement in chemical shift of the aromatic and methyl proton resonances. In addition, the resonance due to the amine proton was not observed which suggested deprotonation in solution. Weight loss by TGA was 4.5%, consistent with a half-molar equivalent of water, and occurred near 110° C. consistent with the endotherm observed in the DSC experiment. Moisture-sorption analysis conducted at 25° C. from 0 to 90% RH (adsorption) and 85 to 0% RH (desorption) showed Form D to be a hygroscopic, showing approximately 26 wt % water at 90% RH. In comparison, Forms C and F (acetone and dioxane solvates) showed approximately 47 and 22 wt % water at 90% RH, respectively. XRPD analysis following the moisture-sorption experiment afforded a pattern consistent with Form D. Solubility studies were conducted at pH 2, 7, and 12 for Form D and showed 29, 33, and 59 mg/mL respectively. Solubility concentrations were determined using area-percent calculations with an HPLC calibration curve. Slurry experiments were performed on 50/50 mixtures of Forms C, D, and F to determine their propensity for conversion and to see if a unique form could be generated. Upon slurrying mixtures of Form D with Form C or Form F in ethyl acetate, acetonitrile, and isopropanol conversion to Form D was observed in all solvents.

6.2.11.6. Characterization of Polymorphic Form F of Diazoxide Potassium Salt.

Form F of diazoxide potassium salt is a dioxane solvate with a 2:1 ratio of diazoxide/solvent. It is a crystalline form of diazoxide potassium, with endothermic events at 191 and 363° C. in the DSC. The XRPD pattern for Form F is unique compared to all other forms observed. FTIR (ATR) spectroscopy showed differences between forms. $^1$H NMR spectra were found to be consistent with the structure of diazoxide with a half-molar equivalent of dioxane present. NMR data also indicated that the magnetic environment of the diazoxide structure had changed as evidenced by a movement in chemical shift of the aromatic and methyl proton resonances. In addition, the resonance due to the amine proton was not observed which suggested deprotonation in solution. Weight loss by TGA was 13.1%, consistent with a half-molar equivalent of dioxane, and occurs near 180° C. consistent with the endotherm observed in the DSC experiment. Moisture-sorption analysis conducted at 25° C. from 0 to 90% RH (adsorption) and 85 to 0% RH (desorption) showed Form F to be a hygroscopic solid, showing approximately 22 wt % water at 90% RH. In comparison, Forms C and D (acetone solvate and hemihydrate) showed approximately 47 and 26 wt % water at 90% RH, respectively. XRPD analysis following the moisture-sorption experiment afforded a pattern consistent with Form D. Slurry experiments were performed on 50/50 mixtures of Forms C, D, and F to determine their propensity for conversion and to see if a unique form could be generated. Upon slurrying mixtures of Form F with Form C and Form D in ethyl acetate, acetonitrile, and isopropanol conversion to Form D was observed in all solvents.

B. In Vivo Obesity Testing

1. Obesity Animal Model

Formulations of salts of any of the compounds of Formulae I-IV prepared as described herein can be tested for efficacy in an animal model of obesity as described by Surwit et al. (*Endocrinology* 141:3630-3637 (2000)). Briefly, 4-week-old B6 male mice are housed 5/cage in a temperature-controlled (22° C.) room with a 12-h light, 12-h dark cycle. The high fat (HF) and low fat (LF) experimental diets contain 58% and 11% of calories from fat, respectively. A group of mice are fed the HF diet for the first 4 weeks of the study; the remaining 15 mice are fed the LF diet. The mice assigned to the LF diet are maintained on this diet throughout the study as a reference group of lean control mice. At week 4, all HF-fed mice a reassigned to 2 groups of mice. The first group remains on the HF diet throughout the study as the obese control group. The remaining 3 groups of mice are fed the HF diet and administered the controlled release formulation of salts of any of the compounds of Formulae I-IV at about 150 mg of active per kg per day as a single dose administered by oral gavage. Animals are weighed weekly, and food consumption is measured per cage twice weekly until the diets are changed at week 4, whereupon body weight and food intake are determined daily. The feed efficiency (grams of body weight gained per Cal consumed) is calculated on a per cage basis. Samples for analysis of insulin, glucose, and leptin are collected on day 24 (4 days before the diets are changed), on day 32 (4 days after the change), and biweekly thereafter. In all cases food is removed 8 h before samples are collected. Glucose is analyzed by the glucose oxidase method. Insulin and leptin concentrations are determined by double antibody RIA. The insulin assay is based on a rat standard, and the leptin assay uses a mouse standard. At the termination of the study, a postprandial plasma sample is collected and analyzed for triglyceride and nonesterified fatty acid concentrations. After 4 weeks of drug treatment, a subset of 10 animals from each group is killed. The epididymal white adipose tissue (EWAT), retroperitoneal (RP) fat, interscapular brown adipose tissue (IBAT) fat pads, and gastrocnemius muscle are removed, trimmed, and weighed. The percent body fat is estimated from the weight of the epididymal fat pad. A subset of five animals from each group is injected i.p. with 0.5 g/kg glucose. At 30 min post injection, a plasma sample is collected and analyzed for glucose content by the glucose oxidase method.

2. Treatment of Obesity in Humans

Formulations of salts of any of the compounds of Formulae I-IV prepared as described herein can be tested for efficacy in obese humans, as described by Alemzadeh (Alemzadeh et al., *J Clin Endocr Metab* 83:1911-1915 (1998)). Subjects consist of moderate-to-morbidly obese adults with a body mass index (BMI) greater than or equal to 30 kg/m$^2$. Each subject undergoes a complete physical examination at the initial evaluation, body weight being measured on a standard electronic scale and body composition being measured by DEXA.

Before initiation of the study, all subjects are placed on a hypocaloric diet for a lead-in period of 1 week. This is designed to exclude subjects who are unlikely to be compliant and to ensure stable body weight before treatment. Up to 50 subjects are tested at each dosage of drug. Daily dosage is set at 100, 200, and 300 mg/day. The daily dose is divided into 2 doses for administration. The dose is administered as either one, two or three 50 mg capsules or tablets at each time of administration. Subjects are dosed daily for up to 12 months. Subjects are reviewed weekly, weighed, and asked about any side effects or concurrent illnesses.

Twenty-four-hour dietary recall is obtained from each subject. The dietary recalls are analyzed using a standard computer software program. All subjects are placed on a hypocaloric diet and encouraged to participate in regular exercise.

Before commencing, and after completion of the study, the following laboratory tests are obtained: blood pressure, fasting plasma glucose, insulin, cholesterol, triglycerides, free fatty acids (FFA), and glycohemoglobin, and measures of rate of appearance and oxidation of plasma derived fatty acids. Additionally, routine chemistry profiles and fasting plasma glucose are obtained weekly to identify those subjects with evidence of glucose intolerance and/or electrolyte abnormalities. Glucose is analyzed in plasma, by the glucose oxidase method.

Insulin concentration is determined by RIA using a double-antibody kit. Cholesterol and triglycerides concentrations are measured by an enzymatic method. Plasma FFA is determined by an enzymatic calorimetric method. SI was assessed by an iv glucose tolerance test (IVGTT) using the modified minimal model. After an overnight fast, a glucose bolus (300 mg/kg) was administered iv, followed (20 min later) by a bolus of insulin. Blood for determination of glucose and insulin is obtained from a contra lateral vein at −30, −15, 0, 2, 3, 4, 5, 6, 8, 10, 19, 22, 25, 30, 40, 50, 70, 100, 140, and 180 min. SI and glucose effectiveness (SG) are calculated using Bergman's modified minimal-model computer program before and after the completion of the study. Acute insulin response to glucose is determined over the first 19 min of the IVGTT, and the glucose disappearance rate (Kg) is determined from 8-19 min of the IVGTT. Body composition is measured by bioelectrical impedance before and at the completion of the study. Resting energy expenditure (REE) is measured by indirect calorimetry after an overnight 12-h fast, with subjects lying supine for a period of 30 min. Urine is collected over the corresponding 24 h, for measurement of total nitrogen and determination of substrate use, before and after the study.

3. Treatment of Obesity in Humans by Coadministering Diazoxide and Phentermine

Evaluation of a prolonged co-administration of solid oral dosage form of salts of any of the compounds of Formulae I-IV thereof in combination with phentermine can be conducted in humans with moderate-to-morbid obesity and a body mass index (BMI) greater than or equal to 30 kg/m². Each subject undergoes a complete physical examination at the initial evaluation, body weight being measured on a standard electronic scale and body composition by DEXA.

Before initiation of the study, all subjects are placed on a hypocaloric diet for a lead-in period of 1 week. This is designed to exclude subjects who are unlikely to be compliant and to ensure stable body weight before treatment. Up to 100 subjects are tested. Daily dosage of salts of any of the compounds of Formulae I-IV is set at 200 mg. The daily dose is divided into 2 doses for administration. The dose is administered as either a 100 mg capsule or a 100 mg tablet at each time of administration. Subjects are dosed daily for up to 12 months. Phentermine is administered as a single daily dose of 15 mg. Subjects are reviewed every two weeks, weighed, and asked about any side effects or concurrent illnesses.

All subjects are continued on a hypocaloric diet and encouraged to participate in regular exercise. Before commencing, and after completion of the study, laboratory tests as described in the example above are obtained.

4. Prevention of Diabetes in Prediabetic Humans

The example describes the use of salts of any of the compounds of Formulae I-IV in a prediabetic subject to prevent the occurrence of diabetes. Subjects included in the study all have elevated risk of developing diabetes as measured by one of two methods. In a fasting glucose assay they have plasma glucose values between 100 and 125 mg/dl indicating impaired fasting glucose, or in an oral glucose tolerance test they have plasma glucose values between 140 and 199 mg/dl at 2 hours post-glucose load indicating they have impaired glucose tolerance. Treatment is initiated in any subject meeting either criteria. Treated subjects receive either 200 mg diazoxide per day as a 100 mg capsule or tablet twice per day or as two 100 mg capsules or tablets once per day. Placebo treated subjects receive either one placebo capsule or tablet twice per day or two placebo capsules or tablets once per day.

Treatment is continued for once year with OGTT or fasting glucose measured monthly.

5. A Sustained Release Coformulation of Diazoxide HCl and Metformin HCl Use to Treat Diabetic Patients A sustained release co-formulation of diazoxide HCl and metformin HCl is produced by forming a compressed tablet matrix that includes 750 mg of metformin HCl and 100 mg of diazoxide HCl. These active ingredients are blended with sodium carboxymethyl cellulose (about 5% (w/w)), hypromellose (about 25% (w/w), and magnesium stearate (<2% (w/w)). The compressed tablet is further coated with a combination of ethylcellulose (80% (w/w)) and methyl cellulose (20% (w/w)) as a thin film to control rate of hydration and drug release.

Type II diabetic patients are treated with the oral dosage form by administration of two tablets once per day or one tablet every 12 hours. Treatment of the patient with the drug is continued until one of two therapeutic endpoints is reached, or for so long as the patient derives therapeutic benefit from administration. The two therapeutic endpoints that would serve as the basis for the decision to cease treatment include the patient reaching a Body Mass Index (BMI (kg/m²)) between 18 and 25 or the re-establishment of normal glucose tolerance in the absence of treatment. The patient is monitored periodically for (a) glucose tolerance using an oral glucose tolerance test, (b) glycemic control using a standard blood glucose assay, (c) weight gain or loss, (d) progression of diabetic complications, and (e) adverse effects associated with the use of these active ingredients.

6. Prevention or Treatment of Weight Gain in a Patient Treated with Olanzapine

Pharmacotherapy for schizophrenia is initiated for a patient meeting DSM III-R criteria for schizophrenia. The patient is administered 10 mg of olanzapine (Zyprexa, Lilly) once per day. Adjunctive therapy to the patient for schizophrenia includes 250 mg equivalent of valproic acid as divalproex sodium (Depakote, Abbott Labs). Weight gain, dyslipidemia and impaired glucose tolerance, and metabolic syndrome are high frequency adverse events in patients treated with this combination of anti-psychotics. Weight gain, dyslipidemia, impaired glucose tolerance or metabolic syndrome are treated by the co-administration of a therapeutically effective dose of a $K_{ATP}$ channel opener. The patient is treated with administration of 200 mg/day of salts of any of the compounds of Formulae I-IV as a once daily tablet formulation. Administration of salts of any of the compounds of Formulae I-IV continues until the weight gain, dyslipidemia, impaired glucose tolerance or metabolic syndrome is corrected or until treatment of the patient with olanzapine is discontinued. Dyslipidemia is detected by measuring circulating concentrations of total, HDL, and LDL cholesterol, triglycerides and non-esterified fatty acids. Impaired glucose tolerance is detected through the use of oral or IV glucose tolerance tests. Metabolic syndrome is detected by measuring its key risk factors including central obesity, dyslipidemia, impaired glucose tolerance, and circulating concentrations of key proinflammatory cytokines.

7. Comparison of Single Doses of Diazoxide Administered as Proglycem® Oral Suspension or as Diazoxide Choline Controlled-Release Tablets in Obese Subjects.

7.1 Experimental Design 7.1.1. Objective of Study.

Clinical studies employing a randomized, open-label, parallel protocol comparing the safety, tolerability and bioavailability (i.e., pharmacokinetics) in obese subjects of Proglycem® (oral suspension) and diazoxide choline salt (controlled-release tablet) were conducted. The study evaluated the safety and tolerability of a single 200 mg does (approximately 2 mg/kg) of diazoxide. The study further compared the single dose pharmacokinetics of an oral suspension of the free base of diazoxide (Proglycem®) with a controlled-release tableted formulation of diazoxide choline salt under fasting conditions in obese subjects.

7.1.2. Rationale for Study.

Diazoxide choline was selected as an alternative molecule for the oral administration of diazoxide because of significantly greater aqueous solubility over diazoxide free base, rapid conversion to diazoxide base on exposure to an aqueous environment, and incompatibility with incorporation into sustained release formulations. The fate of diazoxide choline in an aqueous medium in vitro has been extensively characterized. Without wishing to be bound by theory, once solubilized from the controlled-release tablet formulation, prior to absorption, the salt hydrolyzes to the free base of diazoxide and choline hydroxide. This was extensively characterized using UV/Vis absorbance, and occurred at all physiological relevant pH values from pH 2.0 to pH 8.5. This hydrolysis occurred in deionized water and buffered aqueous solutions, and in polar solvents that contained trace amounts of water. Thus, diazoxide, as the free base, is the molecular form absorbed following oral administration of the choline salt of diazoxide to animals or humans. Serum and plasma assays used in TK and PK analysis measure diazoxide free base concentrations. Dissolution assays measure diazoxide free base. Differences in plasma concentration-time profiles of diazoxide will be dependent on the time course of release of diazoxide choline from the tablet matrix in the intestinal tract. Historically, both oral suspension and immediate release capsule formulations of diazoxide have been commercially available, marketed as Proglycem®. The oral suspension has been shown to be highly bioavailable and rapidly absorbed upon administration. Because of the difficulty in characterizing dissolution from the oral suspension, the in-vitro dissolution of Proglycem® capsules was compared under standardized conditions to that of diazoxide choline controlled-release tablets (50 mg and 200 mg).

7.1.3. Inclusion Criteria.

Inclusion criteria for the present study included age 18 to 65 years old inclusive and BMI between 30 and 45 kg/m$^2$, inclusive, and signed informed consent. Female participants were required to be either postmenopausal for at least 1 year, surgically sterile [bilateral tubal ligation, bilateral oophorectomy, or hysterectomy], or practicing a medically acceptable method of birth control. Inclusion criteria further included freedom from serious medical disorders involving the kidneys, digestive system, heart and blood vessels, lungs, liver, eyes, nerves, brain, skin, endocrine system, bones or blood. Subjects, other than their obese condition, were generally healthy as documented by medical history, physical examination, vital sign, 12-lead ECG, and clinical laboratory assessments. Characteristics of the subjects randomized in the study are provided in Table 33.

TABLE 33

Characteristics of subjects randomized in the study

| Parameter | Proglycem Oral Suspension (n = 15) Mean ± SD (range) | Diazoxide Choline Controlled-Release Tablet (n = 15) Mean ± SD (range) |
| --- | --- | --- |
| Age (yr) | 32.5 ± 12.1 (18-56) | 27.9 ± 12.6 (19-54) |
| BMI (kg/m$^2$) | 32.9 ± 4.3 (30.2-44.8) | 33.8 ± 3.2 (31.4-42.1) |
| Gender (male/female) | 9/6 | 7/8 |

7.1.4. Exclusion Criteria.

Exclusion criteria included treatment with an investigational drug within 28 days prior to dosing, presence or history of a clinically significant disorder, clinical laboratory test values outside of the accepted reference range, reactive screen for HBV, HCV, or HIV, use of any medication affecting body weight, lipid or glucose metabolism within 2 months, use of any systemic prescription medication from 14 days prior to screening to dosing except hormonal contraceptives, use of any drug known to induce or inhibit hepatic drug metabolism from 28 days prior to screening until dosing, positive test for drug of abuse, current tobacco use, positive pregnancy screen, or pregnant or breastfeeding.

7.1.5. Randomization.

A total of 30 subjects were randomized in the present study. Fifteen subjects were randomized to each arm. For convenience, the 30 subjects were broken up into two cohorts. Cohort 1 checked into the clinic on Oct. 12, 2006, was dosed on Oct. 14, 2006, remained in the clinic for 72 hours following dose administration, returning at 96 and 120 hours after dose administration. Cohort 1 included 10 subjects randomized to receive Proglycem Oral Suspension and 5 subjects randomized to receive a Diazoxide Choline Controlled-Release Tablet. Cohort 2 checked into the clinic on Oct. 14, 2006, were dosed on Oct. 16, 2006, remained in the clinic for 72 hours following dose administration, returning at 96 and 120 hours after dose administration. Cohort 2 included 5 subjects randomized to receive Proglycem® Oral Suspension and 10 subjects randomized to receive a diazoxide choline controlled-release tablet. All subjects completed the study.

7.1.6. Dosing.

Subjects randomized to the Proglycem® Oral Suspension arm received a single 200 mg dose (4 mL) taken with 240 mL of room temperature water. Subjects randomized to the diazoxide choline controlled-release tablet arm received a single tablet containing 290 mg of diazoxide choline, which is equivalent to 200 mg of diazoxide. Doses were administered after an overnight fast, and fasting continued until approximately 4.25 hours after dose administration at which time a standardized meal was served.

7.1.7. Safety Monitoring.

Clinical laboratory tests including hematology, clinical serum chemistry and urinalysis were conducted at screening and at end of study. Hematology included measurements of hemoglobin, hematocrit, white blood cell count with differential, red blood cell count and platelet count. Clinical serum chemistry included evaluation of sodium, potassium, BUN, creatinine, total bilirubin, total protein, albumin, alkaline phosphatase, AST, ALT, glucose, total cholesterol, HDL-cholesterol, and triglycerides. Urinalysis included pH, specific gravity, protein, glucose, ketones, bilirubin, blood, nitrites, urobilinogen, leukocytes, and microscopic urine analysis if sample was dipstick positive. All adverse events were recorded. Vital signs were collected at screening, at one hour prior to dosing, and after dose administration at 1, 3, 6, 9, 12, 24, 48, 72 and 120 hours. Continuous two-lead cardiac monitoring (telemetry) was performed on subjects from 24 hours prior to dose administration (to establish baseline data) until 24 hours after dose administration.

7.1.8. Exploratory Endpoints.

Three exploratory endpoints were evaluated in the study. Blood glucose, insulin and non-esterified fatty acids (NEFA) were measured prior to dosing and at 1, 3, 6, 9, 12, 24, and 48 hours post dosing. Blood glucose and insulin levels were also assessed at end of study. Data collected at times 1, 3, 24, and 48 hours after dose administration were obtained under fasting conditions. The remaining data points were post-prandial measures. Samples for pharmacokinetic analysis to evaluate bioavailability were collected prior to dosing and after dose administration at 1, 2, 4, 6, 8, 12, 16, 20, 24, 32, 40, 48, 72, 96, and 120 hours.

7.2. Results 7.2.1. Adverse Events.

The adverse events observed with each of the two formulations are summarized in Tables 34 and 35. With the single exception, a moderate headache requiring treatment with acetaminophen in a subject treated with Proglycem® Oral Suspension, all adverse events were mild. Both formulations appeared to be well tolerated in the study. One subject administered with diazoxide choline controlled-release tablet experienced mild loss of appetite. Because most obese and obese diabetic animal model studies of diazoxide show some reduction in feed consumption, loss of appetite was, therefore, considered part of the pharmacodynamic response to the drug in obese patients, rather than an adverse event.

TABLE 34

Adverse events (AE) in subjects administered Proglycem ® Oral Suspension (n = 15)

| Adverse Event | Hours Post Dosing | | Corrective Treatment | Outcome |
| --- | --- | --- | --- | --- |
| Gastrointestinal | | | | |
| Nausea$^a$ | 2.75 | Mild | None | Resolved |
| Neurological | | | | |
| Headache | 20.0 | Moderate | Therapy required acetaminophen | Resolved |

TABLE 34-continued

Adverse events (AE) in subjects administered Proglycem ® Oral Suspension (n = 15)

| Adverse Event | Hours Post Dosing | | Corrective Treatment | Outcome |
|---|---|---|---|---|
| Headache[b] | 6.25 | Mild | None | Resolved |
| Dizziness[c] | 1.0 | Mild | Assisted to supine position | Resolved |
| Dizziness[c] | 3.25 | Mild | Assisted to supine position | Resolved |
| Dizziness[d] | 1.0 | Mild | Assisted to supine position | Resolved |
| Dizziness[d] | 4.25 | Mild | Assisted to supine position | Resolved |
| Miscellaneous | | | | |
| Chills[b] | 6.25 | Mild | None | Resolved |
| Dermatitis from ECG patches[a] | 4.75 | Mild | None | Resolved |

Number of subjects with at least one AE = 5, AEs followed by the same superscript letter are the same subject

TABLE 35

Adverse events (AE) in subjects administered Diazoxide Choline Controlled-Release Tablet (n = 15)

| Adverse Event | Hours Post Dosing | | Corrective Treatment | Outcome |
|---|---|---|---|---|
| Gastrointestinal | | | | |
| Nausea[e] | 1.5 | Mild | None | Resolved |
| Dry Heaves[e] | 1.6 | Mild | None | Resolved |
| Neurological | | | | |
| Lightheaded | 12.0 | Mild | Assisted to supine position | Resolved |
| Dizziness[g] | 20.0 | Mild | None | Resolved |
| Miscellaneous | | | | |
| Chills[f] | 2.0 | Mild | None | Resolved |
| Back Pain[f] | 2.0 | Mild | None | Resolved |
| Warm[g] | 20.0 | Mild | None | Resolved |

Number of subjects with at least one AE = 4, AEs followed by the same superscript letter are the same subject

7.2.2. Clinical Chemistry.

A summary of fasting glucose, fasting insulin, NEFA, and serum sodium (Na), potassium (K) and creatinine level is provided in Table 36. Neither treatment resulted in significant changes in serum Na, K or creatinine from baseline to end of study. Treatment with diazoxide primarily impacts glucose-stimulated insulin secretion rather than basal insulin secretion. Fasting glucose levels increased slightly in the first 3 hours following dose administration. This increase was more pronounced in the Proglycem® Oral Suspension arm as compared to the diazoxide choline controlled-release tablet arm. These results are consistent with the differences in measured rates of dissolution from these formulations (see Table 5 herein) and the PK levels (see FIGS. 24 and 25 herein). In this study, there is no evidence for a reduction in fasting insulin after the administration of the single dose of diazoxide. There is also no evidence for a significant increase in fasting glucose as measured at 24 or 48 hours after dose administration. The most sensitive pharmacodynamic response measure is NEFA. Diazoxide treatment normally results in a short-term increase in NEFA, which returns to levels at or below baseline in about 6 hours. Both formulations showed this transient increase in NEFA. Treatment with Proglycem® Oral Suspension resulted in a statistically significant increase ($p<0.001$) in NEFA at 3 hours, which by 6 hours after dose administration had returned to levels well below baseline. Similarly the increase in NEFA at 3 hours after administration of diazoxide choline controlled-release tablets was statistically significant ($p<0.0012$). NEFA levels in the diazoxide choline controlled-release tablet treated subjects also returned to levels well below baseline by 6 hours after dose administration.

TABLE 36

Fasting glucose, fasting insulin, non-esterified fatty acid (NEFA), serum sodium (Na), potassium (K) and creatinine of subjects

| Parameter | Proglycem Oral Suspension (n = 15) Mean ± SD (range) | Diazoxide Choline Controlled-Release Tablet (n = 15) Mean ± SD (range) |
|---|---|---|
| Fasting Glucose (mg/dL) | | |
| Baseline | 93 ± 6 (83-104) | 93 ± 6 (83-108) |
| 1 h post-dose | 99.4 ± 7 (89-117) | 97.9 ± 7 (92-117) |
| 3 h post-dose | 102.8 ± 6 (93-113) | 98.0 ± 7 (90-112) |
| 24 h post-dose | 97 ± 5 (87-106) | 98 ± 8 (88-118) |
| 48 h post-dose | 92 ± 5 (84-103) | 93 ± 5 (83-104) |
| Fasting Insulin (μIU/ml) | | |
| Baseline | 8.6 ± 5.2 (2.9-24.1) | 9.9 ± 3.3 (4.4-16.3) |
| 24 h post-dose | 12.0 ± 8.9 (6.1-41.9) | 11.1 ± 3.3 (5.5-17.0) |
| 48 h post-dose | 9.5 ± 5.7 (4.0-28.9) | 11.1 ± 2.9 (5.3-17.8) |
| NEFA (μmol/L) | | |
| 1 h post-dose | 0.36 ± 0.11 (0.21-0.65) | 0.34 ± 0.14 (0.09-0.67) |
| 3 h post-dose | 0.53 ± 0.13 (0.31-0.78) | 0.55 ± 0.19 (0.28-0.88) |
| 6 h post-dose | 0.13 ± 0.07 (0.07-0.32) | 0.11 ± 0.04 (0.07-0.21) |
| 24 h post-dose | 0.36 ± 0.10 (0.23-0.62) | 0.40 ± 0.18 (0.25-0.97) |
| 48 h post-dose | 0.38 ± 0.13 (0.2-0.66) | 0.39 ± 0.15 (0.17-0.65) |
| Na (mEq/L) | | |
| Baseline | 138.0 ± 2.0 (135-142) | 138.1 ± 2.6 (134-143) |
| End of Study | 138.7 ± 1.1 (137-141) | 139.3 ± 2.3 (135-144) |
| K (mmol/L) | | |
| Baseline | 4.4 ± 0.4 (3.9-5.5) | 4.2 ± 0.3 (3.8-5.1) |
| End of Study | 4.4 ± 0.3 (3.9-5.2) | 4.2 ± 0.3 (3.8-5.2) |
| Creatinine (mg/dL) | | |
| Baseline | 0.9 ± 0.1 (0.7-1.1) | 0.9 ± 0.2 (0.7-1.4) |
| End of Study | 1.0 ± 0.1 (0.8-1.3) | 0.9 ± 0.2 (0.6-1.3) |

All other clinical laboratory tests, including hematology, clinical serum chemistry, and urinalysis were within normal ranges for obese subjects.

7.2.3. Vital Signs.

Figure 22:
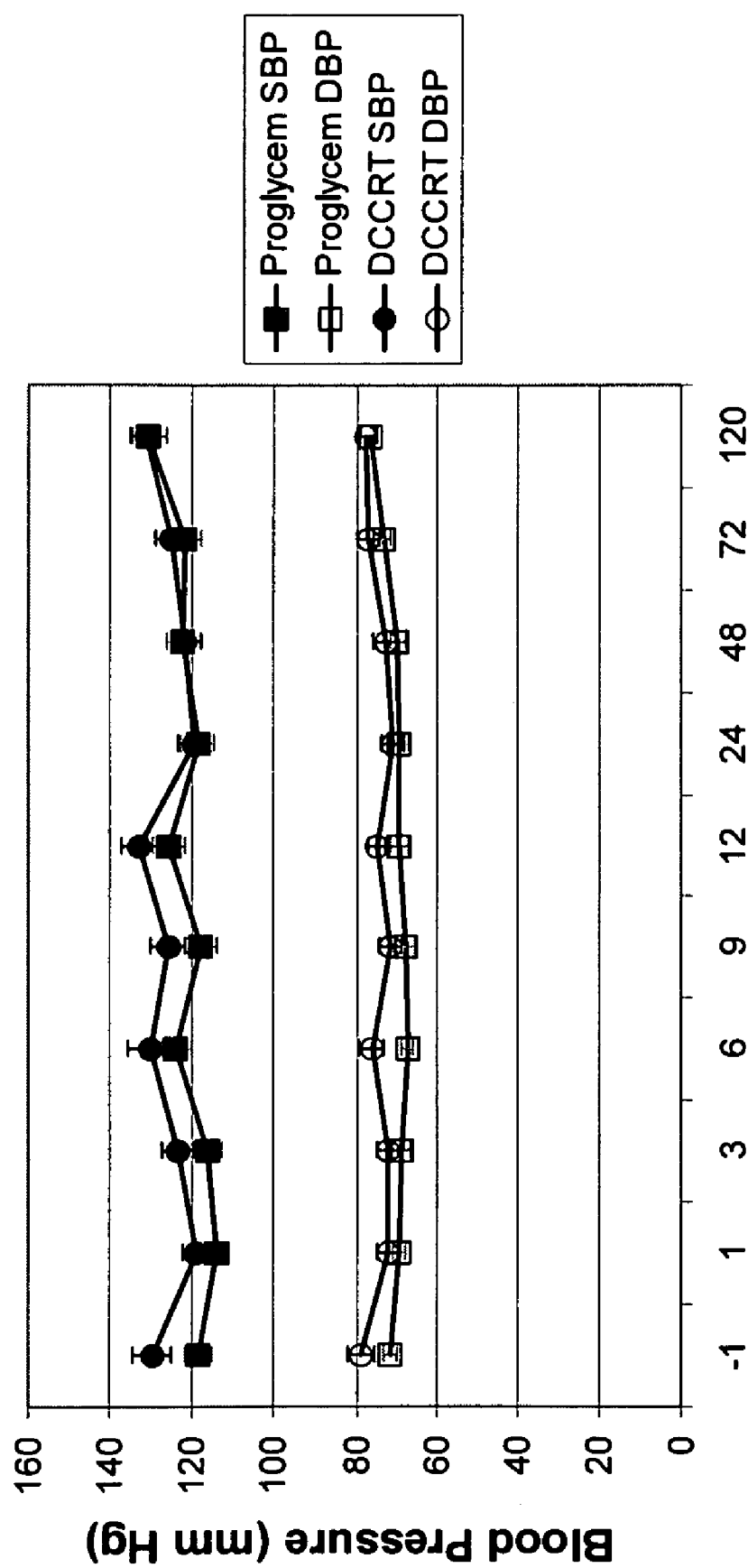
FIG. 22 provides systolic blood pressure (SBP) and diastolic blood pressure (DBP) for Proglycem Oral Suspension (Proglycem) and Diazoxide Choline Controlled-Release Tablets (DCCRT) at various times following dose administration (mean±SEM).
Figure 23:
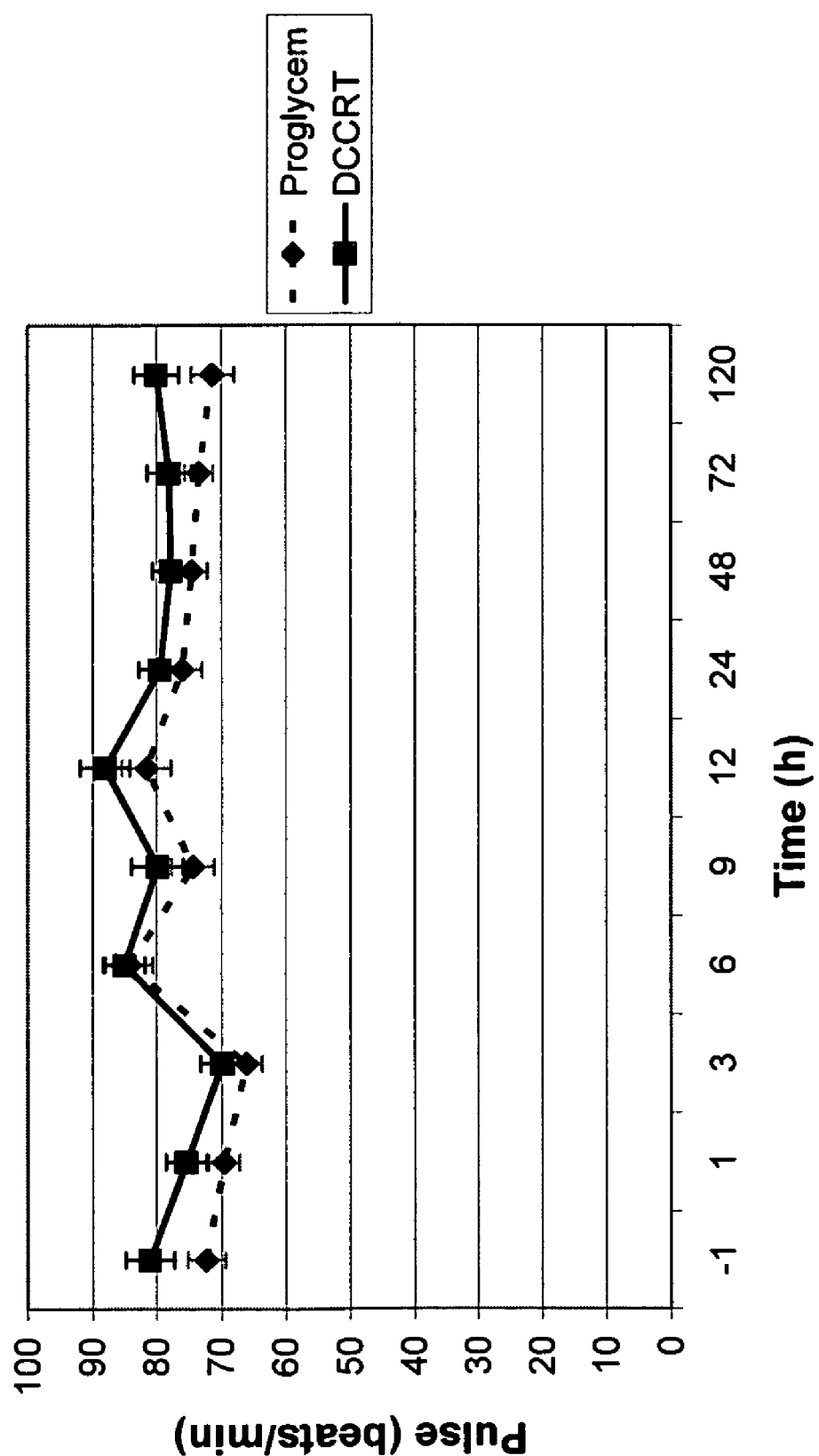
FIG. 23 provides pulse rate for Proglycem Oral Suspension (Proglycem) and Diazoxide Choline Controlled-Release Tablets (DCCRT) at various times following dose administration (mean±SEM).

A graph depicting sitting blood pressure at baseline and at various times following dose administration is provided in FIG. 22. Neither treatment was associated with a sustained reduction or increase in blood pressure, nor was there any clear trend from baseline over 6, 9, 12, or 24 hours after dose administration. Pulse rates dropped incrementally from baseline levels in the period from dose administration to 3 hours post dosing (FIG. 23). Pulse rates rose to levels equivalent to baseline or slightly above baseline in the period from 6 to 12 hours after dose administration, and remained at baseline levels from 24 hours after dose administration to the end of the study (FIG. 23). Review of the baseline cardiac telemetry data for all subjects was conducted the morning of dosing. Based on the absence of clinical significant abnormalities, all subjects were allowed to proceed with dosing. The cardiac telemetry data from study time 0 to 24 hours after dose administration was evaluated. No clinically significant abnormalities (e.g. arrhythmias) were observed.

7.2.4. Preliminary Evaluation of Diazoxide Plasma Pharmacokinetics.

Figure 24:
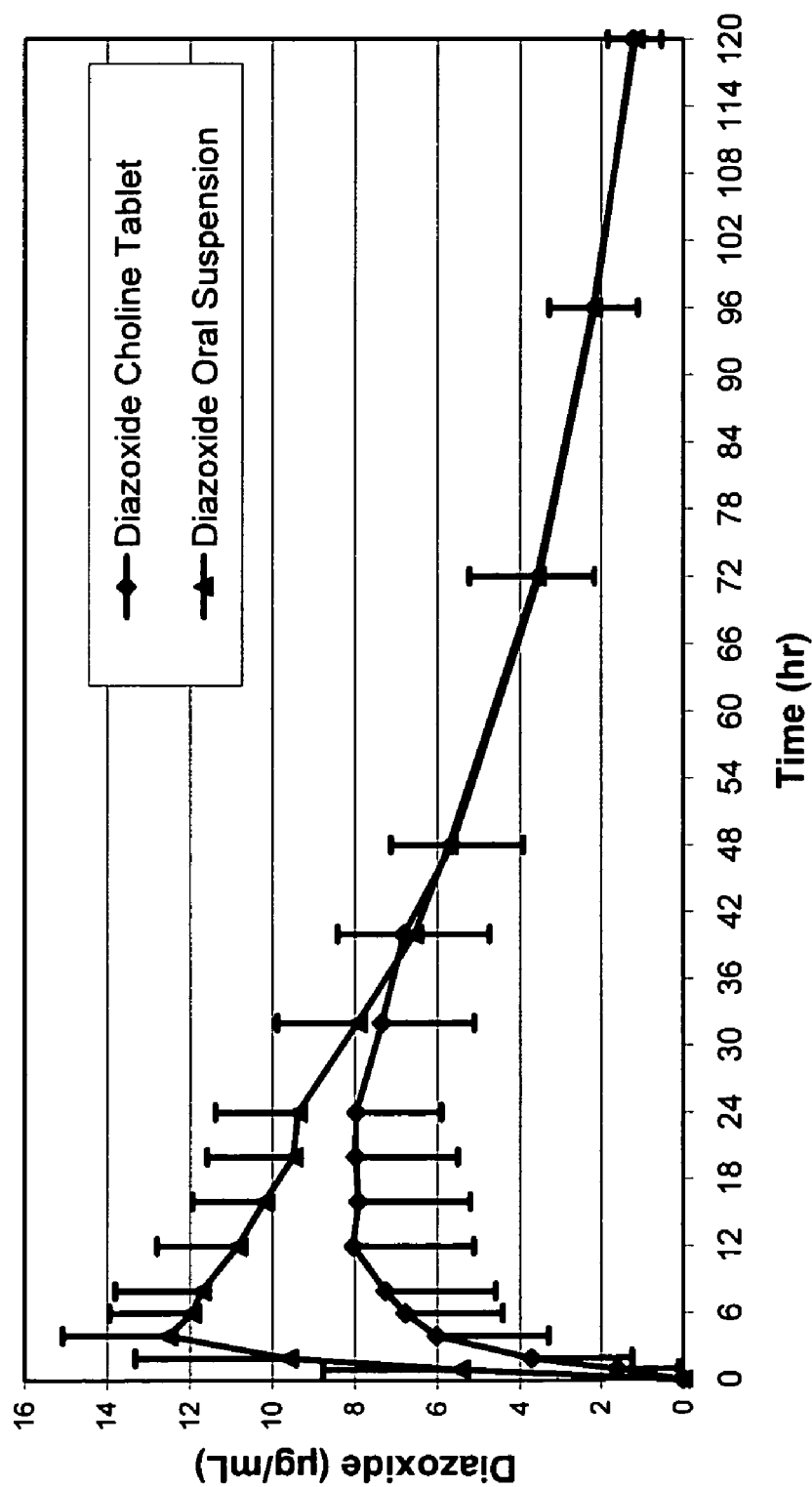
FIG. 24 provides mean plasma diazoxide (±SD) concentrations after a 200 mg dose of diazoxide (linear coordinates).
Figure 25:
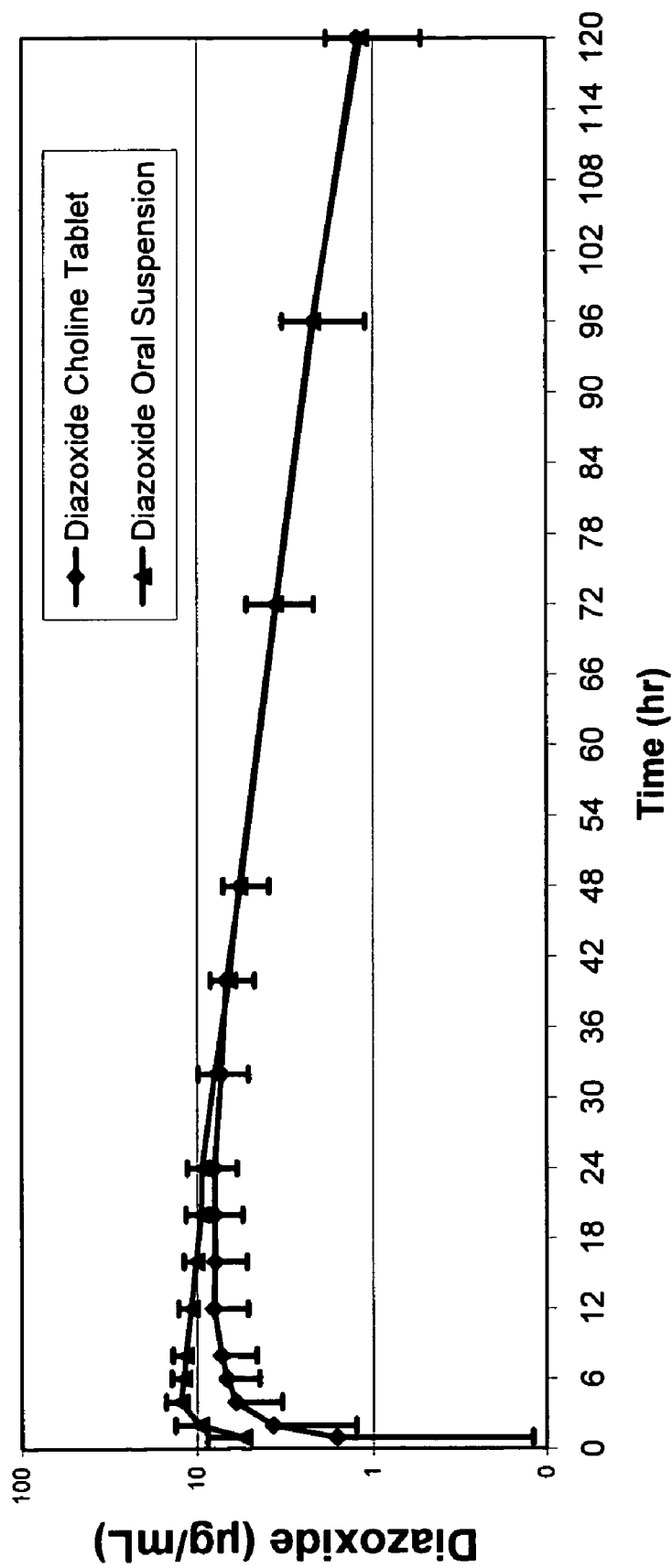
FIG. 25 provides mean plasma diazoxide (±SD) concentrations after a 200 mg dose of diazoxide (semilog coordinates).
Figure 26:
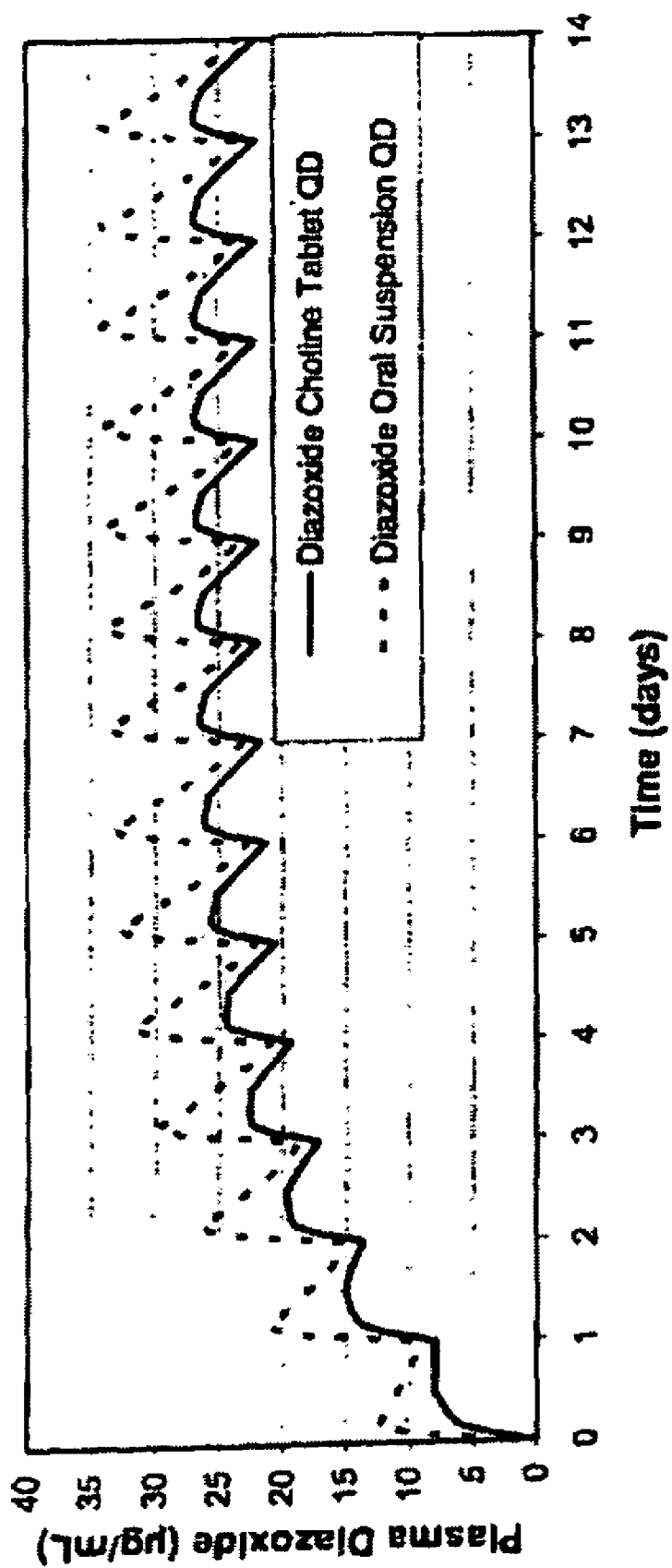
FIG. 26 provides simulations to steady-state of once daily dosing with 200 mg diazoxide.

Compared to the Proglycem® Oral Suspension, the diazoxide choline controlled-release tablet had a 30% lower peak exposure (Cmax) and a 15% lower total exposure (AUC) when the formulations were administered orally as 200 mg equivalents of diazoxide (Table 37). The timing of the peak plasma concentration (Tmax) occurred at a median time of 4 hr after administration of the oral suspension and 20 hr after administration of the diazoxide choline controlled-release tablet. The terminal half-life for diazoxide was similar with both formulations (29 hr for the oral suspension and 32 hr for the tablet). The two formulations had similar between-patient variability for Cmax and AUC. The most notable difference between the two formulations following a single dose was the lower, broader peak of the concentration-time profile of the tablet formulation (FIGS. 24 and 25). The peak concentration for the tablet averaged about 30% less and occurred about 16 hours later than the suspension. FIGS. 24 and 25 illustrate that the mean peak concentration was virtually unchanged between 12-hr and 24-hr post-dose following administration of the diazoxide choline controlled-release tablet formulation. Because of a more sustained release pattern, the tablet formulation was predicted to have a greater accumulation factor with chronic dosing than was the oral suspensions (3.96 vs. 2.84). Simulations of repeated once-daily dosing with the two formulations (assuming linear pharmacokinetics) predicted that the two formulations would have similar trough concentrations at steady-state (22-23 µg/mL) (see FIG. 26).

Oral Suspension in obese patients indicates that both formulations were well tolerated. With a single exception, moderate headache requiring treatment with acetaminophen in one subject treated with Proglycem®, all adverse events were mild. Diazoxide choline controlled-release tablets appear to have a better CNS safety profile than Proglycem® Oral Suspension as evidenced by the absence of headaches and reduced rate of dizziness. Exploratory endpoints showed no detrimental impact. Preliminary pharmacokinetic analysis showed that compared to Proglycem® Oral Suspension, the diazoxide choline controlled-release tablet had a 30% lower peak exposure (Cmax) and a 15% lower total exposure (AUC) for the same 200 mg diazoxide equivalent dose. The timing of the peak plasma concentration (Tmax) occurred at a median time of 4 hr after administration of the oral suspension and 20 hr after administration of the diazoxide choline tablet. The terminal half-life for diazoxide is similar with both formulations (29 hr for the oral suspension and 32 hr for the tablet). The two formulations had similar between-patient variability for Cmax and AUC.

All patents and other references cited in the specification are indicative of the level of skill of those skilled in the art to which the invention pertains, and are incorporated by reference in their entireties, including any tables and figures, to the same extent as if each reference had been incorporated by reference in its entirety individually.

One skilled in the art would readily appreciate that the present invention is well adapted to obtain the ends and advantages mentioned, as well as those inherent therein. The methods, variances, and compositions described herein as presently representative of preferred embodiments are exemplary and are not intended as limitations on the scope.

TABLE 37

Summary Statistics for Plasma Diazoxide Pharmacokinetic Parameters after a Single Dose of Two Formulations

|  | Cmax µg/mL | Tmax hr | AUC (0-24) µg·hr/mL | AUC (0-120) µg·hr/mL | AUC (0-∞) µg·hr/mL | $\lambda z$ 1/hr | $T^{1/2}$ hr | Accum Factor |
|---|---|---|---|---|---|---|---|---|
| *Diazoxide Choline Controlled-Release Tablets* | | | | | | | | |
| N | 15 | 15 | 15 | 15 | 15 | 15 | 15 | 15 |
| Mean | 9.25 | 22.1 | 166 | 553 | 618 | 0.0242 | 31.9 | 3.96 |
| Geomean | 9.07 | 19.6 | 157 | 531 | 588 | 0.0229 | 30.2 | 3.74 |
| St Dev | 1.89 | 11.5 | 54 | 160 | 198 | 0.0085 | 10.6 | 1.48 |
| SEM | 0.49 | 3.0 | 14 | 41 | 51 | 0.0022 | 2.7 | 0.38 |
| CV % | 20.5% | 52.0% | 32.5% | 28.9% | 32.0% | 35.2% | 33.3% | 37.5% |
| Median | 9.08 | 20.0 | 164 | 518 | 586 | 0.0237 | 29.3 | 3.80 |
| Min | 5.53 | 8.00 | 74.6 | 261 | 274 | 0.0144 | 15.9 | 2.26 |
| Max | 13.2 | 48.0 | 266 | 842 | 1024 | 0.0437 | 48.3 | 7.84 |
| *Diazoxide Oral Suspension (Proglycem)* | | | | | | | | |
| N | 15 | 15 | 15 | 15 | 15 | 15 | 15 | 15 |
| Mean | 13.5 | 6.67 | 245 | 643 | 696 | 0.0256 | 28.6 | 2.84 |
| Geomean | 13.3 | 5.36 | 243 | 629 | 677 | 0.0249 | 27.9 | 2.79 |
| St Dev | 2.3 | 5.49 | 35 | 142 | 173 | 0.0068 | 6.3 | 0.57 |
| SEM | 0.6 | 1.42 | 9 | 37 | 45 | 0.0018 | 1.6 | 0.15 |
| CV % | 17.1% | 82.3% | 14.4% | 22.1% | 24.9% | 26.7% | 22.0% | 20.0% |
| Median | 13.3 | 4.00 | 245 | 620 | 671 | 0.0234 | 29.6 | 2.86 |
| Min | 10.1 | 2.00 | 183 | 464 | 488 | 0.0180 | 16.1 | 1.84 |
| Max | 18.0 | 24.0 | 314 | 926 | 1054 | 0.0430 | 38.5 | 4.25 |

7.3. Conclusions of Comparison of Single Doses of Diazoxide Administered as Proglycem® Oral Suspension or as Diazoxide Choline Controlled-Release Tablets in Obese Subjects.

The present clinical study on the comparison of a single dose of diazoxide choline controlled-release tablet with an equivalent dose of diazoxide administered as Proglycem®

Changes therein and other uses will occur to those skilled in the art, which are encompassed within the spirit of the invention, are defined by the scope of the claims.

Definitions provided herein are not intended to be limiting from the meaning commonly understood by one of skill in the art unless indicated otherwise.

The inventions illustratively described herein may suitably be practiced in the absence of any element or elements, limitation or limitations, not specifically disclosed herein. Thus, for example, the terms "comprising", "including," "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein. Other embodiments are within the following claims. In addition, where features or aspects of the invention are described in terms of Markush groups, those skilled in the art will recognize that the invention is also thereby described in terms of any individual member or subgroup of members of the Markush group.

That which is claimed is:

1. A salt comprising:
a KATP channel opener selected from the group consisting of Formula III and Formula IV, and a counter ion as shown below

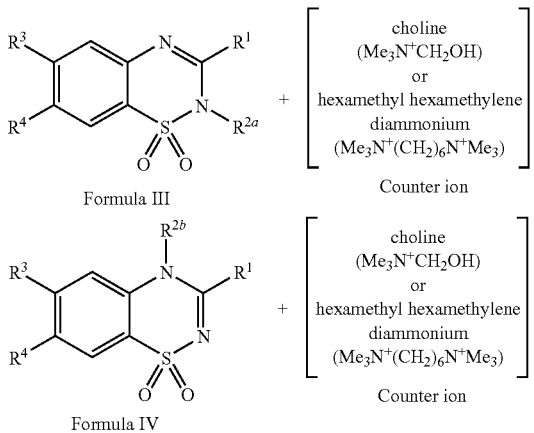

Formula III

Formula IV wherein:
$R^1$ is selected from the group consisting of hydrogen, lower alkyl, substituted lower alkyl, and cycloalkyl provided however that when $R^1$ is a substituted lower alkyl, then the substituent does not include an amino group;
$R^{2a}$ is hydrogen;
$R^{2b}$ is hydrogen;
$R^3$ is selected from the group consisting of hydrogen, halogen, lower alkyl, substituted lower alkyl, cycloalkyl and substituted cycloalkyl provided however that when $R^3$ is a substituted lower alkyl, then the substituent does not include an amino group;
$R^4$ is selected from the group consisting of hydrogen, halogen, lower alkyl, substituted lower alkyl, cycloalkyl and substituted cycloalkyl provided however that when $R^4$ is a substituted lower alkyl, then the substituent does not include an amino group.

2. The salt according to claim 1 wherein said KATP channel opener is diazoxide.

3. The salt according to claim 1 wherein said KATP channel opener is diazoxide and said counter ion is choline.

4. The salt according to claim 1 wherein said KATP channel opener is diazoxide and said counter ion is hexamethyl hexamethylene diammonium.

5. A pharmaceutical formulation comprising the salt of claim 1 and at least one pharmaceutically acceptable excipient.

6. The formulation according to claim 5 wherein the pharmaceutical formulation is an oral dosage form.

7. The formulation according to claim 6 which is an enteric coated formulation.

8. The formulation according to claim 7 wherein the enteric coating is selected from the group consisting of: (a) a compression coating on a tablet, (b) a thin film on a tablet, and (c) a coating on microparticles wherein the microparticles can be further encapsulated.

9. The formulation according to claim 6 wherein the formulation is a sustained release formulation.

10. The formulation according to claim 9 wherein the period of release is 8-24 hours following administration.

11. The formulation according to claim 9 wherein the formulation comprises a component selected from the group consisting of: (a) a pH sensitive polymeric coating, (b) a hydrogel, (c) a film coating that controls the rate of diffusion of the salt from a coated matrix, (d) n erodable matrix that controls rate of salt release, (e) polymer coated pellets, granules or microparticles of salt which can be further encapsulated or compressed into a tablet, (f) an osmotic pump system containing the salt, (g) a compression coated tablet form of the salt, and (h) combinations thereof.

12. The formulation according to claim 5 for a single administration that contains between 10 and 2000 mg of the salt.

13. The formulation according to claim 5 for a single administration that contains between 300 and 500 mg of the salt.

14. The formulation according to claim 9 wherein the period of release is 2-30 hours following administration.

* * * * *

UNITED STATES PATENT AND TRADEMARK OFFICE
CERTIFICATE OF CORRECTION

PATENT NO. : 7,572,789 B2  Page 1 of 1
APPLICATION NO. : 12/391990
DATED : August 11, 2009
INVENTOR(S) : Neil M. Cowen and Khaled A. Yamout It is certified that error appears in the above-identified patent and that said Letters Patent is hereby corrected as shown below:

Title Page; In Item (75), please correct inventors listed from "Neil M. Cowen, Carlsbad, CA (US); Kenneth B. Kashkin, Sparta, NJ (US); Khaled A. Yamout, Carlsbad, CA (US);" to -- Neil M. Cowen, Carlsbad, CA (US); Khaled A. Yamout, Carlsbad, CA (US); --.

Claim 1, Column 113 line 40 and line 48, the description in both counter ion formulas replace "choline ($Me_3N+CH_2OH$) ..." with -- choline ($Me_3N+CH_2CH_2OH$) ... --.

Claim 11, Column 114 line 44, replace "... (d) n erodable matrix that ..." with -- (d) an erodible matrix that ... --.

Signed and Sealed this

Fifth Day of January, 2010

David J. Kappos
*Director of the United States Patent and Trademark Office*